United States Patent
Ma et al.

(10) Patent No.: US 9,322,020 B2
(45) Date of Patent: Apr. 26, 2016

(54) RNA INTERFERENCE MEDIATED INHIBITION OF ISOCITRATE DEHYDROGENASE (IDH1) GENE EXPRESSION

(75) Inventors: Yong Ma, Daly City, CA (US); Duncan Brown, Berkeley, CA (US); Steven Bartz, Seattle, WA (US)

(73) Assignee: Sirna Therapeutics, Inc., Cambridge, MA (US)

( * ) Notice: Subject to any disclaimer, the term of this patent is extended or adjusted under 35 U.S.C. 154(b) by 0 days.

(21) Appl. No.: 14/123,822

(22) PCT Filed: Jun. 1, 2012

(86) PCT No.: PCT/US2012/040332
§ 371 (c)(1),
(2), (4) Date: Dec. 4, 2013

(87) PCT Pub. No.: WO2012/170284
PCT Pub. Date: Dec. 13, 2012

(65) Prior Publication Data
US 2014/0094503 A1    Apr. 3, 2014

Related U.S. Application Data

(60) Provisional application No. 61/493,570, filed on Jun. 6, 2011.

(51) Int. Cl.
*C12N 15/113* (2010.01)
*C07H 21/02* (2006.01)

(52) U.S. Cl.
CPC ............ *C12N 15/1137* (2013.01); *C07H 21/02* (2013.01); *C12N 2310/14* (2013.01); *C12N 2310/315* (2013.01); *C12N 2310/317* (2013.01); *C12N 2310/332* (2013.01); *C12Y 101/01042* (2013.01)

(58) Field of Classification Search
USPC .................................. 536/23.1, 24.5; 514/44
See application file for complete search history.

(56) References Cited

U.S. PATENT DOCUMENTS

2005/0255487 A1    11/2005    Khvorova et al.
2009/0176725 A1    7/2009    Morrissey et al.

FOREIGN PATENT DOCUMENTS

WO    WO2010105243 A1 *    3/2010

* cited by examiner

*Primary Examiner* — Terra C Gibbs
(74) *Attorney, Agent, or Firm* — McCarter & English, LLP; Maria Laccotripe Zacharakis; Deborah L. Nagle

(57) ABSTRACT

The present invention relates to compounds, compositions, and methods for the study, diagnosis, and treatment of traits, diseases and conditions that respond to the modulation of IDH1 and mutant IDH1 gene expression and/or activity, and/or modulate an IDH1 or mutant IDH1 gene expression pathway. Specifically, the invention relates to double-stranded nucleic acid molecules, including small nucleic acid molecules such as short interfering nucleic acid (siNA), short interfering RNA (siRNA), double-stranded RNA (dsRNA), micro-RNA (miRNA), and short hairpin RNA (shRNA) molecules, that are capable of mediating or that mediate RNA interference (RNAi) against IDH1 or mutant IDH1 gene expression.

14 Claims, 14 Drawing Sheets

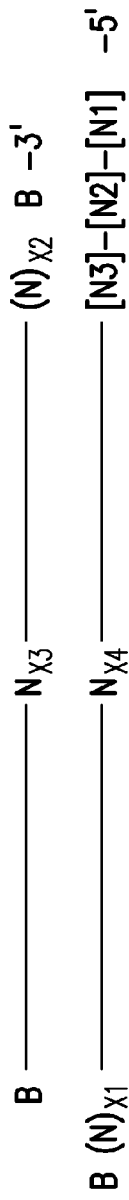

$B \longrightarrow N_{X3} \longrightarrow (N)_{X2}\ B\ -3'$ $B\ (N)_{X1} \longrightarrow N_{X4} \longrightarrow [N3]-[N2]-[N1]\ -5'$ N = Nucleotide (optionally non-nucleotide)
X1 and X2 are independently integers from 0 to 4
X3 is an integer from 15 to 30
X4 is an integer from 12 to 27

Each (N) is independently a 2'-OMe, 2'-F, 2'-deoxy or LNA nucleotide or any combination thereof
Each N is independently a 2'-OMe, 2'-F, ribo-, or 2'-deoxy nucleotide or any combination thereof
Each [N1], [N2], [N3] is independently a 2'-OMe, 2'-F, ribo-, or 2'-deoxy nucleotide or any combination thereof
B = an optional CAP
Optional phosphorothioates, e.g., between (N),(N) nucleotides; N,N nucleotides; or (N),N nucleotides

| $N_{X3}$ Y/R | $N_{X4}$ Y/R | [N3]-[N2]-[N1] |
|---|---|---|
| (5+) 2'-F/OH<br>Optional PS | (5+) 2'-F/OH<br>Optional PS | 2'-H, 2'-F, 2'-F<br>or<br>'2-OMe, 2-F, 2-H<br>or<br>2'-F, 2'-F, 2'-F<br>or<br>2'-H, 2'-F, 2'-H<br>or<br>2'-OH, 2'-OH, 2'-OH |
| (5+) 2'-OMe/OH<br>Optional PS | (5+) 2'-OMe/OH<br>Optional PS | |
| (5+) 2'-F/H<br>Optional PS | (5+) 2'-F/OMe<br>Optional PS | |
| (5+) 2'-OMe/F<br>Optional PS | (5+) 2'-F/OMe<br>Optional PS | |

| $(N)_{X1}$ = 2'-OMe/F/H/LNA + Optional PS |
|---|
| $(N)_{X2}$ = 2'-OMe/F/H/LNA + Optional PS |

FIG. 3

```
                              11th nucleotide position based on
                                 5'-end of antisense strand
                                           ↓
1.  5'-           B-N N N N N N N N N N N N N N N N N (N N)-B      -3'
2.  3'-      B-(N N) N N N N N N N N N N N N N N N N N N3 N2 N1     -5'
3.  5'- ------[N N] N N N N N N N N N N N N N N N N N N N N N ------ -3'
```

1. = sense strand (passenger strand)
2. = antisense strand (guide strand)
3. = target polynucleotide sequence i. The guide strand is complementary to the target sequence (see exception vii below) and the passenger strand is complementary to the guide strand.
ii. Overhang nucleotides (NN) in the guide strand can be complementary to nucleotides [NN] in target sequence.
iii. Overhang nucleotides (NN) in the passenger strand can comprise nucleotides [NN] in target sequence.
iv. Position $N$ of the passenger strand can comprise a ribonucleotide. For the representative 19 base pair 21-mer duplex shown, position $N$ is 9 nucleotides in from the 5' end of the passenger strand. However, in duplexes of differing length, the position $N$ is determined based on the 5'-end of the guide strand by counting 11 nucleotide positions in from the 5'-terminus of the guide strand and picking the corresponding base paired nucleotide in the passenger strand. Generally, cleavage by Ago2 takes place between positions 10 and 11 as indicated by the arrow.
v. Position $\underline{N}$ of the antisense strand is 14 nucleotides from the 5' end of the antisense strand and can be a ribonucleotide or modified nucleotide, such as a 2'-deoxy-2'-fluoro nucleotide, but is preferably not a 2'-O-alkyl nucleotide.
vi. N3, N2, and N1 positions of the antisense strand can have modification on the 2'-sugar position and/or phosphate backbone.
vii. When N of the target sequence is an A and the corresponding complementary nucleotide in the antisense strand is a U at positons 1, 2, or 3 from 5' end of the antisense strand, and the 2'-sugar modification is a 2'-deoxy modification, a thymidine can be used in place of a 2'-deoxy uridine.
viii. Representative 2 nucleotide overhangs are shown, but can vary for example from 0 to about 4 nucleotides.
x. B = terminal cap which can be present or absent
xi. This generalized motif can be applied to all Stab chemistries herein (see Table 6).

FIG. 4C

SEQUENCE LISTING

<160> NUMBER OF SEQ ID NOS: 516

<210> SEQ ID NO 1
<211> LENGTH: 19
<212> TYPE: RNA
<213> ORGANISM: Artificial Sequence
<220> FEATURE:
<223> OTHER INFORMATION: Synthetic

<400> SEQUENCE: 1
auuggaucua cauagcuau                                          19

<210> SEQ ID NO 2
<211> LENGTH: 19
<212> TYPE: RNA
<213> ORGANISM: Artificial Sequence
<220> FEATURE:
<223> OTHER INFORMATION: Synthetic

<400> SEQUENCE: 2
gcauaauguu ggcgucaaa                                              19

<210> SEQ ID NO 3
<211> LENGTH: 19
<212> TYPE: RNA
<213> ORGANISM: Artificial Sequence
<220> FEATURE:
<223> OTHER INFORMATION: Synthetic

<400> SEQUENCE: 3
aaaccuauca ucauagguc                                              19

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
aaccuaucau cauaggucg                                              19

<210> SEQ ID NO 5
<211> LENGTH: 19
<212> TYPE: RNA
<213> ORGANISM: Artificial Sequence
<220> FEATURE:
<223> OTHER INFORMATION: Synthetic

<400> SEQUENCE: 5
accuaucauc auaggucgu                                              19

<210> SEQ ID NO 6
<211> LENGTH: 19
<212> TYPE: RNA
<213> ORGANISM: Artificial Sequence
<220> FEATURE:
<223> OTHER INFORMATION: Synthetic

<400> SEQUENCE: 6
ccuaucauca uaggucguc                                              19

<210> SEQ ID NO 7
<211> LENGTH: 19
<212> TYPE: RNA
<213> ORGANISM: Artificial Sequence
<220> FEATURE:
<223> OTHER INFORMATION: Synthetic

<400> SEQUENCE: 7
cuaucaucau aggucguca                                              19

<210> SEQ ID NO 8
<211> LENGTH: 19
<212> TYPE: RNA
<213> ORGANISM: Artificial Sequence
<220> FEATURE:
<223> OTHER INFORMATION: Synthetic

<400> SEQUENCE: 8
uaucaucaua ggucgucau                                              19

<210> SEQ ID NO 9
<211> LENGTH: 19
<212> TYPE: RNA
<213> ORGANISM: Artificial Sequence

```
<220> FEATURE:
<223> OTHER INFORMATION: Synthetic

<400> SEQUENCE: 9
aucaucauag gucgucaug                                                    19

<210> SEQ ID NO 10
<211> LENGTH: 19
<212> TYPE: RNA
<213> ORGANISM: Artificial Sequence
<220> FEATURE:
<223> OTHER INFORMATION: Synthetic

<400> SEQUENCE: 10
ucaucauagg ucgucaugc                                                    19

<210> SEQ ID NO 11
<211> LENGTH: 19
<212> TYPE: RNA
<213> ORGANISM: Artificial Sequence
<220> FEATURE:
<223> OTHER INFORMATION: Synthetic

<400> SEQUENCE: 11
caucauaggu cgucaugcu                                                    19

<210> SEQ ID NO 12
<211> LENGTH: 19
<212> TYPE: RNA
<213> ORGANISM: Artificial Sequence
<220> FEATURE:
<223> OTHER INFORMATION: Synthetic

<400> SEQUENCE: 12
aucauagguc gucaugcuu                                                    19

<210> SEQ ID NO 13
<211> LENGTH: 19
<212> TYPE: RNA
<213> ORGANISM: Artificial Sequence
<220> FEATURE:
<223> OTHER INFORMATION: Synthetic

<400> SEQUENCE: 13
ucauaggucg ucaugcuua                                                    19

<210> SEQ ID NO 14
<211> LENGTH: 19
<212> TYPE: RNA
<213> ORGANISM: Artificial Sequence
<220> FEATURE:
<223> OTHER INFORMATION: Synthetic

<400> SEQUENCE: 14
cauaggucgu caugcuuau                                                    19

<210> SEQ ID NO 15
<211> LENGTH: 19
<212> TYPE: RNA
<213> ORGANISM: Artificial Sequence
<220> FEATURE:
<223> OTHER INFORMATION: Synthetic

<400> SEQUENCE: 15
auaggucguc augcuuaug                                                    19
```

<210> SEQ ID NO 16
<211> LENGTH: 19
<212> TYPE: RNA
<213> ORGANISM: Artificial Sequence
<220> FEATURE:
<223> OTHER INFORMATION: Synthetic

<400> SEQUENCE: 16
uaggucguca ugcuuaugg                                                19

<210> SEQ ID NO 17
<211> LENGTH: 19
<212> TYPE: RNA
<213> ORGANISM: Artificial Sequence
<220> FEATURE:
<223> OTHER INFORMATION: Synthetic

<400> SEQUENCE: 17
aggucgucau gcuuauggg                                                19

<210> SEQ ID NO 18
<211> LENGTH: 19
<212> TYPE: RNA
<213> ORGANISM: Artificial Sequence
<220> FEATURE:
<223> OTHER INFORMATION: Synthetic

<400> SEQUENCE: 18
ggucgucaug cuuaugggg                                                19

<210> SEQ ID NO 19
<211> LENGTH: 19
<212> TYPE: RNA
<213> ORGANISM: Artificial Sequence
<220> FEATURE:
<223> OTHER INFORMATION: Synthetic

<400> SEQUENCE: 19
gucgucaugc uuaugggga                                                19

<210> SEQ ID NO 20
<211> LENGTH: 19
<212> TYPE: RNA
<213> ORGANISM: Artificial Sequence
<220> FEATURE:
<223> OTHER INFORMATION: Synthetic

<400> SEQUENCE: 20
ucgucaugcu uaugggau                                                 19

<210> SEQ ID NO 21
<211> LENGTH: 19
<212> TYPE: RNA
<213> ORGANISM: Artificial Sequence
<220> FEATURE:
<223> OTHER INFORMATION: Synthetic

<400> SEQUENCE: 21
cgucaugcuu augggauc                                                 19

<210> SEQ ID NO 22
<211> LENGTH: 19
<212> TYPE: RNA
<213> ORGANISM: Artificial Sequence
<220> FEATURE:
<223> OTHER INFORMATION: Synthetic

```
<400> SEQUENCE: 22
gucaugcuua ugggauca                                              19

<210> SEQ ID NO 23
<211> LENGTH: 19
<212> TYPE: RNA
<213> ORGANISM: Artificial Sequence
<220> FEATURE:
<223> OTHER INFORMATION: Synthetic

<400> SEQUENCE: 23
ugaagaaggu gguguguu                                              19

<210> SEQ ID NO 24
<211> LENGTH: 19
<212> TYPE: RNA
<213> ORGANISM: Artificial Sequence
<220> FEATURE:
<223> OTHER INFORMATION: Synthetic

<400> SEQUENCE: 24
uccaaauggc ucugucuaa                                             19

<210> SEQ ID NO 25
<211> LENGTH: 19
<212> TYPE: RNA
<213> ORGANISM: Artificial Sequence
<220> FEATURE:
<223> OTHER INFORMATION: Synthetic

<400> SEQUENCE: 25
gagcaaagcu ugauaacaa                                             19

<210> SEQ ID NO 26
<211> LENGTH: 19
<212> TYPE: RNA
<213> ORGANISM: Artificial Sequence
<220> FEATURE:
<223> OTHER INFORMATION: Synthetic

<400> SEQUENCE: 26
agcaaagcuu gauaacaau                                             19

<210> SEQ ID NO 27
<211> LENGTH: 19
<212> TYPE: RNA
<213> ORGANISM: Artificial Sequence
<220> FEATURE:
<223> OTHER INFORMATION: Synthetic

<400> SEQUENCE: 27
agguuuaccc aaugugcaa                                             19

<210> SEQ ID NO 28
<211> LENGTH: 19
<212> TYPE: RNA
<213> ORGANISM: Artificial Sequence
<220> FEATURE:
<223> OTHER INFORMATION: Synthetic

<400> SEQUENCE: 28 cauugaguu cauggauaa                                              19

<210> SEQ ID NO 29
```

```
<211> LENGTH: 19
<212> TYPE: RNA
<213> ORGANISM: Artificial Sequence
<220> FEATURE:
<223> OTHER INFORMATION: Synthetic

<400> SEQUENCE: 29
acuuuaaguu cauaccuga                                                19

<210> SEQ ID NO 30
<211> LENGTH: 19
<212> TYPE: RNA
<213> ORGANISM: Artificial Sequence
<220> FEATURE:
<223> OTHER INFORMATION: Synthetic

<400> SEQUENCE: 30
aaaccuauca ucauagguu                                                19

<210> SEQ ID NO 31
<211> LENGTH: 19
<212> TYPE: RNA
<213> ORGANISM: Artificial Sequence
<220> FEATURE:
<223> OTHER INFORMATION: Synthetic

<400> SEQUENCE: 31
aaccuaucau cauagguug                                                19

<210> SEQ ID NO 32
<211> LENGTH: 19
<212> TYPE: RNA
<213> ORGANISM: Artificial Sequence
<220> FEATURE:
<223> OTHER INFORMATION: Synthetic

<400> SEQUENCE: 32
accuaucauc auagguugu                                                19

<210> SEQ ID NO 33
<211> LENGTH: 19
<212> TYPE: RNA
<213> ORGANISM: Artificial Sequence
<220> FEATURE:
<223> OTHER INFORMATION: Synthetic

<400> SEQUENCE: 33
ccuaucauca uagguuguc                                                19

<210> SEQ ID NO 34
<211> LENGTH: 19
<212> TYPE: RNA
<213> ORGANISM: Artificial Sequence
<220> FEATURE:
<223> OTHER INFORMATION: Synthetic

<400> SEQUENCE: 34
cuaucaucau agguuguca                                                19

<210> SEQ ID NO 35
<211> LENGTH: 19
<212> TYPE: RNA
<213> ORGANISM: Artificial Sequence
<220> FEATURE:
<223> OTHER INFORMATION: Synthetic

<400> SEQUENCE: 35
```
uaucaucaua gguugucau                                        19

<210> SEQ ID NO 36
<211> LENGTH: 19
<212> TYPE: RNA
<213> ORGANISM: Artificial Sequence
<220> FEATURE:
<223> OTHER INFORMATION: Synthetic

<400> SEQUENCE: 36
aucaucauag guugucaug                                        19

<210> SEQ ID NO 37
<211> LENGTH: 19
<212> TYPE: RNA
<213> ORGANISM: Artificial Sequence
<220> FEATURE:
<223> OTHER INFORMATION: Synthetic

<400> SEQUENCE: 37
ucaucauagg uugucaugc                                        19

<210> SEQ ID NO 38
<211> LENGTH: 19
<212> TYPE: RNA
<213> ORGANISM: Artificial Sequence
<220> FEATURE:
<223> OTHER INFORMATION: Synthetic

<400> SEQUENCE: 38
caucauaggu ugucaugcu                                        19

<210> SEQ ID NO 39
<211> LENGTH: 19
<212> TYPE: RNA
<213> ORGANISM: Artificial Sequence
<220> FEATURE:
<223> OTHER INFORMATION: Synthetic

<400> SEQUENCE: 39
aucauagguu gucaugcuu                                        19

<210> SEQ ID NO 40
<211> LENGTH: 19
<212> TYPE: RNA
<213> ORGANISM: Artificial Sequence
<220> FEATURE:
<223> OTHER INFORMATION: Synthetic

<400> SEQUENCE: 40
ucauagguug ucaugcuua                                        19

<210> SEQ ID NO 41
<211> LENGTH: 19
<212> TYPE: RNA
<213> ORGANISM: Artificial Sequence
<220> FEATURE:
<223> OTHER INFORMATION: Synthetic

<400> SEQUENCE: 41
cauagguugu caugcuuau                                        19

<210> SEQ ID NO 42
<211> LENGTH: 19
<212> TYPE: RNA

```
<213> ORGANISM: Artificial Sequence
<220> FEATURE:
<223> OTHER INFORMATION: Synthetic

<400> SEQUENCE: 42
auagguuguc augcuuaug                                                   19

<210> SEQ ID NO 43
<211> LENGTH: 19
<212> TYPE: RNA
<213> ORGANISM: Artificial Sequence
<220> FEATURE:
<223> OTHER INFORMATION: Synthetic

<400> SEQUENCE: 43
uagguuguca ugcuuaugg                                                   19

<210> SEQ ID NO 44
<211> LENGTH: 19
<212> TYPE: RNA
<213> ORGANISM: Artificial Sequence
<220> FEATURE:
<223> OTHER INFORMATION: Synthetic

<400> SEQUENCE: 44
agguugucau gcuuauggg                                                   19

<210> SEQ ID NO 45
<211> LENGTH: 19
<212> TYPE: RNA
<213> ORGANISM: Artificial Sequence
<220> FEATURE:
<223> OTHER INFORMATION: Synthetic

<400> SEQUENCE: 45
gguugucaug cuuaugggg                                                   19

<210> SEQ ID NO 46
<211> LENGTH: 19
<212> TYPE: RNA
<213> ORGANISM: Artificial Sequence
<220> FEATURE:
<223> OTHER INFORMATION: Synthetic

<400> SEQUENCE: 46
guugucaugc uuaugggga                                                   19

<210> SEQ ID NO 47
<211> LENGTH: 19
<212> TYPE: RNA
<213> ORGANISM: Artificial Sequence
<220> FEATURE:
<223> OTHER INFORMATION: Synthetic

<400> SEQUENCE: 47
uugucaugcu uauggggau                                                   19

<210> SEQ ID NO 48
<211> LENGTH: 19
<212> TYPE: RNA
<213> ORGANISM: Artificial Sequence
<220> FEATURE:
<223> OTHER INFORMATION: Synthetic

<400> SEQUENCE: 48
ugucaugcuu auggggauc                                                   19
```

```
<210> SEQ ID NO 49
<211> LENGTH: 19
<212> TYPE: RNA
<213> ORGANISM: Artificial Sequence
<220> FEATURE:
<223> OTHER INFORMATION: Synthetic

<400> SEQUENCE: 49
aaccuaucau cauagguca                                                    19

<210> SEQ ID NO 50
<211> LENGTH: 19
<212> TYPE: RNA
<213> ORGANISM: Artificial Sequence
<220> FEATURE:
<223> OTHER INFORMATION: Synthetic

<400> SEQUENCE: 50
accuaucauc auaggucau                                                    19

<210> SEQ ID NO 51
<211> LENGTH: 19
<212> TYPE: RNA
<213> ORGANISM: Artificial Sequence
<220> FEATURE:
<223> OTHER INFORMATION: Synthetic

<400> SEQUENCE: 51
ccuaucauca uaggucauc                                                    19

<210> SEQ ID NO 52
<211> LENGTH: 19
<212> TYPE: RNA
<213> ORGANISM: Artificial Sequence
<220> FEATURE:
<223> OTHER INFORMATION: Synthetic

<400> SEQUENCE: 52
cuaucaucau aggucauca                                                    19

<210> SEQ ID NO 53
<211> LENGTH: 19
<212> TYPE: RNA
<213> ORGANISM: Artificial Sequence
<220> FEATURE:
<223> OTHER INFORMATION: Synthetic

<400> SEQUENCE: 53
uaucaucaua ggucaucau                                                    19

<210> SEQ ID NO 54
<211> LENGTH: 19
<212> TYPE: RNA
<213> ORGANISM: Artificial Sequence
<220> FEATURE:
<223> OTHER INFORMATION: Synthetic

<400> SEQUENCE: 54
aucaucauag gucaucaug                                                    19

<210> SEQ ID NO 55
<211> LENGTH: 19
<212> TYPE: RNA
<213> ORGANISM: Artificial Sequence
<220> FEATURE:
```

<223> OTHER INFORMATION: Synthetic

<400> SEQUENCE: 55
ucaucauagg ucaucaugc                                                      19

<210> SEQ ID NO 56
<211> LENGTH: 19
<212> TYPE: RNA
<213> ORGANISM: Artificial Sequence
<220> FEATURE:
<223> OTHER INFORMATION: Synthetic

<400> SEQUENCE: 56
caucauaggu caucaugcu                                                      19

<210> SEQ ID NO 57
<211> LENGTH: 19
<212> TYPE: RNA
<213> ORGANISM: Artificial Sequence
<220> FEATURE:
<223> OTHER INFORMATION: Synthetic

<400> SEQUENCE: 57
aucauagguc aucaugcuu                                                      19

<210> SEQ ID NO 58
<211> LENGTH: 19
<212> TYPE: RNA
<213> ORGANISM: Artificial Sequence
<220> FEATURE:
<223> OTHER INFORMATION: Synthetic

<400> SEQUENCE: 58
ucauagguca ucaugcuua                                                      19

<210> SEQ ID NO 59
<211> LENGTH: 19
<212> TYPE: RNA
<213> ORGANISM: Artificial Sequence
<220> FEATURE:
<223> OTHER INFORMATION: Synthetic

<400> SEQUENCE: 59
cauaggucau caugcuuau                                                      19

<210> SEQ ID NO 60
<211> LENGTH: 19
<212> TYPE: RNA
<213> ORGANISM: Artificial Sequence
<220> FEATURE:
<223> OTHER INFORMATION: Synthetic

<400> SEQUENCE: 60
auaggucauc augcuuaug                                                      19

<210> SEQ ID NO 61
<211> LENGTH: 19
<212> TYPE: RNA
<213> ORGANISM: Artificial Sequence
<220> FEATURE:
<223> OTHER INFORMATION: Synthetic

<400> SEQUENCE: 61
uaggucauca ugcuuaugg                                                      19

```
<210> SEQ ID NO 62
<211> LENGTH: 19
<212> TYPE: RNA
<213> ORGANISM: Artificial Sequence
<220> FEATURE:
<223> OTHER INFORMATION: Synthetic

<400> SEQUENCE: 62
aggucaucau gcuuauggg                                                        19

<210> SEQ ID NO 63
<211> LENGTH: 19
<212> TYPE: RNA
<213> ORGANISM: Artificial Sequence
<220> FEATURE:
<223> OTHER INFORMATION: Synthetic

<400> SEQUENCE: 63
ggucaucaug cuuaugggg                                                        19

<210> SEQ ID NO 64
<211> LENGTH: 19
<212> TYPE: RNA
<213> ORGANISM: Artificial Sequence
<220> FEATURE:
<223> OTHER INFORMATION: Synthetic

<400> SEQUENCE: 64
gucaucaugc uuaugggga                                                        19

<210> SEQ ID NO 65
<211> LENGTH: 19
<212> TYPE: RNA
<213> ORGANISM: Artificial Sequence
<220> FEATURE:
<223> OTHER INFORMATION: Synthetic

<400> SEQUENCE: 65
ucaucaugcu uaugggggau                                                       19

<210> SEQ ID NO 66
<211> LENGTH: 19
<212> TYPE: RNA
<213> ORGANISM: Artificial Sequence
<220> FEATURE:
<223> OTHER INFORMATION: Synthetic

<400> SEQUENCE: 66
caucaugcuu augggauc                                                         19

<210> SEQ ID NO 67
<211> LENGTH: 19
<212> TYPE: RNA
<213> ORGANISM: Artificial Sequence
<220> FEATURE:
<223> OTHER INFORMATION: Synthetic

<400> SEQUENCE: 67
aucaugcuua ugggauca                                                         19

<210> SEQ ID NO 68
<211> LENGTH: 21
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 68
auuggaucua cauagcuaut t                                              21

<210> SEQ ID NO 69
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 69
auagcuaugu agauccaauu u                                              21

<210> SEQ ID NO 70
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 70
gcauaauguu ggcgucaaat t                                              21

<210> SEQ ID NO 71
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 71
uuugacgcca acauuaugcu u                                              21

<210> SEQ ID NO 72
<211> LENGTH: 21
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 72
aaaccuauca ucauagguct t                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 73
gaccuaugau gauagguuut t                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 74
aaaccuauca ucauagguct t                                              21

<210> SEQ ID NO 75
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 75
gaccuaugau gauagguuuu u                                              21

<210> SEQ ID NO 76
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(19)
<223> OTHER INFORMATION: ribonucleotide unmodified or modified as
      described for this sequence

<400> SEQUENCE: 76
aaccuaucau cauaggucgt t                                              21

<210> SEQ ID NO 77
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 77
cgaccuauga ugauagguut t                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 78
aaccuaucau cauaggucgt t                                              21

<210> SEQ ID NO 79
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 79
cgaccuauga ugaugguuu u                                               21

<210> SEQ ID NO 80
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
```

<400> SEQUENCE: 80
accuaucauc auaggucgut t                                            21

<210> SEQ ID NO 81
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 81
acgaccuaug augauaggut t                                            21

<210> SEQ ID NO 82
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 82
accuaucauc auaggucgut t                                            21

<210> SEQ ID NO 83
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 83
acgaccuaug augauagguu u                                            21

<210> SEQ ID NO 84
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 84
ccuaucauca uaggucguct t                                            21

<210> SEQ ID NO 85
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as described for this sequence

<400> SEQUENCE: 85
gacgaccuau gaugauaggt t                                              21

<210> SEQ ID NO 86
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 86
ccuaucauca uaggucguct t                                              21

<210> SEQ ID NO 87
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 87
gacgaccuau gaugauaggu u                                              21

<210> SEQ ID NO 88
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as described for this sequence

<400> SEQUENCE: 88
cuaucaucau aggucgucat t                                              21

<210> SEQ ID NO 89
<211> LENGTH: 21
<212> TYPE: DNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 89
ugacgaccua ugaugauagt t                                              21

<210> SEQ ID NO 90
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this
      sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 90
cuaucaucau aggucgucat t                                              21

<210> SEQ ID NO 91
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 91
ugacgaccua ugaugauagu u                                              21

<210> SEQ ID NO 92
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 92
augacgaccu augaugauat t                                              21

<210> SEQ ID NO 93
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 93
uaucaucaua ggucgucaut t                                              21

<210> SEQ ID NO 94
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 94
uaucaucaua ggucgucaut t                                              21

<210> SEQ ID NO 95
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 95
augacgaccu augaugauau u                                              21

<210> SEQ ID NO 96
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 96
aucaucauag gucgucaugt t                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
``` described for this sequence

<400> SEQUENCE: 97
caugacgacc uaugaugaut t         21

<210> SEQ ID NO 98
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 98
aucaucauag gucgucaugt t         21

<210> SEQ ID NO 99
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 99
caugacgacc uaugaugauu u         21

<210> SEQ ID NO 100
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 100
gcaugacgac cuaugaugat t         21

<210> SEQ ID NO 101
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 101
ucaucauagg ucgucaugct t                                              21

<210> SEQ ID NO 102
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 102
ucaucauagg ucgucaugct t                                              21

<210> SEQ ID NO 103
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 103
gcaugacgac cuaugaugau u                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 104
agcaugacga ccuaugaugt t                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 105
caucauaggu cgucaugcut t                                              21

<210> SEQ ID NO 106

```
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 106
caucauaggu cgucaugcut t                                                    21

<210> SEQ ID NO 107
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 107
agcaugacga ccuaugaugu u                                                    21

<210> SEQ ID NO 108
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 108
aagcaugacg accuaugaut t                                                    21

<210> SEQ ID NO 109
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 109 aucauaggguc gucaugcuut t                                                   21

<210> SEQ ID NO 110
<211> LENGTH: 21
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 110
aucauagguc gucaugcuut t                                                  21

<210> SEQ ID NO 111
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 111
aagcaugacg accuaugauu u                                                  21

<210> SEQ ID NO 112
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 112
uaagcaugac gaccuaugat t                                                  21

<210> SEQ ID NO 113
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 113
ucauaggucg ucaugcuuat t                                                  21

<210> SEQ ID NO 114
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
```

```
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 114
ucauaggucg ucaugcuuat t                                              21

<210> SEQ ID NO 115
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 115
uaagcaugac gaccuaugau u                                              21

<210> SEQ ID NO 116
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 116
auaagcauga cgaccuaugt t                                              21

<210> SEQ ID NO 117
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 117
cauaggucgu caugcuuaut t                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
```

```
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 118
cauaggucgu caugcuuaut t                                              21

<210> SEQ ID NO 119
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 119
auaagcauga cgaccuaugu u                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 120
auaggucguc augcuuaugt t                                              21

<210> SEQ ID NO 121
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 121
cauaagcaug acgaccuaut t                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
```

<222> LOCATION: (21)..(21)
<223> OTHER INFORMATION: inverted abasic cap

<400> SEQUENCE: 122
auaggucguc augcuuaugt t                                              21

<210> SEQ ID NO 123
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 123
cauaagcaug acgaccuauu u                                              21

<210> SEQ ID NO 124
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 124
ccauaagcau gacgaccuat t                                              21

<210> SEQ ID NO 125
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 125
uaggucguca ugcuuauggt t                                              21

<210> SEQ ID NO 126
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 126
uaggucguca ugcuuauggt t          21

<210> SEQ ID NO 127
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 127
ccauaagcau gacgaccuau u          21

<210> SEQ ID NO 128
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 128
aggucgucau gcuuagggt t          21

<210> SEQ ID NO 129
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 129
cccauaagca ugacgaccut t          21

<210> SEQ ID NO 130
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 130
aggucgucau gcuuagggt t          21

-continued

```
<210> SEQ ID NO 131
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 131
cccauaagca ugacgaccuu u                                             21

<210> SEQ ID NO 132
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 132
ccccauaagc augacgacct t                                             21

<210> SEQ ID NO 133
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 133
ggucgucaug cuuauggggt t                                             21

<210> SEQ ID NO 134
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 134
ggucgucaug cuuauggggt t                                             21

<210> SEQ ID NO 135
<211> LENGTH: 21
<212> TYPE: RNA
<213> ORGANISM: Artificial Sequence
```

-continued

```
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 135
ccccauaagc augacgaccu u                                          21

<210> SEQ ID NO 136
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 136
gucgucaugc uuaugggat t                                           21

<210> SEQ ID NO 137
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 137
uccccauaag caugacgact t                                          21

<210> SEQ ID NO 138
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 138
gucgucaugc uuaugggat t                                           21

<210> SEQ ID NO 139
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

<222> LOCATION: (20)..(21)
<223> OTHER INFORMATION: 2'-O-methyl

<400> SEQUENCE: 139
uccccauaag caugacgacu u                                             21

<210> SEQ ID NO 140
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 140
auccccauaa gcaugacgat t                                             21

<210> SEQ ID NO 141
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 141
ucgucaugcu uauggggaut t                                             21

<210> SEQ ID NO 142
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 142
ucgucaugcu uauggggaut t                                             21

<210> SEQ ID NO 143
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 143
auccccauaa gcaugacgau u     21

<210> SEQ ID NO 144
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 144
cgucaugcuu augggauct t     21

<210> SEQ ID NO 145
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 145
gauccccaua agcaugacgt t     21

<210> SEQ ID NO 146
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 146
cgucaugcuu augggauct t     21

<210> SEQ ID NO 147
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 147
gauccccaua agcaugacgu u     21

```
<210> SEQ ID NO 148
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 148
gucaugcuua uggggaucat t                                              21

<210> SEQ ID NO 149
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 149
ugauccccau aagcaugact t                                              21

<210> SEQ ID NO 150
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this
 sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 150
gucaugcuua uggggaucat t                                              21

<210> SEQ ID NO 151
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 151
ugauccccau aagcaugacu u                                              21

<210> SEQ ID NO 152
<211> LENGTH: 21
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 152
ugaagaaggu ggugguguut t                                              21

<210> SEQ ID NO 153
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 153
aacaccacca ccuucuucau u                                              21

<210> SEQ ID NO 154
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 154 uccaauggc ucugucuaat t                                               21

<210> SEQ ID NO 155
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 155
uuagacagag ccauuuggau u                                              21
```

```
<210> SEQ ID NO 156
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 156
gagcaaagcu ugauaacaat t                                           21

<210> SEQ ID NO 157
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 157
uuguuaucaa gcuuugcucu u                                           21

<210> SEQ ID NO 158
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 158
agcaaagcuu gauaacaaut t                                           21

<210> SEQ ID NO 159
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 159
```
auuguuauca agcuuugcuu u                                          21

<210> SEQ ID NO 160
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 160
agguuuaccc aaugugcaat t                                          21

<210> SEQ ID NO 161
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 161
uugcacauug gguaaaccuu u                                          21

<210> SEQ ID NO 162
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 162
cauuugaguu cauggauaat t                                          21

<210> SEQ ID NO 163
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

```
<400> SEQUENCE: 163
uuauccauga acucaaaugu u                                              21

<210> SEQ ID NO 164
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 164
acuuuaaguu cauaccugat t                                              21

<210> SEQ ID NO 165
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 165
ucagguauga acuuaaaguu u                                              21

<210> SEQ ID NO 166
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 166
aaaccuauca ucauagguuu u                                              21

<210> SEQ ID NO 167
<211> LENGTH: 21
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 167
aaccuaugau gauagguuuu u                                              21

<210> SEQ ID NO 168
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 168
aaaccuauca ucauagguut t                                              21

<210> SEQ ID NO 169
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 169
aaccuaugau gauagguuut t                                              21

<210> SEQ ID NO 170
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 170
aaccuaucau cauagguugu u                                              21

<210> SEQ ID NO 171
```

```
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 171
caaccuauga ugauagguuu u                                              21

<210> SEQ ID NO 172
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 172
aaccuaucau cauagguugt t                                              21

<210> SEQ ID NO 173
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 173
caaccuauga ugauagguut t                                              21

<210> SEQ ID NO 174
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 174
accuaucauc auagguuguu u                                              21
```

<210> SEQ ID NO 175
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 175
acaaccuaug augauagguu u                                              21

<210> SEQ ID NO 176
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 176
acaaccuaug augauaggut t                                              21

<210> SEQ ID NO 177
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 177
accuaucauc auagguugut t                                              21

<210> SEQ ID NO 178
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

```
<400> SEQUENCE: 178 ccaucauca uagguugucu u                                              21

<210> SEQ ID NO 179
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 179
gacaaccuau gaugauaggu u                                             21

<210> SEQ ID NO 180
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 180 ccaucauca uagguuguct t                                              21

<210> SEQ ID NO 181
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 181
gacaaccuau gaugauaggt t                                             21

<210> SEQ ID NO 182
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
```

```
<222> LOCATION: (21)..(21)
<223> OTHER INFORMATION: inverted abasic cap

<400> SEQUENCE: 182
cuaucaucau agguugucau u                                            21

<210> SEQ ID NO 183
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 183
ugacaaccua ugaugauagu u                                            21

<210> SEQ ID NO 184
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 184
cuaucaucau agguugucat t                                            21

<210> SEQ ID NO 185
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 185
ugacaaccua ugaugauagt t                                            21

<210> SEQ ID NO 186
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
```

```
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 186
uaucaucaua gguugucauu u                                              21

<210> SEQ ID NO 187
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 187
augacaaccu augaugauau u                                              21

<210> SEQ ID NO 188
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 188
augacaaccu augaugauat t                                              21

<210> SEQ ID NO 189
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 189
uaucaucaua gguugucaut t                                              21

<210> SEQ ID NO 190
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
```

```
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 190
aucaucauag guugucaugu u                                              21

<210> SEQ ID NO 191
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 191
caugacaacc uaugaugauu u                                              21

<210> SEQ ID NO 192
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 192
aucaucauag guugucaugt t                                              21

<210> SEQ ID NO 193
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 193
caugacaacc uaugaugaut t                                              21

<210> SEQ ID NO 194
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
```

```
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 194
ucaucauagg uugucaugcu u                                              21

<210> SEQ ID NO 195
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 195
gcaugacaac cuaugaugau u                                              21

<210> SEQ ID NO 196
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 196
gcaugacaac cuaugaugat t                                              21

<210> SEQ ID NO 197
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 197
ucaucauagg uugucaugct t                                              21

<210> SEQ ID NO 198
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 198
caucauaggu ugucaugcuu u                                      21

<210> SEQ ID NO 199
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 199
agcaugacaa ccuaugaugu u                                      21

<210> SEQ ID NO 200
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 200
agcaugacaa ccuaugaugt t                                      21

<210> SEQ ID NO 201
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 201
caucauaggu ugucaugcut t                                      21

<210> SEQ ID NO 202
<211> LENGTH: 21
<212> TYPE: RNA
<213> ORGANISM: Artificial Sequence
<220> FEATURE:
```

-continued

```
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 202
caucauaggu ugucaugcuu u                                                 21

<210> SEQ ID NO 203
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
```

```
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 203
agcaugacaa ccuaugaugu u                                              21

<210> SEQ ID NO 204
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 204
agcaugacaa ccuaugaugu u                                              21

<210> SEQ ID NO 205
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
```

```
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 205
caucauaggu ugucaugcuu u                                       21

<210> SEQ ID NO 206
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-O-methyl
```

```
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 206
agcaugacaa ccuaugaugu u                                              21

<210> SEQ ID NO 207
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
```

```
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 207
caucauaggu ugucaugcuu u                                             21

<210> SEQ ID NO 208
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
```

<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 208
caucauaggu ugucaugcuu u                                          21

<210> SEQ ID NO 209
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 209
agcaugacaa ccuaugaugu u                                          21

<210> SEQ ID NO 210
<211> LENGTH: 21
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 210
agcaugacaa ccuaugaugu u                                          21

<210> SEQ ID NO 211
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-fluoro
```

```
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 211
caucauaggu ugucaugcuu u                                              21

<210> SEQ ID NO 212
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
```

```
<223> OTHER INFORMATION: inverted abasic cap

<400> SEQUENCE: 212
aucauagguu gucaugcuuu u                                              21

<210> SEQ ID NO 213
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 213
aagcaugaca accuaugauu u                                              21

<210> SEQ ID NO 214
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 214
aagcaugaca accuaugaut t                                              21

<210> SEQ ID NO 215
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 215
aucauagguu gucaugcuut t                                              21

<210> SEQ ID NO 216
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
```

```
-continued

<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 216
aucauagguu gucaugcuuu u                                              21

<210> SEQ ID NO 217
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 217
aagcaugaca accuaugauu u                                              21

<210> SEQ ID NO 218
```

```
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 218
aagcaugaca accuaugauu u                                            21

<210> SEQ ID NO 219
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
```

```
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 219
aucauagguu gucaugcuuu u                                              21

<210> SEQ ID NO 220
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
```

```
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 220
aagcaugaca accuaugauu u                                              21

<210> SEQ ID NO 221
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 221
aagcaugaca accuaugauu u                                              21
```

<210> SEQ ID NO 222
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 222
aucauagguu gucaugcuuu u                                             21

<210> SEQ ID NO 223
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)

```
<223> OTHER INFORMATION: inverted abasic cap
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 223
aucauagguu gucaugcuuu u                                              21

<210> SEQ ID NO 224
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-O-methyl
<220> FEATURE:
<221> NAME/KEY: misc_feature
```

```
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-O-methyl
<220> FEATURE:
<221> NAME/KEY: misc_feature
<222> LOCATION: (12)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 224
aagcaugaca accaugauu u                                             21

<210> SEQ ID NO 225
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(8)
<223> OTHER INFORMATION: 2'-O-methyl
<220> FEATURE:
<221> NAME/KEY: misc_feature
<222> LOCATION: (9)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
```

```
<221> NAME/KEY: misc_feature
<222> LOCATION: (12)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 225
aucauagguu gucaugcuuu u                                              21

<210> SEQ ID NO 226
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 226
ucauagguug ucaugcuuau u                                              21

<210> SEQ ID NO 227
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
```

<400> SEQUENCE: 227
uaagcaugac aaccuaugau u                                          21

<210> SEQ ID NO 228
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 228
uaagcaugac aaccuaugat t                                          21

<210> SEQ ID NO 229
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 229
ucauagguug ucaugcuuat t                                          21

<210> SEQ ID NO 230
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 230
cauagguugu caugcuuauu u                                          21

<210> SEQ ID NO 231
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:

```
<221> NAME/KEY: misc_feature
<222> LOCATION: (20)..(21)
<223> OTHER INFORMATION: phosphorothioate linkage

<400> SEQUENCE: 231
auaagcauga caaccuaugu u                                              21

<210> SEQ ID NO 232
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 232
auaagcauga caaccuaugt t                                              21

<210> SEQ ID NO 233
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 233
cauagguugu caugcuuaut t                                              21

<210> SEQ ID NO 234
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 234
auagguuguc augcuuaugu u                                              21

<210> SEQ ID NO 235
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 235
cauaagcaug acaaccuauu u                                              21

<210> SEQ ID NO 236
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 236
auagguuguc augcuuaugt t                                              21

<210> SEQ ID NO 237
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 237
cauaagcaug acaaccuaut t                                              21

<210> SEQ ID NO 238
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 238
uagguuguca ugcuuauggu u                                              21

<210> SEQ ID NO 239
<211> LENGTH: 21
<212> TYPE: RNA
<213> ORGANISM: Artificial Sequence
<220> FEATURE:
```

<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 239
ccauaagcau gacaaccuau u                                               21

<210> SEQ ID NO 240
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 240
ccauaagcau gacaaccuat t                                               21

<210> SEQ ID NO 241
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 241
uagguuguca ugcuuauggt t                                               21

<210> SEQ ID NO 242
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 242
agguugucau gcuuaugggu u                                               21

<210> SEQ ID NO 243
<211> LENGTH: 21

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 243
cccauaagca ugacaaccuu u                                              21

<210> SEQ ID NO 244
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 244
agguugucau gcuuaugggt t                                              21

<210> SEQ ID NO 245
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 245
cccauaagca ugacaaccut t                                              21

<210> SEQ ID NO 246
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 246
gguugucaug cuuauggggu u                                              21
```

```
<210> SEQ ID NO 247
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 247
ccccauaagc augacaaccu u                                              21

<210> SEQ ID NO 248
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 248
ccccauaagc augacaacct t                                              21

<210> SEQ ID NO 249
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 249
gguugucaug cuuauggggt t                                              21

<210> SEQ ID NO 250
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 250
```
guugucaugc uuaugggau u                                                21

<210> SEQ ID NO 251
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 251
uccccauaag caugacaacu u                                               21

<210> SEQ ID NO 252
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 252
guugucaugc uuaugggat t                                                21

<210> SEQ ID NO 253
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 253
uccccauaag caugacaact t                                               21

<210> SEQ ID NO 254
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)

<223> OTHER INFORMATION: inverted abasic cap

<400> SEQUENCE: 254
uugucaugcu uaugggauu u                                              21

<210> SEQ ID NO 255
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 255
auccccauaa gcaugacaau u                                             21

<210> SEQ ID NO 256
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 256
auccccauaa gcaugacaat t                                             21

<210> SEQ ID NO 257
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 257
uugucaugcu uaugggaut t                                              21

<210> SEQ ID NO 258
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

```
<220> FEATURE:
<221> NAME/KEY: misc_feature
<222> LOCATION: (21)..(21)
<223> OTHER INFORMATION: inverted abasic cap

<400> SEQUENCE: 258
ugucaugcuu auggggaucu u                                              21

<210> SEQ ID NO 259
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 259 gaucccaua agcaugacau u                                               21

<210> SEQ ID NO 260
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 260 gaucccaua agcaugacat t                                               21

<210> SEQ ID NO 261
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 261
ugucaugcuu auggggauct t                                              21

<210> SEQ ID NO 262
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
```

```
<220> FEATURE:
<221> NAME/KEY: misc_feature
<222> LOCATION: (21)..(21)
<223> OTHER INFORMATION: inverted abasic cap

<400> SEQUENCE: 262
aaccuaucau cauaggucat t                                              21

<210> SEQ ID NO 263
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 263
ugaccuauga ugauagguuu u                                              21

<210> SEQ ID NO 264
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 264
aaccuaucau cauaggucat t                                              21

<210> SEQ ID NO 265
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 265
ugaccuauga ugauagguut t                                              21

<210> SEQ ID NO 266
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap
```

<400> SEQUENCE: 266
accuaucauc auaggucaut t        21

<210> SEQ ID NO 267
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 267
augaccuaug augauagguu u        21

<210> SEQ ID NO 268
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 268
accuaucauc auaggucaut t        21

<210> SEQ ID NO 269
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 269
augaccuaug augauaggut t        21

<210> SEQ ID NO 270
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 270
ccuaucauca uaggucauct t        21

```
<210> SEQ ID NO 271
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 271
gaugaccuau gaugauaggu u                                              21

<210> SEQ ID NO 272
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 272
ccuaucauca uaggucauct t                                              21

<210> SEQ ID NO 273
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 273
gaugaccuau gaugauaggt t                                              21

<210> SEQ ID NO 274
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 274
cuaucaucau aggucaucat t                                              21

<210> SEQ ID NO 275
<211> LENGTH: 21
```

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 275
ugaugaccua ugaugauagu u                                              21

<210> SEQ ID NO 276
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 276
cuaucaucau aggucaucat t                                              21

<210> SEQ ID NO 277
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 277
ugaugaccua ugaugauagt t                                              21

<210> SEQ ID NO 278
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 278
uaucaucaua ggucaucaut t                                              21

<210> SEQ ID NO 279
<211> LENGTH: 21
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (20)..(21)
<223> OTHER INFORMATION: 2'-O-methyl

<400> SEQUENCE: 279
augaugaccu augaugauau u                                              21

<210> SEQ ID NO 280
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 280
augaugaccu augaugauat t                                              21

<210> SEQ ID NO 281
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 281
uaucaucaua ggucaucaut t                                              21

<210> SEQ ID NO 282
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 282
aucaucauag gucaucaugt t                                              21

<210> SEQ ID NO 283
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
```

```
<400> SEQUENCE: 283
caugaugacc uaugaugauu u                                          21

<210> SEQ ID NO 284
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 284
aucaucauag gucaucaugt t                                          21

<210> SEQ ID NO 285
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 285
caugaugacc uaugaugaut t                                          21

<210> SEQ ID NO 286
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 286
ucaucauagg ucaucaugct t                                          21

<210> SEQ ID NO 287
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 287
gcaugaugac cuaugaugau u                                          21
```

```
<210> SEQ ID NO 288
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 288
gcaugaugac cuaugaugat t                                                   21

<210> SEQ ID NO 289
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 289
ucaucauagg ucaucaugct t                                                   21

<210> SEQ ID NO 290
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 290
caucauaggu caucaugcut t                                                   21

<210> SEQ ID NO 291
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 291
agcaugauga ccuaugaugu u                                                   21

<210> SEQ ID NO 292
<211> LENGTH: 21
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 292
agcaugauga ccuaugaugt t                                              21

<210> SEQ ID NO 293
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 293
caucauaggu caucaugcut t                                              21

<210> SEQ ID NO 294
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 294
aucauagguc aucaugcuut t                                              21

<210> SEQ ID NO 295
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 295
aagcaugaug accuaugauu u                                              21

<210> SEQ ID NO 296
<211> LENGTH: 21
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 296
aagcaugaug accuaugaut t                                              21

<210> SEQ ID NO 297
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 297
aucauagguc aucaugcuut t                                              21

<210> SEQ ID NO 298
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 298
ucauagguca ucaugcuuat t                                              21

<210> SEQ ID NO 299
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 299
uaagcaugau gaccuaugau u                                              21

<210> SEQ ID NO 300
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
``` described for this sequence

<400> SEQUENCE: 300
uaagcaugau gaccuaugat t                                              21

<210> SEQ ID NO 301
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 301
ucauagguca ucaugcuuat t                                              21

<210> SEQ ID NO 302
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 302
cauaggucau caugcuuaut t                                              21

<210> SEQ ID NO 303
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 303
auaagcauga ugaccuaugu u                                              21

<210> SEQ ID NO 304
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 304
auaagcauga ugaccuaugt t                                              21

<210> SEQ ID NO 305
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 305
cauaggucau caugcuuaut t                                              21

<210> SEQ ID NO 306
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 306
cauaggucau caugcuuauu u                                              21

<210> SEQ ID NO 307
<211> LENGTH: 21
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 307
auaagcauga ugaccuaugu u                                              21

<210> SEQ ID NO 308
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
```

```
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 308
auaagcauga ugaccuaugu u                                              21

<210> SEQ ID NO 309
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-deoxy
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 309
auaagcauga ugaccuaugu u                                              21

<210> SEQ ID NO 310
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
```

```
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 310
auaagcauga ugaccuaugu u                                              21

<210> SEQ ID NO 311
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 311
auaagcauga ugaccuaugu u                                              21

<210> SEQ ID NO 312
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
```

```
<222> LOCATION: (6)..(6)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 312
auaagcauga ugaccuaugu u                                              21

<210> SEQ ID NO 313
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 313
auaagcauga ugaccuaugu u                                              21

<210> SEQ ID NO 314
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
```

```
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (15)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 314
auaagcauga ugaccuaugu u                                              21

<210> SEQ ID NO 315
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 315
auaagcauga ugaccuaugu u                                              21
```

<210> SEQ ID NO 316
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 316
auaagcauga ugaccuaugu u                                          21

<210> SEQ ID NO 317
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)

-continued

```
<223> OTHER INFORMATION: phosphorothioate linkage

<400> SEQUENCE: 317
auaagcauga ugaccuaugu u                                              21

<210> SEQ ID NO 318
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 318
auaagcauga ugaccuaugu u                                              21

<210> SEQ ID NO 319
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
```

```
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 319
auaagcauga ugaccuaugu u                                           21

<210> SEQ ID NO 320
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 320
auaagcauga ugaccuaugu u                                           21

<210> SEQ ID NO 321
<211> LENGTH: 21
<212> TYPE: RNA
<213> ORGANISM: Artificial Sequence
<220> FEATURE:
<223> OTHER INFORMATION: Synthetic
<220> FEATURE:
```

<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 321
auaagcauga ugaccuaugu u                                      21

<210> SEQ ID NO 322
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

```
<220> FEATURE:
<221> NAME/KEY: misc_feature
<222> LOCATION: (20)..(21)
<223> OTHER INFORMATION: phosphorothioate linkage

<400> SEQUENCE: 322
auaagcauga ugaccuaugu u                                              21

<210> SEQ ID NO 323
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 323
auaagcauga ugaccuaugu u                                              21

<210> SEQ ID NO 324
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
```

```
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 324
auaagcauga ugaccuaugu u                                              21

<210> SEQ ID NO 325
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 325
auaagcauga ugaccuaugu u                                              21

<210> SEQ ID NO 326
<211> LENGTH: 21
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 326
auaagcauga ugaccuaugu u                                           21

<210> SEQ ID NO 327
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
```

-continued

```
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 327
auaagcauga ugaccuaugu u                                              21

<210> SEQ ID NO 328
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 328
auaagcauga ugaccuaugu u                                              21

<210> SEQ ID NO 329
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
```

```
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 329
auaagcauga ugaccuaugu u                                              21

<210> SEQ ID NO 330
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 330
auaagcauga ugaccuaugu u                                              21

<210> SEQ ID NO 331
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
```

```
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 331
auaagcauga ugaccuaugu u                                              21

<210> SEQ ID NO 332
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
```

```
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 332
cauaggucau caugcuuauu u                                              21

<210> SEQ ID NO 333
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
```

```
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 333
auaagcauga ugaccuaugu u                                              21

<210> SEQ ID NO 334
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
```

```
<220> FEATURE:
<221> NAME/KEY: misc_feature
<222> LOCATION: (21)..(21)
<223> OTHER INFORMATION: inverted abasic cap

<400> SEQUENCE: 334
cauaggucau caugcuuauu u                                              21

<210> SEQ ID NO 335
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (7)..(8)
<223> OTHER INFORMATION: 2'-deoxy-2'-fluoro
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 335
cauaggucau caugcuuauu u                                              21

<210> SEQ ID NO 336
<211> LENGTH: 21
<212> TYPE: RNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 336
auaagcauga ugaccuaugu u                                              21

<210> SEQ ID NO 337
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
```

```
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 337
auaagcauga ugaccuaugu u                                              21

<210> SEQ ID NO 338
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 338
auaagcauga ugaccuaugu u                                              21

<210> SEQ ID NO 339
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
```

<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 339
auaagcauga ugaccuaugu u                                              21

<210> SEQ ID NO 340
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl

```
<220> FEATURE:
<221> NAME/KEY: misc_feature
<222> LOCATION: (20)..(21)
<223> OTHER INFORMATION: phosphorothioate linkage

<400> SEQUENCE: 340
auaagcauga ugaccuaugu u                                              21

<210> SEQ ID NO 341
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 341
auaagcauga ugaccuaugu u                                              21

<210> SEQ ID NO 342
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
```

-continued

```
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 342
auaagcauga ugaccuaugu u                                              21

<210> SEQ ID NO 343
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(8)
<223> OTHER INFORMATION: 2'-deoxy
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
```

<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 343
auaagcauga ugaccuaugu u                                              21

<210> SEQ ID NO 344
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 344
auaagcauga ugaccuaugu u                                              21

<210> SEQ ID NO 345
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:

```
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 345
auaagcauga ugaccuaugu u                                              21

<210> SEQ ID NO 346
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
```

-continued

<220> FEATURE:
<221> NAME/KEY: misc_feature
<222> LOCATION: (20)..(21)
<223> OTHER INFORMATION: phosphorothioate linkage

<400> SEQUENCE: 346
auaagcauga ugaccuaugu u                                              21

<210> SEQ ID NO 347
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 347
auaagcauga ugaccuaugu u                                              21

<210> SEQ ID NO 348
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)

```
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 348
auaagcauga ugaccuaugu u                                           21

<210> SEQ ID NO 349
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
```

```
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 349
auaagcauga ugaccuaugu u                                              21

<210> SEQ ID NO 350
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 350
auaagcauga ugaccuaugu u                                              21

<210> SEQ ID NO 351
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
```

<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 351
auaagcauga ugaccuaugu u                                               21

<210> SEQ ID NO 352
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl

```
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 352
auaagcauga ugaccuaugu u                                              21

<210> SEQ ID NO 353
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 353
auaagcauga ugaccuaugu u                                              21

<210> SEQ ID NO 354
<211> LENGTH: 21
<212> TYPE: RNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 354
auaagcauga ugaccuaugu u                                               21

<210> SEQ ID NO 355
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
```

```
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 355
auaagcauga ugaccuaugu u                                              21

<210> SEQ ID NO 356
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
```

<400> SEQUENCE: 356
auaagcauga ugaccuaugu u                                              21

<210> SEQ ID NO 357
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 357
auaagcauga ugaccuaugu u                                              21

<210> SEQ ID NO 358
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl

```
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 358
auaagcauga ugaccuaugu u                                              21

<210> SEQ ID NO 359
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(15)
```

<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 359
auaagcauga ugaccuaugu u                                           21

<210> SEQ ID NO 360
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 360
auaagcauga ugaccuaugu u                                              21

<210> SEQ ID NO 361
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 361
auaagcauga ugaccuaugu u                                              21

<210> SEQ ID NO 362
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:

```
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 362
auaagcauga ugaccuaugu u                                              21

<210> SEQ ID NO 363
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
```

-continued

```
<220> FEATURE:
<221> NAME/KEY: misc_feature
<222> LOCATION: (20)..(21)
<223> OTHER INFORMATION: phosphorothioate linkage

<400> SEQUENCE: 363
auaagcauga ugaccuaugu u                                              21

<210> SEQ ID NO 364
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(13)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 364
auaagcauga ugaccuaugu u                                              21

<210> SEQ ID NO 365
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
```

```
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 365
auaagcauga ugaccuaugu u                                             21

<210> SEQ ID NO 366
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 366
auaagcauga ugaccuaugu u                                             21

<210> SEQ ID NO 367
<211> LENGTH: 21
<212> TYPE: RNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 367
auaagcauga ugaccuaugu u                                              21

<210> SEQ ID NO 368
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
```

```
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 368
auaagcauga ugaccuaugu u                                     21

<210> SEQ ID NO 369
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 369
auaagcauga ugaccuaugu u                                     21

<210> SEQ ID NO 370
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
```

```
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 370
auaagcauga ugaccuaugu u                                          21

<210> SEQ ID NO 371
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
```

```
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 371
auaagcauga ugaccuaugu u                                              21

<210> SEQ ID NO 372
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 372
auaagcauga ugaccuaugu u                                              21

<210> SEQ ID NO 373
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (2)..(2)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 373
auaagcauga ugaccuaugu u                                              21

<210> SEQ ID NO 374
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 374
auaagcauga ugaccuaugu u                                              21

<210> SEQ ID NO 375
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 375
auaagcauga ugaccuaugu u                                              21

<210> SEQ ID NO 376
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 376
auaagcauga ugaccuaugu u                                              21

<210> SEQ ID NO 377
<211> LENGTH: 21
<212> TYPE: RNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 377
auaagcauga ugaccuaugu u                                              21

<210> SEQ ID NO 378
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 378
auaagcauga ugaccuaugu u                                              21

<210> SEQ ID NO 379
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 379
auaagcauga ugaccuaugu u                                              21

<210> SEQ ID NO 380
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 380
auaagcauga ugaccuaugu u                                              21

<210> SEQ ID NO 381
<211> LENGTH: 21
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 381
auaagcauga ugaccuaugu u                                              21

<210> SEQ ID NO 382
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 382
auaagcauga ugaccuaugu u                                              21

<210> SEQ ID NO 383
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 383
auaagcauga ugaccuaugu u                                              21

<210> SEQ ID NO 384
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (16)..(16)
```

```
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 384
auaagcauga ugaccuaugu u                                              21

<210> SEQ ID NO 385
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 385
auaagcauga ugaccuaugu u                                              21

<210> SEQ ID NO 386
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 386
auaagcauga ugaccuaugu u                                              21

<210> SEQ ID NO 387
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
```

```
<222> LOCATION: (20)..(21)
<223> OTHER INFORMATION: 2'-O-methyl

<400> SEQUENCE: 387
auaagcauga ugaccuaugu u                                              21

<210> SEQ ID NO 388
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 388
auaagcauga ugaccuaugu u                                              21

<210> SEQ ID NO 389
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (15)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 389
auaagcauga ugaccuaugu u                                              21

<210> SEQ ID NO 390
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
```

```
<221> NAME/KEY: misc_feature
<222> LOCATION: (20)..(21)
<223> OTHER INFORMATION: 2'-O-methyl

<400> SEQUENCE: 390
auaagcauga ugaccuaugu u                                              21

<210> SEQ ID NO 391
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 391
auaagcauga ugaccuaugu u                                              21

<210> SEQ ID NO 392
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 392
auaagcauga ugaccuaugu u                                              21

<210> SEQ ID NO 393
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
```

```
<220> FEATURE:
<221> NAME/KEY: misc_feature
<222> LOCATION: (20)..(21)
<223> OTHER INFORMATION: 2'-O-methyl

<400> SEQUENCE: 393
auaagcauga ugaccuaugu u                                              21

<210> SEQ ID NO 394
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 394
auaagcauga ugaccuaugu u                                              21

<210> SEQ ID NO 395
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl

<400> SEQUENCE: 395
auaagcauga ugaccuaugu u                                              21

<210> SEQ ID NO 396
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-deoxy-2'-fluoro
<220> FEATURE:
<221> NAME/KEY: misc_feature
<222> LOCATION: (4)..(5)
```

-continued

```
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(13)
<223> OTHER INFORMATION: 2'-O-methyl
<220> FEATURE:
<221> NAME/KEY: misc_feature
<222> LOCATION: (14)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 396
auaagcauga ugaccuaugu u                                              21

<210> SEQ ID NO 397
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(6)
<223> OTHER INFORMATION: 2'-O-methyl
<220> FEATURE:
<221> NAME/KEY: misc_feature
```

<222> LOCATION: (7)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 397
cauaggucau caugcuuauu u                                      21

<210> SEQ ID NO 398
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
    described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 398
auaggucauc augcuuaugt t                                      21

<210> SEQ ID NO 399
<211> LENGTH: 21

```
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 399
cauaagcaug augaccuauu u                                              21

<210> SEQ ID NO 400
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 400
auaggucauc augcuuaugt t                                              21

<210> SEQ ID NO 401
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 401
cauaagcaug augaccuaut t                                              21

<210> SEQ ID NO 402
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 402
uaggucauca ugcuuauggt t                                              21

<210> SEQ ID NO 403
<211> LENGTH: 21
<212> TYPE: RNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (20)..(21)
<223> OTHER INFORMATION: 2'-O-methyl

<400> SEQUENCE: 403
ccauaagcau gaugaccuau u                                              21

<210> SEQ ID NO 404
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 404
ccauaagcau gaugaccuat t                                              21

<210> SEQ ID NO 405
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 405
uaggucauca ugcuuauggt t                                              21

<210> SEQ ID NO 406
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 406
aggucaucau gcuuaugggt t                                              21

<210> SEQ ID NO 407
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl
```

<400> SEQUENCE: 407
cccauaagca ugaugaccuu u                                              21

<210> SEQ ID NO 408
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 408
aggucaucau gcuuaugggt t                                              21

<210> SEQ ID NO 409
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 409
cccauaagca ugaugaccut t                                              21

<210> SEQ ID NO 410
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 410
ggucaucaug cuuauggggt t                                              21

<210> SEQ ID NO 411
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 411
ccccauaagc augaugaccu u                                              21

```
<210> SEQ ID NO 412
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 412
ccccauaagc augaugacct t                                            21

<210> SEQ ID NO 413
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 413
ggucaucaug cuuauggggt t                                            21

<210> SEQ ID NO 414
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 414
ccccauaagc augaugaccu u                                            21
```

<210> SEQ ID NO 415
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 415
ggucaucaug cuuauggggu u                                             21

<210> SEQ ID NO 416
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl

```
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 416
ccccauaagc augaugaccu u                                              21

<210> SEQ ID NO 417
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (19)..(21)
<223> OTHER INFORMATION: 2'-O-methyl
<220> FEATURE:
<221> NAME/KEY: misc_feature
<222> LOCATION: (20)..(21)
```

```
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 417
ggucaucaug cuuauggggu u                                              21

<210> SEQ ID NO 418
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (8)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 418
ccccauaagc augaugaccu u                                              21

<210> SEQ ID NO 419
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
```

```
<222> LOCATION: (1)..(4)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 419
ccccauaagc augaugaccu u                                              21

<210> SEQ ID NO 420
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
```

<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 420
ggucaucaug cuuauggggu u                                      21

<210> SEQ ID NO 421
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(18)
<223> OTHER INFORMATION: 2'-O-methyl
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

```
<220> FEATURE:
<221> NAME/KEY: misc_feature
<222> LOCATION: (21)..(21)
<223> OTHER INFORMATION: inverted abasic cap

<400> SEQUENCE: 421
ggucaucaug cuuauggggu u                                              21

<210> SEQ ID NO 422
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(17)
<223> OTHER INFORMATION: 2'-O-methyl
<220> FEATURE:
<221> NAME/KEY: misc_feature
<222> LOCATION: (18)..(19)
<223> OTHER INFORMATION: 2'-deoxy-2'-fluoro
<220> FEATURE:
<221> NAME/KEY: misc_feature
<222> LOCATION: (20)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage

<400> SEQUENCE: 422
ccccauaagc augaugaccu u                                              21

<210> SEQ ID NO 423
<211> LENGTH: 21
<212> TYPE: RNA
<213> ORGANISM: Artificial Sequence
<220> FEATURE:
```

<223> OTHER INFORMATION: Synthetic
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (1)..(2)
<223> OTHER INFORMATION: 2'-O-methyl
<220> FEATURE:
<221> NAME/KEY: misc_feature
<222> LOCATION: (3)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(21)
<223> OTHER INFORMATION: 2'-O-methyl
<220> FEATURE:
<221> NAME/KEY: misc_feature
<222> LOCATION: (20)..(21)
<223> OTHER INFORMATION: phosphorothioate linkage
<220> FEATURE:
<221> NAME/KEY: misc_feature
<222> LOCATION: (21)..(21)
<223> OTHER INFORMATION: inverted abasic cap

<400> SEQUENCE: 423
ggucaucaug cuuauggggu u                                                    21

<210> SEQ ID NO 424
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:

```
<221> NAME/KEY: misc_feature
<222> LOCATION: (21)..(21)
<223> OTHER INFORMATION: inverted abasic cap

<400> SEQUENCE: 424
gucaucaugc uuauggggat t                                              21

<210> SEQ ID NO 425
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 425
uccccauaag caugaugacu u                                              21

<210> SEQ ID NO 426
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 426
gucaucaugc uuauggggat t                                              21

<210> SEQ ID NO 427
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 427
uccccauaag caugaugact t                                              21

<210> SEQ ID NO 428
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap
```

```
<400> SEQUENCE: 428
ucaucaugcu uaugggga ut t                                              21

<210> SEQ ID NO 429
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 429
auccccauaa gcaugaugau u                                               21

<210> SEQ ID NO 430
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 430
auccccauaa gcaugaugat t                                               21

<210> SEQ ID NO 431
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 431
ucaucaugcu uaugggga ut t                                              21

<210> SEQ ID NO 432
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 432
caucaugcuu auggggauct t                                               21
```

<210> SEQ ID NO 433
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 433 gaucccaua agcaugaugu u     21

<210> SEQ ID NO 434
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 434
caucaugcuu augggauct t     21

<210> SEQ ID NO 435
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 435 gaucccaua agcaugaugt t     21

<210> SEQ ID NO 436
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence
<220> FEATURE:
<221> NAME/KEY: misc_feature
<222> LOCATION: (1)..(1)
<223> OTHER INFORMATION: inverted abasic cap
<220> FEATURE:
<221> NAME/KEY: misc_feature
<222> LOCATION: (21)..(21)
<223> OTHER INFORMATION: inverted abasic cap

<400> SEQUENCE: 436
aucaugcuua ugggaucat t     21

<210> SEQ ID NO 437
<211> LENGTH: 21
<212> TYPE: RNA

```
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: 2'-O-methyl

<400> SEQUENCE: 437
ugauccccau aagcaugauu u                                              21

<210> SEQ ID NO 438
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 438
aucaugcuua ugggaucat t                                               21

<210> SEQ ID NO 439
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide unmodified or modified as
      described for this sequence

<400> SEQUENCE: 439
ugauccccau aagcaugaut t                                              21

<210> SEQ ID NO 440
<211> LENGTH: 19
<212> TYPE: RNA
<213> ORGANISM: Artificial Sequence
<220> FEATURE:
<223> OTHER INFORMATION: Synthetic

<400> SEQUENCE: 440
auagcuaugu agauccaau                                                 19

<210> SEQ ID NO 441
<211> LENGTH: 19
<212> TYPE: RNA
<213> ORGANISM: Artificial Sequence
<220> FEATURE:
<223> OTHER INFORMATION: Synthetic

<400> SEQUENCE: 441
uuugacgcca acauuaugc                                                 19

<210> SEQ ID NO 442
<211> LENGTH: 19
<212> TYPE: RNA
<213> ORGANISM: Artificial Sequence
<220> FEATURE:
<223> OTHER INFORMATION: Synthetic

<400> SEQUENCE: 442
```
gaccuaugau gauagguuu                                                  19

<210> SEQ ID NO 443
<211> LENGTH: 19
<212> TYPE: RNA
<213> ORGANISM: Artificial Sequence
<220> FEATURE:
<223> OTHER INFORMATION: Synthetic

<400> SEQUENCE: 443 cgaccauga ugauagguu                                                   19

<210> SEQ ID NO 444
<211> LENGTH: 19
<212> TYPE: RNA
<213> ORGANISM: Artificial Sequence
<220> FEATURE:
<223> OTHER INFORMATION: Synthetic

<400> SEQUENCE: 444
acgaccuaug augauaggu                                                  19

<210> SEQ ID NO 445
<211> LENGTH: 19
<212> TYPE: RNA
<213> ORGANISM: Artificial Sequence
<220> FEATURE:
<223> OTHER INFORMATION: Synthetic

<400> SEQUENCE: 445
gacgaccuau gaugauagg                                                  19

<210> SEQ ID NO 446
<211> LENGTH: 19
<212> TYPE: RNA
<213> ORGANISM: Artificial Sequence
<220> FEATURE:
<223> OTHER INFORMATION: Synthetic

<400> SEQUENCE: 446
ugacgaccua ugaugauag                                                  19

<210> SEQ ID NO 447
<211> LENGTH: 19
<212> TYPE: RNA
<213> ORGANISM: Artificial Sequence
<220> FEATURE:
<223> OTHER INFORMATION: Synthetic

<400> SEQUENCE: 447
augacgaccu augaugaua                                                  19

<210> SEQ ID NO 448
<211> LENGTH: 19
<212> TYPE: RNA
<213> ORGANISM: Artificial Sequence
<220> FEATURE:
<223> OTHER INFORMATION: Synthetic

<400> SEQUENCE: 448
caugacgacc uaugaugau                                                  19

<210> SEQ ID NO 449
<211> LENGTH: 19
<212> TYPE: RNA

```
<213> ORGANISM: Artificial Sequence
<220> FEATURE:
<223> OTHER INFORMATION: Synthetic

<400> SEQUENCE: 449
gcaugacgac cuaugauga                                              19

<210> SEQ ID NO 450
<211> LENGTH: 19
<212> TYPE: RNA
<213> ORGANISM: Artificial Sequence
<220> FEATURE:
<223> OTHER INFORMATION: Synthetic

<400> SEQUENCE: 450
agcaugacga ccuaugaug                                              19

<210> SEQ ID NO 451
<211> LENGTH: 19
<212> TYPE: RNA
<213> ORGANISM: Artificial Sequence
<220> FEATURE:
<223> OTHER INFORMATION: Synthetic

<400> SEQUENCE: 451
aagcaugacg accuaugau                                              19

<210> SEQ ID NO 452
<211> LENGTH: 19
<212> TYPE: RNA
<213> ORGANISM: Artificial Sequence
<220> FEATURE:
<223> OTHER INFORMATION: Synthetic

<400> SEQUENCE: 452
uaagcaugac gaccuauga                                              19

<210> SEQ ID NO 453
<211> LENGTH: 19
<212> TYPE: RNA
<213> ORGANISM: Artificial Sequence
<220> FEATURE:
<223> OTHER INFORMATION: Synthetic

<400> SEQUENCE: 453
auaagcauga cgaccuaug                                              19

<210> SEQ ID NO 454
<211> LENGTH: 19
<212> TYPE: RNA
<213> ORGANISM: Artificial Sequence
<220> FEATURE:
<223> OTHER INFORMATION: Synthetic

<400> SEQUENCE: 454
cauaagcaug acgaccuau                                              19

<210> SEQ ID NO 455
<211> LENGTH: 19
<212> TYPE: RNA
<213> ORGANISM: Artificial Sequence
<220> FEATURE:
<223> OTHER INFORMATION: Synthetic

<400> SEQUENCE: 455
ccauaagcau gacgaccua                                              19
```

<210> SEQ ID NO 456
<211> LENGTH: 19
<212> TYPE: RNA
<213> ORGANISM: Artificial Sequence
<220> FEATURE:
<223> OTHER INFORMATION: Synthetic

<400> SEQUENCE: 456
cccauaagca ugacgaccu                                          19

<210> SEQ ID NO 457
<211> LENGTH: 19
<212> TYPE: RNA
<213> ORGANISM: Artificial Sequence
<220> FEATURE:
<223> OTHER INFORMATION: Synthetic

<400> SEQUENCE: 457
ccccauaagc augacgacc                                          19

<210> SEQ ID NO 458
<211> LENGTH: 19
<212> TYPE: RNA
<213> ORGANISM: Artificial Sequence
<220> FEATURE:
<223> OTHER INFORMATION: Synthetic

<400> SEQUENCE: 458
uccccauaag caugacgac                                          19

<210> SEQ ID NO 459
<211> LENGTH: 19
<212> TYPE: RNA
<213> ORGANISM: Artificial Sequence
<220> FEATURE:
<223> OTHER INFORMATION: Synthetic

<400> SEQUENCE: 459
auccccauaa gcaugacga                                          19

<210> SEQ ID NO 460
<211> LENGTH: 19
<212> TYPE: RNA
<213> ORGANISM: Artificial Sequence
<220> FEATURE:
<223> OTHER INFORMATION: Synthetic

<400> SEQUENCE: 460
gauccccaua agcaugacg                                          19

<210> SEQ ID NO 461
<211> LENGTH: 19
<212> TYPE: RNA
<213> ORGANISM: Artificial Sequence
<220> FEATURE:
<223> OTHER INFORMATION: Synthetic

<400> SEQUENCE: 461
ugauccccau aagcaugac                                          19

<210> SEQ ID NO 462
<211> LENGTH: 19
<212> TYPE: RNA
<213> ORGANISM: Artificial Sequence
<220> FEATURE:

<223> OTHER INFORMATION: Synthetic

<400> SEQUENCE: 462
aacaccacca ccuucuuca                                                    19

<210> SEQ ID NO 463
<211> LENGTH: 19
<212> TYPE: RNA
<213> ORGANISM: Artificial Sequence
<220> FEATURE:
<223> OTHER INFORMATION: Synthetic

<400> SEQUENCE: 463
uuagacagag ccauuugga                                                    19

<210> SEQ ID NO 464
<211> LENGTH: 19
<212> TYPE: RNA
<213> ORGANISM: Artificial Sequence
<220> FEATURE:
<223> OTHER INFORMATION: Synthetic

<400> SEQUENCE: 464
uuguuaucaa gcuuugcuc                                                    19

<210> SEQ ID NO 465
<211> LENGTH: 19
<212> TYPE: RNA
<213> ORGANISM: Artificial Sequence
<220> FEATURE:
<223> OTHER INFORMATION: Synthetic

<400> SEQUENCE: 465
auuguuauca agcuuugcu                                                    19

<210> SEQ ID NO 466
<211> LENGTH: 19
<212> TYPE: RNA
<213> ORGANISM: Artificial Sequence
<220> FEATURE:
<223> OTHER INFORMATION: Synthetic

<400> SEQUENCE: 466
uugcacauug gguaaaccu                                                    19

<210> SEQ ID NO 467
<211> LENGTH: 19
<212> TYPE: RNA
<213> ORGANISM: Artificial Sequence
<220> FEATURE:
<223> OTHER INFORMATION: Synthetic

<400> SEQUENCE: 467
uuauccauga acucaaaug                                                    19

<210> SEQ ID NO 468
<211> LENGTH: 19
<212> TYPE: RNA
<213> ORGANISM: Artificial Sequence
<220> FEATURE:
<223> OTHER INFORMATION: Synthetic

<400> SEQUENCE: 468
ucagguauga acuuaaagu                                                    19

```
<210> SEQ ID NO 469
<211> LENGTH: 19
<212> TYPE: RNA
<213> ORGANISM: Artificial Sequence
<220> FEATURE:
<223> OTHER INFORMATION: Synthetic

<400> SEQUENCE: 469
aaccuaugau gauagguuu                                                    19

<210> SEQ ID NO 470
<211> LENGTH: 19
<212> TYPE: RNA
<213> ORGANISM: Artificial Sequence
<220> FEATURE:
<223> OTHER INFORMATION: Synthetic

<400> SEQUENCE: 470
caaccuauga ugauagguu                                                    19

<210> SEQ ID NO 471
<211> LENGTH: 19
<212> TYPE: RNA
<213> ORGANISM: Artificial Sequence
<220> FEATURE:
<223> OTHER INFORMATION: Synthetic

<400> SEQUENCE: 471
acaaccuaug augauaggu                                                    19

<210> SEQ ID NO 472
<211> LENGTH: 19
<212> TYPE: RNA
<213> ORGANISM: Artificial Sequence
<220> FEATURE:
<223> OTHER INFORMATION: Synthetic

<400> SEQUENCE: 472
gacaaccuau gaugauagg                                                    19

<210> SEQ ID NO 473
<211> LENGTH: 19
<212> TYPE: RNA
<213> ORGANISM: Artificial Sequence
<220> FEATURE:
<223> OTHER INFORMATION: Synthetic

<400> SEQUENCE: 473
ugacaaccua ugaugauag                                                    19

<210> SEQ ID NO 474
<211> LENGTH: 19
<212> TYPE: RNA
<213> ORGANISM: Artificial Sequence
<220> FEATURE:
<223> OTHER INFORMATION: Synthetic

<400> SEQUENCE: 474
augacaaccu augaugaua                                                    19

<210> SEQ ID NO 475
<211> LENGTH: 19
<212> TYPE: RNA
<213> ORGANISM: Artificial Sequence
<220> FEATURE:
<223> OTHER INFORMATION: Synthetic
```

```
<400> SEQUENCE: 475
caugacaacc uaugaugau                                                  19

<210> SEQ ID NO 476
<211> LENGTH: 19
<212> TYPE: RNA
<213> ORGANISM: Artificial Sequence
<220> FEATURE:
<223> OTHER INFORMATION: Synthetic

<400> SEQUENCE: 476
gcaugacaac cuaugauga                                                  19

<210> SEQ ID NO 477
<211> LENGTH: 19
<212> TYPE: RNA
<213> ORGANISM: Artificial Sequence
<220> FEATURE:
<223> OTHER INFORMATION: Synthetic

<400> SEQUENCE: 477
agcaugacaa ccuaugaug                                                  19

<210> SEQ ID NO 478
<211> LENGTH: 19
<212> TYPE: RNA
<213> ORGANISM: Artificial Sequence
<220> FEATURE:
<223> OTHER INFORMATION: Synthetic

<400> SEQUENCE: 478
aagcaugaca accuaugau                                                  19

<210> SEQ ID NO 479
<211> LENGTH: 19
<212> TYPE: RNA
<213> ORGANISM: Artificial Sequence
<220> FEATURE:
<223> OTHER INFORMATION: Synthetic

<400> SEQUENCE: 479
uaagcaugac aaccuauga                                                  19

<210> SEQ ID NO 480
<211> LENGTH: 19
<212> TYPE: RNA
<213> ORGANISM: Artificial Sequence
<220> FEATURE:
<223> OTHER INFORMATION: Synthetic

<400> SEQUENCE: 480
auaagcauga caaccuaug                                                  19

<210> SEQ ID NO 481
<211> LENGTH: 19
<212> TYPE: RNA
<213> ORGANISM: Artificial Sequence
<220> FEATURE:
<223> OTHER INFORMATION: Synthetic

<400> SEQUENCE: 481
cauaagcaug acaaccuau                                                  19

<210> SEQ ID NO 482
<211> LENGTH: 19
```

```
<212> TYPE: RNA
<213> ORGANISM: Artificial Sequence
<220> FEATURE:
<223> OTHER INFORMATION: Synthetic

<400> SEQUENCE: 482
ccauaagcau gacaaccua                                                    19

<210> SEQ ID NO 483
<211> LENGTH: 19
<212> TYPE: RNA
<213> ORGANISM: Artificial Sequence
<220> FEATURE:
<223> OTHER INFORMATION: Synthetic

<400> SEQUENCE: 483
cccauaagca ugacaaccu                                                    19

<210> SEQ ID NO 484
<211> LENGTH: 19
<212> TYPE: RNA
<213> ORGANISM: Artificial Sequence
<220> FEATURE:
<223> OTHER INFORMATION: Synthetic

<400> SEQUENCE: 484
ccccauaagc augacaacc                                                    19

<210> SEQ ID NO 485
<211> LENGTH: 19
<212> TYPE: RNA
<213> ORGANISM: Artificial Sequence
<220> FEATURE:
<223> OTHER INFORMATION: Synthetic

<400> SEQUENCE: 485
uccccauaag caugacaac                                                    19

<210> SEQ ID NO 486
<211> LENGTH: 19
<212> TYPE: RNA
<213> ORGANISM: Artificial Sequence
<220> FEATURE:
<223> OTHER INFORMATION: Synthetic

<400> SEQUENCE: 486
auccccauaa gcaugacaa                                                    19

<210> SEQ ID NO 487
<211> LENGTH: 19
<212> TYPE: RNA
<213> ORGANISM: Artificial Sequence
<220> FEATURE:
<223> OTHER INFORMATION: Synthetic

<400> SEQUENCE: 487
gauccccaua agcaugaca                                                    19

<210> SEQ ID NO 488
<211> LENGTH: 19
<212> TYPE: RNA
<213> ORGANISM: Artificial Sequence
<220> FEATURE:
<223> OTHER INFORMATION: Synthetic

<400> SEQUENCE: 488
```

```
ugaccuauga ugauagguu                                          19

<210> SEQ ID NO 489
<211> LENGTH: 19
<212> TYPE: RNA
<213> ORGANISM: Artificial Sequence
<220> FEATURE:
<223> OTHER INFORMATION: Synthetic

<400> SEQUENCE: 489
augaccuaug augauaggu                                          19

<210> SEQ ID NO 490
<211> LENGTH: 19
<212> TYPE: RNA
<213> ORGANISM: Artificial Sequence
<220> FEATURE:
<223> OTHER INFORMATION: Synthetic

<400> SEQUENCE: 490
gaugaccuau gaugauagg                                          19

<210> SEQ ID NO 491
<211> LENGTH: 19
<212> TYPE: RNA
<213> ORGANISM: Artificial Sequence
<220> FEATURE:
<223> OTHER INFORMATION: Synthetic

<400> SEQUENCE: 491
ugaugaccua ugaugauag                                          19

<210> SEQ ID NO 492
<211> LENGTH: 19
<212> TYPE: RNA
<213> ORGANISM: Artificial Sequence
<220> FEATURE:
<223> OTHER INFORMATION: Synthetic

<400> SEQUENCE: 492
augaugaccu augaugaua                                          19

<210> SEQ ID NO 493
<211> LENGTH: 19
<212> TYPE: RNA
<213> ORGANISM: Artificial Sequence
<220> FEATURE:
<223> OTHER INFORMATION: Synthetic

<400> SEQUENCE: 493
caugaugacc uaugaugau                                          19

<210> SEQ ID NO 494
<211> LENGTH: 19
<212> TYPE: RNA
<213> ORGANISM: Artificial Sequence
<220> FEATURE:
<223> OTHER INFORMATION: Synthetic

<400> SEQUENCE: 494
gcaugaugac cuaugauga                                          19

<210> SEQ ID NO 495
<211> LENGTH: 19
<212> TYPE: RNA
<213> ORGANISM: Artificial Sequence
```

```
<220> FEATURE:
<223> OTHER INFORMATION: Synthetic

<400> SEQUENCE: 495
agcaugauga ccuaugaug                                          19

<210> SEQ ID NO 496
<211> LENGTH: 19
<212> TYPE: RNA
<213> ORGANISM: Artificial Sequence
<220> FEATURE:
<223> OTHER INFORMATION: Synthetic

<400> SEQUENCE: 496
aagcaugaug accuaugau                                          19

<210> SEQ ID NO 497
<211> LENGTH: 19
<212> TYPE: RNA
<213> ORGANISM: Artificial Sequence
<220> FEATURE:
<223> OTHER INFORMATION: Synthetic

<400> SEQUENCE: 497
uaagcaugau gaccuauga                                          19

<210> SEQ ID NO 498
<211> LENGTH: 19
<212> TYPE: RNA
<213> ORGANISM: Artificial Sequence
<220> FEATURE:
<223> OTHER INFORMATION: Synthetic

<400> SEQUENCE: 498
auaagcauga ugaccuaug                                          19

<210> SEQ ID NO 499
<211> LENGTH: 19
<212> TYPE: RNA
<213> ORGANISM: Artificial Sequence
<220> FEATURE:
<223> OTHER INFORMATION: Synthetic

<400> SEQUENCE: 499
cauaagcaug augaccuau                                          19

<210> SEQ ID NO 500
<211> LENGTH: 19
<212> TYPE: RNA
<213> ORGANISM: Artificial Sequence
<220> FEATURE:
<223> OTHER INFORMATION: Synthetic

<400> SEQUENCE: 500
ccauaagcau gaugaccua                                          19

<210> SEQ ID NO 501
<211> LENGTH: 19
<212> TYPE: RNA
<213> ORGANISM: Artificial Sequence
<220> FEATURE:
<223> OTHER INFORMATION: Synthetic

<400> SEQUENCE: 501
cccauaagca ugaugaccu                                          19
```

<210> SEQ ID NO 502
<211> LENGTH: 19
<212> TYPE: RNA
<213> ORGANISM: Artificial Sequence
<220> FEATURE:
<223> OTHER INFORMATION: Synthetic

<400> SEQUENCE: 502
ccccauaagc augaugacc                                                    19

<210> SEQ ID NO 503
<211> LENGTH: 19
<212> TYPE: RNA
<213> ORGANISM: Artificial Sequence
<220> FEATURE:
<223> OTHER INFORMATION: Synthetic

<400> SEQUENCE: 503
uccccauaag caugaugac                                                    19

<210> SEQ ID NO 504
<211> LENGTH: 19
<212> TYPE: RNA
<213> ORGANISM: Artificial Sequence
<220> FEATURE:
<223> OTHER INFORMATION: Synthetic

<400> SEQUENCE: 504
auccccauaa gcaugauga                                                    19

<210> SEQ ID NO 505
<211> LENGTH: 19
<212> TYPE: RNA
<213> ORGANISM: Artificial Sequence
<220> FEATURE:
<223> OTHER INFORMATION: Synthetic

<400> SEQUENCE: 505
gauccccaua agcaugaug                                                    19

<210> SEQ ID NO 506
<211> LENGTH: 19
<212> TYPE: RNA
<213> ORGANISM: Artificial Sequence
<220> FEATURE:
<223> OTHER INFORMATION: Synthetic

<400> SEQUENCE: 506
ugauccccau aagcaugau                                                    19

<210> SEQ ID NO 507
<211> LENGTH: 200
<212> TYPE: DNA
<213> ORGANISM: Homo sapiens

<400> SEQUENCE: 507
cggtcttcag agaagccatt atctgcaaaa atatcccccg gcttgtgagt ggatgggtaa       60
aacctatcat cataggtcgt catgcttatg gggatcaata cagagcaact gattttgttg      120
ttcctgggcc tggaaaagta gagataaacct acacaccaag tgacggaacc caaaaggtga    180
catacctggt acataacttt                                                  200

<210> SEQ ID NO 508
<211> LENGTH: 200

```
<212> TYPE: DNA
<213> ORGANISM: Homo sapiens

<400> SEQUENCE: 508
cggtcttcag agaagccatt atctgcaaaa atatccccg gcttgtgagt ggatgggtaa      60
aacctatcat cataggtcat catgcttatg gggatcaata cagagcaact gattttgttg     120
ttcctgggcc tggaaaagta gagataacct acacaccaag tgacggaacc caaaaggtga    180
catacctggt acataacttt                                                200

<210> SEQ ID NO 509
<211> LENGTH: 200
<212> TYPE: DNA
<213> ORGANISM: Homo sapiens

<400> SEQUENCE: 509
cggtcttcag agaagccatt atctgcaaaa atatccccg gcttgtgagt ggatgggtaa      60
aacctatcat cataggttgt catgcttatg gggatcaata cagagcaact gattttgttg    120
ttcctgggcc tggaaaagta gagataacct acacaccaag tgacggaacc caaaaggtga    180
catacctggt acataacttt                                                200

<210> SEQ ID NO 510
<211> LENGTH: 414
<212> TYPE: PRT
<213> ORGANISM: Homo sapiens

<400> SEQUENCE: 510
```

Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

```
Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
            245                 250                 255

Gln Ala Met Lys Ser Glu Gly Gly Phe Ile Trp Ala Cys Lys Asn Tyr
        260                 265                 270

Asp Gly Asp Val Gln Ser Asp Ser Val Ala Gln Gly Tyr Gly Ser Leu
    275                 280                 285

Gly Met Met Thr Ser Val Leu Val Cys Pro Asp Gly Lys Thr Val Glu
290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
            325                 330                 335

Thr Arg Gly Leu Ala His Arg Ala Lys Leu Asp Asn Asn Lys Glu Leu
        340                 345                 350

Ala Phe Phe Ala Asn Ala Leu Glu Glu Val Ser Ile Glu Thr Ile Glu
    355                 360                 365

Ala Gly Phe Met Thr Lys Asp Leu Ala Ala Cys Ile Lys Gly Leu Pro
370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
            405                 410

<210> SEQ ID NO 511
<211> LENGTH: 1245
<212> TYPE: DNA
<213> ORGANISM: Homo sapiens

<400> SEQUENCE: 511
atgtccaaaa aaatcagtgg cggttctgtg gtagagatgc aaggagatga aatgacacga      60
atcatttggg aattgattaa agagaaactc attttteect acgtggaatt ggatctacat     120
agctatgatt taggcataga gaatcgtgat gccaccaacg accaagtcac caaggatgct     180
gcagaagcta taagaagca taatgttggc gtcaaatgtg ccactatcac teetgatgag      240 aagagggttg aggagttcaa gttgaaacaa atgtggaaat caccaaatgg caccatacga     300
aatattctgg gtggcacggt cttcagagaa gccattatct gcaaaaatat ccccggctt      360 gtgagtggat gggtaaaacc tatcatcata ggtcgtcatg cttatgggga tcaatacaga     420
gcaactgatt tgttgttcc tgggcctgga aagtagaga taacctacac accaagtgac      480
ggaacccaaa aggtgacata cctggtacat aactttgaag aaggtggtgg tgttgccatg     540
gggatgtata atcaagataa gtcaattgaa gattttgcac acagttcctt ccaaatggct     600
ctgtctaagg gttggcettt gtatctgagc accaaaaaca ctattctgaa gaaatatgat     660
gggcgtttta agacatcett tcaggagata tatgacaagc agtacaagtc ccagtttgaa     720
gctcaaaaga tctggtatga gcataggctc atcgacgaca tggtggccca agctatgaaa     780
tcagagggag gcttcatctg ggcctgtaaa aactatgatg gtgacgtgca gtcggactct     840
gtggcccaag gtatggctc tctcggcatg atgaccagcg tgctggttg tccagatggc     900 aagacagtag aagcagaggc tgcccacggg actgtaaccc gtcactaccg catgtaccag     960
aaaggacagg agacgtccac caatcccatt gcttccattt ttgcctggac cagagggtta    1020
gcccacagag caaagcttga taacaataaa gagcttgcct tctttgcaaa tgcctttgaa    1080
```

```
gaagtctcta ttgagacaat tgaggctggc ttcatgacca aggacttggc tgcttgcatt    1140
aaaggtttac ccaatgtgca acgttctgac tacttgaata catttgagtt catggataaa    1200
cttggagaaa acttgaagat caaactagct caggccaaac tttaa                    1245
```

<210> SEQ ID NO 512
<211> LENGTH: 414
<212> TYPE: PRT
<213> ORGANISM: Homo sapiens

<400> SEQUENCE: 512

```
Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly His His Ala Tyr Gly Asp Gln Tyr Arg Ala Thr Asp Phe
130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
```

```
                340             345             350
Ala Phe Phe Ala Asn Ala Leu Glu Glu Val Ser Ile Glu Thr Ile Glu
            355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 513
<211> LENGTH: 1245
<212> TYPE: DNA
<213> ORGANISM: Homo sapiens

<400> SEQUENCE: 513
atgtccaaaa aaatcagtgg cggttctgtg gtagagatgc aaggagatga aatgacacga       60
atcatttggg aattgattaa agagaaactc atttttccct acgtggaatt ggatctacat      120
agctatgatt taggcataga gaatcgtgat gccaccaacg accaagtcac caaggatgct      180
gcagaagcta taaagaagca taatgttggc gtcaaatgtg ccactatcac tcctgatgag      240
aagagggttg aggagttcaa gttgaaacaa atgtggaaat caccaaatgg caccatacga      300 atattctgg gtggcacggt cttcagaaa gccattatct gcaaaatat ccccggctt        360 gtgagtggat gggtaaaacc tatcatcata ggtcatcatg cttatgggga tcaatacaga      420
gcaactgatt ttgttgttcc tgggcctgga aaagtagaga taacctacac accaagtgac      480
ggaacccaaa aggtgacata cctggtacat aactttgaag aaggtggtgg tgttgccatg      540
gggatgtata atcaagataa gtcaattgaa gattttgcac acagttcctt ccaaatggct      600
ctgtctaagg gttggccttt gtatctgagc accaaaaaca ctattctgaa gaaatatgat      660
gggcgtttta agacatctt tcaggagata tatgacaagc agtacaagtc ccagtttgaa      720
gctcaaaaga tctggtatga gcataggctc atcgacgaca tggtggccca agctatgaaa      780
tcagagggag gcttcatctg ggcctgtaaa aactatgatg gtgacgtgca gtcggactct      840
gtggcccaag gtatggctc tctcggcatg atgaccagcg tgctggtttg tccagatggc      900
aagacagtag aagcagaggc tgcccacggg actgtaaccc gtcactaccg catgtaccag      960
aaaggacagg agacgtccac caatcccatt gcttccattt ttgcctggac cagagggtta     1020
gcccacagag caaagcttga taacaataaa gagcttgcct tctttgcaaa tgctttggaa     1080
gaagtctcta ttgagacaat tgaggctggc ttcatgacca aggacttggc tgcttgcatt     1140
aaaggtttac ccaatgtgca acgttctgac tacttgaata catttgagtt catggataaa     1200
cttggagaaa acttgaagat caaactagct caggccaaac tttaa                     1245

<210> SEQ ID NO 514
<211> LENGTH: 414
<212> TYPE: PRT
<213> ORGANISM: Homo sapiens

<400> SEQUENCE: 514

Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
```

```
              35                  40                  45
Arg Asp Ala Thr Asn Asp Gln Val Thr Lys Asp Ala Glu Ala Ile
 50                  55                  60

Lys Lys His Asn Val Gly Val Lys Cys Ala Thr Ile Thr Pro Asp Glu
 65                  70                  75                  80

Lys Arg Val Glu Glu Phe Lys Leu Lys Gln Met Trp Lys Ser Pro Asn
                 85                  90                  95

Gly Thr Ile Arg Asn Ile Leu Gly Gly Thr Val Phe Arg Glu Ala Ile
                100                 105                 110

Ile Cys Lys Asn Ile Pro Arg Leu Val Ser Gly Trp Val Lys Pro Ile
            115                 120                 125

Ile Ile Gly Cys His Ala Tyr Gly Asp Gln Tyr Arg Ala Thr Asp Phe
            130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 515
<211> LENGTH: 1245
<212> TYPE: DNA
<213> ORGANISM: Homo sapiens

<400> SEQUENCE: 515
```

```
atgtccaaaa aaatcagtgg cggttctgtg gtagagatgc aaggagatga atgacacga      60 atcatttggg aattgattaa agagaaactc attttcccct acgtggaatt ggatctacat    120
agctatgatt taggcataga gaatcgtgat gccaccaacg accaagtcac caaggatgct    180
gcagaagcta taaagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagaaa gccattatct gcaaaaatat cccccggctt    360
gtgagtggat gggtaaaacc tatcatcata ggttgtcatg cttatgggga tcaatacaga    420
gcaactgatt ttgttgttcc tgggcctgga aaagtagaga taacctacac accaagtgac    480
ggaacccaaa aggtgacata cctggtacat aactttgaag aaggtggtgg tgttgccatg    540
gggatgtata atcaagataa gtcaattgaa gattttgcac acagttcctt ccaaatggct    600
ctgtctaagg gttggccttt gtatctgagc accaaaaaca ctattctgaa gaaatatgat    660
gggcgtttta agacatcttt tcaggagata tatgacaagc agtacaagtc ccagtttgaa    720
gctcaaaaga tctggtatga gcataggctc atcgacgaca tggtggccca agctatgaaa    780
tcagagggag gcttcatctg ggcctgtaaa aactatgatg tgacgtgca gtcggactct    840 gtggcccaag ggtatggctc tctcggcatg atgaccagcg tgctggtttg tccagatggc    900
aagacagtag aagcagaggc tgcccacggg actgtaaccc gtcactaccg catgtaccag    960
aaaggacagg agacgtccac caatcccatt gcttccattt ttgcctggac cagagggtta   1020
gcccacagag caaagcttga taacaataaa gagcttgcct tctttgcaaa tgctttggaa   1080
gaagtctcta ttgagacaat tgaggctggc ttcatgacca aggacttggc tgcttgcatt   1140 aaaggttta ccaatgtgca acgttctgac tacttgaata catttgagtt catggataaa   1200
cttggagaaa acttgaagat caaactagct caggccaaac tttaa                    1245
```

<210> SEQ ID NO 516
<211> LENGTH: 2339
<212> TYPE: DNA
<213> ORGANISM: Homo sapiens

<400> SEQUENCE: 516

```
cctgtggtcc cgggtttctg cagagtctac ttcagaagcg gaggcactgg gagtccggtt     60
tgggattgcc aggctgtggt tgtgagtctg agcttgtgag cggctgtggc gccccaactc    120
ttcgccagca tatcatcccg gcaggcgata aactacattc agttgagtct gcaagactgg    180
gaggaactgg ggtgataaga aatctattca ctgtcaaggt ttattgaagt caaaatgtcc    240
aaaaaaatca gtggcggttc tgtggtagag atgcaaggag atgaaatgac acgaatcatt    300
tgggaattga ttaaagagaa actcattttt ccctacgtgg aattggatct acatagctat    360
gatttaggca tagagaatcg tgatgccacc aacgaccaag tcaccaagga tgctgcagaa    420
gctataaaga agcataatgt tggcgtcaaa tgtgccacta tcactcctga tgaagagg     480 gttgaggagt tcaagttgaa acaaatgtgg aaatcaccaa atggcaccat acgaaatatt    540
ctgggtggca cggtcttcag agaagccatt atctgcaaaa atatcccccg gcttgtgagt    600
ggatgggtaa aacctatcat cataggtcgt catgcttatg gggatcaata cagagcaact    660
gattttgttg ttcctgggcc tggaaaagta gagataacct acacaccaag tgacggaacc    720
caaaaggtga cataccttggt acataacttt gaagaaggtg gtggtgttgc catggggatg    780
tataatcaag ataagtcaat tgaagatttt gcacacagtt ccttccaaat ggctctgtct    840
aagggttggc ctttgtatct gagcaccaaa aacactattc tgaagaaata tgatgggcgt    900
```

```
tttaaagaca tctttcagga gatatatgac aagcagtaca agtcccagtt tgaagctcaa    960
aagatctggt atgagcatag gctcatcgac gacatggtgg cccaagctat gaaatcagag   1020
ggaggcttca tctgggcctg taaaaactat gatggtgacg tgcagtcgga ctctgtggcc   1080
caagggtatg gctctctcgg catgatgacc agcgtgctgg tttgtccaga tggcaagaca   1140
gtagaagcag aggctgccca cgggactgta acccgtcact accgcatgta ccagaaagga   1200
caggagacgt ccaccaatcc cattgcttcc attttgcct ggaccagagg gttagcccac    1260
agagcaaagc ttgataacaa taaagagctt gccttctttg caaatgcttt ggaagaagtc   1320
tctattgaga caattgaggc tggcttcatg accaaggact tggctgcttg cattaaaggt   1380
ttacccaatg tgcaacgttc tgactacttg aatacatttg agttcatgga taaacttgga   1440
gaaaacttga agatcaaact agctcaggcc aaactttaag ttcatacctg agctaagaag   1500
gataattgtc ttttggtaac taggtctaca ggtttacatt tttctgtgtt acactcaagg   1560
ataaaggcaa aatcaatttt gtaatttgtt tagaagccag agtttatctt ttctataagt   1620
ttacagcctt tttcttatat atacagttat tgccacctt gtgaacatgg caagggactt    1680
ttttacaatt tttattttat tttctagtac cagcctagga attcggttag tactcatttg   1740
tattcactgt cacttttct catgttctaa ttataaatga ccaaaatcaa gattgctcaa    1800
aagggtaaat gatagccaca gtattgctcc ctaaaatatg cataaagtag aaattcactg   1860
ccttcccctc ctgtccatga ccttgggcac agggaagttc tggtgtcata gatatcccgt   1920
tttgtgaggt agagctgtgc attaaacttg cacatgactg gaacgaagta tgagtgcaac   1980
tcaaatgtgt tgaagatact gcagtcattt ttgtaaagac cttgctgaat gtttccaata   2040
gactaaatac tgtttaggcc gcaggagagt tggaatccg gaataaatac tacctggagg    2100
tttgtcctct ccattttct ctttctcctc ctggcctggc ctgaatatta tactactcta    2160
aatagcatat ttcatccaag tgcaataatg taagctgaat cttttttgga cttctgctgg   2220
cctgttttat ttcttttata taaatgtgat ttctcagaaa ttgatattaa acactatctt   2280
atcttctcct gaactgttga ttttaattaa aattaagtgc taattaccaa aaaaaaaaa    2339
```

RNA INTERFERENCE MEDIATED INHIBITION OF ISOCITRATE DEHYDROGENASE (IDH1) GENE EXPRESSION

CROSS-REFERENCE TO RELATED APPLICATIONS

The present application is the §371 National Stage application of PCT International Application serial no. PCT/US2012/040332, having an international filing date of Jun. 1, 2012, which claims the benefit of U.S. Provisional Application No. 61/493,570, filed Jun. 6, 2011.

SEQUENCE LISTING

The sequence listing submitted via EFS, in compliance with 37 CFR §1.52(e)(5), is incorporated herein by reference. The sequence listing text file submitted via EFS contains the file "SIRONC00004USPCT-SEQLIST-03DEC2013", created on Dec. 3, 2013, which is 237,568 bytes in size.

BACKGROUND OF THE INVENTION

Cytosolic isocitrate dehydrogenase, also known as isocitrate dehydrogenanse 1 (IDH1), is an enzyme that catalyzes the oxidative carboxylation of isocitrate to produce $CO_2$ and α-ketoglutarate (αKG). Somatic mutations in IDH1 have been identified in colorectal cancers, gliomas (e.g., grade II-III astrocytomas, oligodendrogliomas and glioblastomas), patients with acute myeloid leukemia (AML), prostate, B-acute lymphoblastic leukemia, and a variety of other malignanices with lower frequencies (Sjöblom et. al., 2006, Science 314:268-274; Parsons et al., 2008, Science 321:1807-1812; Bleeker et al., 2009, Hum. Mutat. 30:7-11; Yan et al., 2009, N. Engl. J. Med. 360:765-773; Yan et al., 2009, N. Engl. J. Med. 360:765-773; Mardis et al., 2009, N. Engl. J. Med. 361:1058-1066). Importantly, gliomas and AML are two of the most malignant types of tumors, having the worst prognoses.

The IDH1 mutation found within these malignancies is a heterozygous mutation affecting Arg132, an amino acid that forms part of a catalytic arginine triad (along with Arg100 and Arg 109) involved in binding to isocitrate. Due the location of the mutation, it was originally hypothesized that the mutated protein would lack enzymatic activity; however, it was later discovered that rather than being catalytically inactive, the mutant form possesses the novel enzymatic activity of reducing αKG to 2-hydroxyglutarate (2HG) (Dang et al., 2009 Nature 462:739-744). The arginine at amino acid position 132 of IDH1 has been found to be mutated to histidine (R132H), cysteine (R132C), glycine (R132G), serine (R132S), leucine (R132L) and valine (R132V) (Yen et al., 2010, Oncogene 29:6409-6417).

PCT International patent application published as WO 2010/105243 (Dang et al.) describes methods for treating patients with cell proliferation-related disorders characterized by the presence of a mutant isocitrate dehydrogenase by administering a nucleic acid based inhibitor (e.g., siRNA) that targets mRNA encoding mutant IDH1 proteins that demonstrate 2HG neoactivity. siRNA having specific sense and antisense sequences are provided in the application; however, the disclosure does not show either the down-regulation of IDH1 gene expression and/or decrease in IDH protein levels or the result of such down-regulation in any functional assays.

There remains a need for molecules that inhibit IDH1 and mutant forms thereof. Alteration of gene expression, specifically IDH1 and mutant IDH1 gene expression, through RNA interference (hereinafter "RNAi") is one approach for meeting this need. RNAi is induced by short single-stranded RNA ("ssRNA") or double-stranded RNA ("dsRNA") molecules. The short dsRNA molecules, called "short interfering nucleic acids ("siNA")" or "short interfering RNA" or "siRNA" or "RNAi inhibitors" silence the expression of messenger RNAs ("mRNAs") that share sequence homology to the siNA. This can occur via cleavage of the mRNA mediated by an endonuclease complex containing a siNA, commonly referred to as an RNA-induced silencing complex (RISC). Cleavage of the target RNA typically takes place in the middle of the region complementary to the guide sequence of the siNA duplex (Elbashir et al., 2001, Genes Dev., 15:188). In addition, RNA interference can also involve small RNA (e.g., micro-RNA or miRNA) mediated gene silencing, presumably through cellular mechanisms that either inhibit translation or that regulate chromatin structure and thereby prevent transcription of target gene sequences (see for example Alishire, 2002, Science, 297:1818-1819; Volpe et al., 2002, Science, 297:1833-1837; Jenuwein, 2002, Science, 297:2215-2218; and Hall et al., 2002, Science, 297:2232-2237). Despite significant advances in the field of RNAi, there remains a need for agents that can inhibit IDH1 and mutant IDH1 gene expression and that can treat disease associated with mutant IDH1 expression, such as cancer.

SUMMARY OF THE INVENTION

The invention provides a solution to the problem of treating diseases that respond to modulation of IDH1 gene expression, or a derivative and/or mutant thereof, using novel short interfering nucleic acid (siNA) molecules. The novel siNA molecules described as part of the invention can be used to modulate wild-type IDH1 gene expression and/or to modulate the gene expression of one or more derivatives and/or mutant forms of IDH1. For example, the novel siNA molecules can be used to modulate gene expression of mutant forms of the IDH1 protein that are expressed in certain types of cancers (e.g., cancers of the central nervous system and AML), such as IDH1-R132H, IDH1-R132C, IDH1-R132G, IDH1-R132S, IDH1-R132L and IDH1-R132V. Wild-type IDH1 and mutant forms of IDH1 are together referred to herein as "IDH1-related" proteins and genes.

The present invention provides compounds, compositions, and methods useful for modulating the expression of IDH1-related genes, specifically those IDH1-related genes associated with cell-proliferation-related disorders (e.g., cancers of the central nervous system and AML), and for treating conditions associated with such disorders by RNA interference (RNAi) using small nucleic acid molecules.

In particular, the instant invention features small nucleic acid molecules, i.e., short interfering nucleic acid (siNA) molecules including, but not limited to, short interfering RNA (siRNA), double-stranded RNA (dsRNA), micro-RNA (miRNA), short hairpin RNA (shRNA) and circular RNA molecules and methods used to modulate the expression of IDH1-related genes and/or other genes involved in pathways of IDH1-related gene expression and/or activity.

In one aspect, the invention provides double-stranded short interfering nucleic acid (siNA) molecules that inhibit the expression of an IDH1-related gene in a cell or mammal, wherein the double-stranded siNAs comprise a sense and an antisense strand. The antisense strand comprises a sequence that is complementary to at least a part of an RNA associated with the expression of an IDH1-related gene. The sense strand comprises a sequence that is complementary to the antisense strand. In various embodiments, at least one strand of the siNA molecule comprises at least a 15 nucleotide sequence selected from the group of sequences consisting of SEQ ID NOs: 1-506.

In certain embodiments, double-stranded short interfering nucleic acid (siNA) molecules are provided wherein the antisense strand comprises at least 15 nucleotides having sequence complementarity to a target sequence set forth in Table 1a. In one embodiment, the "at least 15 nucleotides" are 15 contiguous nucleotides. The sense strand of the siNA comprises a region that is complementary to the antisense strand. In specific embodiments, the antisense strand of an siNA of the invention comprises at least 15 nucleotides of an antisense sequence selected from Table 1b (SEQ ID NOs: 440-506). In other embodiments, the sense strand comprises at least 15 nucleotides of a sense strand sequence as set forth in Table 1b (SEQ ID NOs: 1-67). In further embodiments, double-stranded siNA molecules of the invention comprise at least 15 nucleotides of a sense strand selected from Table 1b (SEQ ID NOs: 1-67) and at least 15 nucleotides of an antisense strand selected from Table 1b (SEQ ID NOs: 440-506). In each of the embodiment above, the "at least 15 nucleotides" are 15 contiguous nucleotides.

In certain embodiments of this aspect of the invention, double-stranded short interfering nucleic acid (siNA) molecules are provided wherein the antisense and/or sense strand comprises at least one nucleotide sequence selected from SEQ ID NOs: 68-439, provided in Table 1c. In other embodiment, the antisense strand comprises a modified sequence as set forth in Table 1c that has sequence complementarity to a target sequence of the invention. In other embodiments, siNA molecules of the invention comprise at least two sequences selected from SEQ ID NOs: 68-439, provided in Table 1c, wherein one of the at least two sequences is complementary to another of the at least two sequences, and one of the at least two sequences is complementary to a sequence of a mRNA generated in the expression of an IDH1-related gene.

In certain embodiments, the present invention provides a double-stranded short interfering nucleic acid (siNA) molecule that modulates the expression of an IDH1-related gene, wherein the siNA molecule comprises a sense strand and an antisense strand, wherein each strand is independently 15 to 30 nucleotides in length, and wherein the antisense strand comprises at least 15 nucleotides having sequence complementary to any of:

```
                                          (SEQ ID NO: 7)
5'-CUAUCAUCAUAGGUCGUCA-3';

(SEQ ID NO: 11)
5'-CAUCAUAGGUCGUCAUGCU-3';

(SEQ ID NO: 12)
5'-AUCAUAGGUCGUCAUGCUU-3';

(SEQ ID NO: 13)
5'-UCAUAGGUCGUCAUGCUUA-3';

(SEQ ID NO: 38)
5'-CAUCAUAGGUUGUCAUGCU-3';

(SEQ ID NO: 39)
5'-AUCAUAGGUUGUCAUGCUU-3';

(SEQ ID NO: 40)
5'-UCAUAGGUUGUCAUGCUUA-3';
```

```
                                          (SEQ ID NO: 41)
5'-CAUAGGUUGUCAUGCUUAU-3';

(SEQ ID NO: 59)
5'-CAUAGGUCAUCAUGCUUAU-3';
or,
                                          (SEQ ID NO: 63)
5'-GGUCAUCAUGCUUAUGGGG-3'.
```

In one embodiment, the "at least 15 nucleotides" are 15 contiguous nucleotides.

In some embodiments, the antisense strand of an siNA molecule of the invention comprises at least 15 nucleotides having identity to any of:

```
                                          (SEQ ID NO: 446)
5'-UGACGACCUAUGAUGAUAG-3';

(SEQ ID NO: 450)
5'-AGCAUGACGACCUAUGAUG-3';

(SEQ ID NO: 451)
5'-AAGCAUGACGACCUAUGAU-3';

(SEQ ID NO: 452)
5'-UAAGCAUGACGACCUAUGA-3';

(SEQ ID NO: 477)
5'-AGCAUGACAACCUAUGAUG-3';

(SEQ ID NO: 478)
5'-AAGCAUGACAACCUAUGAU-3';

(SEQ ID NO: 479)
5'-UAAGCAUGACAACCUAUGA-3';

(SEQ ID NO: 480)
5'-AUAAGCAUGACAACCUAUG-3';

(SEQ ID NO: 498)
5'-AUAAGCAUGAUGACCUAUG-3';
or,
                                          (SEQ ID NO: 502)
5'-CCCCAUAAGCAUGAUGACC-3'.
```

In one embodiment, the "at least 15 nucleotides" are 15 contiguous nucleotides. Thus, the antisense strand of the siNA molecule comprises at least a 15 nucleotide sequence of any of SEQ ID NO: 446, 450, 451, 452, 477, 478, 479, 480, 498, or 502.

In some embodiments, the sense strand of an siNA molecule of the invention comprises at least 15 nucleotides having identity to any of:

```
                                          (SEQ ID NO: 7)
5'-CUAUCAUCAUAGGUCGUCA-3';

(SEQ ID NO: 11)
5'-CAUCAUAGGUCGUCAUGCU-3';

(SEQ ID NO: 12)
5'-AUCAUAGGUCGUCAUGCUU-3';

(SEQ ID NO: 13)
5'-UCAUAGGUCGUCAUGCUUA-3';

(SEQ ID NO: 38)
5'-CAUCAUAGGUUGUCAUGCU-3';

(SEQ ID NO: 39)
5'-AUCAUAGGUUGUCAUGCUU-3';
```

```
                                            (SEQ ID NO: 40)
5'-UCAUAGGUUGUCAUGCUUA-3';

(SEQ ID NO: 41)
5'-CAUAGGUUGUCAUGCUUAU-3';

(SEQ ID NO: 59)
5'-CAUAGGUCAUCAUGCUUAU-3';
or, (SEQ ID NO: 63)
5'-GGUCAUCAUGCUUAUGGGG-3'.
```

In one embodiment, the "at least 15 nucleotides" are 15 contiguous nucleotides. Thus, the sense strand of the siNA molecule comprises at least a 15 nucleotide sequence of any of SEQ ID NO: 7, 11, 12, 13, 38, 39, 40, 41, 59, or 63.

In some embodiments, an siNA molecule of the invention comprises any of:

```
                                            (SEQ ID NO: 7)
5'-CUAUCAUCAUAGGUCGUCA-3'
and (SEQ ID NO: 446)
5'-UGACGACCUAUGAUGAUAG-3';

(SEQ ID NO: 11)
5'-CAUCAUAGGUCGUCAUGCU-3'
and (SEQ ID NO: 450)
5'-AGCAUGACGACCUAUGAUG-3';

(SEQ ID NO: 12)
5'-AUCAUAGGUCGUCAUGCUU-3'
and (SEQ ID NO: 451)
5'-AAGCAUGACGACCUAUGAU-3';

(SEQ IN NO: 13)
5'-UCAUAGGUCGUCAUGCUUA-3'
and (SEQ ID NO: 452)
5'-UAAGCAUGACGACCUAUGA-3';

(SEQ ID NO: 38)
5'-CAUCAUAGGUUGUCAUGCU-3'
and (SEQ ID NO: 477)
5'-AGCAUGACAACCUAUGAUG-3';

(SEQ ID NO: 39)
5'-AUCAUAGGUUGUCAUGCUU-3'
and (SEQ ID NO: 478)
5'-AAGCAUGACAACCUAUGAU-3';

(SEQ ID NO: 40)
5'-UCAUAGGUUGUCAUGCUUA-3'
and (SEQ ID NO: 479)
5'-UAAGCAUGACAACCUAUGA-3';

(SEQ ID NO: 41)
5'-CAUAGGUUGUCAUGCUUAU-3'
and (SEQ ID NO: 480)
5'-AUAAGCAUGACAACCUAUG-3';

(SEQ ID NO: 59)
5'-CAUAGGUCAUCAUGCUUAU-3'
and (SEQ ID NO: 498)
5'-AUAAGCAUGAUGACCUAUG-;
or, (SEQ ID NO: 63)
5'-GGUCAUCAUGCUUAUGGGG-3'
and (SEQ ID NO: 502)
5'-CCCCAUAAGCAUGAUGACC-3'.
```

In another embodiment, the siNA molecule comprises at least a 15 nucleotide sequence of both SEQ ID NO: 7 and 446; or both SEQ ID NO: 11 and 450; or both SEQ ID NO: 12 and 451; or both SEQ ID NO: 13 and 452; or both SEQ ID NO: 38 and 477; or both SEQ ID NO: 39 and 478; or both SEQ ID NO: 40 and 479; or both SEQ ID NO: 41 and 480; or both SEQ ID NO: 59 and 498; or both SEQ ID NO: 63 and 502.

In some embodiments of the invention, all of the nucleotides of siNAs of the invention are unmodified. In other embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) of the nucleotide positions independently in either one or both strands of an siNA molecule are modified. Modifications include nucleic acid sugar modifications, base modifications, backbone (internucleotide linkage) modifications, non-nucleotide modifications, and/or any combination thereof. In certain instances, purine and pyrimidine nucleotides are differentially modified. For example, purine and pyrimidine nucleotides can be differentially modified at the 2'-sugar position (i.e., at least one purine has a different modification from at least one pyrimidine in the same or different strand at the 2'-sugar position). In certain instances the purines are unmodified in one or both strands, while the pyrimidines in one or both strands are modified. In certain other instances, the pyrimidines are unmodified in one or both strands, while the purines in one or both strands are modified. In some instances, at least one modified nucleotide is a 2'-deoxy-2'-fluoro nucleotide, a 2'-deoxy nucleotide, or a 2'-O-alkyl nucleotide. In some instances, at least 5 or more of the pyrimidine nucleotides in one or both strands are either all 2'-deoxy-2'-fluoro or all 2'-O-methyl pyrimidine nucleotides. In some instances, at least 5 or more of the purine nucleotides in one or both strands are either all 2'-deoxy-2'-fluoro or all 2'-O-methyl purine nucleotides. In certain instances, wherein the siNA molecules comprise one or more modifications as described herein, the nucleotides at positions 1, 2, and 3 at the 5' end of the guide (antisense) strand are unmodified.

In certain embodiments, the siNA molecules of the invention have 3' overhangs of one, two, three, or four nucleotide(s) on one or both of the strands. In other embodiments, the siNA molecules lack overhangs (i.e., have blunt ends). Preferably, the siNA molecule has 3' overhangs of two nucleotides on both the sense and antisense strands. The overhangs can be modified or unmodified. Examples of modified nucleotides in the overhangs include, but are not limited to, 2'-O-alkyl nucleotides, 2'-deoxy-2'-fluoro nucleotides, locked nucleic acid (LNA) nucleotides, or 2'-deoxy nucleotides. The overhanging nucleotides in the antisense strand can comprise nucleotides that are complementary to nucleotides in the IDH1-related target sequence. Likewise, the overhangs in the sense strand can comprise nucleotides that are present in the IDH1-related target sequence. In certain instances, the siNA molecules of the invention have two 3' overhanging nucleotides on the antisense strand that are 2'-O-alkyl (e.g., 2'-O-methyl) nucleotides and two 3' overhanging nucleotides on the sense strand that are 2'-deoxy nucleotides. In other instances, the siNA molecules of the invention have two 3' overhanging nucleotides that are 2'-O-alkyl (e.g., 2'-O-methyl) nucleotides on both the antisense strand and the sense strand. In certain embodiments, the 2'-O-alkyl nucleotides are 2'-O-methyl uridine nucleotides. In certain instances, the 3' overhangs also comprise one or more phosphorothioate linkages between nucleotides of the overhang.

In some embodiments, the siNA molecules of the invention have caps (also referred to herein as "terminal caps." The cap can be present at the 5'-terminus (5'-cap) or at the 3'-terminus (3'-cap) or can be present on both termini, such as at the 5' and 3' termini of the sense strand of the siNA.

In some embodiments, the siNA molecules of the invention are phosphorylated at the 5' end of the antisense strand. The phosphate group can be a phosphate, a diphosphate or a triphosphate.

In some embodiments, the antisense strand of an siNA molecule of the invention comprises at least 15 nucleotides having sequence identity to any of SEQ ID NOs: 91, 107, 111, 115, 199, 213, 227, 231, 303, or 411. In other embodiments, the sense strand of an siNA molecule of the invention comprises at least 15 nucleotides having sequence identity of any of SEQ ID NOs: 90, 106, 110, 114, 198, 212, 226, 230, 302, or 410. In a further embodiment, the "at least 15 nucleotides" are 15 contiguous nucleotides.

In some embodiments, an siNA molecule of the invention comprises any of: SEQ ID NO: 90 and 91; SEQ ID NO: 106 and 107; SEQ ID NO: 110 and 111; SEQ ID NO: 114 and 115; SEQ ID NO: 198 and 199; SEQ ID NO: 212 and 213; SEQ ID NO: 226 and 227; SEQ ID NO: 230 and 231; SEQ ID NO: 302 and 303; or SEQ ID NO: 410 and 411.

The double-stranded siNA molecules of the invention can be symmetric or asymmetric. Each strand of these double-stranded siNAs independently can range in nucleotide length from between 3 and 30 nucleotides. Generally, each strand of the siNA molecules of the invention is about 15 to 30 (i.e., about 15, 16, 17, 18, 19, 20, 21, 22, 23, 24, 25, 26, 27, 28, 29, or 30) nucleotides in length.

The siNA molecules of the invention, which are double stranded or have a duplex structure, independently comprise about 3 to about 30 (e.g., about 3, 4, 5, 6, 7, 8, 9, 10, 11, 12, 13, 14, 15, 16, 17, 18, 19, 20, 21, 22, 23, 24, 25, 26, 27, 28, 29, or 30) base pairs. Generally, the duplex structure of siNAs of the invention is between 15 and 30 base pairs, more generally between 18 and 25 base pairs, yet more generally between 19 and 24 base pairs, and most generally between 19 and 21 base pairs in length.

In certain embodiments, double-stranded short interfering nucleic acid (siNA) molecules are provided, wherein the molecule has a sense strand and an antisense strand and comprises formula (A):

B—$N_{X3}$—$(N)_{X2}$B-3'

B$(N)_{X1}$—$N_{X4}$—[N3]-[N2]-[N1]-5'     (A)

wherein, the upper strand is the sense strand and the lower strand is the antisense strand of the double-stranded nucleic acid molecule; wherein the antisense strand comprises at least a 15 nucleotide sequence of SEQ ID NO: 446, SEQ ID NO: 450, SEQ ID NO: 451, SEQ ID NO: 452, SEQ ID NO: 477, SEQ ID NO: 478, SEQ ID NO: 479, SEQ ID NO: 480, SEQ ID NO: 498, or SEQ ID NO: 502; and the sense strand comprises a sequence having complementarity to the antisense strand;

each N is independently either a nucleotide that is unmodified or chemically modified, or a non-nucleotide;

each B is a terminal cap that is present or absent;

(N) represents overhanging nucleotides, each of which is independently unmodified or chemically modified;

X1 and X2 are independently integers from 0 to 4;
X3 is an integer from 15 to 30;
X4 is an integer from 12 to 27; and,
[N1]-[N2]-[N3] are modified nucleotides or ribonucleotides, and wherein [N1]-[N2]-[N3] is selected from the groups consisting of:
(a) [N1] is a 2'-deoxy-2'-fluoro nucleotide, [N2] is a 2'-deoxy-2'-fluoro nucleotide, and [N3] is a 2'-deoxy-2'-fluoro nucleotide;
(b) [N1] is a 2'-deoxy-2'-fluoro nucleotide, [N2] is a 2'-deoxy-2'-fluoro nucleotide, and [N3] is a 2'-deoxy nucleotide;
(c) [N1] is a 2'-deoxy nucleotide, [N2] is a 2'-deoxy-2'-fluoro nucleotide, and [N3] is a 2'-O-methyl nucleotide;
(d) [N1] is a 2'-deoxy nucleotide, [N2] is a 2'-deoxy-2'-fluoro nucleotide, and [N3] is a 2'-deoxy nucleotide; and,
(e) [N1] is a ribonucleotide, [N2] is a ribonucleotide, and [N3] is a ribonucleotide.

In one embodiment, the invention features a double-stranded short interfering nucleic acid (siNA) molecule of formula (A); wherein:
(a) one or more pyrimidine nucleotides in $N_{X4}$ positions are independently 2'-deoxy-2'-fluoro nucleotides, 2'-O-alkyl nucleotides, 2'-deoxy nucleotides, ribonucleotides, or any combination thereof;
(b) one or more purine nucleotides in $N_{X4}$ positions are independently 2'-deoxy-2'-fluoro nucleotides, 2'-O-alkyl nucleotides, 2'-deoxy nucleotides, ribonucleotides, or any combination thereof;
(c) one or more pyrimidine nucleotides in $N_{X3}$ positions are independently 2'-deoxy-2'-fluoro nucleotides, 2'-O-alkyl nucleotides, 2'-deoxy nucleotides, ribonucleotides, or any combination thereof; and,
(d) one or more purine nucleotides in $N_{X3}$ positions are independently 2'-deoxy-2'-fluoro nucleotides, 2'-O-alkyl nucleotides, 2'-deoxy nucleotides, ribonucleotides, or any combination thereof.

The present invention further provides compositions comprising the double-stranded nucleic acid molecules described herein with, optionally, a pharmaceutically acceptable carrier or diluent.

The administration of the composition can be carried out by known methods, wherein the nucleic acid is introduced into a desired target cell in vitro or in vivo.

Commonly used techniques for introduction of the nucleic acid molecules of the invention into cells, tissues, and organisms include the use of various carrier systems, reagents and vectors. Non-limiting examples of such carrier systems suitable for use in the present invention include conjugates, nucleic-acid-lipid particles, lipid nanoparticles (LNP), liposomes, lipoplexes, micelles, virosomes, virus like particles (VLP), nucleic acid complexes, and mixtures thereof.

The compositions of the invention can be in the form of an aerosol, dispersion, solution (e.g., an injectable solution), a cream, ointment, tablet, powder, suspension or the like. These compositions may be administered in any suitable way, e.g. orally, sublingually, buccally, parenterally, nasally, or topically. In some embodiments, the compositions are aerosolized and delivered via inhalation.

The molecules and compositions of the present invention have utility over a broad range of therapeutic applications. Accordingly another aspect of this invention relates to the use of the molecules and compositions of the invention in treating a subject. The invention thus provides a method for treating a subject, such as a human, suffering from a condition which is mediated by the action, or by the loss of action, of an IDH1- related gene or protein, wherein the method comprises administering to the subject an effective amount of a double-stranded short interfering nucleic acid (siNA) molecule of the invention. In certain embodiments, the condition is cancer (e.g., glioma, glioblastoma, AML).

These and other aspects of the invention will be apparent upon reference to the following Detailed Description and attached figures. Moreover, it is contemplated that any method or composition described herein can be implemented with respect to any other method or composition described herein and that different embodiments may be combined.

Additionally, patents, patent applications, and other documents are cited throughout the specification to describe and more specifically set forth various aspects of this invention. Each of these references cited herein is hereby incorporated by reference in its entirety, including the drawings.

BRIEF DESCRIPTION OF THE DRAWINGS

FIG. 2 shows non-limiting examples of chemically modified siNA constructs of the present invention using a generalized structure of a representative siNA duplex. The specific modifications shown in the figure can be utilized alone or in combination with other modifications of the figure, in addition to other modifications and features described herein with reference to any siNA molecule of the invention. In the figure, N strands for any nucleotide or optionally a non-nucleotide as described herein. The upper strand, having B—$N_{X3}$—$(N)_{X2}$—B-3' is the sense (or passenger) strand of the siNA, whereas the lower strand, having B$(N)_{X1}$—$N_{X4}$-[N3]-[N2]-[N1]-5' is the antisense (or guide) strand of the siNA. Nucleotides (or optional non-nucleotides) of internal portions of the sense strand are designated $N_{X3}$ and nucleotides (or optional non-nucleotides) of internal portions of the antisense strand are designated $N_{X4}$. Nucleotides (or optional non-nucleotides) of the internal portions are generally base paired between the two strands, but can optionally lack base pairing (e.g., have mismatches or gaps) in some embodiments. Nucleotides (or optional non-nucleotides) of overhang regions are designated by parenthesis (N). Nucleotides of the 5'-terminal portion of the antisense strand are designated [N] ([N1], [N2], [N3]). Terminal caps are optionally present at the 5' and/or 3' end of the sense strand and further optionally present at the 3'-end of the antisense strand. Generally, each strand can independently range from about 15 to about 30 nucleotides in length, but can vary depending on the presence of any overhanging nucleotides. In certain embodiments, X1 and X2 are independently integers from 0 to 4; X3 is an integer from 15 to 30; and X4 is an integer from 12 to 27. Various modifications are shown for the nucleotides of the sense and antisense strands of the siNA constructs. The [N3], [N2], and [N1] nucleotides are chemically modified with either 2'-deoxy, 2'-deoxy-2'-fluoro or 2'-methoxy modifications and can also include ribose nucleotides. The (N) overhang nucleotide positions can be chemically modified as described herein (e.g., 2'-O-methyl, 2'-deoxy-2'-fluoro, 2'-deoxy, LNA, universal bases, etc.) and can be either derived from a corresponding target nucleic acid sequence or not. The constructs shown in the figure can also comprise phosphorothioate linkages as described herein. For example, phosphorothioate linkages can exist between any N and/or (N) positions. Such phosphorothioate incorporation can be utilized between purine "R" and pyrimidine "Y" positions or for stabilization of pyrimidine linkages in general. Furthermore, although not depicted on the figure, the constructs shown in the figure can optionally include a ribonucleotide at the $9^{th}$ position from the 5'-end of the sense strand or the $11^{th}$ position based on the 5'-end of the guide strand by counting 11 nucleotide positions in from the 5'-terminus of the guide strand. Similarly, the antisense strand can include a ribonucleotide or a 2'-deoxy-2'-fluoro nucleotide at the $14^{th}$ position from the 5' end, or alternately can be selected or designed so that a 2'-O-alkyl nucleotide (e.g., a 2'-O-methyl purine) is not present at this position. Furthermore, although not shown in the figure, the 5'-terminal position of the antisense strand can comprise a terminal phosphate group as described herein.

FIG. 3 shows non-limiting examples of certain combinations of modifications applied to the representative siNA duplex described in FIG. 2. The table shown below the representative structure provides specific combinations of $(N)_{X1}$, $(N)_{X2}$, $N_{X3}$, $N_{X4}$, and [N3]-[N2]-[N1] nucleotide (and optional non-nucleotide) positions. For example, combinations of 5 or more (e.g., 5, 6, 7, 8, 9, or 10 or more) $N_{X3}$ and 5 or more (e.g., 5, 6, 7, 8, 9, or 10 or more) $N_{X4}$ pyrimidine "Y" and purine "R" nucleotides are specified, each of which can independently have specific $(N)_{X1}$ and/or $(N)_{X2}$, substitutions as shown in the figure, in addition to optional phosphorothioate substitutions. The 5'-terminal antisense strand [N3]-[N2]-[N1] nucleotides are modified with either 2'-deoxy, 2'-deoxy-2'-fluoro or 2'-methoxy modifications, or are ribonucleotides, as depicted.

FIGS. 4A-C show non-limiting examples of different siNA constructs of the invention. The criteria of the representative structures shown in FIGS. 2 and 3 can be applied to any of the structures shown in FIG. 4A-C.

Figure 1:
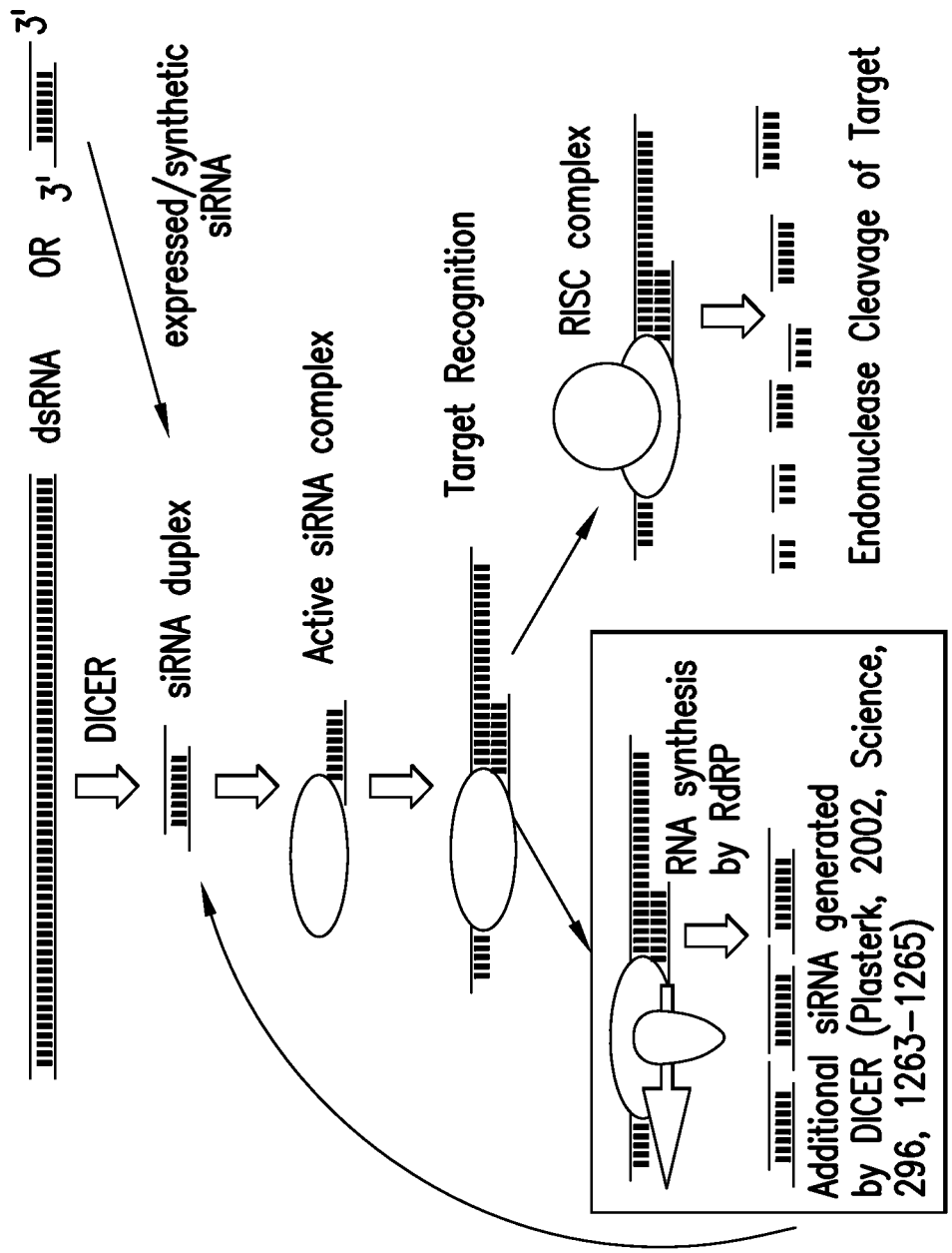
FIG. 1 shows a non-limiting proposed mechanistic representation of target RNA degradation involved in RNAi. Double-stranded RNA (dsRNA), which is generated by RNA-dependent RNA polymerase (RdRP) from foreign single-stranded RNA, for example viral, transposon, or other exogenous RNA, activates the DICER enzyme that in turn generates siNA duplexes. Alternately, synthetic or expressed siNA can be introduced directly into a cell by appropriate means. An active siNA complex recognizes a target RNA, resulting in degradation of the target RNA by the RISC endonuclease complex or in the synthesis of additional RNA by RNA-dependent RNA polymerase (RdRP), which can activate DICER and result in additional siNA molecules, thereby amplifying the RNAi response.
Figure 4A:
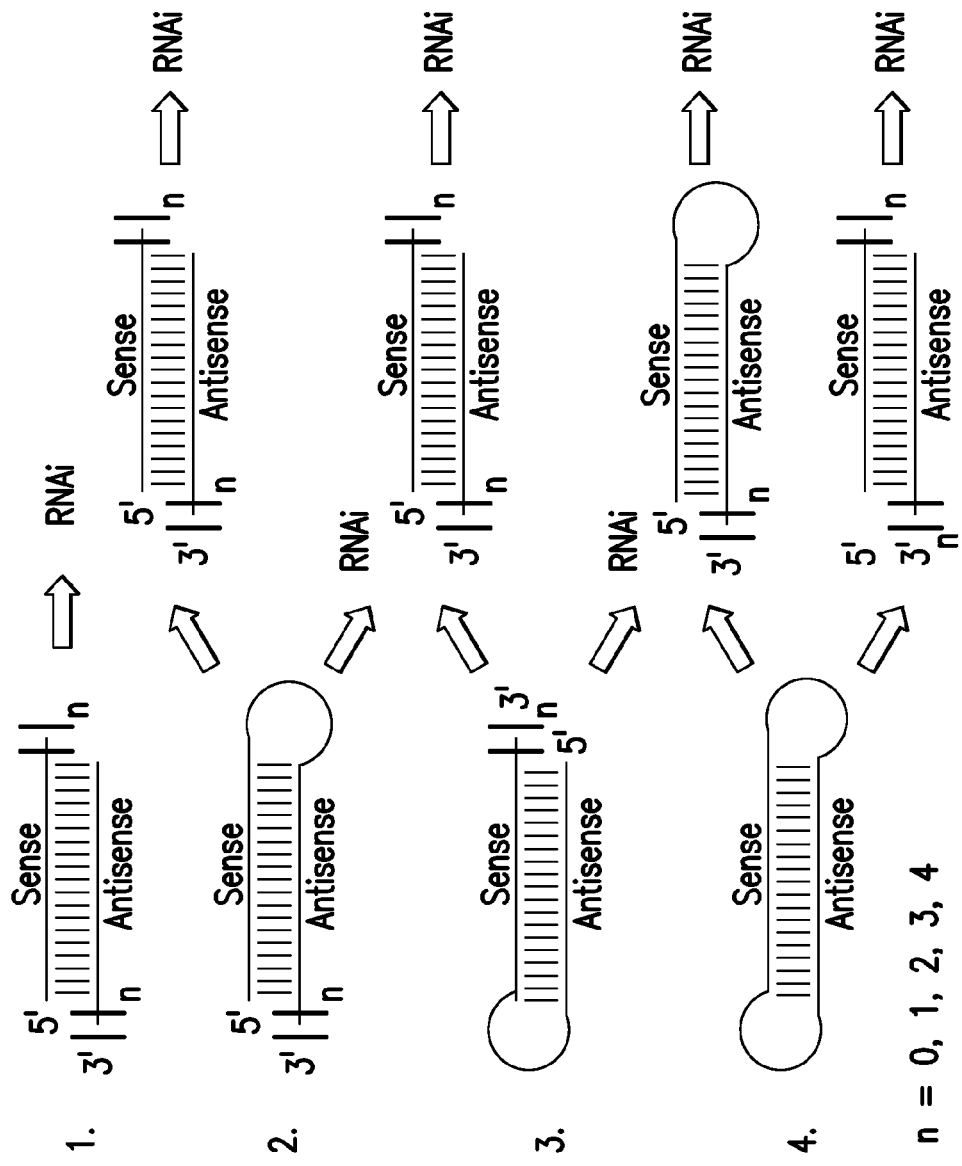

The examples shown in FIG. 4A (constructs 1, 2, and 3) have 19 representative base pairs; however, different embodiments of the invention include any number of base pairs described herein. Bracketed regions represent nucleotide overhangs, for example, comprising about 1, 2, 3, or 4 nucleotides in length, preferably about 2 nucleotides. Constructs 1 and 2 can be used independently for RNAi activity. Construct 2 can comprise a polynucleotide or non-nucleotide linker, which can optionally be designed as a biodegradable linker. In one embodiment, the loop structure shown in construct 2 can comprise a biodegradable linker that results in the formation of construct 1 in vivo and/or in vitro. In another example, construct 3 can be used to generate construct 2 under the same principle wherein a linker is used to generate the active siNA construct 2 in vivo and/or in vitro, which can optionally utilize another biodegradable linker to generate the active siNA construct 1 in vivo and/or in vitro. As such, the stability and/or activity of the siNA constructs can be modulated based on the design of the siNA construct for use in vivo or in vitro and/or in vitro.

Figure 4B:
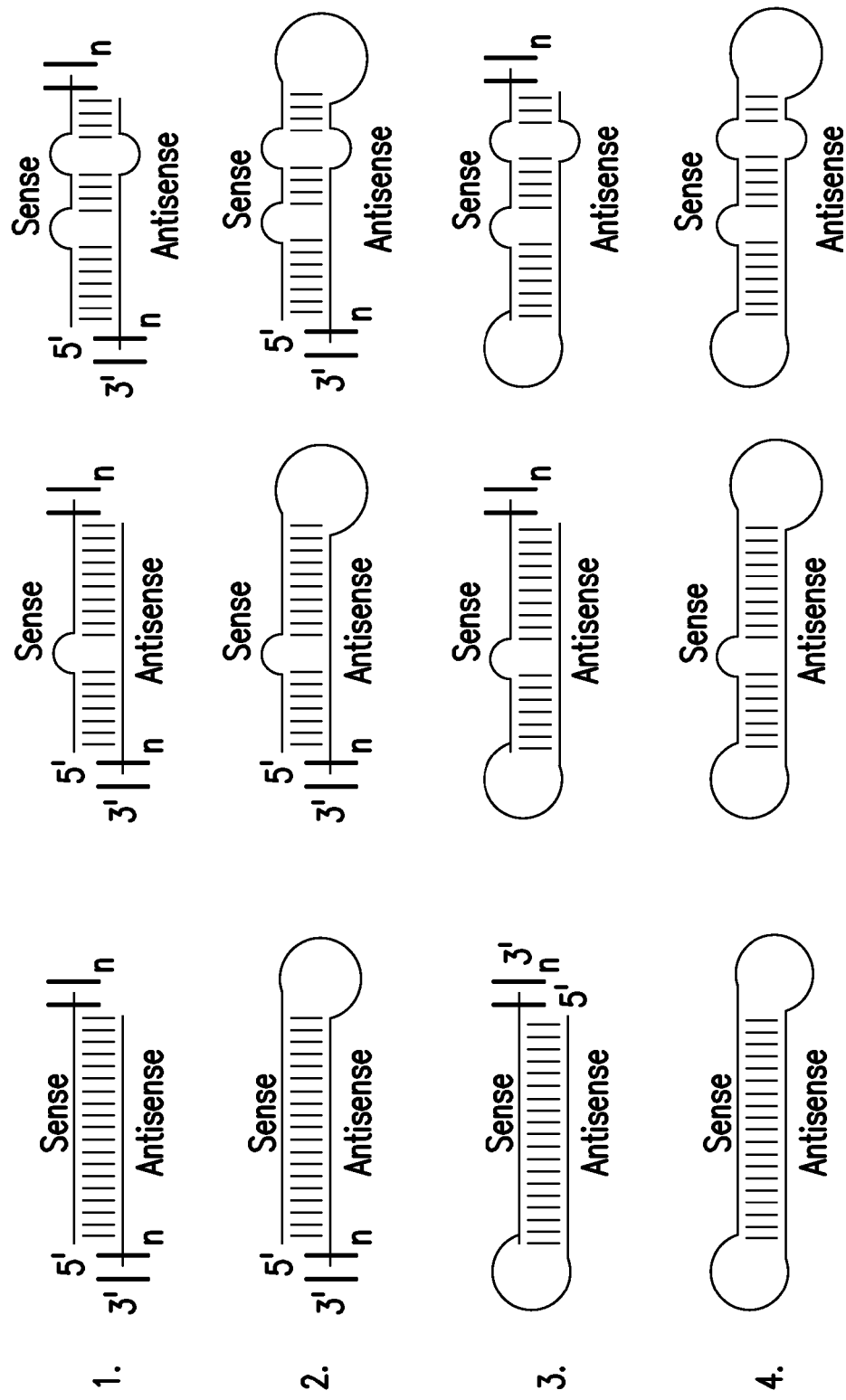

The examples shown in FIG. 4B represent different variations of double-stranded nucleic acid molecules of the invention, such as microRNA or siRNA, that can include overhangs, bulges, loops, and stem-loops resulting from partial complementarity. The bulges, loops, and stem-loops can result from any degree of partial complementarity, such as mismatches or bulges of about 1, 2, 3, 4, 5, 6, 7, 8, 9, 10 or more nucleotides in one or both strands of the double-stranded nucleic acid molecule of the invention.

The example in FIG. 4C represents a model double-stranded nucleic acid molecule of the invention comprising a 19 base pair duplex of two 21 nucleotide sequences having dinucleotide 3'-overhangs. The top strand (1) represents the sense strand (passenger strand), the middle strand (2) represents the antisense (guide strand), and the lower strand (3) represents a target polynucleotide sequence. The dinucleotide overhangs (NN) can comprise a sequence derived from the target polynucleotide. For example, the 3'-(NN) sequence in the guide strand can be complementary to the 5'-[NN] sequence of the target polynucleotide. In addition, the 5'-(NN) sequence of the passenger strand can comprise the same sequence as the 5'-[NN] sequence of the target polynucleotide sequence. In other embodiments, the overhangs (NN) are not derived from the target polynucleotide sequence, for example where the 3'-(NN) sequence in the guide strand are not complementary to the 5'-[NN] sequence of the target polynucleotide and the 5'-(NN) sequence of the passenger strand can comprise different sequence from the 5'-[NN] sequence of the target polynucleotide sequence. In additional embodiments, any (NN) nucleotides are chemically modified, e.g., as 2'-O-methyl, 2'-deoxy-2'-fluoro, and/or other modifications herein. Furthermore, the passenger strand can comprise a ribonucleotide position N of the passenger strand. For the representative 19 base pair 21 mer duplex shown, position N can be 9 nucleotides in from the 5' end of the passenger strand. However, in duplexes of differing length, the position N is determined based on the 5'-end of the guide strand by counting 11 nucleotide positions in from the 5'-terminus of the guide strand and picking the corresponding base paired nucleotide in the passenger strand. Cleavage by Ago2 takes place between positions 10 and 11 as indicated by the arrow. In additional embodiments, there are two ribonucleotides, at positions 10 and 11 based on the 5'-end of the guide strand by counting 10 and 11 nucleotide positions in from the 5'-terminus of the guide strand and picking the corresponding base paired nucleotides in the passenger strand. The antisense strand nucleotide N can also be a ribonucleotide or modified nucleotide and is located at position 14 from the 5'-end terminus of the guide strand. The modification can be, for example, a 2'-deoxy-2'-fluoro modification, but is preferably not a 2'-O-alkyl modification. Position N3, N2, and N1 of the antisense strand comprise modified nucleotides.

Figure 5:
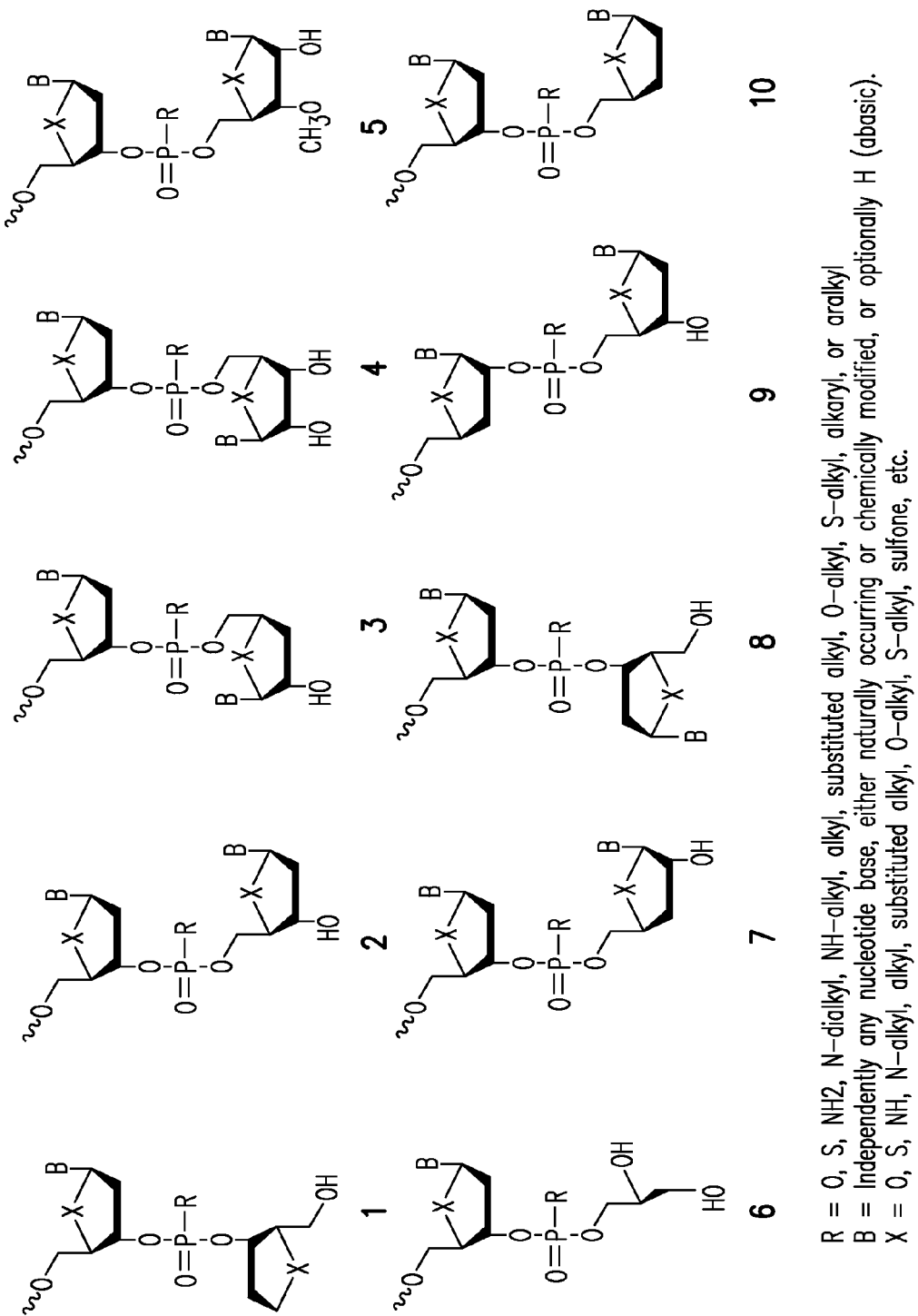

FIG. 5 shows non-limiting examples of different stabilization chemistries (1-10) that can be used, for example, to stabilize the 5' and/or 3'-ends of siNA sequences of the invention, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide (when X=O). In addition to modified and unmodified backbone chemistries indicated in the figure, these chemistries can be combined with different sugar and base nucleotide modifications as described herein.

Figure 6:
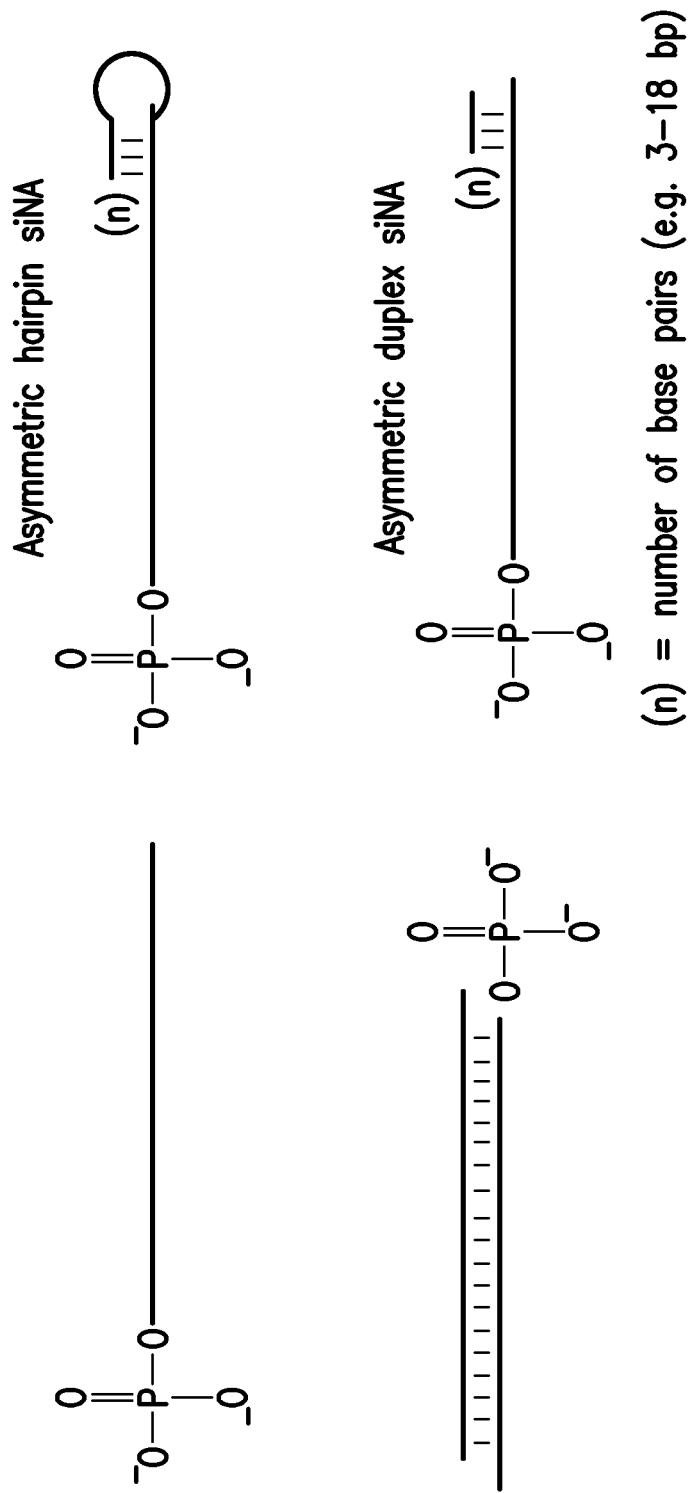

FIG. 6 shows non-limiting examples of phosphorylated siNA molecules of the invention, including linear and duplex constructs and asymmetric derivatives thereof.

Figure 7:
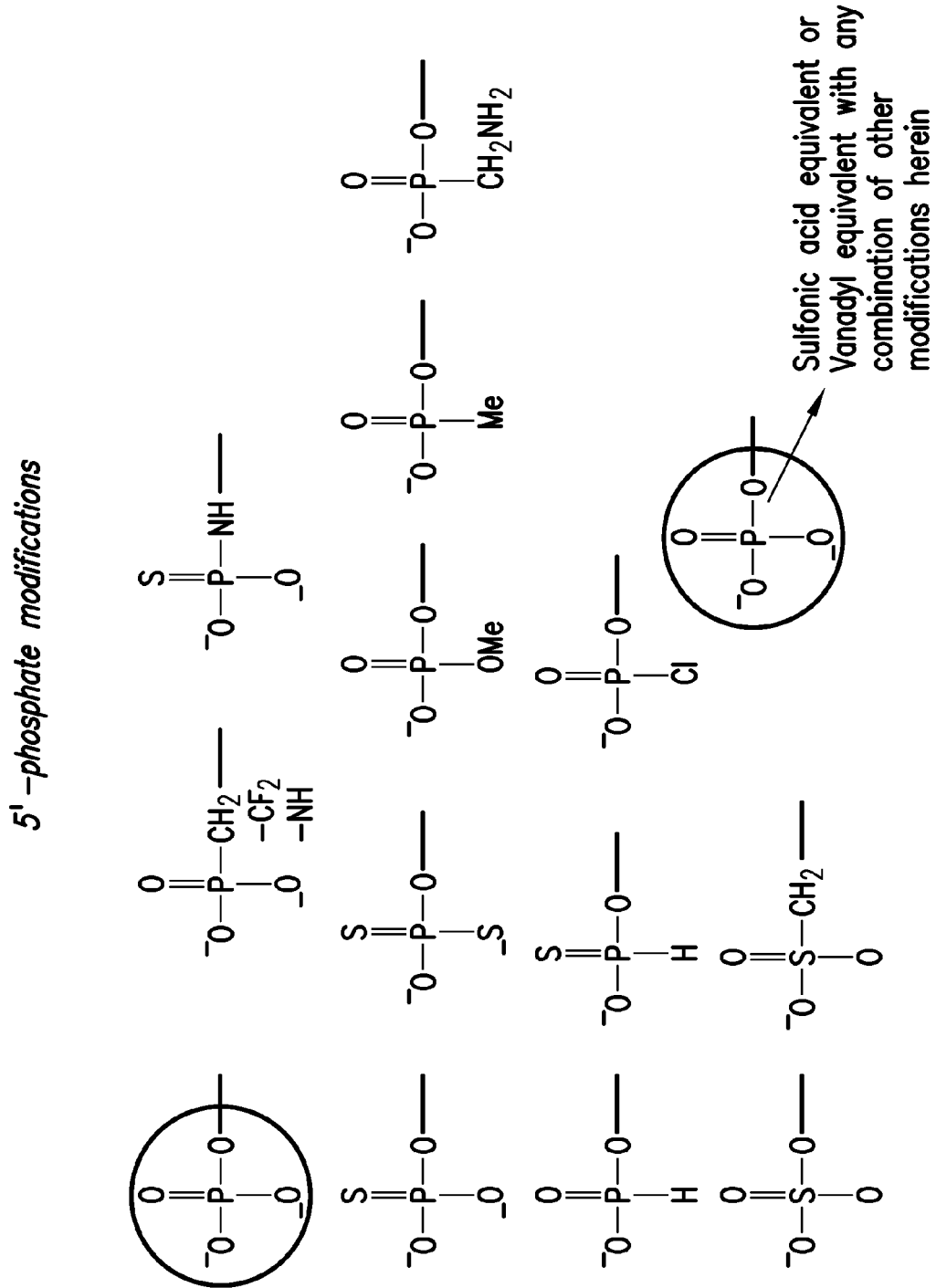

FIG. 7 shows non-limiting examples of chemically modified terminal phosphate groups of the invention.

Figure 8:
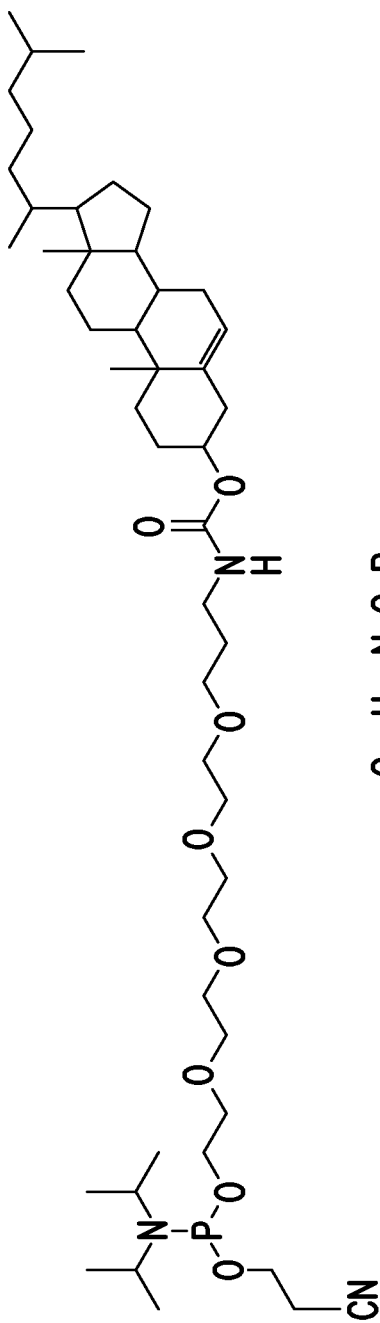

FIG. 8 shows a non-limiting example of a cholesterol linked phosphoramidite that can be used to synthesize cholesterol conjugated siNA molecules of the invention. An example is shown with the cholesterol moiety linked to the 5'-end of the sense strand of an siNA molecule.

Figure 9:
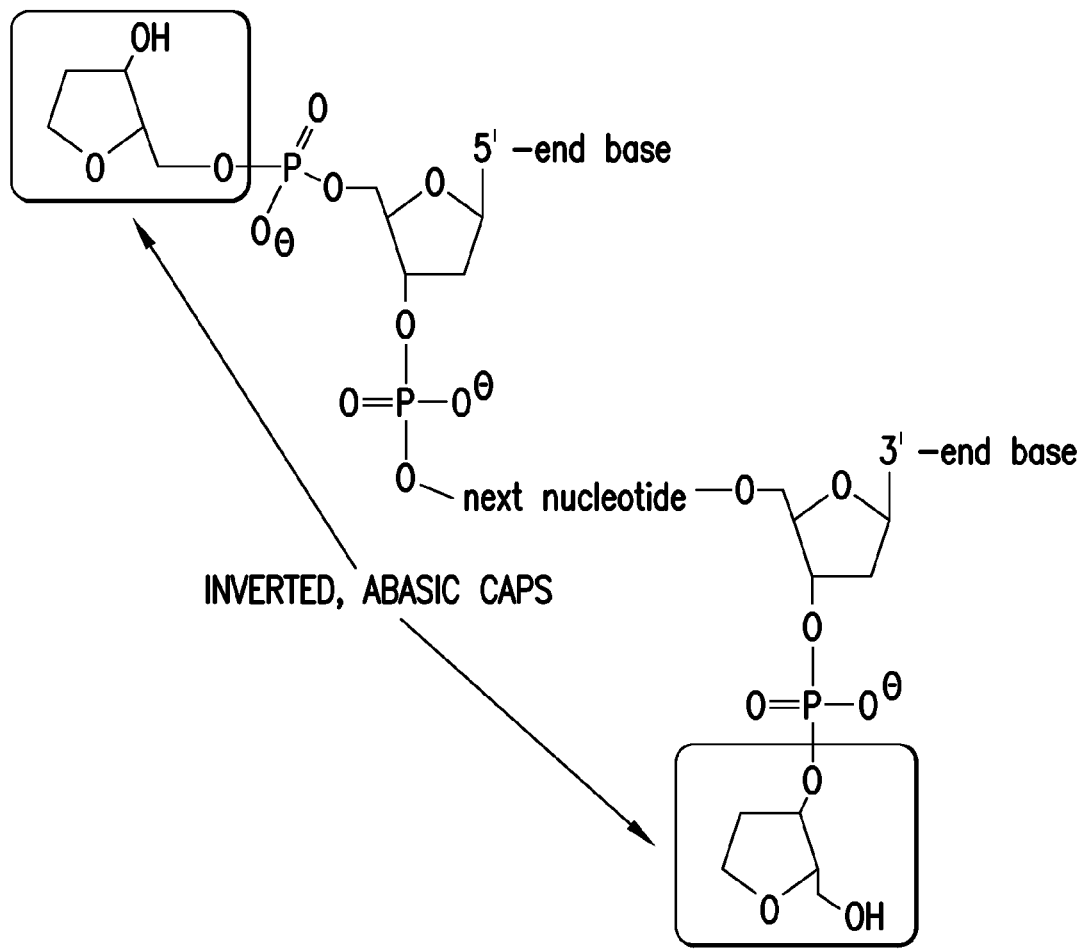

FIG. 9 depicts an embodiment of 5' and 3' inverted abasic cap linked to a nucleic acid strand.

Figure 10:
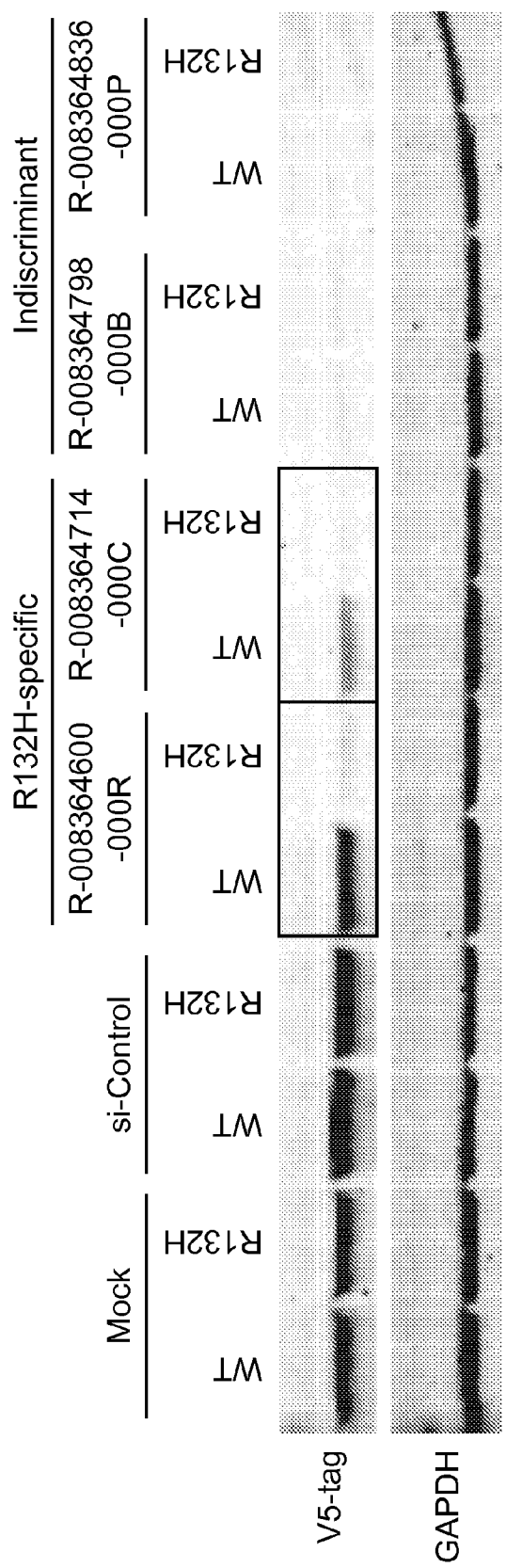

FIG. 10 shows preferential IDH1 R132H-specific RNAi knockdown in MOG-G-UVM human glioma cells. Samples were prepared 72 hours post-transfection with 20 nM siNA. The particular siNA transfected is identified by the siNA duplex ID number (e.g., R-008364600-000R; see Table 1c).

Figure 11A:
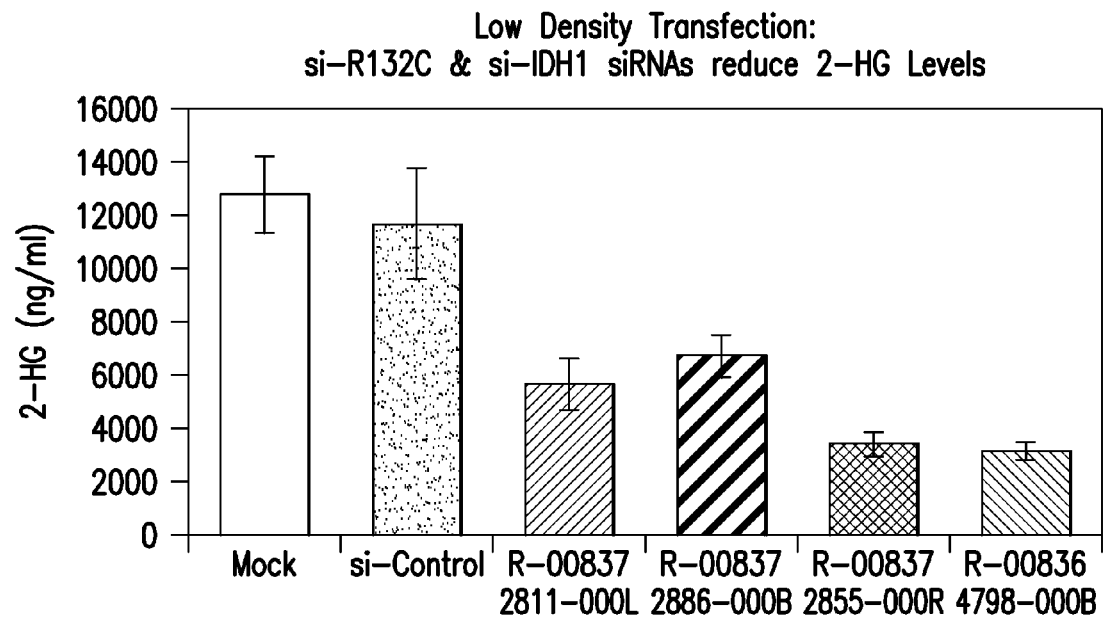
Figure 11B:
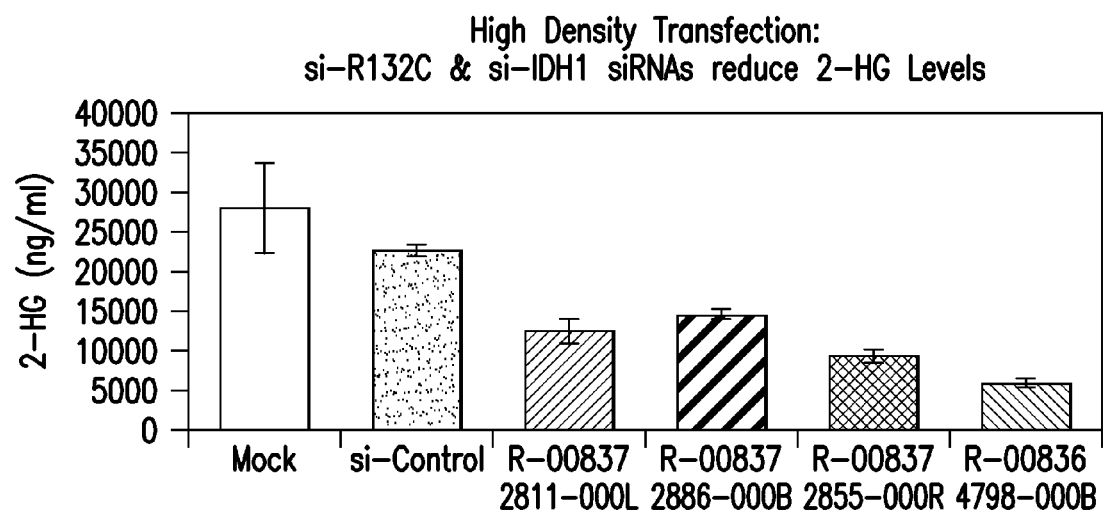

FIGS. 11A and 11B show a decrease in 2-hydroxyglutarate (2-HG) production and secretion into cell culture media with RNAi knockdown of IDH1 R132C (n=4 for each column). Figures A and B differ only by cell plating density at the beginning of each experiment. Samples were prepared 96 hours post-transfection with siNA. The particular siNA transfected is identified by the siNA duplex ID number (e.g., R-008364600-000R; see Table 1c).

Figure 12:
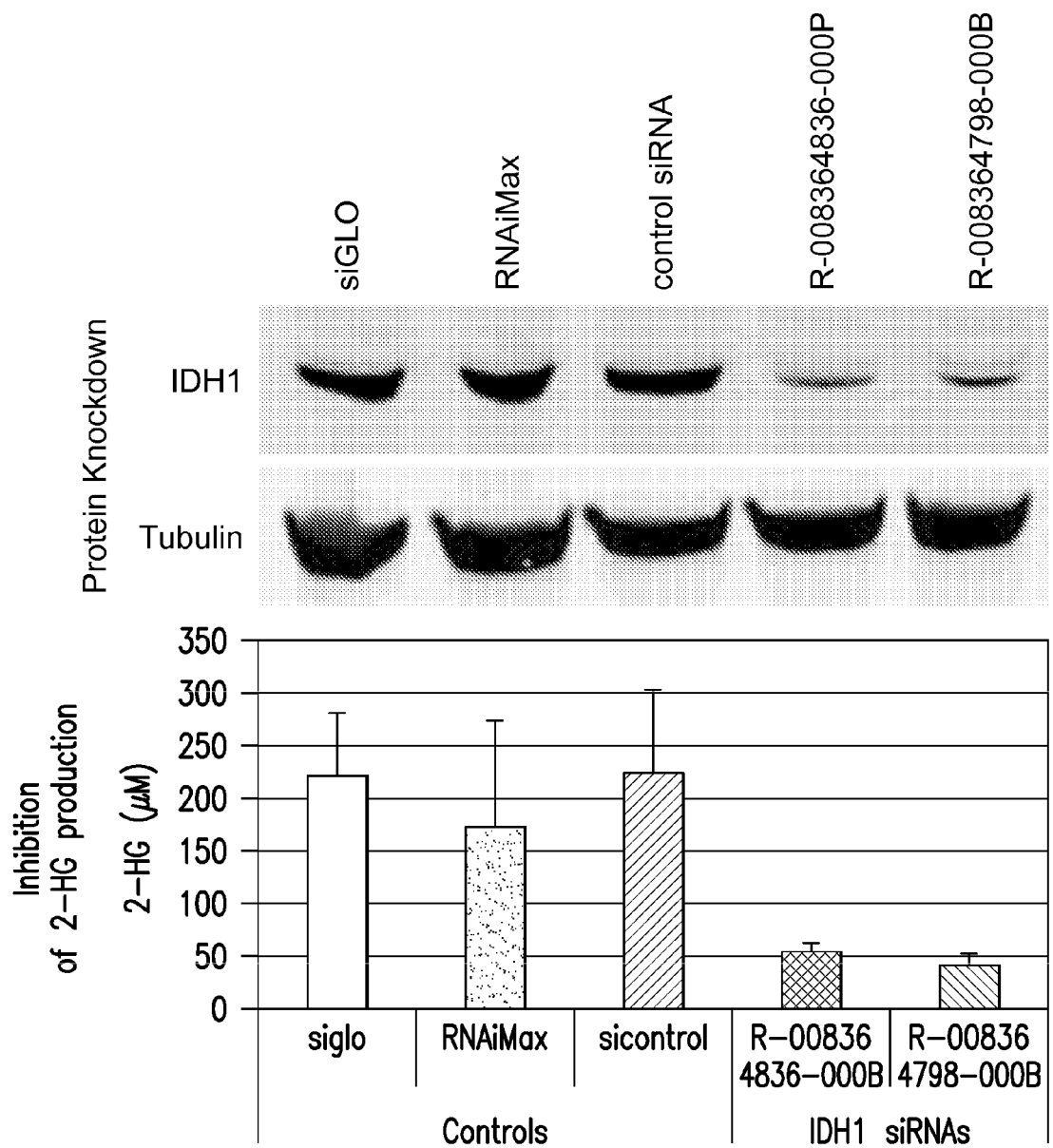

FIG. 12 shows the correlation between IDH1 siNA knockdown and a decrease in hydroxyglutarate (2-HG) secretion.

DETAILED DESCRIPTION OF THE INVENTION

A. Terms and Definitions

The following terminology and definitions apply as used in the present application.

As used in this specification and the appended claims, the singular forms "a," "an," and "the" include plural referents unless the content clearly dictates otherwise. Thus, for example, reference to "a cell" includes a combination of two or more cells, and the like.

Any concentration range, percentage range, ratio range or integer range is to be understood to include the value of any integer within the recited range, and when appropriate, fractions thereof (such as one tenth and one hundredth of an integer), unless otherwise indicated.

About" or "approximately," as used herein, in reference to a number are generally taken to include numbers that fall within a range of 5% in either direction (greater than or less than) of the number unless otherwise stated or otherwise evident from the context (except where such number would exceed 100% of a possible value). Where ranges are stated, the endpoints are included within the range unless otherwise stated or otherwise evident from the context.

The term "abasic" as used herein refers to its meaning as is generally accepted in the art. The term generally refers to sugar moieties lacking a nucleobase or having a hydrogen atom (H) or other non-nucleobase chemical groups in place of a nucleobase at the 1' position of the sugar moiety, see for example Adamic et al., U.S. Pat. No. 5,998,203. In one embodiment, an abasic moiety of the invention is a ribose, deoxyribose, or dideoxyribose sugar.

The term "acyclic nucleotide" as used herein refers to its meaning as is generally accepted in the art. The term generally refers to any nucleotide having an acyclic ribose sugar, for example where any of the ribose carbon/carbon or carbon/oxygen bonds are independently or in combination absent from the nucleotide.

The term "alkyl" as used herein refers to its meaning as is generally accepted in the art. The term generally refers to saturated or unsaturated hydrocarbons, including straight-chain, branched-chain, alkenyl, alkynyl groups and cyclic groups, but excludes aromatic groups. Notwithstanding the foregoing, alkyl also refers to non-aromatic heterocyclic groups. Preferably, the alkyl group has 1 to 12 carbons. More preferably, it is a lower alkyl of from 1 to 7 carbons, more preferably 1 to 4 carbons. The alkyl group can be substituted or unsubstituted. When substituted, the substituted group(s) is preferably, hydroxyl, halogen, cyano, C1-C4 alkoxy, =O, =S, $NO_2$, SH, $NH_2$, or $NR_1R_2$, where $R_1$ and $R_2$ independently are H or C1-C4 alkyl.

The phrase "antisense region" as used herein refers to its meaning as is generally accepted in the art. With reference to exemplary nucleic acid molecules of the invention, the term refers to a nucleotide sequence of an siNA molecule having complementarity to a target nucleic acid sequence. In addition, the antisense region of an siNA molecule can optionally comprise a nucleic acid sequence having complementarity to a sense region of the siNA molecule. In one embodiment, the antisense region of the siNA molecule is referred to as the antisense strand or guide strand.

The phrase "asymmetric hairpin" refers to a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

The term "biodegradable" as used herein refers to its meaning as is generally accepted in the art. The term generally refers to degradation in a biological system, for example, enzymatic degradation or chemical degradation.

The term "biodegradable linker" as used herein refers to its meaning as is generally accepted in the art. With reference to exemplary nucleic acid molecules of the invention, the term refers to a linker molecule that is designed to connect one molecule to another molecule, and which is susceptible to degradation in a biological system. The linker can be a nucleic acid or non-nucleic acid based linker. For example, a biodegradable linker can be used to attach a ligand or biologically active molecule to an siNA molecule of the invention. Alternately, a biodegradable linker can be used to connect the sense and antisense strands of an siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The phrase "biologically active molecule" as used herein refers to its meaning as is generally accepted in the art. With reference to exemplary nucleic acid molecules of the invention, the term refers to compounds or molecules that are capable of eliciting or modifying a biological response in a system and/or are capable of modulating the pharmacokinetics and/or pharmacodynamics of other biologically active molecules. Examples of biologically active molecules, include siNA molecules alone or in combination with other molecules including, but not limited to therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, polyamines, polyamides, polyethylene glycol, other polyethers, 2-5A chimeras, siNA, dsRNA, allozymes, aptamers, decoys and analogs thereof.

The phrase "biological system" as used herein refers to its meaning as is generally accepted in the art. The term generally refers to material, in a purified or unpurified form, from biological sources including, but not limited to, human or animal, wherein the system comprises the components required for RNAi activity. Thus, the phrase includes, for example, a cell, tissue, subject, or organism, or extract thereof. The term also includes reconstituted material from a biological source.

The phrase "blunt end" as used herein refers to its meaning as is generally accepted in the art. With reference to exemplary nucleic acid molecules of the invention, the term refers to termini of a double-stranded siNA molecule having no overhanging nucleotides. For example, the two strands of a double-stranded siNA molecule having blunt ends align with each other with matched base-pairs without overhanging nucleotides at the termini. A siNA duplex molecule of the invention can comprise blunt ends at one or both termini of the duplex, such as termini located at the 5'-end of the antisense strand, the 5'-end of the sense strand, or both termini of the duplex.

The term "cap" (also referred to herein as "terminal cap") as used herein refers to its meaning as is generally accepted in the art. With reference to exemplary nucleic acid molecules of the invention, the term refers to a moiety, which can be a chemically modified nucleotide or non-nucleotide that can be incorporated at one or more termini of one or more nucleic acid molecules of the invention. These terminal modifications protect the nucleic acid molecule from exonuclease degradation, and can help in delivery and/or localization within a cell. The cap can be present at the 5'-terminus (5'-cap) or at the 3'-terminal (3'-cap) or can be present on both termini of any nucleic acid molecule of the invention. A cap can be present at the 5'-end, 3-end and/or 5' and 3'-ends of the sense strand of a nucleic acid molecule of the invention. Additionally, a cap can optionally be present at the 3'-end of the antisense strand of a nucleic acid molecule of the invention. In non-limiting examples, the 5'-cap includes, but is not limited to, LNA; glyceryl; inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide; 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety. Non-limiting examples of the 3'-cap include, but are not limited to, LNA; glyceryl; inverted deoxy abasic residue (moiety); 4',5'-methylene nucleotide; 1-(beta-D-erythrofuranosyl) nucleotide; 4'-thio nucleotide; carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate; phosphorothioate and/or phosphorodithioate; bridging or non bridging methylphosphonate; and 5'-mercapto moieties (for more details see Beaucage and Iyer, 1993, *Tetrahedron* 49, 1925; incorporated by reference herein). FIG. 5 shows some non-limiting examples of various caps.

The term "cell" as used herein refers to its meaning as is generally accepted in the art. With reference to exemplary nucleic acid molecules of the invention, the term is used in its usual biological sense, and does not refer to an entire multi-cellular organism, e.g., specifically does not refer to a human being. The cell can be present in an organism, e.g., birds, plants and mammals, such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

The phrase "chemical modification" as used herein refers to its meaning as is generally accepted in the art. With reference to exemplary nucleic acid molecules of the invention, the term refers to any modification of the chemical structure of the nucleotides that differs from nucleotides of native siRNA or RNA in general. The term "chemical modification" encompasses the addition, substitution, or modification of native siRNA or RNA at the sugar, base, or internucleotide linkage, as described herein or as is otherwise known in the art. In certain embodiments, the term "chemical modification" can refer to certain forms of RNA that are naturally occurring in certain biological systems, for example to 2'-O-methyl modifications or inosine modifications.

The term "complementarity" or "complementary" as used herein refers to its meaning as is generally accepted in the art. With reference to exemplary nucleic acid molecules of the invention, the terms generally refer to the formation or existence of hydrogen bond(s) between one nucleic acid sequence and another nucleic acid sequence by either traditional Watson-Crick or other non-traditional types of bonding as described herein. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, *CSH Symp. Quant. Biol. LII* pp. 123-133; Frier et al., 1986, *Proc. Nat. Acad. Sci. USA* 83:9373-9377; Turner et al., 1987, *J. Am. Chem. Soc.* 109:3783-3785). Perfect complementary means that all the contiguous residues of a nucleic acid sequence will hydrogen bond with the same number of contiguous residues in a second nucleic acid sequence. Partial complementarity can include various mismatches or non-based paired nucleotides (e.g., 1, 2, 3, 4, 5, 6, 7, 8, 9, 10 or more mismatches, non-nucleotide linkers, or non-based paired nucleotides) within the nucleic acid molecule, which can result in bulges, loops, or overhangs that result between the sense strand or sense region and the antisense strand or antisense region of the nucleic acid molecule or between the antisense strand or antisense region of the nucleic acid molecule and a corresponding target nucleic acid molecule. Such partial complementarity can be represented by a % complementarity that is determined by the number of non-base paired nucleotides, i.e., about 50%, 60%, 70%, 80%, 90% etc. depending on the total number of nucleotides involved. Such partial complementarity is permitted to the extent that the nucleic acid molecule (e.g., siNA) maintains its function, for example the ability to mediate sequence specific RNAi.

The terms "composition" or "formulation" as used herein refer to their generally accepted meaning in the art. These terms generally refer to a composition or formulation, such as in a pharmaceutically acceptable carrier or diluent, in a form suitable for administration, e.g., systemic or local administration, into a cell or subject, including, for example, a human. Suitable forms, in part, depend upon the use or the route of entry, for example oral, transdermal, inhalation, or by injection. Such forms should not prevent the composition or formulation from reaching a target cell (i.e., a cell to which the negatively charged nucleic acid is desirable for delivery). For example, compositions injected into the blood stream should be soluble. Other factors are known in the art, and include considerations such as toxicity and forms that prevent the composition or formulation from exerting its effect. As used herein, pharmaceutical formulations include formulations for human and veterinary use. Non-limiting examples of agents suitable for formulation with the nucleic acid molecules of the instant invention include: Lipid Nanoparticles (see for example Semple et al., 2010, *Nat Biotechnol.*, February; 28(2):172-6.); P-glycoprotein inhibitors (such as Pluronic P85); biodegradable polymers, such as poly(DL-lactide-coglycolide) microspheres for sustained release delivery (Emerich, D F et al., 1999, *Cell Transplant*, 8, 47-58); and loaded nanoparticles, such as those made of polybutylcyanoacrylate. Other non-limiting examples of delivery strategies for the nucleic acid molecules of the instant invention include material described in Boado et al., 1998, *J. Pharm. Sci.*, 87, 1308-1315; Tyler et al., 1999, *FEBS Lett.*, 421, 280-284; Pardridge et al., 1995, *PNAS USA.*, 92, 5592-5596; Boado, 1995, *Adv. Drug Delivery Rev.*, 15, 73-107; Aldrian-Herrada et al., 1998, *Nucleic Acids Res.*, 26, 4910-4916; and Tyler et al., 1999, *PNAS USA.*, 96, 7053-7058. A "pharmaceutically acceptable composition" or "pharmaceutically acceptable formulation" can refer to a composition or formulation that allows for the effective distribution of the nucleic acid molecules of the instant invention to the physical location most suitable for their desired activity.

The phrase "cytotoxic/cytostatic agents" refer to compounds that cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, hematopoietic growth factors, monoclonal antibody targeted therapeutic agents, topoisomerase inhibitors, proteasome inhibitors and ubiquitin ligase inhibitors.

The term "gene" or "target gene" as used herein refers to their meaning as is generally accepted in the art. The terms generally refer a nucleic acid (e.g., DNA or RNA) sequence that comprises partial length or entire length coding sequences necessary for the production of a polypeptide. The target gene can also include the UTR or non-coding region of the nucleic acid sequence. A gene or target gene can also encode a functional RNA (fRNA) or non-coding RNA (ncRNA), such as small temporal RNA (stRNA), micro RNA (miRNA), small nuclear RNA (snRNA), short interfering RNA (siRNA), small nucleolar RNA (snRNA), ribosomal RNA (rRNA), transfer RNA (tRNA) and precursor RNAs thereof. Such non-coding RNAs can serve as target nucleic acid molecules for siNA mediated RNA interference in modulating the activity of fRNA or ncRNA involved in functional or regulatory cellular processes. Aberrant fRNA or ncRNA activity leading to disease can therefore be modulated by siNA molecules of the invention. siNA molecules targeting fRNA and ncRNA can also be used to manipulate or alter the genotype or phenotype of a subject, organism or cell, by intervening in cellular processes such as genetic imprinting, transcription, translation, or nucleic acid processing (e.g., transamination, methylation etc.). The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus. Non-limiting examples of plants include monocots, dicots, or gymnosperms. Non-limiting examples of animals include vertebrates or invertebrates. Non-limiting examples of fungi include molds or yeasts. For a review, see for example Snyder and Gerstein, 2003, Science, 300, 258-260.

The phrase "homologous sequence" as used herein refers to its meaning as is generally accepted in the art. The term generally refers a nucleotide sequence that is shared by one or more polynucleotide sequences, such as genes, gene transcripts and/or non-coding polynucleotides. For example, a homologous sequence can be a nucleotide sequence that is shared by two or more genes encoding related but different proteins, such as different members of a gene family, different protein epitopes, different protein isoforms or completely divergent genes. A homologous sequence can be a nucleotide sequence that is shared by two or more non-coding polynucleotides, such as noncoding DNA or RNA, regulatory sequences, introns, and sites of transcriptional control or regulation. Homologous sequences can also include sequence regions shared by more than one polynucleotide sequence. Homology does not need to be perfect identity (100%), as partially homologous sequences are also contemplated by and within the scope of the instant invention (e.g., at least 95%, 94%, 93%, 92%, 91%, 90%, 89%, 88%, 87%, 86%, 85%, 84%, 83%, 82%, 81%, 80% etc.). Percent homology is the number of matching nucleotides between two sequences divided by the total length being compared, multiplied by 100.

The term "IDH1" refers to isocitrate dehydrogenase 1 (also known as cytosolic isocitrate dehydrogenase). Table 5 lists the NCBI Genbank Accession number disclosing the nucleotide sequence encoding the wild-type human IDH1 protein. The term "IDH1-related" encompasses IDH1 genes or proteins, including both wild-type IDH1 genes and encoded proteins, and derivatives thereof, including mutant forms and/or splice variants of wild-type IDH1 genes and encoded proteins and/or peptides. For example, various mutant forms of human IDH1 have been identified wherein the arginine at position 132 is mutated to histidine (IDH1-R132H), cysteine (IDH1-R132C), glycine (IDH1-R132G), serine (IDH1-R132S), leucine (IDH1-R132L) and valine (IDH1-R132V). These mutant forms, and polynucleotides encoding them, are each encompassed by the term "IDH1-related."

The phrase "improved RNAi activity" refers to an increase in RNAi activity measured in vitro and/or in vivo, where the RNAi activity is a reflection of both the ability of the siNA to mediate RNAi and the stability of the siNAs of the invention. In this invention, the product of these activities can be increased in vitro and/or in vivo compared to an all RNA siNA or an siNA containing a plurality of ribonucleotides. In some cases, the activity or stability of the siNA molecule can be decreased (i.e., less than ten-fold), but the overall activity of the siNA molecule is enhanced in vitro and/or in vivo.

The term "including" (and any form thereof, such as "includes" and "include"), "comprising" (and any form thereof, such as "has" or "have") or "containing" (and any form thereof ("contains" or "contain") are inclusive and open-ended and do not exclude additional, unrecited elements or method steps.

The terms "inhibit," "down-regulate," or "reduce" as used herein refers to their meanings as generally accepted in the art. With reference to exemplary nucleic acid molecules of the invention, the term generally refers to the reduction in the expression of a gene, or in the level of RNA molecules or equivalent RNA molecules encoding one or more proteins or protein subunits, or in the activity of one or more proteins or protein subunits, below that observed in the absence of the nucleic acid molecules (e.g., siNA) of the invention. Down-regulation can also be associated with post-transcriptional silencing, such as RNAi mediated cleavage or by alteration in DNA methylation patterns or DNA chromatin structure.

The terms "intermittent" or "intermittently" as used herein refers to their meaning as generally accepted in the art. The terms generally refer to periodic stopping and starting at either regular or irregular intervals.

The terms "internucleoside linkage" or "internucleoside linker" or "internucleotide linkage" or "internucleotide linker" are used herein interchangeably and refer to any linker or linkage between two nucleoside units, as is known in the art, including, for example, but not as limitation, phosphate, analogs of phosphate, phosphonate, guanidium, hydroxylamine, hydroxylhydrazinyl, amide, carbamate, alkyl, and substituted alkyl linkages. Internucleoside linkages constitute the backbone of a nucleic acid molecule.

The terms "mammalian" or "mammal" as used herein refers to their meanings as generally accepted in the art. The terms generally refer to any warm blooded vertebrate species, such as a human, mouse, rat, dog, cat, hamster, guinea pig, rabbit, livestock, and the like.

The phrase "metered dose inhaler" or "MDI" refers to a unit comprising a can, a secured cap covering the can and a formulation metering valve situated in the cap. MDI systems includes a suitable channeling device. Suitable channeling devices comprise for example, a valve actuator and a cylindrical or cone-like passage through which medicament can be delivered from the filled canister via the metering valve to the nose or mouth of a patient such as a mouthpiece actuator.

The term "microRNA" or "miRNA" as used herein refers to its meaning as is generally accepted in the art. The term generally refers a small double-stranded RNA that regulates the expression of target messenger RNAs either by mRNA cleavage, translational repression/inhibition or heterochromatic silencing (see for example Ambros, 2004, Nature, 431, 350-355; Bartel, 2004, Cell, 116, 281-297; Cullen, 2004, Virus Research., 102, 3-9; He et al., 2004, Nat. Rev. Genet., 5, 522-531; Ying et al., 2004, Gene, 342, 25-28; and Sethupathy et al., 2006, RNA, 12:192-197).

The term "modulate" as used herein refers to its meaning as is generally accepted in the art. With reference to exemplary nucleic acid molecules of the invention, the term refers to when the expression of a gene, or the level of one or more RNA molecules (coding or non-coding), or activity the of one or more RNA molecules or proteins or protein subunits, is up-regulated or down-regulated, such that expression, level, or activity is greater than or less than that observed in the absence of the molecule that effects modulation. For example, the term "modulate" in some embodiments can refer to inhibition and, in other embodiments, can refer to potentiation or up-regulation, e.g., of gene expression.

The phrase "modified nucleotide" as used herein refers to its meaning as is generally accepted in the art. The term generally refers a nucleotide, which contains a modification in the chemical structure of the base, sugar and/or phosphate of the unmodified (or natural) nucleotide as is generally known in the art. Non-limiting examples of modified nucleotides are described herein and in U.S. application Ser. No. 12/064,014 (published as US 20090176725).

The phrase "non-base paired" refers to nucleotides that are not base paired between the sense strand or sense region and the antisense strand or antisense region of a double-stranded siNA molecule. Non-base paired nucleotides can include, for example, but not as limitation, mismatches, overhangs, and single stranded loops.

The term "non-nucleotide" refers to any group or compound which can be incorporated into a polynucleotide chain in the place of one or more nucleotide units, such as for example but not limitation, abasic moieties or alkyl chains. The group or compound is "abasic" in that it does not contain a commonly recognized nucleotide base, such as adenosine, guanine, cytosine, uracil or thymine and, therefore, lacks a nucleobase at the 1'-position.

The term "nucleotide" is used as is generally recognized in the art. Nucleotides generally comprise a nucleobase, a sugar, and an internucleoside linkage, e.g., a phosphate. The base can be a natural base (standard), a modified base, or a base analog, as are well known in the art. Such bases are generally located at the 1' position of a nucleotide sugar moiety. Additionally, the nucleotides can be unmodified or modified at the sugar, internucleoside linkage, and/or base moiety, (also referred to interchangeably as nucleotide analogs, modified nucleotides, non-natural nucleotides, non-standard nucleotides and others; see, for example, U.S. application Ser. No. 12/064,014 (published as US 20090176725)).

The term "overhang" as used herein refers to its meaning as is generally accepted in the art. With reference to exemplary double stranded nucleic acid molecules, the term generally refers to the terminal portion of a nucleotide sequence that is not base paired between the two strands of a double-stranded nucleic acid molecule (see, for example, FIG. 4). Overhangs, when present, are typically at the 3'-end of one or both strands in a siNA duplex.

The term "parenteral" as used herein refers to its meaning as is generally accepted in the art. The term generally refers methods or techniques of administering a molecule, drug, agent, or compound in a manner other than through the digestive tract and includes epicutaneous, subcutaneous, intravascular (e.g., intravenous), intramuscular, or intrathecal injection or infusion techniques and the like.

The phrase "pathway target" refers to any target involved in pathways of gene expression or activity. For example, any given target can have related pathway targets that can include upstream, downstream, or modifier genes in a biologic pathway. These pathway target genes can provide additive or synergistic effects in the treatment of diseases, conditions, and traits herein.

The term "phosphorothioate" refers to an internucleotide phosphate linkage comprising one or more sulfur atoms in place of an oxygen atom. Hence, the term phosphorothioate refers to both phosphorothioate and phosphorodithioate internucleotide linkages.

The term "position 1" refers to the position of the first nucleotide at the end of a strand, e.g., antisense strand. All positions referred to herein are the positions of a nucleotide counting from the end of a strand, for example, positions 1-3 from the 5' end of the antisense strand refer to the three nucleotides at positions 1, 2, and 3 counting from the 5' end of the antisense strand.

The term "ribonucleotide" as used herein refers to its meaning as is generally accepted in the art. The term generally refers to a nucleotide with a hydroxyl group at the 2' position of a β-D-ribofuranose moiety.

The term "RNA" as used herein refers to its generally accepted meaning in the art. Generally, the term RNA refers to a molecule comprising at least one ribofuranoside moiety. The term can include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

The phrase "RNA interference" or term "RNAi" refer to the biological process of inhibiting or down regulating gene expression in a cell, as is generally known in the art, and which is mediated by short interfering nucleic acid molecules, see for example Zamore and Haley, 2005, *Science*, 309, 1519-1524; Vaughn and Martienssen, 2005, *Science*, 309, 1525-1526; Zamore et al., 2000, *Cell*, 101, 25-33; Bass, 2001, *Nature*, 411, 428-429; Elbashir et al., 2001, *Nature*, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science*, 297, 1818-1819; Volpe et al., 2002, *Science*, 297, 1833-1837; Jenuwein, 2002, *Science*, 297, 2215-2218; and Hall et al., 2002, *Science*, 297, 2232-2237; Hutvagner and Zamore, 2002, *Science*, 297, 2056-60; McManus et al., 2002, *RNA*, 8, 842-850; Reinhart et al., 2002, *Gene & Dev.*, 16, 1616-1626; and Reinhart & Bartel, 2002, *Science*, 297, 1831). Additionally, the term RNAi is meant to be equivalent to other terms used to describe sequence specific RNA interference, such as post transcriptional gene silencing, translational inhibition, transcriptional inhibition, or epigenetics. For example, siNA molecules of the invention can be used to epigenetically silence genes at either the post-transcriptional level or the pre-transcriptional level. In a non-limiting example, epigenetic modulation of gene expression by siNA molecules of the invention can result from siNA mediated modification of chromatin structure or methylation patterns to alter gene expression (see, for example, Verdel et al., 2004, *Science,* 303, 672-676; Pal-Bhadra et al., 2004, *Science,* 303, 669-672; Allshire, 2002, *Science,* 297, 1818-1819; Volpe et al., 2002, *Science,* 297, 1833-1837; Jenuwein, 2002, *Science,* 297, 2215-2218; and Hall et al., 2002, *Science,* 297, 2232-2237). In another non-limiting example, modulation of gene expression by siNA molecules of the invention can result from siNA mediated cleavage of RNA (either coding or non-coding RNA) via RISC, or via translational inhibition, as is known in the art, or modulation can result from transcriptional inhibition (see for example Janowski et al., 2005, *Nature Chemical Biology,* 1, 216-222).

The phrase "RNAi inhibitor" refers to any molecule that can down regulate, reduce or inhibit RNA interference function or activity in a cell or organism. An RNAi inhibitor can down regulate, reduce or inhibit RNAi (e.g., RNAi mediated cleavage of a target polynucleotide, translational inhibition, or transcriptional silencing) by interacting or interfering with the function of any component of the RNAi pathway, including protein components such as RISC, or nucleic acid components such as miRNAs or siRNAs. A RNAi inhibitor can be an siNA molecule, an antisense molecule, an aptamer, or a small molecule that interacts with or interferes with the function of RISC, a miRNA, an siRNA, or any other component of the RNAi pathway in a cell or organism. By inhibiting RNAi (e.g., RNAi mediated cleavage of a target polynucleotide, translational inhibition, or transcriptional silencing), a RNAi inhibitor of the invention can be used to modulate (e.g., up-regulate or down regulate) the expression of a target gene.

The phrase "sense region" as used herein refers to its meaning as is generally accepted in the art. With reference to exemplary nucleic acid molecules of the invention, the term refers to a nucleotide sequence of an siNA molecule having complementarity to an antisense region of the siNA molecule. In addition, the sense region of an siNA molecule can comprise a nucleic acid sequence having homology or sequence identity with a target nucleic acid sequence. In one embodiment, the sense region of the siNA molecule is also referred to as the sense strand or passenger strand.

The phrases "short interfering nucleic acid," "siNA," "short interfering RNA," "siRNA," "short interfering nucleic acid molecule," "short interfering oligonucleotide molecule," or "chemically modified short interfering nucleic acid molecule" refer to any nucleic acid molecule capable of inhibiting or down regulating gene expression or viral replication by mediating RNA interference ("RNAi") or gene silencing in a sequence-specific manner. These terms can refer to both individual nucleic acid molecules, a plurality of such nucleic acid molecules, or pools of such nucleic acid molecules. The siNA can be a double-stranded nucleic acid molecule comprising self-complementary sense and antisense strands, wherein the antisense strand comprises a nucleotide sequence that is complementary to a nucleotide sequence in a target nucleic acid molecule or a portion thereof and the sense strand comprises a nucleotide sequence corresponding to the target nucleic acid sequence or a portion thereof. The siNA can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof and the sense region comprises a nucleotide sequence corresponding to the target nucleic acid sequence or a portion thereof. The siNA can be a circular single-stranded polynucleotide having two or more loop structures and a stem comprising self-complementary sense and antisense regions, wherein the antisense region comprises nucleotide sequence that is complementary to a nucleotide sequence in a target nucleic acid molecule or a portion thereof and the sense region comprises a nucleotide sequence corresponding to the target nucleic acid sequence or a portion thereof, and wherein the circular polynucleotide can be processed either in vivo or in vitro to generate an active siNA molecule capable of mediating RNAi. The siNA can also comprise a single-stranded polynucleotide having a nucleotide sequence complementary to nucleotide sequence in a target nucleic acid molecule or a portion thereof (for example, where such siNA molecule does not require the presence within the siNA molecule of a nucleotide sequence corresponding to the target nucleic acid sequence or a portion thereof), wherein the single-stranded polynucleotide can further comprise a terminal phosphate group, such as a 5'-phosphate (see for example, Martinez et al., 2002, *Cell,* 110, 563-574 and Schwarz et al., 2002, *Molecular Cell,* 10, 537-568), or 5',3'-diphosphate.

The term "subject" as used herein refers to its meaning as is generally accepted in the art. The term generally refers an organism to which the nucleic acid molecules of the invention can be administered. A subject can be a mammal or mammalian cells, including a human or human cells. The term also refers to an organism which is a donor or recipient of explanted cells or the cells themselves.

The phrase "systemic administration" as used herein refers to its meaning as is generally accepted in the art. The term generally refers in vivo systemic absorption or accumulation of drugs in the blood stream followed by distribution throughout the entire body.

The term "target" as used with the term "IDH1" or "IDH1-related" refers to any IDH1-related target protein, peptide, or polypeptide, or encoding polynucleotide/nucleic acid sequence (such as target DNA or target RNA), including but not limited to those listed in Table 2 and Table 5. Thus, IDH1-related targets both wild-type IDH1 protein and its encoding gene, as well as derivatives thereof, including mutant forms and/or splice variants of wild-type IDH1 genes and encoded proteins and/or peptides. For example, various mutant forms of human IDH1 have been identified wherein the arginine at position 132 is mutated to histidine (IDH1-R132H), cysteine (IDH1-R132C), glycine (IDH1-R132G), serine (IDH1-R132S), leucine (IDH1-R132L) and valine (IDH1-R132V).

The phrase "target site" as used herein refers to its meaning as is generally accepted in the art. The term generally refers to a sequence within a target nucleic acid molecule (e.g., RNA) that is "targeted," e.g., for cleavage mediated by an siNA construct which contains sequences within its antisense region that are complementary to the target sequence.

The phrase "therapeutically effective amount" as used herein refers to its meaning as is generally accepted in the art. The term generally refers to the amount of the compound or composition that will elicit the biological or medical response of a cell, tissue, system, animal or human that is be sought by the researcher, veterinarian, medical doctor or other clinician. For example, if a given clinical treatment is considered effective when there is at least a 25% reduction in a measurable parameter associated with a disease or disorder, a therapeutically effective amount of a drug for the treatment of that disease or disorder is that amount necessary to effect at least a 25% reduction in that parameter.

The phrase "universal base" as used herein refers to its meaning as is generally accepted in the art. The term universal base generally refers to nucleotide base analogs that form base pairs with each of the natural DNA/RNA bases with little or no discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, for example, Loakes, 2001, *Nucleic Acids Research*, 29, 2437-2447).

The term "up-regulate" as used herein refers to its meaning as is generally accepted in the art. With reference to exemplary nucleic acid molecules of the invention, the term refers to an increase in either the expression of a gene, or the level of RNA molecules or equivalent RNA molecules encoding one or more proteins or protein subunits, or the activity of one or more RNAs, proteins or protein subunits, above that observed in the absence of the nucleic acid molecules (e.g., siNA) of the invention. In certain instances, up-regulation or promotion of gene expression with an siNA molecule is above that level observed in the presence of an inactive or attenuated molecule. In other instances, up-regulation or promotion of gene expression with siNA molecules is above that level observed in the presence of, for example, an siNA molecule with scrambled sequence or with mismatches. In still other instances, up-regulation or promotion of gene expression with a nucleic acid molecule of the instant invention is greater in the presence of the nucleic acid molecule than in its absence. In some instances, up-regulation or promotion of gene expression is associated with inhibition of RNA mediated gene silencing, such as RNAi mediated cleavage or silencing of a coding or non-coding RNA target that down-regulates, inhibits, or silences the expression of the gene of interest to be up-regulated. The down-regulation of gene expression can, for example, be induced by a coding RNA or its encoded protein, such as through negative feedback or antagonistic effects. The down-regulation of gene expression can, for example, be induced by a non-coding RNA having regulatory control over a gene of interest, for example by silencing expression of the gene via translational inhibition, chromatin structure, methylation, RISC mediated RNA cleavage, or translational inhibition. As such, inhibition or down-regulation of targets that down-regulate, suppress, or silence a gene of interest can be used to up-regulate expression of the gene of interest toward therapeutic use.

The term "vector" as used herein refers to its meaning as is generally accepted in the art. The term vector generally refers to any nucleic acid- and/or viral-based expression system or technique used to deliver one or more nucleic acid molecules.

B. siNA Molecules of the Invention

The present invention provides compositions and methods comprising siNAs targeted to IDH1-related polynucleotide sequences that can be used to treat diseases and/or physiological conditions, e.g., cell-proliferation-related disorders associated with expression of an IDH1-related gene or protein, including but not limited to cancers of the central nervous system (e.g., gliomas) and AML. In particular aspects and embodiments of the invention, the nucleic acid molecules of the invention comprise at least a 15 nucleotide sequence of the sequences shown in Table 1a and Table 1b. The siNAs can be provided in several forms. For example, an siNA of the invention can be isolated as one or more siNA compounds, or it may take the form of a transcriptional cassette in a nucleic acid plasmid. The siNA may also be chemically synthesized.

The siNA may also include modifications and/or modification patterns, such as those shown in, for example, Table 1c and Table 6. Thus, in various embodiments, at least one strand or region of the nucleic acids of the invention comprises at least a 15 nucleotide sequence selected from the group of sequences consisting of SEQ ID NOs: 1-506. The siNAs can be administered alone or co-administered with other siNA molecules or with conventional agents that treat an IDH1-related disease or condition.

The siNA molecules of the invention can be used to mediate gene silencing, specifically of an IDH1-related gene, via interaction with RNA transcripts or alternately by interaction with particular gene sequences. Such interaction results in modulation of gene silencing either at the transcriptional level or post-transcriptional level such as, for example, but not limited to, RNAi or through cellular processes that modulate the chromatin structure or methylation patterns of the target and prevent transcription of the target gene, with the nucleotide sequence of the target thereby mediating silencing. More specifically, the target is any of IDH1-related RNA, DNA, or mRNA.

In one aspect, the invention provides short interfering nucleic acid (siNA) molecules for inhibiting the expression of an IDH1-related gene in a cell or mammal. The siNA can be single-stranded or double-stranded. When double-stranded, the siNA comprises a sense and an antisense strand. The antisense strand is complementary to at least a part of an mRNA formed in the expression of an IDH1-related gene. The sense strand comprises a region that is complementary to the antisense strand. In specific embodiments, the antisense strand comprises at least 15 nucleotides of an antisense sequence selected from Table 1b (SEQ ID NOs: 440-506). Generally, the double-stranded siNA comprises at least 15 nucleotides of a sense strand selected from Table 1b (SEQ ID NOs: 1-67) and at least 15 nucleotides of an antisense strand selected from Table 1b (SEQ ID NOs: 440-506). In another embodiment, the "at least 15 nucleotides" is 15 contiguous nucleotides.

One or more of the nucleotides of the siNAs of the invention are optionally modified. In further embodiments of chemically modified siNA, some siNAs of the invention comprise at least one nucleotide sequence selected from SEQ ID NOs: 68-439, provided in Table 1c. In other embodiments, the siNA comprises at least two sequences selected from SEQ ID NOs: 68-439, provided in Table 1c, wherein one of the at least two sequences is complementary to another of the at least two sequences and one of the at least two sequences is complementary to a sequence of a mRNA generated in the expression of an IDH1-related gene. Examples of certain modified siNAs of the invention are in Table 1c.

The double stranded RNA molecules of the invention can comprise two distinct and separate strands that can be symmetric or asymmetric and are complementary, i.e., two single-stranded RNA molecules, or can comprise one single-stranded molecule in which two complementary portions, e.g., a sense region and an antisense region, are base-paired, and are covalently linked by one or more single-stranded "hairpin" areas (i.e. loops) resulting in, for example, a single-stranded short-hairpin polynucleotide or a circular single-stranded polynucleotide.

The linker can be polynucleotide linker or a non-nucleotide linker. In some embodiments, the linker is a non-nucleotide linker. In some embodiments, a hairpin or circular siNA molecule of the invention contains one or more loop motifs, wherein at least one of the loop portions of the siNA molecule is biodegradable. For example, a single-stranded hairpin siNA molecule of the invention is designed such that degradation of the loop portion of the siNA molecule in vivo can generate a double-stranded siNA molecule with 3'-terminal overhangs, such as 3'-terminal nucleotide overhangs comprising 1, 2, 3 or 4 nucleotides. Or alternatively, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

In symmetric siNA molecules of the invention, each strand, the sense (passenger) strand and antisense (guide) strand, are independently about 15 to about 30 (e.g., about 15, 16, 17, 18, 19, 20, 21, 22, 23, 24, 25, 26, 27, 28, 29, or 30) nucleotides in length. Generally, each strand of the symmetric siNA molecules of the invention are about 19-24 (e.g., about 19, 20, 21, 22, 23 or 24) nucleotides in length.

In asymmetric siNA molecules, the antisense region or strand of the molecule is about 15 to about 30 (e.g., about 15, 16, 17, 18, 19, 20, 21, 22, 23, 24, 25, 26, 27, 28, 29, or 30) nucleotides in length, wherein the sense region is about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides in length. Generally, each strand of the asymmetric siNA molecules of the invention is about 19-24 (e.g., about 19, 20, 21, 22, 23 or 24) nucleotides in length.

In yet other embodiments, siNA molecules of the invention comprise single stranded hairpin siNA molecules, wherein the siNA molecules are about 25 to about 70 (e.g., about 25, 26, 27, 28, 29, 30, 31, 32, 33, 34, 35, 36, 40, 45, 50, 55, 60, 65, or 70) nucleotides in length.

In still other embodiments, siNA molecules of the invention comprise single-stranded circular siNA molecules, wherein the siNA molecules are about 38 to about 70 (e.g., about 38, 40, 45, 50, 55, 60, 65, or 70) nucleotides in length.

In still other embodiments, siNA molecules of the invention comprise single-stranded non-circular siNA molecules, wherein the siNA molecules are independently about 15 to about 30 (e.g., about 15, 16, 17, 18, 19, 20, 21, 22, 23, 24, 25, 26, 27, 28, 29, or 30) nucleotides in length.

In various symmetric embodiments, the siNA duplexes of the invention independently comprise about 15 to about 30 (e.g., about 15, 16, 17, 18, 19, 20, 21, 22, 23, 24, 25, 26, 27, 28, 29, or 30) base pairs. Generally, the duplex structure of the siNAs contains between 15 and 30, more generally between 18 and 25, yet more generally between 19 and 24, and most generally between 19 and 21 base pairs.

In yet other embodiments, where the duplex siNA molecules of the invention are asymmetric, the siNA molecules comprise about 3 to 25 (e.g., about 3, 4, 5, 6, 7, 8, 9, 10, 11, 12, 13, 14, 15, 16, 17, 18, 19, 20, 21, 22, 23, 24, or 25) base pairs. Generally, the duplex structure of the siNA contains between 15 and 25, more generally between 18 and 25, yet more generally between 19 and 24, and most generally between 19 and 21 base pairs.

In still other embodiments, where the siNA molecules of the invention are hairpin or circular structures, the siNA molecules comprise about 15 to about 30 (e.g., about 15, 16, 17, 18, 19, 20, 21, 22, 23, 24, 25, 26, 27, 28, 29, or 30) base pairs.

The sense strand and antisense strand, or the sense region and antisense region, of the siNA molecules of the invention can be complementary. Also, the antisense strand or antisense region can be complementary to a nucleotide sequence or a portion thereof of an IDH1-related target RNA, such as for example, but not limited to, those sequences represented by the NCBI Genbank Accession No. shown in Table 5 or those disclosed in Table 2. The sense strand or sense region of the siNA can comprise a nucleotide sequence of an IDH1-related gene or a portion thereof. In certain embodiments, the sense region or sense strand of an siNA molecule of the invention is complementary to that portion of the antisense region or antisense strand of the siNA molecule that is complementary to an IDH1-related target polynucleotide sequence, such as for example, but not limited to, those sequences represented by the NCBI Genbank Accession No. shown in Table 5 or those disclosed in Table 2.

In some embodiments, siNA molecules of the invention have perfect complementarity between the sense strand or sense region and the antisense strand or antisense region of the siNA molecule. In other or the same embodiments, the antisense strand of the siNA molecules of the invention is perfectly complementary to a corresponding IDH1-related target nucleic acid molecule.

In yet other embodiments, siNA molecules of the invention have partial complementarity (i.e., less than 100% complementarity) between the sense strand or sense region and the antisense strand or antisense region of the siNA molecule or between the antisense strand or antisense region of the siNA molecule and a corresponding IDH1-related target nucleic acid molecule. Thus, in some embodiments, the double-stranded nucleic acid molecules of the invention, have between about 15 to about 30 (e.g., about 15, 16, 17, 18, 19, 20, 21, 22, 23, 24, 25, 26, 27, 28, 29, or 30) nucleotides in one strand that are complementary to the nucleotides of the other strand. In other embodiments, the molecules have between about 15 to about 30 (e.g., about 15, 16, 17, 18, 19, 20, 21, 22, 23, 24, 25, 26, 27, 28, 29, or 30) nucleotides in the sense region that are complementary to the nucleotides of the antisense region of the double-stranded nucleic acid molecule. In certain embodiments, the double-stranded nucleic acid molecules of the invention have between about 15 to about 30 (e.g., about 15, 16, 17, 18, 19, 20, 21, 22, 23, 24, 25, 26, 27, 28, 29, or 30) nucleotides in the antisense strand that are complementary to a nucleotide sequence of a corresponding IDH1-related target nucleic acid molecule.

In other embodiments, the siNA molecule can contain one or more nucleotide deletions, substitutions, mismatches and/or additions; provided, however, that the siNA molecule maintains its activity, for example, to mediate RNAi. In a non-limiting example, the deletion, substitution, mismatch and/or addition can result in a loop or bulge, or alternately a wobble or other alternative (non Watson-Crick) base pair. Thus, in some embodiments, for example, the double-stranded nucleic acid molecules of the invention, have 1 or more (e.g., 1, 2, 3, 4, 5, or 6) nucleotides, in one strand or region that are mismatches or non-base-paired with the other strand or region. In other embodiments, the double-stranded nucleic acid molecules of the invention, have 1 or more (e.g., 1, 2, 3, 4, 5, or 6) nucleotides in each strand or region that are mismatches or non-base-paired with the other strand or region. In a preferred embodiment, the siNA of the invention contains no more than 3 mismatches. If the antisense strand of the siNA contains mismatches to a target sequence, it is preferable that the area of mismatch not be located in the center of the region of complementarity.

In other embodiments, the siNA molecule can contain at least one sequence selected from SEQ ID NOs: 1-67 and SEQ ID NOs: 440-506 (shown in Table 1b) having one or more nucleotide deletions, substitutions, mismatches and/or additions to said sequence(s) provided, however, that the siNA molecule maintains its activity, for example, to mediate RNAi. In a non-limiting example, the deletion, substitution, mismatch and/or addition can result in a loop or bulge, or alternately a wobble or other alternative (non Watson-Crick) base pair.

The invention also comprises double-stranded nucleic acid (siNA) molecules as otherwise described hereinabove in which the first strand and second strand are complementary to each other and wherein at least one strand is hybridisable to a polynucleotide sequence selected from SEQ ID NOs: 1-67 and SEQ ID NOs: 440-506 (shown in Table 1b) under conditions of high stringency, and wherein any of the nucleotides is unmodified or chemically modified. Hybridization techniques are well known to the skilled artisan (see for instance, Sambrook et al., Molecular Cloning: A Laboratory Manual, 2nd Ed., Cold Spring Harbor Laboratory Press, Cold Spring Harbor, N.Y. (1989)). Preferred stringent hybridization conditions include overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA; followed by washing the filters in 0.1×SSC at about 65° C. In one specific embodiment, the first strand has about 15, 16, 17, 18, 19, 20 or 21 nucleotides that are complementary to the nucleotides of the other strand and at least one strand is hybridisable to a polynucleotide sequence selected from SEQ ID NOs: 1-67 and SEQ ID NOs: 440-506 (shown in Table 1b). In a more preferred embodiment, the first strand has about 15, 16, 17, 18, 19, 20 or 21 nucleotides that are complementary to the nucleotides of the other strand and at least one strand is hybridisable to SEQ ID NO: 7, SEQ ID NO: 446, SEQ ID NO: 11, SEQ ID NO: 450, SEQ ID NO: 12, SEQ ID NO: 451, SEQ ID NO: 13, SEQ ID NO: 452; SEQ ID NO: 38, SEQ ID NO: 477, SEQ ID NO: 39, SEQ ID NO: 478, SEQ ID NO: 40, SEQ ID NO: 479, SEQ ID NO: 41, SEQ ID NO: 480, SEQ ID NO: 59, SEQ ID NO: 498, SEQ ID NO: 63 or SEQ ID NO: 502; under conditions of high stringency, and wherein any of the nucleotides is unmodified or chemically modified.

In certain embodiments, the siNA molecules of the invention comprise overhangs of about 1 to about 4 (e.g., about 1, 2, 3 or 4) nucleotides. The nucleotides in the overhangs can be the same or different nucleotides. In some embodiments, the overhangs occur at the 3'-end at one or both strands of the double-stranded nucleic acid molecule. For example, a double-stranded nucleic acid molecule of the invention can comprise a nucleotide or non-nucleotide overhang at the 3'-end of the antisense strand/region, the 3'-end of the sense strand/region, or both the antisense strand/region and the sense strand/region of the double-stranded nucleic acid molecule.

In some embodiments, the nucleotides comprising the overhanging portion of an siNA molecule of the invention comprise sequences based on an IDH1-related target polynucleotide sequence in which the nucleotides comprising the overhanging portion of the antisense strand/region of an siNA molecule of the invention are complementary to nucleotides in the IDH1-related target polynucleotide sequence and/or the nucleotides comprising the overhanging portion of the sense strand/region of an siNA molecule of the invention can comprise nucleotides in the IDH1-related target polynucleotide sequence. Thus, in some embodiments, the overhang comprises a two nucleotide overhang that is complementary to a portion of the IDH1-related target polynucleotide sequence. In other embodiments, however, the overhang comprises a two nucleotide overhang that is not complementary to a portion of the IDH1-related target polynucleotide sequence. In certain embodiments, the overhang comprises a 3'-UU overhang that is not complementary to a portion of the IDH1-related target polynucleotide sequence. In other embodiments, the overhang comprises a UU overhang at the 3' end of the antisense strand and a TT overhang at the 3' end of the sense strand. In other embodiments, the overhang comprises nucleotides as described in the examples, Tables, and Figures herein.

In any of the embodiments of the siNA molecules described herein having 3'-terminal nucleotide overhangs, the overhangs are optionally chemically modified at one or more nucleic acid sugar, base, or backbone positions. Representative, but not limiting examples of modified nucleotides in the overhanging portion of a double-stranded nucleic acid (siNA) molecule of the invention include: 2'-O-alkyl (e.g., 2'-O-methyl), 2'-deoxy, 2'-deoxy-2'-fluoro, 2'-deoxy-2'-fluoroarabino (FANA), 4'-thio, 2'-O-trifluoromethyl, 2'-O-ethyl-trifluoromethoxy, 2'-O-difluoromethoxy-ethoxy, universal base, acyclic, or 5-C-methyl nucleotides. In more preferred embodiments, the overhang nucleotides are each independently, a 2'-O-alkyl nucleotide, a 2'-O-methyl nucleotide, a 2'-deoxy-2-fluoro nucleotide, or a 2'-deoxy ribonucleotide. In some instances the overhanging nucleotides are linked by one or more phosphorothioate linkages.

In yet other embodiments, siNA molecules of the invention comprise duplex nucleic acid molecules with blunt ends (i.e., without nucleotide overhangs), where both ends are blunt, or alternatively, where one of the ends is blunt. In some embodiments, the siNA molecules of the invention comprise one blunt end, for example wherein the 5'-end of the antisense strand and the 3'-end of the sense strand do not have any overhanging nucleotides, or wherein the 3'-end of the antisense strand and the 5'-end of the sense strand do not have any overhanging nucleotides. In other embodiments, siNA molecules of the invention comprise two blunt ends, for example wherein the 3'-end of the antisense strand and the 5'-end of the sense strand, as well as the 5'-end of the antisense strand and 3'-end of the sense strand, do not have any overhanging nucleotides.

In any of the embodiments or aspects of the siNA molecules of the invention, the sense strand and/or the antisense strand can further have a cap, such as described herein or as known in the art, at the 3'-end, the 5'-end, or both of the 3' and 5'-ends of the sense strand and/or antisense strand. In the case of a hairpin siNA molecule, the cap can be at either one or both of the terminal nucleotides of the polynucleotide. In some embodiments, the cap is at one or both ends of the sense strand of a double-stranded siNA molecule. In other embodiments, the cap is at the 3'-end of antisense (guide) strand. In preferred embodiments, a cap is at the 3'-end of the sense strand and at the 5'-end of the sense strand.

Representative but non-limiting examples of such terminal caps include an inverted abasic nucleotide, an inverted deoxy abasic nucleotide, an inverted nucleotide moiety, a group shown in FIG. 5, a glyceryl modification, an alkyl or cycloalkyl group, a heterocycle, or any other cap as is generally known in the art.

Any of the embodiments of the siNA molecules of the invention can have a 5' phosphate termini. In some embodiments, the siNA molecules lack terminal phosphates.

Any siNA molecule or construct of the invention can comprise one or more chemical modifications. Modifications can be used to improve in vitro or in vivo characteristics such as stability, activity, toxicity, immune response (e.g., prevent stimulation of an interferon response, an inflammatory or pro-inflammatory cytokine response, or a Toll-like Receptor response), and/or bioavailability.

Applicants describe herein chemically modified siNA molecules with improved RNAi activity and/or stability compared to corresponding unmodified siNA molecules. Various chemically modified siNA motifs disclosed herein provide the capacity to maintain RNAi activity that is substantially similar to unmodified or minimally modified active siRNA (see for example Elbashir et al., 2001, *EMBO* 1, 20:6877-6888) while at the same time providing nuclease resistance and pharmacokinetic properties suitable for use in therapeutic applications.

In various embodiments, the siNA molecules of the invention comprise modifications wherein any (e.g., one or more, or all) nucleotides present in the sense and/or antisense strand are modified nucleotides (e.g., wherein one nucleotide is modified, some nucleotides (i.e., a plurality or more than one) are modified, or all nucleotides are modified nucleotides). In some embodiments, the siNA molecules of the invention are partially modified (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, or 59 nucleotides are modified) with chemical modifications. In some embodiments, an siNA molecule of the invention comprises at least about 8, 10, 12, 14, 16, 18, 20, 22, 24, 26, 28, 30, 32, 34, 36, 38, 40, 42, 44, 46, 48, 50, 52, 54, 56, 58, or 60 nucleotides that are modified nucleotides. In other embodiments, the siNA molecules of the invention are completely modified (100% modified) with chemical modifications, i.e., the siNA molecule does not contain any ribonucleotides. In some of embodiments, one or more of the nucleotides in the sense strand of the siNA molecules of the invention are modified. In the same or other embodiments, one or more of the nucleotides in the antisense strand of the siNA molecules of the invention are modified.

The chemical modification within a single siNA molecule can be the same or different. In some embodiments, at least one strand has at least one chemical modification. In other embodiments, each strand has at least one chemical modification, which can be the same or different, such as sugar, base, or backbone (i.e., internucleotide linkage) modifications. In other embodiments, siNA molecules of the invention contain at least 2, 3, 4, 5, or more different chemical modifications.

Non-limiting examples of chemical modifications that are suitable for use in the present invention, are disclosed in U.S. patent application Ser. Nos. 10/444,853, 10/981,966, and 12/064,014 (published as US 20040192626, US 20050266422, and US 20090176725, respectively), and in references cited therein, and include sugar, base, and phosphate modifications, non-nucleotide modifications, and/or any combination thereof. These U.S. patent application Ser. Nos. 10/444,853, 10/981,966, 12/064,014 are incorporated hereby as references for the purpose of describing chemical modifications that are suitable for use with the siNAs of the invention.

In certain specific embodiments of the invention, at least one modified nucleotide is a 2'-deoxy-2-fluoro nucleotide, a 2'-deoxy nucleotide, a 2'-O-alkyl (e.g., 2'-O-methyl) nucleotide, or a locked nucleic acid (LNA) nucleotide, as is generally recognized in the art.

In yet other embodiment of the invention, at least one nucleotide has a ribo-like, Northern or A form helix configuration (see e.g., Saenger, Principles of Nucleic Acid Structure, Springer-Verlag ed., 1984). Non-limiting examples of nucleotides having a Northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl nucleotides; 2'-deoxy-2'-fluoro nucleotides; 2'-deoxy-2'-chloro nucleotides; 2'-azido nucleotides; 2'-trifluoromethyl nucleotides; 2'-O-ethyl-trifluoromethoxy nucleotides; 2'-O-difluoromethoxy-ethoxy nucleotides; 4'-thio nucleotides; and 2'-O-methyl nucleotides.

In various embodiments, a majority (e.g., greater than 50%) of the pyrimidine nucleotides present in the double-stranded siNA molecule comprises a sugar modification. In some of the same and/or other embodiments, a majority (e.g., greater than 50%) of the purine nucleotides present in the double-stranded siNA molecule comprises a sugar modification.

In some embodiments, the pyrimidine nucleotides in the antisense strand are 2'-O-methyl or 2'-deoxy-2'-fluoro pyrimidine nucleotides and the purine nucleotides present in the antisense strand are 2'-O-methyl nucleotides or 2'-deoxy nucleotides. In other embodiments, the pyrimidine nucleotides in the sense strand are 2'-deoxy-2'-fluoro pyrimidine nucleotides and the purine nucleotides present in the sense strand are 2'-O-methyl or 2'-deoxy purine nucleotides.

In certain embodiments of the invention, all the pyrimidine nucleotides in the complementary region on the sense strand are 2'-deoxy-2'-fluoro pyrimidine nucleotides. In certain embodiments, all of the pyrimidine nucleotides in the complementary region of the antisense strand are 2'-deoxy-2'-fluoro pyrimidine nucleotides. In certain embodiments, all the purine nucleotides in the complementary region on the sense strand are 2'-deoxy purine nucleotides. In certain embodiments, all of the purines in the complementary region on the antisense strand are 2'-O-methyl purine nucleotides. In certain embodiments, all of the pyrimidine nucleotides in the complementary regions on the sense strand are 2'-deoxy-2'-fluoro pyrimidine nucleotides; all of the pyrimidine nucleotides in the complementary region of the antisense strand are 2'-deoxy-2'-fluoro pyrimidine nucleotides; all the purine nucleotides in the complementary region on the sense strand are 2'-deoxy purine nucleotides and all of the purines in the complementary region on the antisense strand are 2'-O-methyl purine nucleotides.

In some embodiments, at least 5 or more of the pyrimidine nucleotides in one or both strands are 2'-deoxy-2'-fluoro pyrimidine nucleotides. In some embodiments, at least 5 or more of the pyrimidine nucleotides in one or both strands are 2'-O-methyl pyrimidine nucleotides. In some embodiments, at least 5 or more of the purine nucleotides in one or both strands are 2'-deoxy-2'-fluoro purine nucleotides. In some embodiments, at least 5 or more of the purine nucleotides in one or both strands are 2'-O-methyl purine nucleotides.

In certain embodiments, the purines and pyrimidines are differentially modified at the 2'-sugar position (i.e., at least one purine has a different modification from at least one pyrimidine in the same or different strand at the 2'-sugar position). For example, in some instances, at least 5 or more of the pyrimidine nucleotides in one or both strands are 2'-deoxy-2'-fluoro pyrimidine nucleotides and at least 5 or more purine nucleotides in one or both strands are 2'-O-methyl purine nucleotides. In other instances at least 5 or more of the pyrimidine nucleotides in one or both strands are 2'-O-methyl pyrimidine nucleotides and at least 5 or more purine nucleotides in one or both strands are 2'-deoxy-2'-fluoro purine nucleotides.

Further non-limiting examples of sense and antisense strands of such siNA molecules having various modifications and modifications patterns are shown in FIGS. 2 and 3.

Any of the above described modifications, or combinations thereof, including those in the references cited, can be applied to any of the siNA molecules of the invention.

The modified siNA molecules of the invention can comprise modifications at various locations within the siNA molecule. In some embodiments, the double-stranded siNA molecule of the invention comprises modified nucleotides at internal base paired positions within the siNA duplex. In other embodiments, a double-stranded siNA molecule of the invention comprises modified nucleotides at non-base paired or overhang regions of the siNA molecule. In yet other embodiments, a double-stranded siNA molecule of the invention comprises modified nucleotides at terminal positions of the siNA molecule. For example, such terminal regions include the 3'-position and/or 5'-position of the sense and/or antisense strand or region of the siNA molecule. Additionally, any of the modified siNA molecules of the invention can have a modification in one or both oligonucleotide strands of the siNA duplex, for example in the sense strand, the antisense strand, or both strands. Moreover, with regard to chemical modifications of the siNA molecules of the invention, each strand of the double-stranded siNA molecules of the invention can have one or more chemical modifications, such that each strand comprises a different pattern of chemical modifications.

Any of the above described modifications, or combinations thereof, including those in the references cited, can be applied to any of the embodiments of the present invention.

In certain embodiments each strand of a double-stranded siNA molecule of the invention comprises a different pattern of chemical modifications, such as any Stabilization chemistries ("Stab") modification chemistries described herein (see Table 6) or any combination thereof, i.e., different combinations of defined Stab chemistry sense and antisense strands. Further, non-limiting examples of modification schemes that could give rise to different patterns of modifications are shown in Table 6. The stabilization chemistries referred to in Table 6 as "Stab," can be combined in any combination of sense/antisense chemistries, such as Stab 7/8, Stab 7/11, Stab 8/8, Stab 18/8, Stab 18/11, Stab 12/13, Stab 7/13, Stab 18/13, Stab 7/19, Stab 8/19, Stab 18/19, Stab 7/20, Stab 8/20, Stab 18/20, Stab 7/32, Stab 8/32, or Stab 18/32 or any other combination of Stabilization chemistries.

In any of the siNAs of the invention, one or more (for example 1, 2, 3, 4 or 5) nucleotides at the 5'-end of the guide strand or guide region (also known as the antisense strand or antisense region) of the siNA molecule are ribonucleotides.

In certain embodiments, the present invention provides a double-stranded short interfering nucleic acid (siNA) molecule that modulates the expression of IDH1 or a derivative or mutant thereof, wherein the siNA molecule comprises a sense strand and an antisense strand; wherein each strand is independently 15 to 30 nucleotides in length; and wherein the antisense strand comprises at least 15 nucleotides having sequence complementary to any of:

```
                                           (SEQ ID NO: 7)
5'-CUAUCAUCAUAGGUCGUCA-3';

(SEQ ID NO: 11)
5'-CAUCAUAGGUCGUCAUGCU-3';

(SEQ ID NO: 12)
5'-AUCAUAGGUCGUCAUGCUU-3';

(SEQ ID NO: 13)
5'-UCAUAGGUCGUCAUGCUUA-3';

(SEQ ID NO: 38)
5'-CAUCAUAGGUUGUCAUGCU-3';

(SEQ ID NO: 39)
5'-AUCAUAGGUUGUCAUGCUU-3';

(SEQ ID NO: 40)
5'-UCAUAGGUUGUCAUGCUUA-3';

(SEQ ID NO: 41)
5'-CAUAGGUUGUCAUGCUUAU-3';

(SEQ ID NO: 59)
5'-CAUAGGUCAUCAUGCUUAU-3';
or, (SEQ ID NO: 63)
5'-GGUCAUCAUGCUUAUGGGG-3'.
```

In one embodiment, the "at least 15 nucleotides" are 15 contiguous nucleotides.

In some embodiments, the antisense strand of an siNA molecule of the invention comprises at least 15 nucleotides having identity of any of:

```
                                         (SEQ ID NO: 446)
5'-UGACGACCUAUGAUGAUAG-3';

(SEQ ID NO: 450)
5'-AGCAUGACGACCUAUGAUG-3';

(SEQ ID NO: 451)
5'-AAGCAUGACGACCUAUGAU-3';

(SEQ ID NO: 452)
5'-UAAGCAUGACGACCUAUGA-3';

(SEQ ID NO: 477)
5'-AGCAUGACAACCUAUGAUG-3';

(SEQ ID NO: 478)
5'-AAGCAUGACAACCUAUGAU-3';

(SEQ ID NO: 479)
5'-UAAGCAUGACAACCUAUGA-3';

(SEQ ID NO: 480)
5'-AUAAGCAUGACAACCUAUG-3';

(SEQ ID NO: 498)
5'-AUAAGCAUGAUGACCUAUG-3';
or, (SEQ ID NO: 502)
5'-CCCCAUAAGCAUGAUGACC-3'.
```

In one embodiment, the "at least 15 nucleotides" are 15 contiguous nucleotides. Thus, the antisense strand of the siNA molecule comprises at least a 15 nucleotide sequence of any of SEQ ID NO: 446, 450, 451, 452, 477, 478, 479, 480, 498, or 502.

In some embodiments, the sense strand of an siNA molecule of the invention comprises at least 15 nucleotides having identity to any of:

```
                                           (SEQ ID NO: 7)
5'-CUAUCAUCAUAGGUCGUCA-3';

(SEQ ID NO: 11)
5'-CAUCAUAGGUCGUCAUGCU-3';

(SEQ ID NO: 12)
5'-AUCAUAGGUCGUCAUGCUU-3';

(SEQ ID NO: 13)
5'-UCAUAGGUCGUCAUGCUUA-3';

(SEQ ID NO: 38)
5'-CAUCAUAGGUUGUCAUGCU-3';

(SEQ ID NO: 39)
5'-AUCAUAGGUUGUCAUGCUU-3';
```

```
                                            (SEQ ID NO: 40)
5'-UCAUAGGUUGUCAUGCUUA-3';

(SEQ ID NO: 41)
5'-CAUAGGUUGUCAUGCUUAU-3';

(SEQ ID NO: 59)
5'-CAUAGGUCAUCAUGCUUAU-3';
or, (SEQ ID NO: 63)
5'-GGUCAUCAUGCUUAUGGGG-3'.
```

In one embodiment, the "at least 15 nucleotides" are 15 contiguous nucleotides. Thus, the sense strand of the siNA molecule comprises at least a 15 nucleotide sequence of any of SEQ ID NO: 7, 11, 12, 13, 38, 39, 40, 41, 59, or 63.

In some embodiments, an siNA molecule of the invention comprises any of:

```
                                            (SEQ ID NO: 7)
5'-CUAUCAUCAUAGGUCGUCA-3'
and (SEQ ID NO: 446)
5'-UGACGACCUAUGAUGAUAG-3';

(SEQ ID NO: 11)
5'-CAUCAUAGGUCGUCAUGCU-3'
and (SEQ ID NO: 450)
5'-AGCAUGACGACCUAUGAUG-3';

(SEQ ID NO: 12)
5'-AUCAUAGGUCGUCAUGCUU-3'
and (SEQ ID NO: 451)
5'-AAGCAUGACGACCUAUGAU-3';

(SEQ IN NO: 13)
5'-UCAUAGGUCGUCAUGCUUA-3'
and (SEQ ID NO: 452)
5'-UAAGCAUGACGACCUAUGA-3';

(SEQ ID NO: 38)
5'-CAUCAUAGGUUGUCAUGCU-3'
and (SEQ ID NO: 477)
5'-AGCAUGACAACCUAUGAUG-3';

(SEQ ID NO: 39)
5'-AUCAUAGGUUGUCAUGCUU-3'
and (SEQ ID NO: 478)
5'-AAGCAUGACAACCUAUGAU-3';

(SEQ ID NO: 40)
5'-UCAUAGGUUGUCAUGCUUA-3'
and (SEQ ID NO: 479)
5'-UAAGCAUGACAACCUAUGA-3';

(SEQ ID NO: 41)
5'-CAUAGGUUGUCAUGCUUAU-3'
and (SEQ ID NO: 480)
5'-AUAAGCAUGACAACCUAUG-3';
```

```
                                            (SEQ ID NO: 59)
5'-CAUAGGUCAUCAUGCUUAU-3'
and (SEQ ID NO: 498)
5'-AUAAGCAUGAUGACCUAUG-;
or, (SEQ ID NO: 63)
5'-GGUCAUCAUGCUUAUGGGG-3'
and (SEQ ID NO: 502)
5'-CCCCAUAAGCAUGAUGACC-3'.
```

In another embodiment, the siNA molecule comprises at least a 15 nucleotide sequence of both SEQ ID NO: 7 and 446; or both SEQ ID NO: 11 and 450; or both SEQ ID NO: 12 and 451; or both SEQ ID NO: 13 and 452; or both SEQ ID NO: 38 and 477; or both SEQ ID NO: 39 and 478; or both SEQ ID NO: 40 and 479; or both SEQ ID NO: 41 and 480; or both SEQ ID NO: 59 and 498; or both SEQ ID NO: 63 and 502.

In some embodiments, the siNA molecule can contain one or more nucleotide deletions, substitutions, mismatches and/or additions within the at least 15 nucleotide sequence of SEQ ID NO: 7, SEQ ID NO: 446, SEQ ID NO: 11, SEQ ID NO: 450, SEQ ID NO: 12, SEQ ID NO: 451, SEQ ID NO: 13, SEQ ID NO: 452; SEQ ID NO: 38, SEQ ID NO: 477, SEQ ID NO: 39, SEQ ID NO: 478, SEQ ID NO: 40, SEQ ID NO: 479, SEQ ID NO: 41, SEQ ID NO: 480, SEQ ID NO: 59, SEQ ID NO: 498, SEQ ID NO: 63 or SEQ ID NO: 502; provided, however, that the siNA molecule maintains its activity, for example, to mediate RNAi. In a non-limiting example, the deletion, substitution, mismatch and/or addition can result in a loop or bulge, or alternately a wobble or other alternative (non Watson-Crick) base pair.

In some embodiments, the antisense strand of an siNA molecule of the invention comprises at least 15 nucleotides having sequence identity to any of SEQ ID NOs: 91, 107, 111, 115, 199, 213, 227, 231, 303, or 411. In other embodiments, the sense strand of an siNA molecule of the invention comprises at least 15 nucleotides having sequence identity to any of SEQ ID NOs: 90, 106, 110, 114, 198, 212, 226, 230, 302, or 410. In a further embodiment, the "at least 15 nucleotides" are 15 contiguous nucleotides.

In some embodiments, an siNA molecule of the invention comprises any of: SEQ ID NO: 90 and 91; SEQ ID NO: 106 and 107; SEQ ID NO: 110 and 111; SEQ ID NO: 114 and 115; SEQ ID NO: 198 and 199; SEQ ID NO: 212 and 213; SEQ ID NO: 226 and 227; SEQ ID NO: 230 and 231; SEQ ID NO: 302 and 303; or SEQ ID NO: 410 and 411.

In certain embodiments, double-stranded short interfering nucleic acid (siNA) molecules are provided, wherein the molecule has a sense strand and an antisense strand and comprises formula (A):

$$B-N_{X3}-(N)_{X2}B-3'$$

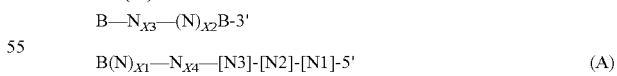

wherein, the upper strand is the sense strand and the lower strand is the antisense strand of the double-stranded nucleic acid molecule; wherein the antisense strand comprises at least a 15 nucleotide sequence of SEQ ID NO: 446, SEQ ID NO: 450, SEQ ID NO: 451, SEQ ID NO: 452, SEQ ID NO: 477, SEQ ID NO: 478, SEQ ID NO: 479, SEQ ID NO: 480, SEQ ID NO: 498, or SEQ ID NO: 502, and the sense strand comprises a sequence having complementarity to the antisense strand;

each N is independently either a nucleotide that is unmodified or chemically modified, or a non-nucleotide;

each B is a terminal cap that is present or absent;

(N) represents overhanging nucleotides, each of which is independently unmodified or chemically modified;

X1 and X2 are independently integers from 0 to 4;

X3 is an integer from 15 to 30;

X4 is an integer from 12 to 27; and,

[N1]-[N2]-[N3] are modified nucleotides or ribonucleotides, and wherein [N1]-[N2]-[N3] is selected from the groups consisting of:
- (a) [N1] is a 2'-deoxy-2'-fluoro nucleotide, [N2] is a 2'-deoxy-2'-fluoro nucleotide, and [N3] is a 2'-deoxy-2'-fluoro nucleotide;
- (b) [N1] is a 2'-deoxy-2'-fluoro nucleotide, [N2] is a 2'-deoxy-2'-fluoro nucleotide, and [N3] is a 2'-deoxy nucleotide;
- (c) [N1] is a 2'-deoxy nucleotide, [N2] is a 2'-deoxy-2'-fluoro nucleotide, and [N3] is a 2'-O-methyl nucleotide;
- (d) [N1] is a 2'-deoxy nucleotide, [N2] is a 2'-deoxy-2'-fluoro nucleotide, and [N3] is a 2'-deoxy nucleotide; and,
- (e) [N1] is a ribonucleotide, [N2] is a ribonucleotide, and [N3] is a ribonucleotide.

In some embodiments, the siNA molecule of formula A can contain one or more nucleotide deletions, substitutions, mismatches and/or additions to the at least 15 nucleotide sequence of SEQ ID NO: 446, SEQ ID NO: 450, SEQ ID NO: 451, SEQ ID NO: 452, SEQ ID NO: 477, SEQ ID NO: 478, SEQ ID NO: 479, SEQ ID NO: 480, SEQ ID NO: 498, or SEQ ID NO: 502; provided, however, that the siNA molecule maintains its activity, for example, to mediate RNAi. In a non-limiting example, the deletion, substitution, mismatch and/or addition can result in a loop or bulge, or alternately a wobble or other alternative (non Watson-Crick) base pair.

In one embodiment, the invention features a double-stranded short interfering nucleic acid (siNA) molecule of formula (A); wherein:
- (a) one or more pyrimidine nucleotides in $N_{X4}$ positions are independently 2'-deoxy-2'-fluoro nucleotides, 2'-O-alkyl nucleotides, 2'-deoxy nucleotides, ribonucleotides, or any combination thereof;
- (b) one or more purine nucleotides in $N_{X4}$ positions are independently 2'-deoxy-2'-fluoro nucleotides, 2'-O-alkyl nucleotides, 2'-deoxy nucleotides, ribonucleotides, or any combination thereof;
- (c) one or more pyrimidine nucleotides in $N_{X3}$ positions are independently 2'-deoxy-2'-fluoro nucleotides, 2'-O-alkyl nucleotides, 2'-deoxy nucleotides, ribonucleotides, or any combination thereof; and,
- (d) one or more purine nucleotides in $N_{X3}$ positions are independently 2'-deoxy-2'-fluoro nucleotides, 2'-O-alkyl nucleotides, 2'-deoxy nucleotides, ribonucleotides, or any combination thereof.

In certain embodiments, the invention features a double-stranded short interfering nucleic acid (siNA) molecule of formula (A); wherein:
- (a) 1, 2, 3, 4, 5 or more pyrimidine nucleotides in $N_{X4}$ positions are 2'-deoxy-2'-fluoro nucleotides;
- (b) 1, 2, 3, 4, 5 or more purine nucleotides in $N_{X4}$ positions are 2'-O-alkyl nucleotides;
- (c) 1, 2, 3, 4, 5 or more pyrimidine nucleotides in $N_{X3}$ positions are 2'-deoxy-2'-fluoro nucleotides; and,
- (d) 1, 2, 3, 4, 5 or more purine nucleotides in $N_{X3}$ positions are 2'-deoxy nucleotides.

In certain embodiments, the invention features a double-stranded short interfering nucleic acid (siNA) molecule of formula (A); wherein:
- (a) 1, 2, 3, 4, 5 or more pyrimidine nucleotides in $N_{X4}$ positions are 2'-O-alkyl nucleotides;
- (b) 1, 2, 3, 4, 5 or more purine nucleotides in $N_{X4}$ positions are ribonucleotides;
- (c) 1, 2, 3, 4, 5 or more pyrimidine nucleotides in $N_{X3}$ positions are 2'-O-alkyl nucleotides; and,
- (d) 1, 2, 3, 4, 5 or more purine nucleotides in $N_{X3}$ positions are ribonucleotides.

In certain embodiments, the invention features a double-stranded short interfering nucleic acid (siNA) molecule of formula (A); wherein:
- (a) 1, 2, 3, 4, 5 or more pyrimidine nucleotides in $N_{X4}$ positions are 2'-deoxy-2'-fluoro nucleotides;
- (b) 1, 2, 3, 4, 5 or more purine nucleotides in $N_{X4}$ positions are 2'-O-alkyl nucleotides;
- (c) 1, 2, 3, 4, 5 or more pyrimidine nucleotides in $N_{X3}$ positions are 2'-O-alkyl nucleotides; and,
- (d) 1, 2, 3, 4, 5 or more purine nucleotides in $N_{X3}$ positions are 2'-deoxy-2'-fluoro nucleotides.

In certain embodiments, the invention features a double-stranded short interfering nucleic acid (siNA) molecule of formula (A) further comprising one or more phosphorothioate internucleotide linkages.

In some embodiments, siNA molecules having formula A comprise a terminal phosphate group at the 5'-end of the antisense strand or antisense region of the nucleic acid molecule.

In various embodiments, siNA molecules having formula A comprise each X1 and X2=1 or 2; X3=18, 19, 20, 21, 22, 23 or 24; and, X4=15, 16, 17, 18, 19, 20 or 21.

In certain embodiments, siNA molecules having formula A comprise X1=2 and X2=2.

In one specific embodiment, an siNA molecule having formula A comprises each X1 and X2=2; X3=19; and, X4=16.

In certain embodiments, siNA molecules having formula A comprise caps (B) at the 3' and 5' ends of the sense strand or sense region.

In certain embodiments, siNA molecules having formula A comprise caps (B) at the 3'-end of the antisense strand or antisense region.

In various embodiments, siNA molecules having formula A comprise caps (B) at the 3' and 5' ends of the sense strand or sense region and caps (B) at the 3'-end of the antisense strand or antisense region.

In yet other embodiments, siNA molecules having formula A comprise caps (B) only at the 5'-end of the sense (upper) strand of the double-stranded nucleic acid molecule.

In some embodiments, siNA molecules having formula A further comprise one or more phosphorothioate internucleotide linkages between the nucleotides. In certain embodiments, siNA molecules having formula A comprise one or more phosphorothioate internucleotide linkages between the first terminal (N) and the adjacent nucleotide on the 3'end of the sense strand, antisense strand, or both sense strand and antisense strands of the nucleic acid molecule. For example, a double-stranded nucleic acid molecule can comprise X1 and/or X2=2 having overhanging nucleotide positions with a phosphorothioate internucleotide linkage, e.g., (NsN) where "s" indicates phosphorothioate.

In some embodiments, one or more of the nucleotides of siNA molecules having formula A has a universal base.

In certain embodiments, siNA molecules having formula A have at position 14 from the 5'-end of the antisense strand a ribonucleotide when the nucleotide at that position 14 is a purine. In other embodiments, siNA molecules having formula A have at position 14 from the 5'-end of the antisense strand a ribonucleotide, a 2'-deoxy-2'-fluoro nucleotide, or a 2'-O-methyl nucleotide when the nucleotide at that position 14 is a pyrimidine nucleotide. In particularly preferred embodiments, position 14 from the 5'-end of the antisense strand is a 2'-deoxy-2'-fluoro nucleotide regardless of whether it is a purine or a pyrimidine.

In some embodiments, siNA molecules having formula A comprises (N) nucleotides in the antisense strand (lower strand) that are complementary to nucleotides in an IDH1-related target polynucleotide sequence, which also has complementarity to the N and [N] nucleotides of the antisense (lower) strand.

Any of the above described modifications, or combinations thereof, discussed above as applicable to siNAs of the invention, including those in the references cited, can be applied to any of the embodiments to siNA molecules having formula A.

C. Generation/Synthesis of siNA Molecules

The siNAs of the invention can be obtained using a number of techniques known to those of skill in the art. For example the siNA can be chemically synthesized or may be encoded by plasmid (e.g., transcribed as sequences that automatically fold into duplexes with hairpin loops.) siNA can also be generated by cleavage of longer dsRNA (e.g., dsRNA greater than about 25 nucleotides in length) by the *E coli* RNase II or Dicer. These enzymes process the dsRNA into biologically active siNA (see, e.g., Yang et al., PNAS USA 99:9942-9947 (2002); Calegari et al. *PNAS USA* 99:14236 (2002); Byron et al. Ambion Tech Notes 10 (1):4-6 (2009); Kawaski et al., *Nucleic Acids Res.*, 31:981-987 (2003); Knight and Bass, *Science*, 293:2269-2271 (2001); and Roberston et al., *J. Biol. Chem* 243:82 (1969).

1. Chemical Synthesis

Preferably, siNA of the invention are chemically synthesized. Oligonucleotides (e.g., certain modified oligonucleotides or portions of oligonucleotides lacking ribonucleotides) are synthesized using protocols known in the art (for example, as described in: Caruthers et al., 1992, *Methods in Enzymology* 211, 3-19; Thompson et al., International PCT Publication No. WO 99/54459; Wincott et al., 1995, *Nucleic Acids Res.* 23, 2677-2684; Wincott et al., 1997, *Methods Mol. Bio.*, 74, 59; Brennan et al., 1998, *Biotechnol Bioeng.*, 61, 33-45; and Brennan, U.S. Pat. No. 6,001,311). The synthesis of oligonucleotides makes use of common nucleic acid protecting and coupling groups, such as dimethoxytrityl at the 5'-end, and phosphoramidites at the 3'-end.

siNA molecules without modifications are synthesized using procedures as described in Usman et al., 1987, *J. Am. Chem. Soc.*, 109, 7845; and Scaringe et al., 1990, *Nucleic Acids Res.*, 18, 5433. These syntheses makes use of common nucleic acid protecting and coupling groups, such as dimethoxytrityl at the 5'-end, and phosphoramidites at the 3'-end that can be used for certain siNA molecules of the invention.

In certain embodiments, the siNA molecules of the invention are synthesized, deprotected, and analyzed according to methods described in U.S. Pat. Nos. 6,995,259, 6,686,463, 6,673,918, 6,649,751, 6,989,442, and 7,205,399.

In a non-limiting synthesis example, small scale syntheses are conducted on a 394 Applied Biosystems, Inc. synthesizer using a 0.2 µmol scale protocol with a 2.5 min coupling step for 2'-O-methylated nucleotides and a 45 second coupling step for 2'-deoxy nucleotides or 2'-deoxy-2'-fluoro nucleotides. Table 7 outlines the amounts and the contact times of the reagents used in the synthesis cycle.

Alternatively, the siNA molecules of the present invention can be synthesized separately and joined together post-synthetically, for example, by ligation (e.g., Moore et al., 1992, *Science* 256, 9923; Draper et al., International PCT Publication No. WO 93/23569; Shabarova et al., 1991, *Nucleic Acids Research* 19, 4247; Bellon et al., 1997, *Nucleosides & Nucleotides*, 16, 951; and Bellon et al., 1997, *Bioconjugate Chem.* 8, 204), or by hybridization following synthesis and/or deprotection.

Various siNA molecules of the invention can also be synthesized using the teachings of Scaringe et al., U.S. Pat. Nos. 5,889,136; 6,008,400; and 6,111,086.

2. Vector Expression

Alternatively, siNA molecules of the invention that interact with and down-regulate gene encoding target IDH1-related molecules can be expressed and delivered from transcription units (see, for example, Couture et al., 1996, *TIG.*, 12, 510) inserted into DNA or RNA vectors. The recombinant vectors can be DNA plasmids or viral vectors. siNA expressing viral vectors can be constructed based on, but not limited to, adeno-associated virus, retrovirus, adenovirus, or alphavirus.

In some embodiments, pol III based constructs are used to express nucleic acid molecules of the invention. Transcription of the siNA molecule sequences can be driven from a promoter for eukaryotic RNA polymerase I (pol I), RNA polymerase II (pol II), or RNA polymerase III (pol III). (see, for example, Thompson, U.S. Pat. Nos. 5,902,880 and 6,146,886). (See also, Izant and Weintraub, 1985, *Science*, 229, 345; McGarry and Lindquist, 1986, *Proc. Natl. Acad. Sci.*, USA 83, 399; Scanlon et al., 1991, *Proc. Natl. Acad. Sci. USA*, 88, 10591-5; Kashani-Sabet et al., 1992, *Antisense Res. Dev.*, 2, 3-15; Dropulic et al., 1992, *J. Virol.*, 66, 1432-41; Weerasinghe et al., 1991, *J. Virol.*, 65, 5531-4; Ojwang et al., 1992, *Proc. Natl. Acad. Sci. USA*, 89, 10802-6; Chen et al., 1992, *Nucleic Acids Res.*, 20, 4581-9; Sarver et al., 1990 *Science*, 247, 1222-1225; Thompson et al., 1995, *Nucleic Acids Res.*, 23, 2259; Good et al., 1997, *Gene Therapy*, 4, 45). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (see Elroy-Stein and Moss, 1990, *Proc. Natl. Acad. Sci. USA*, 87, 6743-7; Gao and Huang 1993, *Nucleic Acids Res.*, 21, 2867-72; Lieber et al., 1993, *Methods Enzymol.*, 217, 47-66; Zhou et al., 1990, *Mol. Cell. Biol.*, 10, 4529-37). Several investigators have demonstrated that nucleic acid molecules expressed from such promoters can function in mammalian cells (e.g., Kashani-Sabet et al., 1992, supra; Ojwang et al., 1992, supra; Chen et al., 1992, supra; Yu et al., 1993, *Proc. Natl. Acad. Sci. USA*, 90, 6340-4; L'Huillier et al., 1992, *EMBO J.*, 11, 4411-8; Lisziewicz et al., 1993, *Proc. Natl. Acad. Sci. U.S.A*, 90, 8000-4; Thompson et al., 1995, *Nucleic Acids Res.*, 23, 2259; and Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as siNA in cells (Thompson et al., 1995, supra; Couture and Stinchcomb, 1996, supra; Noonberg et al., 1994, *Nucleic Acid Res.*, 22, 2830; Noonberg et al., U.S. Pat. No. 5,624,803; Good et al., 1997, *Gene Ther.*, 4, 45; and Beigelman et al., International PCT Publication No. WO 96/18736. The above siNA transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture et al., 1996, TIG, 12, 510).

Vectors used to express the siNA molecules of the invention can encode one or both strands of an siNA duplex, or a single self-complementary strand that self hybridizes into an siNA duplex. The nucleic acid sequences encoding the siNA molecules of the instant invention can be operably linked in a manner that allows expression of the siNA molecule (see for example Paul et al., 2002, Nature Biotechnology, 19, 505; Miyagishi and Taira, 2002, Nature Biotechnology, 19, 497; and Lee et al., 2002, Nature Biotechnology, 19, 500).

D. Carrier/Delivery Systems

The siNA molecules of the invention are added directly, or can be complexed with cationic lipids, packaged within liposomes, or as a recombinant plasmid or viral vectors which express the siNA molecules, or otherwise delivered to target cells or tissues. Methods for the delivery of nucleic acid molecules are described in, for example, Akhtar et al., 1992, Trends Cell Bio., 2, 139; Delivery Strategies for Antisense Oligonucleotide Therapeutics, ed. Akhtar, 1995; Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192. Beigelman et al., U.S. Pat. No. 6,395,713 and Sullivan et al., PCT International application publication no. WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example, Gonzalez et al., 1999, Bioconjugate Chem., 10, 1068-1074; Wang et al., International PCT Publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722).

In one aspect, the present invention provides carrier systems containing the siNA molecules described herein. In some embodiments, the carrier system is a lipid-based carrier system, cationic lipid, or liposome nucleic acid complexes, a liposome, a micelle, a virosome, a lipid nanoparticle or a mixture thereof. In other embodiments, the carrier system is a polymer-based carrier system such as a cationic polymer-nucleic acid complex. In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. In another embodiment, the carrier system is a lipid nanoparticle ("LNP") formulation.

In certain embodiments, the siNA molecules of the invention are formulated with a lipid nanoparticle composition such as is described in U.S. patent application Ser. Nos. 11/353,630, 11/586,102, 61/189,295, 61/204,878, 61/235,476, 61/249,807, and 61/298,022. In certain embodiments, the siNA molecules of the invention are formulated with a lipid nanoparticle composition comprising a cationic lipid/Cholesterol/PEG-C-DMA/DSPC in a 40/48/2/10 ratio, a cationic lipid/Cholesterol/PEG-DMG/DSPC in a 40/48/2/10 ratio, or a cationic lipid/Cholesterol/PEG-DMG in a 60/38/2 ratio. In certain embodiments, the cationic lipid is Octyl CLinDMA, DLinDMA, L-278, DLinKC2DMA, or MC3 (see Table 9).

In various embodiments, lipid nanoparticle formulations described in Table 8 are applied to any siNA molecule or combination of siNA molecules herein.

In certain other embodiments, the invention features a composition comprising an siNA molecule of the invention formulated with any of the cationic lipid formulations described in PCT International application publication nos. WO 2010/021865; WO 2010/080724; WO 2010/042877; WO 2010/105209 and WO 2011/022460; and in U.S. Patent Application Nos. 61/249,807; 61/298,022; 61/322,054; 61/347,640; 61/351,373; 61/382,067; 61/384,486; and 61/388,201.

In other embodiments, the invention features conjugates and/or complexes of siNA molecules of the invention. Such conjugates and/or complexes can be used to facilitate delivery of siNA molecules into a biological system, such as a cell. The conjugates and complexes provided by the instant invention can impart therapeutic activity by transferring therapeutic compounds across cellular membranes, altering the pharmacokinetics, and/or modulating the localization of nucleic acid molecules of the invention. Non-limiting, examples of such conjugates are described in U.S. Publication Nos. US 2008/0152661 and US 2004/0162260 (e.g., CDM-LBA, CDM-Pip-LBA, CDM-PEG, CDM-NAG, etc.) and U.S. patent application Ser. No. 10/201,394; and U.S. Pat. Nos. 7,833,992; 6,528,631; 6,335,434; 6,235,886; 6,153,737; 5,214,136; and 5,138,045.

In various embodiments, polyethylene glycol (PEG) can be covalently attached to siNA compounds of the present invention. The attached PEG can be any molecular weight, preferably from about 100 to about 50,000 daltons (Da).

In yet other embodiments, the invention features compositions or formulations comprising surface-modified liposomes containing poly(ethylene glycol) lipids (PEG-modified, or long-circulating liposomes or stealth liposomes) and siNA molecules of the invention, such as is disclosed in for example, International PCT Publication No. WO 96/10391; Ansell et al., International PCT Publication No. WO 96/10390; Holland et al., International PCT Publication No. WO 96/10392.

In some embodiments, the siNA molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid molecules of the invention are formulated as described in U.S. Patent Application Publication No. 2003/0077829.

In other embodiments, siNA molecules of the invention are complexed with membrane disruptive agents such as those described in U.S. Patent Application Publication No. 2001/0007666. In still other embodiments, the membrane disruptive agent or agents and the siNA molecule are also complexed with a cationic lipid or helper lipid molecule, such as those lipids described in U.S. Pat. No. 6,235,310.

In certain embodiments, siNA molecules of the invention are complexed with delivery systems as described in U.S. Patent Application Publication Nos. 2003/077829; 2005/0287551; 2005/0164220; 2005/0191627; 2005/0118594;

2005/0153919; 2005/0085486; and 2003/0158133; and International PCT Publication Nos. WO 00/03683 and WO 02/087541.

In some embodiments, a liposomal formulation of the invention comprises an siNA molecule of the invention (e.g., siNA) formulated or complexed with compounds and compositions described in U.S. Pat. Nos. 6,858,224; 6,534,484; 6,287,591; 6,835,395; 6,586,410; 6,858,225; 6,815,432; 6,586,001; 6,120,798; 6,977,223; 6,998,115; 5,981,501; 5,976,567; 5,705,385; and U.S. Patent Application Publication Nos. 2006/0019912; 2006/0019258; 2006/0008909; 2005/0255153; 2005/0079212; 2005/0008689; 2003/0077829, 2005/0064595, 2005/0175682, 2005/0118253; 2004/0071654; 2005/0244504; 2005/0265961 and 2003/0077829.

Alternatively, recombinant plasmids and viral vectors, as discussed above, which express siNAs of the invention, can be used to deliver the molecules of the invention. Delivery of siNA molecule expressing vectors can be systemic, such as by intravenous or intra-muscular administration, by administration to target cells ex-planted from a subject followed by reintroduction into the subject, or by any other means that would allow for introduction into the desired target cell (for a review see Couture et al., 1996, *TIG.*, 12, 510). Such recombinant plasmids can also be administered directly or in conjunction with a suitable delivery reagents, including, for example, the Mirus Transit LT1 lipophilic reagent; lipofectin; lipofectamine; cellfectin; polycations (e.g., polylysine) or liposomes lipid-based carrier system, cationic lipid, or liposome nucleic acid complexes, a micelle, a virosome, a lipid nanoparticle.

E. Kits

The present invention also provides nucleic acids in kit form. The kit may comprise a container. The kit typically contains a nucleic acid of the invention with instructions for its administration. In certain instances, the nucleic acids may have a targeting moiety attached. Methods of attaching targeting moieties (e.g. antibodies, proteins) are known to those of skill in the art. In certain instances, the nucleic acids are chemically modified. In other embodiments, the kit contains more than one siNA molecule of the invention. The kits may comprise an siNA molecule of the invention with a pharmaceutically acceptable carrier or diluent. The kits may further comprise excipients.

F. Therapeutic Uses/Pharmaceutical Compositions

The present body of knowledge in IDH1 research indicates the need for methods to assay IDH1 activity and for compounds that regulate wild-type and/or mutant IDH1 expression for research, diagnostic, and therapeutic use. As described infra, the nucleic acid molecules of the present invention can be used in assays to diagnose one or more disease states related to IDH1 and/or mutant IDH1 levels. In addition, the nucleic acid molecules and pharmaceutical compositions can be used to treat one or more disease states related to IDH1-related RNA levels.

1. Disease States Associated with IDH1 and/or Mutant IDH1

Particular disease states that can be associated with the expression of IDH1-related genes and/or proteins include cell-proliferation-related disorders, including cancers of the central nervous system (e.g., gliomas (e.g., glioblastomas, astrocytomas, oligodendrogliomas, supratentorial) and primitive neuroectodermal tumors (e.g., medulloblastomas)) and disorders of hematopoiesis characterized by the proliferation of myeloid cells (e.g., AML, myelodysplastic syndrome (MDS), myeloproliferative neoplasm (MPN)).

It is understood that the siNA molecules of the invention can degrade the target IDH1-related mRNA (and thus inhibit the diseases associated with IDH1-related gene or protein expression). Inhibition of a disease can be evaluated by directly measuring the progress of the disease in a subject. It can also be inferred through observing a change or reversal in a condition associated with the disease. Additionally, the siNA molecules of the invention can be used as a prophylaxis. Thus, the use of the nucleic acid molecules and pharmaceutical compositions of the invention can be used to ameliorate, treat, prevent, and/or cure these diseases and others associated with regulation of IDH1-related gene expression.

2. Pharmaceutical Compositions

The siNA molecules of the instant invention provide useful reagents and methods for a variety of therapeutic, prophylactic, veterinary, diagnostic, target validation, genomic discovery, genetic engineering, and pharmacogenomic applications.

a. Formulations

The present invention provides for pharmaceutical compositions of the siNA molecules described, i.e., compositions in a pharmaceutically acceptable carrier or diluent. These formulations or compositions can comprise a pharmaceutically acceptable carrier or diluent as is generally known in the art.

In one embodiment, the invention features a pharmaceutical composition comprising an siNA molecule comprising at least 15 nucleotides of SEQ ID NO: 7, SEQ ID NO: 446, SEQ ID NO: 11, SEQ ID NO: 450, SEQ ID NO: 12, SEQ ID NO: 451, SEQ ID NO: 13, SEQ ID NO: 452, SEQ ID NO: 38, SEQ ID NO: 477, SEQ ID NO: 39, SEQ ID NO: 478, SEQ ID NO: 40, SEQ ID NO: 479, SEQ ID NO: 41, SEQ ID NO: 480, SEQ ID NO: 59, SEQ ID NO: 498, SEQ ID NO: 63, or SEQ ID NO: 502. In another embodiment, the "at least 15 nucleotides" are 15 contiguous nucleotides. In still another embodiment, the invention features a pharmaceutical composition comprising an siNA molecule comprising formula (A).

The siNA molecules of the invention are preferably formulated as pharmaceutical compositions prior to administering to a subject, according to techniques known in the art. Pharmaceutical compositions of the present invention are characterized as being at least sterile and pyrogen-free. Methods for preparing pharmaceutical compositions of the invention are within the skill in the art for example as described in *Remington's Pharmaceutical Science*, 17$^{th}$ ed., Mack Publishing Company, Easton, Pa. (1985).

In some embodiments, pharmaceutical compositions of the invention (e.g., siNA and/or LNP formulations thereof) further comprise conventional pharmaceutical excipients and/or additives. Suitable pharmaceutical excipients include preservatives, flavoring agents, stabilizers, antioxidants, osmolality adjusting agents, buffers, and pH adjusting agents. Suitable additives include physiologically biocompatible buffers (e.g., trimethylamine hydrochloride), addition of chelants (such as, for example, DTPA or DTPA-bisamide) or calcium chelate complexes (as for example calcium DTPA, CaNaDTPA-bisamide), or, optionally, additions of calcium or sodium salts (for example, calcium chloride, calcium ascorbate, calcium gluconate or calcium lactate). In addition, antioxidants and suspending agents can be used.

Non-limiting examples of various types of formulations for local administration include ointments, lotions, creams, gels, foams, preparations for delivery by transdermal patches, powders, sprays, aerosols, capsules or cartridges for use in an inhaler or insufflator or drops (for example eye or nose drops), solutions/suspensions for nebulization, suppositories, pessaries, retention enemas and chewable or suckable tablets or pellets (for example for the treatment of aphthous ulcers) or liposome or microencapsulation preparations.

Ointments, creams and gels, can, for example, can be formulated with an aqueous or oily base with the addition of suitable thickening and/or gelling agent and/or solvents. Non limiting examples of such bases can thus, for example, include water and/or an oil such as liquid paraffin or a vegetable oil such as arachis oil or castor oil, or a solvent such as polyethylene glycol. Various thickening agents and gelling agents can be used depending on the nature of the base. Non-limiting examples of such agents include soft paraffin, aluminum stearate, cetostearyl alcohol, polyethylene glycols, woolfat, beeswax, carboxypolymethylene and cellulose derivatives, and/or glyceryl monostearate and/or non-ionic emulsifying agents.

In one embodiment lotions can be formulated with an aqueous or oily base and will in general also contain one or more emulsifying agents, stabilizing agents, dispersing agents, suspending agents or thickening agents.

In one embodiment powders for external application can be formed with the aid of any suitable powder base, for example, talc, lactose or starch. Drops can be formulated with an aqueous or non-aqueous base also comprising one or more dispersing agents, solubilizing agents, suspending agents or preservatives.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate; or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative, and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The molecule, depending on the vehicle and concentration used, can either be suspended or dissolved in the vehicle. Advantageously, adjuvants such as local anesthetics, preservatives and buffering agents can be dissolved in the vehicle.

In other embodiments, the siNA and LNP compositions and formulations provided herein for use in pulmonary delivery further comprise one or more surfactants. Suitable surfactants or surfactant components for enhancing the uptake of the compositions of the invention include synthetic and natural as well as full and truncated forms of surfactant protein A, surfactant protein B, surfactant protein C, surfactant protein D and surfactant Protein E, di-saturated phosphatidylcholine (other than dipalmitoyl), dipalmitoylphosphatidylcholine, phosphatidylcholine, phosphatidylglycerol, phosphatidylinositol, phosphatidylethanolamine, phosphatidylserine; phosphatidic acid, ubiquinones, lysophosphatidylethanolamine, lysophosphatidylcholine, palmitoyl-lysophosphatidylcholine, dehydroepiandrosterone, dolichols, sulfatidic acid, glycerol-3-phosphate, dihydroxyacetone phosphate, glycerol, glycero-3-phosphocholine, dihydroxyacetone, palmitate, cytidine diphosphate (CDP) diacylglycerol, CDP choline, choline, choline phosphate; as well as natural and artificial lamellar bodies which are the natural carrier vehicles for the components of surfactant, omega-3 fatty acids, polyenic acid, polyenoic acid, lecithin, palmitinic acid, non-ionic block copolymers of ethylene or propylene oxides, polyoxypropylene, monomeric and polymeric, polyoxyethylene, monomeric and polymeric, poly(vinyl amine) with dextran and/or alkanoyl side chains, Brij 35, Triton X-100 and synthetic surfactants ALEC, Exosurf, Survan and Atovaquone, among others. These surfactants can be used either as single or part of a multiple component surfactant in a formulation, or as covalently bound additions to the 5' and/or 3' ends of the nucleic acid component of a pharmaceutical composition herein.

b. Combinations

The siNAs and pharmaceutical formulations according to the invention can be administered to a subject alone or used in combination with or include one or more other therapeutic agents, for example, anti-cancer agents. Thus, combinations of the presently disclosed compounds with other anti-cancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. The siNAs of the invention are also useful in combination with any therapeutic agent used in the cancer. The instant compounds are particularly useful when co-administered with radiation therapy.

In a further embodiment, therefore, the invention provides a combination comprising one or more anti-cancer or chemotherapeutic agent together with an siNA molecule of the invention, such as for example, but not limitation, an siNA molecule comprising at least 15 nucleotides of SEQ ID NO: 7, SEQ ID NO: 446, SEQ ID NO: 11, SEQ ID NO: 450, SEQ ID NO: 12, SEQ ID NO: 451, SEQ ID NO: 13, SEQ ID NO: 452, SEQ ID NO: 38, SEQ ID NO: 477, SEQ ID NO: 39, SEQ ID NO: 478, SEQ ID NO: 40, SEQ ID NO: 479, SEQ ID NO: 41, SEQ ID NO: 480, SEQ ID NO: 59, SEQ ID NO: 498, SEQ ID NO: 63, or SEQ ID NO: 502; or formula (A). In another embodiment, the "at least 15 nucleotides" of the siNA component of the combination is 15 contiguous nucleotides.

In certain embodiments, the instant siNA molecules of the invention are useful in combination with known anti-cancer agents including the following: estrogen receptor modulators, androgen receptor modulators, retinoid receptor modulators, cytotoxic agents, antiproliferative agents, prenyl-protein transferase inhibitors, angiogenesis inhibitors, inhibitors of cell proliferation and survival signaling, apoptosis inducing agents and agents that interfere with cell cycle checkpoints.

Examples of estrogen receptor modulators that can be used in combination with the molecules of the invention include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl) ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

Examples of androgen receptor modulators that can be used in combination with the molecules of the invention include, but are not limited to, finasteride and other 5α-reductase inhibitors, nilutamide, flutamide, bicalutamide, liarozole, and abiraterone acetate.

Examples of such retinoid receptor modulators that can be used in combination with the molecules of the invention include, but are not limited to, bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

Examples of cytotoxic agents that can be used in combination with the molecules of the invention include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound that can be used in combination with the molecules of the invention is tirapazamine.

Examples of proteasome inhibitors that can be used in combination with the molecules of the invention include, but are not limited to, lactacystin and bortezomib.

Examples of microtubule inhibitors/microtubule-stabilising agents that can be used in combination with the molecules of the invention include, but are not limited to, paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors that can be used in combination with the molecules of the invention include, but are not limited to, are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13 (9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-

[2-[N-[2-(dimethylamino)ethyl]-N-methylamino]ethyl]-5-[4-hydroOxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, that can be used in combination with the molecules of the invention include, but are not limited to, inhibitors described in PCT Publications WO 01/30768, WO 01/98278, WO 03/050,064, WO 03/050,122, WO 03/049,527, WO 03/049,679, WO 03/049,678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, and WO05/017190; and in US Patent Application publication no. US2005/0176776. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of histone deacetylase inhibitors that can be used in combination with the compounds of the invention include, but are not limited to, TSA, oxamflatin, PXD101, MG98, valproic acid and scriptaid. Further reference to other histone deacetylase inhibitors may be found in Miller, T. A. et al., *J. Med. Chem.* 46(24):5097-5116 (2003).

Inhibitors of kinases involved in mitotic progression that can be used in combination with the molecules of the invention include, but are not limited to, inhibitors of aurora kinase, inhibitors of Polo-like kinases (PLK) (in particular inhibitors of PLK-1), inhibitors of bub-1 and inhibitors of bub-R1.

Anti-proliferative agents that can be used in combination with the molecules of the invention include, but are not limited to, antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl) urea, N6-[4-deoxy-4-[N2-[2(E),4(E)-tetradecadienoyl]glycylamino]-L-glycero-B-L-manno-heptopyranosyl] adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo (7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabin furanosyl cytosine and 3-aminopyridine-2-carboxaldehyde thiosemicarbazone.

Examples of monoclonal antibody targeted therapeutic agents that can be used in combination with the molecules of the invention include those therapeutic agents which have cytotoxic agents or radioisotopes attached to a cancer cell specific or target cell specific monoclonal antibody, such as, for example, Bexxar.

Examples of prenyl-protein transferase inhibitors that can be used in combination with the molecules of the invention include, but are not limited to, can be found in the following publications and patents: PCT International Application publication no. WO 96/30343, WO 97/18813, WO 97/21701, WO 97/23478, WO 97/38665, WO 98/28980, WO 98/29119, WO 95/32987, WO 94/19357, WO 95/08542, WO 95/11917, WO 95/12612, WO 95/12572, WO 95/10514, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/26246, WO 97/30053, WO 97/44350, and WO 98/02436; U.S. Pat. Nos. 5,420,245, 5,523,430, 5,532,359, 5,510,510, 5,589,485, 5,602,098, 5,661,152, 5,571,792; and. European Patent Application publication nos. 0 618 221, 0 675 112, 0 604 181, 0 696 593. For an example of the role of a prenyl-protein transferase inhibitor on angiogenesis see *European J. of Cancer*, Vol. 35, No. 9, pp. 1394-1401 (1999).

Examples of angiogenesis inhibitors that can be used in combination with the molecules of the invention include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec., Vol.* 238, p. 68 (1994); *FEBS Letters*, Vol. 372, p. 83 (1995); *Clin. Orthop.* Vol. 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonylgumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186), endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)-phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis may also be used in combination with the molecules of the instant invention and include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways that can be used in combination with the compounds of the invention include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in PCT Publication WO 03/013,526 and U.S. Ser. No. 60/349,925 (filed Jan. 18, 2002).

Agents that interfere with cell cycle checkpoints that can be used in combination with the molecules of the invention include, but are not limited to, inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

Agents that interfere with receptor tyrosine kinases (RTKs) that can be used in combination with the molecules of the invention include, but are not limited to, inhibitors of c-Kit, Eph, PDGF, Flt3 and MAPK1. Further agents include inhibitors of RTKs as described by Bume-Jensen and Hunter, *Nature,* 411:355-365, 2001.

Inhibitors of cell proliferation and survival signaling pathway that can be used in combination with the molecules of the invention include, but are not limited to, inhibitors of EGFR (for example gefitinib and erlotinib), inhibitors of ERB-2 (for example trastuzumab), inhibitors of IGFR, inhibitors of cytokine receptors, inhibitors of MAPK1, inhibitors of PI3K (for example LY294002), serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Apoptosis inducing agents that can be used in combination with the molecules of the invention include, but are not limited to, activators of TNF receptor family members (including the TRAIL receptors).

NSAIDs that are selective COX-2 inhibitors that can be used in combination with the molecules of the invention include, but are not limited to, those NSAIDs disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in combination with the molecules of the invention include: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Molecules that have been described as specific inhibitors of COX-2 and are therefore useful in the present invention include, but are not limited to: parecoxib, CELEBREX® and BEXTRA® or a pharmaceutically acceptable salt thereof.

Tyrosine kinase inhibitors that can be used in combination with the molecules of the invention include, but are not limited to, N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD 121974.

Combinations with mol other than traditional anti-cancer compounds are also encompassed in the instant compositions and methods, such as HMG-CoA reductase inhibitors, PPAR-γ (i.e., PPAR-gamma) agonists and PPAR-δ (i.e., PPAR-delta) agonists Examples of HMG-CoA reductase inhibitors that may be used that can be used in combination with the molecules of the invention include, but are not limited to, lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896) and atorvastatin (LIPITOR®; see U.S. Pat. Nos. 5,273,995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314.

PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 31:909-913 (1998); *J. Biol. Chem.* 274:9116-9121 (1999); *Invest. Ophthalmol Vis. Sci.* 41:2309-2317 (2000)). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 119: 709-717 (2001)). Examples of PPAR-γ agonists and PPAR-γ/α agonists that can be used in combination with the compounds of the invention include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in WO 2002/026729).

Another embodiment of the instant invention is the use of the presently disclosed molecules in combination with gene therapy for the treatment of cancer. For an overview of genetic strategies to treating cancer see Hall et al. (*Am J Hum Genet*

61:785-789 (1997)) and Kufe et al. (*Cancer Medicine*, 5th Ed, pp 876-889, BC Decker, Hamilton, 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August 5(8):1105-13 (1998)), and interferon gamma (*J Immunol* 164:217-222 (2000)).

The molecules of the instant invention may also be administered in combination with an inhibitor of inherent multi-drug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A molecule of the present invention may be employed in conjunction with anti-emetic agents to treat nausea or emesis, including acute, delayed, late-phase, and anticipatory emesis, which may result from the use of a molecule of the present invention, alone or with radiation therapy. For the prevention or treatment of emesis, a molecule of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the molecules of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the molecules of the present invention is selected from: 2-(R)-(1-(R)-(3,5-bis(trifluoromethyl)-phenypethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A molecule of the instant invention may also be administered with an agent useful in the treatment of anemia. Such an anemia treatment agent is, for example, a continuous eythropoiesis receptor activator (such as epoetin alfa).

A molecule of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim and PEG-filgrastim.

A molecule of the instant invention may also be administered with an immunologic-enhancing drug, such as levamisole, isoprinosine and Zadaxin.

A molecule of the instant invention may also be useful for treating or preventing cancer in combination with other siNA therapeutics.

The molecules of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A molecule of the instant invention may also be useful for treating or preventing cancer in combination with PARP inhibitors.

A molecule of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®; doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

The combinations referred to above can conveniently be presented for use in the form of a pharmaceutical formulation and thus pharmaceutical compositions comprising a combination as defined above together with a pharmaceutically acceptable diluent or carrier represent a further aspect of the invention.

The individual components of such combinations can be administered either sequentially or simultaneously in separate or combined pharmaceutical formulations.

Thus, the described molecules could be used in combination with one or more known compounds, treatments, or procedures to prevent or treat diseases, disorders, conditions, and traits described herein in a subject or organism as are known in the art, such as other MAPK1 inhibitors.

3. Therapeutic Applications

The present body of knowledge in research on IDH1-related gene expression and protein activity indicates the need for methods that can regulate their expression and/or activity for therapeutic use.

Thus, one aspect of the invention comprises a method of treating a subject including, but not limited to, a human suffering from a condition which is mediated by the action, or by loss of action, of IDH1-related gene expression, which method comprises administering to said subject an effective amount of a double-stranded siNA molecule of the invention. In one embodiment of this aspect, the siNA molecules comprises at least 15 nucleotides of SEQ ID NO: 7, SEQ ID NO: 446, SEQ ID NO: 11, SEQ ID NO: 450, SEQ ID NO: 12, SEQ ID NO: 451, SEQ ID NO: 13, SEQ ID NO: 452; SEQ ID NO: 38, SEQ ID NO: 477, SEQ ID NO: 39, SEQ ID NO: 478, SEQ ID NO: 40, SEQ ID NO: 479, SEQ ID NO: 41, SEQ ID NO: 480, SEQ ID NO: 59, SEQ ID NO: 498, SEQ ID NO: 63 or SEQ ID NO: 502; or formula (A). In another embodiment, the "at least 15 nucleotides" is 15 contiguous nucleotides In another embodiment of this aspect, the condition is or is caused by cancer. Thus, in certain embodiments the molecules and compositions of the instant invention are useful in a method for treating cancer, including the prevention or modulation of the metastases of cancer cells and cancer. Cancers treatable according to this aspect of the invention may include bladder cancer, bladder transitional cell carcinoma, urothelial carcinoma, brain cancer, gliomas, astrocytomas, breast cancer, breast carcinoma, cervical cancer, colorectal cancer, rectal cancer, colorectal carcinoma, colon cancer, hereditary nonpolyposis colorectal cancer, endometrial carcinoma, esophageal cancer, esophageal squamous cell carcinoma, ocular melanoma, uveal melanoma, intraocular melanoma, primary intraocular lymphoma, renal cell carcinoma, clear cell renal cell carcinoma, papillary renal cell carcinoma, leukemia, acute lymocytic leukemia (ALL), acute myeloid leukemia (AML), chronic myeloid (CML), chronic myelomonocytic (CMML), liver cancer, hepatoma, hepatocellular carcinoma, cholangiocarcinoma, lung cancer, small cell lung cancer (SCLC), non-small cell lung cancer (NSCLC), Non-Hodgkin lymphoma, B-cell lymphomas, T-cell lymphomas, precursor T-lymphoblastic lymphoma/leukemia, multiple myeloma, ovarian carcinoma, pancreatic cancer, pancreatic ductal adenocarcinoma, prostate cancer, prostate adenocarcinoma, rhabdomyosarcoma, embryonal rhabdomyosarcoma, skin cancer, melanoma, malignant melanoma, cutaneous melanoma, mucosal melanoma, small intestine carcinomas, stomach cancer, gastric carcinoma, testicular cancer, testicular seminomas, testicular non-seminomas, thyroid cancer, papillary thyroid carcinoma, and papillary adenocarcinomas.

siNA molecules of the invention are also used as reagents in ex vivo applications. For example, siNA reagents are introduced into tissue or cells that are transplanted into a subject for therapeutic effect. The cells and/or tissue can be derived from an organism or subject that later receives the explant, or can be derived from another organism or subject prior to transplantation. The siNA molecules can be used to modulate the expression of one or more genes in the cells or tissue, such that the cells or tissue obtain a desired phenotype or are able to perform a function when transplanted in vivo. In one embodiment, certain IDH1-related target cells from a patient are extracted. These extracted cells are contacted with IDM-related siNAs targeting a specific nucleotide sequence within the cells under conditions suitable for uptake of the siNAs by these cells (e.g., using delivery reagents such as cationic lipids, liposomes and the like or using techniques such as electroporation to facilitate the delivery of siNAs into cells). The cells are then reintroduced back into the same patient or other patients.

G. Administration

Compositions or formulations can be administered in a variety of ways. In certain embodiments, the administration of the siNA molecule is via local administration or systemic administration, either alone as a monotherapy or in combination with additional therapies described herein or as are known in the art.

The invention features contacting the subject or organism with an siNA molecule of the invention via local administration to relevant tissues or cells, such as lung cells and tissues, such as via pulmonary delivery. Local administration can include, for example, inhalation, nebulization, catheterization, implantation, direct injection, dermal/transdermal application, patches, stenting, ear/eye drops, or portal vein administration to relevant tissues, or any other local administration technique, method or procedure, as is generally known in the art.

In yet other embodiments, the invention features contacting the subject or organism with an siNA molecule of the invention via systemic administration (such as via intravenous or subcutaneous administration of siNA) to relevant tissues or cells, such as cancerous tissues or cells in a subject or organism. Systemic administration can include, for example, pulmonary (inhalation, nebulization etc.) intravenous, subcutaneous, intramuscular, catheterization, nasopharangeal, transdermal, or oral/gastrointestinal administration as is generally known in the art.

In one embodiment, the siNA molecules of the invention and formulations or compositions thereof are administered to the liver as is generally known in the art (see for example Wen et al., 2004, *World J GastroenteroL*, 10, 244-9; Murao et al., 2002, *Pharm Res.*, 19, 1808-14; Liu et al., 2003, *gene Ther.*, 10, 180-7; Hong et al., 2003, *J Pharm Pharmacol.*, 54, 51-8; Herrmann et al., 2004, *Arch Virol.*, 149, 1611-7; and Matsuno et al., 2003, *gene Ther.*, 10, 1559-66).

In one embodiment, the invention features the use of methods to deliver the siNA molecules of the instant invention to hematopoietic cells, including monocytes and lymphocytes. These methods are described in detail by Hartmann et al., 1998, *J Phamacol. Exp. Ther.*, 285(2), 920-928; Kronenwett et al., 1998, *Blood*, 91(3), 852-862; Filion and Phillips, 1997, *Biochim. Biophys. Acta.*, 1329(2), 345-356; Ma and Wei, 1996, *Leuk. Res.*, 20(11/12), 925-930; and Bongartz et al., 1994, *Nucleic Acids Research*, 22(22), 4681-8.

In one embodiment, the siNA molecules of the invention and formulations or compositions thereof are administered directly or topically (e.g., locally) to the dermis or follicles as is generally known in the art (see for example Brand, 2001, *Curr. Opin. Mol. Ther.*, 3, 244-8; Regnier et al., 1998, *J. Drug Target*, 5, 275-89; Kanikkannan, 2002, *BioDrugs*, 16, 339-47; Wraight et al., 2001, *Pharmacol. Ther.*, 90, 89-104; and Preat and Dujardin, 2001, STP PharmaSciences, 11, 57-68). In one embodiment, the siNA molecules of the invention and formulations or compositions thereof are administered directly or topically using a hydroalcoholic gel formulation comprising an alcohol (e.g., ethanol or isopropanol), water, and optionally including additional agents such isopropyl myristate and carbomer 980. In other embodiments, the siNA are formulated to be administered topically to the nasal cavity. Topical preparations can be administered by one or more applications per day to the affected area; over skin areas occlusive dressings can advantageously be used. Continuous or prolonged delivery can be achieved by an adhesive reservoir system.

In one embodiment, an siNA molecule of the invention is administered iontophoretically, for example to a particular organ or compartment (e.g., the eye, back of the eye, heart, liver, kidney, bladder, prostate, tumor, CNS etc.). Non-limiting examples of iontophoretic delivery are described in, for example, WO 03/043689 and WO 03/030989, which are incorporated by reference in their entireties herein.

In one embodiment, the siNA molecules of the invention and formulations or compositions thereof are administered to the lung as is described herein and as is generally known in the art. In another embodiment, the siNA molecules of the invention and formulations or compositions thereof are administered to lung tissues and cells as is described in U.S. Patent Publication Nos. 2006/0062758; 2006/0014289; and 2004/0077540.

Non-limiting examples of administration methods of the invention include oral, buccal, sublingual, parenteral (i.e., intraarticularly, intravenously, intraperitoneally, subcutaneously, or intramuscularly), local rectal administration or other local administration. In one embodiment, the composition of the invention can be administered by insufflation and inhalation.

In some embodiments, the pharmaceutical compositions are administered intravenously or intraperitoneally by a bolus injection (see, e.g., U.S. Pat. No. 5,286,634). Lipid nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)).

For therapeutic applications, a pharmaceutically effective dose of the siNA molecules or pharmaceutical compositions of the invention is administered to the subject. A pharmaceutically effective dose is that dose required to prevent, inhibit the occurrence, or treat (alleviate a symptom to some extent, preferably all of the symptoms) a disease state. One skilled in the art can readily determine a therapeutically effective dose of the siNA of the invention to be administered to a given subject, by taking into account factors, such as the size and weight of the subject, the extent of the disease progression or penetration, the age, health, and sex of the subject, the route of administration, and whether the administration is regional or systemic. Generally, an amount between 0.1 µg/kg and 100 mg/kg body weight/day of active ingredients is administered dependent upon potency of the negatively charged polymer. Optimal dosing schedules can be calculated from measurements of drug accumulation in the body of the patient. The siNA molecules of the invention can be administered in a single dose or in multiple doses.

siNA molecules of the instant invention can be administered once monthly, once weekly, once daily (QD), or divided into multiple monthly, weekly, or daily doses, such as, for example, but not limitation, twice daily (BID), three times daily (TID), once every two weeks. Thus, administration can be accomplished via single or divided doses. Persons of ordinary skill in the art can easily estimate repetition rates for dosing based on measured residence times and concentrations of the drug in bodily fluids or tissues.

In addition, the administration can be continuous, i.e., every day, or intermittently. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

The compositions of the present invention, either alone or in combination with other suitable components, can be made into aerosol formulations (i.e., they can be "nebulized") to be administered via inhalation (e.g., intranasally or intratracheally) (see, Brigham et al., *Am. J. Sci.*, 298:278 (1989)). Aerosol formulations can be placed into pressurized acceptable propellants, such as dichlorodifluoromethane, propane, nitrogen, and the like.

In one embodiment, the siNA molecules of the invention and formulations thereof are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the siNA compositions of the invention can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight.

Spray compositions comprising siNA molecules or compositions of the invention can, for example, be formulated as aqueous solutions or suspensions or as aerosols delivered from pressurized packs, such as a metered dose inhaler, with the use of a suitable liquefied propellant. In one embodiment, aerosol compositions of the invention suitable for inhalation can be either a suspension or a solution and generally contain an siNA molecule of the invention and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition can optionally contain additional formulation excipients well known in the art such as surfactants. Non-limiting examples include oleic acid, lecithin or an oligolactic acid or derivative such as those described in WO94/21229 and WO98/34596 and co-solvents for example ethanol. In one embodiment, a pharmaceutical aerosol formulation of the invention comprising a compound of the invention and a fluorocarbon or hydrogen-containing chlorofluorocarbon or mixtures thereof as propellant, optionally in combination with a surfactant and/or a co-solvent.

The aerosol formulations of the invention can be buffered by the addition of suitable buffering agents.

Aerosol formulations can include optional additives including preservatives if the formulation is not prepared sterile. Non-limiting examples include, methyl hydroxybenzoate, anti-oxidants, flavorings, volatile oils, buffering agents and emulsifiers and other formulation surfactants. In one embodiment, fluorocarbon or perfluorocarbon carriers are used to reduce degradation and provide safer biocompatible non-liquid particulate suspension compositions of the invention (e.g., siNA and/or LNP formulations thereof). In another embodiment, a device comprising a nebulizer delivers a composition of the invention (e.g., siNA and/or LNP formulations thereof) comprising fluorochemicals that are bacteriostatic thereby decreasing the potential for microbial growth in compatible devices.

Capsules and cartridges comprising the composition of the invention for use in an inhaler or insufflator, of for example gelatine, can be formulated containing a powder mix for inhalation of a compound of the invention and a suitable powder base such as lactose or starch. In one embodiment, each capsule or cartridge contains an siNA molecule of the invention and one or more excipients. In another embodiment, the compound of the invention can be presented without excipients such as lactose The aerosol compositions of the present invention can be administered into the respiratory system as a formulation including particles of respirable size, e.g. particles of a size sufficiently small to pass through the nose, mouth and larynx upon inhalation and through the bronchi and alveoli of the lungs. In general, respirable particles range from about 0.5 to 10 microns in size. In one embodiment, the particulate range can be from 1 to 5 microns. In another embodiment, the particulate range can be from 2 to 3 microns. Particles of non-respirable size which are included in the aerosol tend to deposit in the throat and be swallowed, and the quantity of non-respirable particles in the aerosol is thus minimized. For nasal administration, a particle size in the range of 10-500 um is preferred to ensure retention in the nasal cavity.

In some embodiments, an siNA composition of the invention is administered topically to the nose for example, for the treatment of rhinitis, via pressurized aerosol formulations, aqueous formulations administered to the nose by pressurized pump or by nebulization. Suitable formulations contain water as the diluent or carrier for this purpose. In certain embodiments, the aqueous formulations for administration of the composition of the invention to the lung or nose can be provided with conventional excipients such as buffering agents, tonicity modifying agents and the like.

The siNA molecules of the invention can be formulated and delivered as particles and/or aerosols as discussed above and dispensed from various aerosolization devices known by those of skill in the art.

Aerosols of liquid or non-liquid particles comprising an siNA molecule or formulation of the invention can be produced by any suitable means, such as with a device comprising a nebulizer (see for example U.S. Pat. No. 4,501,729) such as ultrasonic or air jet nebulizers.

Solid particle aerosols comprising an siNA molecule or formulation of the invention and surfactant can be produced with any solid particulate aerosol generator. One type of solid particle aerosol generator used with the siNA molecules of the invention is an insufflator. A second type of illustrative aerosol generator comprises a metered dose inhaler ("MDI"). MDIs containing siNA molecules or formulations taught herein can be prepared by methods of the art (for example, see Byron, above and WO96/32099).

The siNA molecules can also be formulated as a fluid formulation for delivery from a fluid dispenser, such as those described and illustrated in WO05/044354.

In certain embodiments of the invention, nebulizer devices are used in applications for conscious, spontaneously breathing subjects, and for controlled ventilated subjects of all ages. The nebulizer devices can be used for targeted topical and systemic drug delivery to the lung. In one embodiment, a device comprising a nebulizer is used to deliver an siNA molecule or formulation of the invention locally to lung or pulmonary tissues. In another embodiment, a device comprising a nebulizer is used to deliver an siNA molecule or formulation of the invention systemically.

H. Other Applications/Uses of siNA Molecules of the Invention

The siNA molecules of the invention can also be used for diagnostic applications, research applications, and/or manufacture of medicants.

In one aspect, the invention features a method for diagnosing a disease, trait, or condition in a subject comprising administering to the subject a composition of the invention under conditions suitable for the diagnosis of the disease, trait, or condition in the subject.

In another embodiment, the invention comprises use of a double-stranded nucleic acid according to the invention for use in the manufacture of a medicament. In an embodiment, the medicament is for use in treating a condition that is mediated by the action, or by loss of action, of IDH1-related genes or proteins. In an embodiment, the medicament is for use for the treatment of cell-proliferation-related disorders, including but not limited cancers of the central nervous system and AML.

EXAMPLES

The invention will now be illustrated with the following non-limiting examples. Those of skill in the art will readily recognize a variety of non-critical parameters which can be changed or modified to yield essentially the same results.

Example 1

Design and Synthesis of IDH1 siNA

IDH1 siNA Synthesis—

A series of siNA molecules were designed, synthesized and evaluated for efficacy against IDH1 gene expression. Certain IDH1 sequences were designed and selected by methods set forth in PCT international application serial no. PCT/US2010/036463 (published as WO 2010/138755), which is incorporated by reference for purposes of designing and selecting siNAs. Other sequences were designed and selected using a proprietary algorithm. siNA sequences targeting the human IDH1 mutants were selected to encompass the respective mutant sites. Target sequences within the wildtype human IDH1 gene were primarily selected from those generating high efficacy scores as determined by a proprietary algorithm. The target sequences of selected IDH1-related siNAs are set forth in Table 1a (target sequences). The sense and antisense strands of siNA sequences corresponding to the target sequences in Table 1a are set forth in Table 1b. Various chemically modified siNAs corresponding to a subset of the target sequences in Table 1a are set forth in Table 1c.

TABLE 1a

IDH1-related target sequences (5' to 3'), noting the assigned human target site number (see column 2) and the sequence identification number (SEQ ID NO) (see column 3).

| Target Sequence | Target Site (human) | SEQ ID NO: |
|---|---|---|
| AUUGGAUCUACAUAGCUAU | 342 | 1 |
| GCAUAAUGUUGGCGUCAAA | 432 | 2 |
| AAACCUAUCAUCAUAGGUC | 610a | 3 |
| AACCUAUCAUCAUAGGUCG | 611a | 4 |
| ACCUAUCAUCAUAGGUCGU | 612a | 5 |
| CCUAUCAUCAUAGGUCGUC | 613a | 6 |
| CUAUCAUCAUAGGUCGUCA | 614a | 7 |
| UAUCAUCAUAGGUCGUCAU | 615a | 8 |
| AUCAUCAUAGGUCGUCAUG | 616a | 9 |
| UCAUCAUAGGUCGUCAUGC | 617a | 10 |
| CAUCAUAGGUCGUCAUGCU | 618a | 11 |
| AUCAUAGGUCGUCAUGCUU | 619a | 12 |
| UCAUAGGUCGUCAUGCUUA | 620a | 13 |
| CAUAGGUCGUCAUGCUUAU | 621a | 14 |
| AUAGGUCGUCAUGCUUAUG | 622a | 15 |
| UAGGUCGUCAUGCUUAUGG | 623a | 16 |
| AGGUCGUCAUGCUUAUGGG | 624a | 17 |
| GGUCGUCAUGCUUAUGGGG | 625a | 18 |
| GUCGUCAUGCUUAUGGGGA | 626a | 19 |
| UCGUCAUGCUUAUGGGGAU | 627a | 20 |
| CGUCAUGCUUAUGGGGAUC | 628a | 21 |
| GUCAUGCUUAUGGGGAUCA | 629a | 22 |
| UGAAGAAGGUGGUGGUGUU | 750 | 23 |
| UCCAAAUGGCUCUGUCUAA | 824 | 24 |
| GAGCAAAGCUUGAUAACAA | 1262 | 25 |
| AGCAAAGCUUGAUAACAAU | 1263 | 26 |
| AGGUUUACCCAAUGUGCAA | 1377 | 27 |
| CAUUUGAGUUCAUGGAUAA | 1415 | 28 |
| ACUUUAAGUUCAUACCUGA | 1473 | 29 |
| AAACCUAUCAUCAUAGGUU | 610b | 30 |
| AACCUAUCAUCAUAGGUUG | 611b | 31 |
| ACCUAUCAUCAUAGGUUGU | 612b | 32 |
| CCUAUCAUCAUAGGUUGUC | 613b | 33 |
| CUAUCAUCAUAGGUUGUCA | 614b | 34 |

TABLE 1a-continued

IDH1-related target sequences (5' to 3'), noting the assigned human target site number (see column 2) and the sequence identification number (SEQ ID NO) (see column 3).

| Target Sequence | Target Site (human) | SEQ ID NO: |
|---|---|---|
| UAUCAUCAUAGGUUGUCAU | 615b | 35 |
| AUCAUCAUAGGUUGUCAUG | 616b | 36 |
| UCAUCAUAGGUUGUCAUGC | 617b | 37 |
| CAUCAUAGGUUGUCAUGCU | 618b | 38 |
| AUCAUAGGUUGUCAUGCUU | 619b | 39 |
| UCAUAGGUUGUCAUGCUUA | 620b | 40 |
| CAUAGGUUGUCAUGCUUAU | 621b | 41 |
| AUAGGUUGUCAUGCUUAUG | 622b | 42 |
| UAGGUUGUCAUGCUUAUGG | 623b | 43 |
| AGGUUGUCAUGCUUAUGGG | 624b | 44 |
| GGUUGUCAUGCUUAUGGGG | 625b | 45 |
| GUUGUCAUGCUUAUGGGGA | 626b | 46 |
| UUGUCAUGCUUAUGGGGAU | 627b | 47 |
| UGUCAUGCUUAUGGGGAUC | 628b | 48 |
| AACCUAUCAUCAUAGGUCA | 611c | 49 |
| ACCUAUCAUCAUAGGUCAU | 612c | 50 |
| CCUAUCAUCAUAGGUCAUC | 613c | 51 |

TABLE 1a-continued

IDH1-related target sequences (5' to 3'), noting the assigned human target site number (see column 2) and the sequence identification number (SEQ ID NO) (see column 3).

| Target Sequence | Target Site (human) | SEQ ID NO: |
|---|---|---|
| CUAUCAUCAUAGGUCAUCA | 614c | 52 |
| UAUCAUCAUAGGUCAUCAU | 615c | 53 |
| AUCAUCAUAGGUCAUCAUG | 616c | 54 |
| UCAUCAUAGGUCAUCAUGC | 617c | 55 |
| CAUCAUAGGUCAUCAUGCU | 618c | 56 |
| AUCAUAGGUCAUCAUGCUU | 619c | 57 |
| UCAUAGGUCAUCAUGCUUA | 620c | 58 |
| CAUAGGUCAUCAUGCUUAU | 621c | 59 |
| AUAGGUCAUCAUGCUUAUG | 622c | 60 |
| UAGGUCAUCAUGCUUAUGG | 623c | 61 |
| AGGUCAUCAUGCUUAUGGG | 624c | 62 |
| GGUCAUCAUGCUUAUGGGG | 625c | 63 |
| GUCAUCAUGCUUAUGGGGA | 626c | 64 |
| UCAUCAUGCUUAUGGGGAU | 627c | 65 |
| CAUCAUGCUUAUGGGGAUC | 628c | 66 |
| AUCAUGCUUAUGGGGAUCA | 629c | 67 |

TABLE 1b

Various IDH1-related siNA sense and antisense sequences (5' to 3') corresponding to the selected target site sequences in Table 1a. Antisense sequences are readily identified as being complementary to the sense sequence shown. The SEQ ID NOs listed in column 2 correspond to the sense sequences listed in column 3. The SEQ ID NOs listed in column 5 correspond to the antisense sequences listed in column 4.

| Target Site (human) | SEQ ID NO: | Sense (Target) Sequence (5' to 3') | Antisense Sequence (5' to 3') | SEQ ID NO: |
|---|---|---|---|---|
| 342 | 1 | AUUGGAUCUACAUAGCUAU | AUAGCUAUGUAGAUCCAAU | 440 |
| 432 | 2 | GCAUAAUGUUGGCGUCAAA | UUUGACGCCAACAUUAUGC | 441 |
| 610a | 3 | AAACCUAUCAUCAUAGGUC | GACCUAUGAUGAUAGGUUU | 442 |
| 611a | 4 | AACCUAUCAUCAUAGGUCG | CGACCUAUGAUGAUAGGUU | 443 |
| 612a | 5 | ACCUAUCAUCAUAGGUCGU | ACGACCUAUGAUGAUAGGU | 444 |
| 613a | 6 | CCUAUCAUCAUAGGUCGUC | GACGACCUAUGAUGAUAGG | 445 |
| 614a | 7 | CUAUCAUCAUAGGUCGUCA | UGACGACCUAUGAUGAUAG | 446 |
| 615a | 8 | UAUCAUCAUAGGUCGUCAU | AUGACGACCUAUGAUGAUA | 447 |
| 616a | 9 | AUCAUCAUAGGUCGUCAUG | CAUGACGACCUAUGAUGAU | 448 |
| 617a | 10 | UCAUCAUAGGUCGUCAUGC | GCAUGACGACCUAUGAUGA | 449 |
| 618a | 11 | CAUCAUAGGUCGUCAUGCU | AGCAUGACGACCUAUGAUG | 450 |

TABLE 1b-continued

Various IDH1-related siNA sense and antisense sequences (5' to 3') corresponding to the selected target site sequences in Table 1a. Antisense sequences are readily identified as being complementary to the sense sequence shown. The SEQ ID NOs listed in column 2 correspond to the sense sequences listed in column 3. The SEQ ID NOs listed in column 5 correspond to the antisense sequences listed in column 4.

| Target Site (human) | SEQ ID NO: | Sense (Target) Sequence (5' to 3') | Antisense Sequence (5' to 3') | SEQ ID NO: |
|---|---|---|---|---|
| 619a | 12 | AUCAUAGGUCGUCAUGCUU | AAGCAUGACGACCUAUGAU | 451 |
| 620a | 13 | UCAUAGGUCGUCAUGCUUA | UAAGCAUGACGACCUAUGA | 452 |
| 621a | 14 | CAUAGGUCGUCAUGCUUAU | AUAAGCAUGACGACCUAUG | 453 |
| 622a | 15 | AUAGGUCGUCAUGCUUAUG | CAUAAGCAUGACGACCUAU | 454 |
| 623a | 16 | UAGGUCGUCAUGCUUAUGG | CCAUAAGCAUGACGACCUA | 455 |
| 624a | 17 | AGGUCGUCAUGCUUAUGGG | CCCAUAAGCAUGACGACCU | 456 |
| 625a | 18 | GGUCGUCAUGCUUAUGGGG | CCCCAUAAGCAUGACGACC | 457 |
| 626a | 19 | GUCGUCAUGCUUAUGGGGA | UCCCCAUAAGCAUGACGAC | 458 |
| 627a | 20 | UCGUCAUGCUUAUGGGGAU | AUCCCCAUAAGCAUGACGA | 459 |
| 628a | 21 | CGUCAUGCUUAUGGGGAUC | GAUCCCCAUAAGCAUGACG | 460 |
| 629a | 22 | GUCAUGCUUAUGGGGAUCA | UGAUCCCCAUAAGCAUGAC | 461 |
| 750 | 23 | UGAAGAAGGUGGUGGUGUU | AACACCACCACCUUCUUCA | 462 |
| 824 | 24 | UCCAAAUGGCUCUGUCUAA | UUAGACAGAGCCAUUUGGA | 463 |
| 1262 | 25 | GAGCAAAGCUUGAUAACAA | UUGUUAUCAAGCUUUGCUC | 464 |
| 1263 | 26 | AGCAAAGCUUGAUAACAAU | AUUGUUAUCAAGCUUUGCU | 465 |
| 1377 | 27 | AGGUUUACCCAAUGUGCAA | UUGCACAUUGGGUAAACCU | 466 |
| 1415 | 28 | CAUUUGAGUUCAUGGAUAA | UUAUCCAUGAACUCAAAUG | 467 |
| 1473 | 29 | ACUUUAAGUUCAUACCUGA | UCAGGUAUGAACUUAAAGU | 468 |
| 610b | 30 | AAACCUAUCAUCAUAGGUU | AACCUAUGAUGAUAGGUUU | 469 |
| 611b | 31 | AACCUAUCAUCAUAGGUUG | CAACCUAUGAUGAUAGGUU | 470 |
| 612b | 32 | ACCUAUCAUCAUAGGUUGU | ACAACCUAUGAUGAUAGGU | 471 |
| 613b | 33 | CCUAUCAUCAUAGGUUGUC | GACAACCUAUGAUGAUAGG | 472 |
| 614b | 34 | CUAUCAUCAUAGGUUGUCA | UGACAACCUAUGAUGAUAG | 473 |
| 615b | 35 | UAUCAUCAUAGGUUGUCAU | AUGACAACCUAUGAUGAUA | 474 |
| 616b | 36 | AUCAUCAUAGGUUGUCAUG | CAUGACAACCUAUGAUGAU | 475 |
| 617b | 37 | UCAUCAUAGGUUGUCAUGC | GCAUGACAACCUAUGAUGA | 476 |
| 618b | 38 | CAUCAUAGGUUGUCAUGCU | AGCAUGACAACCUAUGAUG | 477 |
| 619b | 39 | AUCAUAGGUUGUCAUGCUU | AAGCAUGACAACCUAUGAU | 478 |
| 620b | 40 | UCAUAGGUUGUCAUGCUUA | UAAGCAUGACAACCUAUGA | 479 |
| 621b | 41 | CAUAGGUUGUCAUGCUUAU | AUAAGCAUGACAACCUAUG | 480 |
| 622b | 42 | AUAGGUUGUCAUGCUUAUG | CAUAAGCAUGACAACCUAU | 481 |
| 623b | 43 | UAGGUUGUCAUGCUUAUGG | CCAUAAGCAUGACAACCUA | 482 |
| 624b | 44 | AGGUUGUCAUGCUUAUGGG | CCCAUAAGCAUGACAACCU | 483 |
| 625b | 45 | GGUUGUCAUGCUUAUGGGG | CCCCAUAAGCAUGACAACC | 484 |
| 626b | 46 | GUUGUCAUGCUUAUGGGGA | UCCCCAUAAGCAUGACAAC | 485 |

TABLE 1b-continued

Various IDH1-related siNA sense and antisense sequences (5' to 3') corresponding to the selected target site sequences in Table 1a. Antisense sequences are readily identified as being complementary to the sense sequence shown. The SEQ ID NOs listed in column 2 correspond to the sense sequences listed in column 3. The SEQ ID NOs listed in column 5 correspond to the antisense sequences listed in column 4.

| Target Site (human) | SEQ ID NO: | Sense (Target) Sequence (5' to 3') | Antisense Sequence (5' to 3') | SEQ ID NO: |
|---|---|---|---|---|
| 627b | 47 | UUGUCAUGCUUAUGGGGAU | AUCCCCAUAAGCAUGACAA | 486 |
| 628b | 48 | UGUCAUGCUUAUGGGGAUC | GAUCCCCAUAAGCAUGACA | 487 |
| 611c | 49 | AACCUAUCAUCAUAGGUCA | UGACCUAUGAUGAUAGGUU | 488 |
| 612c | 50 | ACCUAUCAUCAUAGGUCAU | AUGACCUAUGAUGAUAGGU | 489 |
| 613c | 51 | CCUAUCAUCAUAGGUCAUC | GAUGACCUAUGAUGAUAGG | 490 |
| 614c | 52 | CUAUCAUCAUAGGUCAUCA | UGAUGACCUAUGAUGAUAG | 491 |
| 615c | 53 | UAUCAUCAUAGGUCAUCAU | AUGAUGACCUAUGAUGAUA | 492 |
| 616c | 54 | AUCAUCAUAGGUCAUCAUG | CAUGAUGACCUAUGAUGAU | 493 |
| 617c | 55 | UCAUCAUAGGUCAUCAUGC | GCAUGAUGACCUAUGAUGA | 494 |
| 618c | 56 | CAUCAUAGGUCAUCAUGCU | AGCAUGAUGACCUAUGAUG | 495 |
| 619c | 57 | AUCAUAGGUCAUCAUGCUU | AAGCAUGAUGACCUAUGAU | 496 |
| 620c | 58 | UCAUAGGUCAUCAUGCUUA | UAAGCAUGAUGACCUAUGA | 497 |
| 621c | 59 | CAUAGGUCAUCAUGCUUAU | AUAAGCAUGAUGACCUAUG | 498 |
| 622c | 60 | AUAGGUCAUCAUGCUUAUG | CAUAAGCAUGAUGACCUAU | 499 |
| 623c | 61 | UAGGUCAUCAUGCUUAUGG | CCAUAAGCAUGAUGACCUA | 500 |
| 624c | 62 | AGGUCAUCAUGCUUAUGGG | CCCAUAAGCAUGAUGACCU | 501 |
| 625c | 63 | GGUCAUCAUGCUUAUGGGG | CCCCAUAAGCAUGAUGACC | 502 |
| 626c | 64 | GUCAUCAUGCUUAUGGGGA | UCCCCAUAAGCAUGAUGAC | 503 |
| 627c | 65 | UCAUCAUGCUUAUGGGGAU | AUCCCCAUAAGCAUGAUGA | 504 |
| 628c | 66 | CAUCAUGCUUAUGGGGAUC | GAUCCCCAUAAGCAUGAUG | 505 |
| 629c | 67 | AUCAUGCUUAUGGGGAUCA | UGAUCCCCAUAAGCAUGAU | 506 |

For each oligonucleotide of a target sequence, the two individual, complementary strands of the siNA were synthesized separately using solid phase synthesis, then purified separately by reversed phase solid phase extraction (SPE). The complementary strands were annealed to form the double strand (duplex) and delivered in the desired concentration and buffer of choice.

Briefly, the single strand oligonucleotides were synthesized using phosphoramidite chemistry on an automated solid-phase synthesizer, using procedures as are generally known in the art (see for example U.S. application Ser. No. 12/064,014, published as US 20090176725). A synthesis column was packed with solid support derivatized with the first nucleoside residue (natural or chemically modified). Synthesis was initiated by detritylation of the acid labile 5'-O-dimethoxytrityl group to release the 5'-hydroxyl. A suitably protected phosphoramidite and a suitable activator in acetonitrile were delivered simultaneously to the synthesis column resulting in coupling of the amidite to the 5'-hydroxyl. The column was then washed with a solvent, such as acetonitrile.

An oxidizing solution, such as an iodine solution, was pumped through the column to oxidize the phosphite triester linkage P(III) to its phosphotriester P(V) analog. Unreacted 5'-hydroxyl groups were capped using reagents such as acetic anhydride in the presence of 2,6-lutidine and N-methylimidazole. The elongation cycle was resumed with the detritylation step for the next phosphoramidite incorporation. This process was repeated until the desired sequence was synthesized. The synthesis concluded with the final 5'-terminus protecting group (trityl or 5'-O-dimethoxytrityl).

Upon completion of the synthesis, the solid-support and associated oligonucleotide were dried under argon pressure or vacuum. Aqueous base was added and the mixture was heated to effect cleavage of the succinyl linkage, removal of the cyanoethyl phosphate protecting group, and deprotection of the exocyclic amine protection.

The following process was performed on single strands that do not contain ribonucleotides. After treating the solid support with the aqueous base, the mixture was filtered to separate the solid support from the deprotected crude synthesis material. The solid support was then rinsed with water, which is combined with the filtrate. The resultant basic solution allows for retention of the 5'-O-dimethoxytrityl group on the 5' terminal position (trityl-on).

For single strands that contain ribonucleotides, the following process was performed. After treating the solid support with the aqueous base, the mixture was filtered to separate the solid support from the deprotected crude synthesis material. The solid support was then rinsed with dimethylsulfoxide (DMSO), which was combined with the filtrate. A fluoride reagent, such as triethylamine trihydrofluoride, was added to the mixture, and the solution was heated. The reaction was quenched with suitable buffer to provide a solution of crude single strand with the 5'-O-dimethoxytrityl group on the final 5' terminal position.

The trityl-on solution of each crude single strand was purified using chromatographic purification, such as SPE RPC purification. The hydrophobic nature of the trityl group permits stronger retention of the desired full-length oligo than the non-tritylated truncated failure sequences. The failure sequences were selectively washed from the resin with a suitable solvent, such as low percent acetonitrile. Retained oligonucleotides were then detritylated on the column with trifluoroacetic acid to remove the acid-labile trityl group. Residual acid was washed from the column, a salt exchange was performed, and a final desalting of the material commenced. The full-length oligo was recovered in a purified form with an aqueous-organic solvent. The final product was then analyzed for purity (HPLC), identity (Maldi-TOF MS), and yield (UV $A_{260}$). The oligos were dried via lyophilization or vacuum condensation.

To anneal, based on the analysis of the product, the dried oligos were dissolved in appropriate buffers followed by mixing equal molar amounts (calculated using the theoretical extinction coefficient) of the sense and antisense oligonucleotide strands. The solution was then analyzed for purity of duplex by chromatographic methods and desired final concentration. If the analysis indicated an excess of either strand, then the additional non-excess strand was titrated until duplexing was complete. When analysis indicated that the target product purity has been achieved, the material was ready for use.

Table 1c shows various chemically-modified siNAs either synthesized using this protocol or that can be synthesized using this protocol or other methods known in the art. Each "siNA duplex ID" number within Table 1c represents a single siNA duplex having a sense and an antisense strand, wherein the sense and antisense strands are comprised of the nucleotides, and chemically-modified forms of those nucleotides, as listed. For example, siNA duplex ID number R-008364807-000W is a double-stranded siNA duplex directed to target site 342 of human IDH1 having the sequence 5'-AUUGGAUCUACAUAGCUAU-3' (SEQ ID NO: 1) (shown in column 4 of Table 1c for this duplex ID no.). There are two entries for duplex R-008364807-000W (see rows 2 and 3 of the table), as for each of the listed siNA duplex ID numbers within Table 1c. These entries differ in the "Modified Sequence" column (column 5) of the table. For each of the duplexes listed in this table, the sequence provided in the "Modified Sequence" column of the first entry of the duplex represents the sense strand (e.g., SEQ ID NO: 68 for duplex R-008364807-000W), and the sequence provided in the "Modified Sequence" column of the second entry of the duplex represents the antisense strand (e.g., SEQ ID NO: 69 for duplex R-008364807-000W). Antisense sequences are readily identified as being complementary to the target sequence (sense sequence) shown.

TABLE 1c

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008364807-000W | 342 | 1 | AUUGGAUCUACAUAGCUAU | B AUUGGAUCUACAUAGCUAUTT B | 68 |
| R-008364807-000W | 342 | 1 | AUUGGAUCUACAUAGCUAU | AUAGCUAUGUAGAUCCAAUUU | 69 |
| R-008364798-000B | 432 | 2 | GCAUAAUGUUGGCGUCAAA | B GCAUAAUGUUGGCGUCAAATT B | 70 |
| R-008364798-000B | 432 | 2 | GCAUAAUGUUGGCGUCAAA | UUUGACGCCAACAUUAUGCUU | 71 |
| R-008415563-000N | 610a | 3 | AAACCUAUCAUCAUAGGUC | AAACCUAUCAUCAUAGGUCTT | 72 |
| R-008415563-000N | 610a | 3 | AAACCUAUCAUCAUAGGUC | GACCUAUGAUGAUAGGUUUTT | 73 |
| R-008405385-000G | 610a | 3 | AAACCUAUCAUCAUAGGUC | B AAACCUAUCAUCAUAGGUCTT B | 74 |
| R-008405385-000G | 610a | 3 | AAACCUAUCAUCAUAGGUC | GACCUAUGAUGAUAGGUUUUU | 75 |
| R-008415522-000K | 611a | 4 | AACCUAUCAUCAUAGGUCG | AACCUAUCAUCAUAGGUCGTT | 76 |
| R-008415522-000K | 611a | 4 | AACCUAUCAUCAUAGGUCG | CGACCUAUGAUGAUAGGUUTT | 77 |
| R-008405184-000D | 611a | 4 | AACCUAUCAUCAUAGGUCG | B AACCUAUCAUCAUAGGUCGTT B | 78 |
| R-008405184-000D | 611a | 4 | AACCUAUCAUCAUAGGUCG | CGACCUAUGAUGAUAGGUUUU | 79 |
| R-008415697-000K | 612a | 5 | ACCUAUCAUCAUAGGUCGU | ACCUAUCAUCAUAGGUCGUTT | 80 |
| R-008415697-000K | 612a | 5 | ACCUAUCAUCAUAGGUCGU | ACGACCUAUGAUGAUAGGUTT | 81 |
| R-008405472-000Y | 612a | 5 | ACCUAUCAUCAUAGGUCGU | B ACCUAUCAUCAUAGGUCGUTT B | 82 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
| --- | --- | --- | --- | --- | --- |
| R-008405472-000Y | 612a | 5 | ACCUAUCAUCAUAGGUCGU | ACGACCUAUGAUGAUAGGUUU | 83 |
| R-008415694-000J | 613a | 6 | CCUAUCAUCAUAGGUCGUC | CCUAUCAUCAUAGGUCGUCTT | 84 |
| R-008415694-000J | 613a | 6 | CCUAUCAUCAUAGGUCGUC | GACGACCUAUGAUGAUAGGTT | 85 |
| R-008405049-000T | 613a | 6 | CCUAUCAUCAUAGGUCGUC | B CCUAUCAUCAUAGGUCGUCTT B | 86 |
| R-008405049-000T | 613a | 6 | CCUAUCAUCAUAGGUCGUC | GACGACCUAUGAUGAUAGGUU | 87 |
| R-008415691-000H | 614a | 7 | CUAUCAUCAUAGGUCGUCA | CUAUCAUCAUAGGUCGUCATT | 88 |
| R-008415691-000H | 614a | 7 | CUAUCAUCAUAGGUCGUCA | UGACGACCUAUGAUGAUAGTT | 89 |
| R-008364795-000A | 614a | 7 | CUAUCAUCAUAGGUCGUCA | B CUAUCAUCAUAGGUCGUCATT B | 90 |
| R-008364795-000A | 614a | 7 | CUAUCAUCAUAGGUCGUCA | UGACGACCUAUGAUGAUAGUU | 91 |
| R-008415629-000F | 615a | 8 | UAUCAUCAUAGGUCGUCAU | AUGACGACCUAUGAUGAUATT | 92 |
| R-008415629-000F | 615a | 8 | UAUCAUCAUAGGUCGUCAU | UAUCAUCAUAGGUCGUCAUTT | 93 |
| R-008404959-000D | 615a | 8 | UAUCAUCAUAGGUCGUCAU | B UAUCAUCAUAGGUCGUCAUTT B | 94 |
| R-008404959-000D | 615a | 8 | UAUCAUCAUAGGUCGUCAU | AUGACGACCUAUGAUGAUAUU | 95 |
| R-008415688-000B | 616a | 9 | AUCAUCAUAGGUCGUCAUG | AUCAUCAUAGGUCGUCAUGTT | 96 |
| R-008415688-000B | 616a | 9 | AUCAUCAUAGGUCGUCAUG | CAUGACGACCUAUGAUGAUTT | 97 |
| R-008405469-000S | 616a | 9 | AUCAUCAUAGGUCGUCAUG | B AUCAUCAUAGGUCGUCAUGTT B | 98 |
| R-008405469-000S | 616a | 9 | AUCAUCAUAGGUCGUCAUG | CAUGACGACCUAUGAUGAUUU | 99 |
| R-008415483-000N | 617a | 10 | UCAUCAUAGGUCGUCAUGC | GCAUGACGACCUAUGAUGATT | 100 |
| R-008415483-000N | 617a | 10 | UCAUCAUAGGUCGUCAUGC | UCAUCAUAGGUCGUCAUGCTT | 101 |
| R-008405310-000S | 617a | 10 | UCAUCAUAGGUCGUCAUGC | B UCAUCAUAGGUCGUCAUGCTT B | 102 |
| R-008405310-000S | 617a | 10 | UCAUCAUAGGUCGUCAUGC | GCAUGACGACCUAUGAUGAUU | 103 |
| R-000372127-000H | 618a | 11 | CAUCAUAGGUCGUCAUGCU | AGCAUGACGACCUAUGAUGTT | 104 |
| R-000372127-000H | 618a | 11 | CAUCAUAGGUCGUCAUGCU | CAUCAUAGGUCGUCAUGCUTT | 105 |
| R-008405466-000R | 618a | 11 | CAUCAUAGGUCGUCAUGCU | B CAUCAUAGGUCGUCAUGCUTT B | 106 |
| R-008405466-000R | 618a | 11 | CAUCAUAGGUCGUCAUGCU | AGCAUGACGACCUAUGAUGUU | 107 |
| R-008415596-000S | 619a | 12 | AUCAUAGGUCGUCAUGCUU | AAGCAUGACGACCUAUGAUTT | 108 |
| R-008415596-000S | 619a | 12 | AUCAUAGGUCGUCAUGCUU | AUCAUAGGUCGUCAUGCUUTT | 109 |
| R-008405253-000C | 619a | 12 | AUCAUAGGUCGUCAUGCUU | B AUCAUAGGUCGUCAUGCUUTT B | 110 |
| R-008405253-000C | 619a | 12 | AUCAUAGGUCGUCAUGCUU | AAGCAUGACGACCUAUGAUUU | 111 |
| R-008415480-000M | 620a | 13 | UCAUAGGUCGUCAUGCUUA | UAAGCAUGACGACCUAUGATT | 112 |
| R-008415480-000M | 620a | 13 | UCAUAGGUCGUCAUGCUUA | UCAUAGGUCGUCAUGCUUATT | 113 |
| R-008405463-000P | 620a | 13 | UCAUAGGUCGUCAUGCUUA | B UCAUAGGUCGUCAUGCUUATT B | 114 |
| R-008405463-000P | 620a | 13 | UCAUAGGUCGUCAUGCUUA | UAAGCAUGACGACCUAUGAUU | 115 |
| R-000372128-000S | 621a | 14 | CAUAGGUCGUCAUGCUUAU | AUAAGCAUGACGACCUAUGTT | 116 |
| R-000372128-000S | 621a | 14 | CAUAGGUCGUCAUGCUUAU | CAUAGGUCGUCAUGCUUAUTT | 117 |
| R-008405382-000F | 621a | 14 | CAUAGGUCGUCAUGCUUAU | B CAUAGGUCGUCAUGCUUAUTT B | 118 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008405382-000F | 621a | 14 | CAUAGGUCGUCAUGCUUAU | AUAAGCAUGACGACCUAUGUU | 119 |
| R-008415477-000F | 622a | 15 | AUAGGUCGUCAUGCUUAUG | AUAGGUCGUCAUGCUUAUGTT | 120 |
| R-008415477-000F | 622a | 15 | AUAGGUCGUCAUGCUUAUG | CAUAAGCAUGACGACCUAUTT | 121 |
| R-008405046-000S | 622a | 15 | AUAGGUCGUCAUGCUUAUG | B AUAGGUCGUCAUGCUUAUGTT B | 122 |
| R-008405046-000S | 622a | 15 | AUAGGUCGUCAUGCUUAUG | CAUAAGCAUGACGACCUAUUU | 123 |
| R-008415519-000D | 623a | 16 | UAGGUCGUCAUGCUUAUGG | CCAUAAGCAUGACGACCUATT | 124 |
| R-008415519-000D | 623a | 16 | UAGGUCGUCAUGCUUAUGG | UAGGUCGUCAUGCUUAUGGTT | 125 |
| R-008405460-000N | 623a | 16 | UAGGUCGUCAUGCUUAUGG | B UAGGUCGUCAUGCUUAUGGTT B | 126 |
| R-008405460-000N | 623a | 16 | UAGGUCGUCAUGCUUAUGG | CCAUAAGCAUGACGACCUAUU | 127 |
| R-008415474-000E | 624a | 17 | AGGUCGUCAUGCUUAUGGG | AGGUCGUCAUGCUUAUGGGTT | 128 |
| R-008415474-000E | 624a | 17 | AGGUCGUCAUGCUUAUGGG | CCCAUAAGCAUGACGACCUTT | 129 |
| R-008405100-000E | 624a | 17 | AGGUCGUCAUGCUUAUGGG | B AGGUCGUCAUGCUUAUGGGTT B | 130 |
| R-008405100-000E | 624a | 17 | AGGUCGUCAUGCUUAUGGG | CCCAUAAGCAUGACGACCUUU | 131 |
| R-008415651-000N | 625a | 18 | GGUCGUCAUGCUUAUGGGG | CCCCAUAAGCAUGACGACCTT | 132 |
| R-008415651-000N | 625a | 18 | GGUCGUCAUGCUUAUGGGG | GGUCGUCAUGCUUAUGGGGTT | 133 |
| R-008405181-000C | 625a | 18 | GGUCGUCAUGCUUAUGGGG | B GGUCGUCAUGCUUAUGGGGTT B | 134 |
| R-008405181-000C | 625a | 18 | GGUCGUCAUGCUUAUGGGG | CCCCAUAAGCAUGACGACCUU | 135 |
| R-008415471-000D | 626a | 19 | GUCGUCAUGCUUAUGGGGA | GUCGUCAUGCUUAUGGGGATT | 136 |
| R-008415471-000D | 626a | 19 | GUCGUCAUGCUUAUGGGGA | UCCCCAUAAGCAUGACGACTT | 137 |
| R-008405457-000G | 626a | 19 | GUCGUCAUGCUUAUGGGGA | B GUCGUCAUGCUUAUGGGGATT B | 138 |
| R-008405457-000G | 626a | 19 | GUCGUCAUGCUUAUGGGGA | UCCCCAUAAGCAUGACGACUU | 139 |
| R-008415516-000C | 627a | 20 | UCGUCAUGCUUAUGGGGAU | AUCCCCAUAAGCAUGACGATT | 140 |
| R-008415516-000C | 627a | 20 | UCGUCAUGCUUAUGGGGAU | UCGUCAUGCUUAUGGGGAUTT | 141 |
| R-008405379-000Z | 627a | 20 | UCGUCAUGCUUAUGGGGAU | B UCGUCAUGCUUAUGGGGAUTT B | 142 |
| R-008405379-000Z | 627a | 20 | UCGUCAUGCUUAUGGGGAU | AUCCCCAUAAGCAUGACGAUU | 143 |
| R-008415593-000R | 628a | 21 | CGUCAUGCUUAUGGGGAUC | CGUCAUGCUUAUGGGGAUCTT | 144 |
| R-008415593-000R | 628a | 21 | CGUCAUGCUUAUGGGGAUC | GAUCCCCAUAAGCAUGACGTT | 145 |
| R-008405178-000W | 628a | 21 | CGUCAUGCUUAUGGGGAUC | B CGUCAUGCUUAUGGGGAUCTT B | 146 |
| R-008405178-000W | 628a | 21 | CGUCAUGCUUAUGGGGAUC | GAUCCCCAUAAGCAUGACGUU | 147 |
| R-008415560-000M | 629a | 22 | GUCAUGCUUAUGGGGAUCA | GUCAUGCUUAUGGGGAUCATT | 148 |
| R-008415560-000M | 629a | 22 | GUCAUGCUUAUGGGGAUCA | UGAUCCCCAUAAGCAUGACTT | 149 |
| R-008404956-000C | 629a | 22 | GUCAUGCUUAUGGGGAUCA | B GUCAUGCUUAUGGGGAUCATT B | 150 |
| R-008404956-000C | 629a | 22 | GUCAUGCUUAUGGGGAUCA | UGAUCCCCAUAAGCAUGACUU | 151 |
| R-008364801-000U | 750 | 23 | UGAAGAAGGUGGUGGUGUU | B UGAAGAAGGUGGUGGUGUUTT B | 152 |
| R-008364801-000U | 750 | 23 | UGAAGAAGGUGGUGGUGUU | AACACCACCACCUUCUUCAUU | 153 |
| R-008364639-000W | 824 | 24 | UCCAAAUGGCUCUGUCUAA | B UCCAAAUGGCUCUGUCUAATT B | 154 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008364639-000W | 824 | 24 | UCCAAAUGGCUCUGUCUAA | UUAGACAGAGCCAUUUGGAUU | 155 |
| R-008364804-000V | 1262 | 25 | GAGCAAAGCUUGAUAACAA | B GAGCAAAGCUUGAUAACAATT B | 156 |
| R-008364804-000V | 1262 | 25 | GAGCAAAGCUUGAUAACAA | UUGUUAUCAAGCUUUGCUCUU | 157 |
| R-008364839-000R | 1263 | 26 | AGCAAAGCUUGAUAACAAU | B AGCAAAGCUUGAUAACAAUTT B | 158 |
| R-008364839-000R | 1263 | 26 | AGCAAAGCUUGAUAACAAU | AUUGUUAUCAAGCUUUGCUUU | 159 |
| R-008364636-000V | 1377 | 27 | AGGUUUACCCAAUGUGCAA | B AGGUUUACCCAAUGUGCAATT B | 160 |
| R-008364636-000V | 1377 | 27 | AGGUUUACCCAAUGUGCAA | UUGCACAUUGGGUAAACCUUU | 161 |
| R-008364836-000P | 1415 | 28 | CAUUUGAGUUCAUGGAUAA | B CAUUUGAGUUCAUGGAUAATT B | 162 |
| R-008364836-000P | 1415 | 28 | CAUUUGAGUUCAUGGAUAA | UUAUCCAUGAACUCAAAUGUU | 163 |
| R-008364735-000W | 1473 | 29 | ACUUUAAGUUCAUACCUGA | B ACUUUAAGUUCAUACCUGATT B | 164 |
| R-008364735-000W | 1473 | 29 | ACUUUAAGUUCAUACCUGA | UCAGGUAUGAACUUAAAGUUU | 165 |
| R-008372792-000Z | 610b | 30 | AAACCUAUCAUCAUAGGUU | B AAACCUAUCAUCAUAGGUUUsU B | 166 |
| R-008372792-000Z | 610b | 30 | AAACCUAUCAUCAUAGGUU | AACCUAUGAUGAUAGGUUUUsU | 167 |
| R-008415684-000S | 610b | 30 | AAACCUAUCAUCAUAGGUU | AAACCUAUCAUCAUAGGUUTT | 168 |
| R-008415684-000S | 610b | 30 | AAACCUAUCAUCAUAGGUU | AACCUAUGAUGAUAGGUUUTT | 169 |
| R-008372838-000G | 611b | 31 | AACCUAUCAUCAUAGGUUG | B AACCUAUCAUCAUAGGUUGUsU B | 170 |
| R-008372838-000G | 611b | 31 | AACCUAUCAUCAUAGGUUG | CAACCUAUGAUGAUAGGUUUsU | 171 |
| R-008415510-000A | 611b | 31 | AACCUAUCAUCAUAGGUUG | AACCUAUCAUCAUAGGUUGTT | 172 |
| R-008415510-000A | 611b | 31 | AACCUAUCAUCAUAGGUUG | CAACCUAUGAUGAUAGGUUTT | 173 |
| R-008372817-000N | 612b | 32 | ACCUAUCAUCAUAGGUUGU | B ACCUAUCAUCAUAGGUUGUUsU B | 174 |
| R-008372817-000N | 612b | 32 | ACCUAUCAUCAUAGGUUGU | ACAACCUAUGAUGAUAGGUUsU | 175 |
| R-008415681-000R | 612b | 32 | ACCUAUCAUCAUAGGUUGU | ACAACCUAUGAUGAUAGGUTT | 176 |
| R-008415681-000R | 612b | 32 | ACCUAUCAUCAUAGGUUGU | ACCUAUCAUCAUAGGUUGUTT | 177 |
| R-008372814-000M | 613b | 33 | CCUAUCAUCAUAGGUUGUC | B CCUAUCAUCAUAGGUUGUCUsU B | 178 |
| R-008372814-000M | 613b | 33 | CCUAUCAUCAUAGGUUGUC | GACAACCUAUGAUGAUAGGUsU | 179 |
| R-008415507-000U | 613b | 33 | CCUAUCAUCAUAGGUUGUC | CCUAUCAUCAUAGGUUGUCTT | 180 |
| R-008415507-000U | 613b | 33 | CCUAUCAUCAUAGGUUGUC | GACAACCUAUGAUGAUAGGTT | 181 |
| R-008372889-000C | 614b | 34 | CUAUCAUCAUAGGUUGUCA | B CUAUCAUCAUAGGUUGUCAUsU B | 182 |
| R-008372889-000C | 614b | 34 | CUAUCAUCAUAGGUUGUCA | UGACAACCUAUGAUGAUAGUsU | 183 |
| R-008415588-000S | 614b | 34 | CUAUCAUCAUAGGUUGUCA | CUAUCAUCAUAGGUUGUCATT | 184 |
| R-008415588-000S | 614b | 34 | CUAUCAUCAUAGGUUGUCA | UGACAACCUAUGAUGAUAGTT | 185 |
| R-008372789-000T | 615b | 35 | UAUCAUCAUAGGUUGUCAU | B UAUCAUCAUAGGUUGUCAUUsU B | 186 |
| R-008372789-000T | 615b | 35 | UAUCAUCAUAGGUUGUCAU | AUGACAACCUAUGAUGAUAUsU | 187 |
| R-008415621-000L | 615b | 35 | UAUCAUCAUAGGUUGUCAU | AUGACAACCUAUGAUGAUATT | 188 |
| R-008415621-000L | 615b | 35 | UAUCAUCAUAGGUUGUCAU | UAUCAUCAUAGGUUGUCAUTT | 189 |
| R-008372868-000J | 616b | 36 | AUCAUCAUAGGUUGUCAUG | B AUCAUCAUAGGUUGUCAUGUsU B | 190 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008372868-000J | 616b | 36 | AUCAUCAUAGGUUGUCAUG | CAUGACAACCUAUGAUGAUUsU | 191 |
| R-008415550-000V | 616b | 36 | AUCAUCAUAGGUUGUCAUG | AUCAUCAUAGGUUGUCAUGTT | 192 |
| R-008415550-000V | 616b | 36 | AUCAUCAUAGGUUGUCAUG | CAUGACAACCUAUGAUGAUTT | 193 |
| R-008372786-000S | 617b | 37 | UCAUCAUAGGUUGUCAUGC | B UCAUCAUAGGUUGUCAUGCUsU B | 194 |
| R-008372786-000S | 617b | 37 | UCAUCAUAGGUUGUCAUGC | GCAUGACAACCUAUGAUGAUsU | 195 |
| R-008415585-000R | 617b | 37 | UCAUCAUAGGUUGUCAUGC | GCAUGACAACCUAUGAUGATT | 196 |
| R-008415585-000R | 617b | 37 | UCAUCAUAGGUUGUCAUGC | UCAUCAUAGGUUGUCAUGCTT | 197 |
| R-008372855-000R | 618b | 38 | CAUCAUAGGUUGUCAUGCU | B CAUCAUAGGUUGUCAUGCUUsU B | 198 |
| R-008372855-000R | 618b | 38 | CAUCAUAGGUUGUCAUGCU | AGCAUGACAACCUAUGAUGUsU | 199 |
| R-008415547-000N | 618b | 38 | CAUCAUAGGUUGUCAUGCU | AGCAUGACAACCUAUGAUGTT | 200 |
| R-008415547-000N | 618b | 38 | CAUCAUAGGUUGUCAUGCU | CAUCAUAGGUUGUCAUGCUTT | 201 |
| R-008415579-000H | 618b | 38 | CAUCAUAGGUUGUCAUGCU | B cAucAuAGGuuGucAuGcuUsU B | 202 |
| R-008415579-000H | 618b | 38 | CAUCAUAGGUUGUCAUGCU | AGcAuGAcAAccuAuGAuGUsU | 203 |
| R-008415622-000V | 618b | 38 | CAUCAUAGGUUGUCAUGCU | agcAuGAcAAccuAuGAuGUsU | 204 |
| R-008415622-000V | 618b | 38 | CAUCAUAGGUUGUCAUGCU | B cAucAuAGGuuGucAuGcuUsU B | 205 |
| R-008415552-000M | 618b | 38 | CAUCAUAGGUUGUCAUGCU | agcAuGAcAAccuAuGAuGUsU | 206 |
| R-008415552-000M | 618b | 38 | CAUCAUAGGUUGUCAUGCU | B cAucAuAGGuuGucAuGcuUsU B | 205 |
| R-008415590-000P | 618b | 38 | CAUCAUAGGUUGUCAUGCU | agcAuGAcAAccuAuGAuGUsU | 204 |
| R-008415590-000P | 618b | 38 | CAUCAUAGGUUGUCAUGCU | B cAucAuAGGuuGucAuGcuUsU B | 207 |
| R-008415668-000S | 618b | 38 | CAUCAUAGGUUGUCAUGCU | agcAuGAcAAccuAuGAuGUsU | 206 |
| R-008415668-000S | 618b | 38 | CAUCAUAGGUUGUCAUGCU | B cAucAuAGGuuGucAuGcuUsU B | 207 |
| R-008415554-000E | 618b | 38 | CAUCAUAGGUUGUCAUGCU | agcAuGAcAAccuAuGAuGUsU | 204 |
| R-008415554-000E | 618b | 38 | CAUCAUAGGUUGUCAUGCU | B cAucAuAGGuuGucAuGcuUsU B | 208 |
| R-008415513-000B | 618b | 38 | CAUCAUAGGUUGUCAUGCU | agcAuGAcAAccuAuGAuGUsU | 206 |
| R-008415513-000B | 618b | 38 | CAUCAUAGGUUGUCAUGCU | B cAucAuAGGuuGucAuGcuUsU B | 208 |
| R-008415624-000M | 618b | 38 | CAUCAUAGGUUGUCAUGCU | agcAuGAcAAccuAuGAuGUsU | 209 |
| R-008415624-000M | 618b | 38 | CAUCAUAGGUUGUCAUGCU | B cAucAuAGGuuGucAuGcuUsU B | 208 |
| R-008415667-000H | 618b | 38 | CAUCAUAGGUUGUCAUGCU | agcAuGAcAAccuAuGAuGUsU | 210 |
| R-008415667-000H | 618b | 38 | CAUCAUAGGUUGUCAUGCU | B cAucAuAGGuuGucAuGcuUsU B | 211 |
| R-008372811-000L | 619b | 39 | AUCAUAGGUUGUCAUGCUU | B AUCAUAGGUUGUCAUGCUUUsU B | 212 |
| R-008372811-000L | 619b | 39 | AUCAUAGGUUGUCAUGCUU | AAGCAUGACAACCUAUGAUUsU | 213 |
| R-008415544-000M | 619b | 39 | AUCAUAGGUUGUCAUGCUU | AAGCAUGACAACCUAUGAUTT | 214 |
| R-008415544-000M | 619b | 39 | AUCAUAGGUUGUCAUGCUU | AUCAUAGGUUGUCAUGCUUTT | 215 |
| R-008415462-000V | 619b | 39 | AUCAUAGGUUGUCAUGCUU | B AucAuAGGuuGucAuGcuuUsU B | 216 |
| R-008415462-000V | 619b | 39 | AUCAUAGGUUGUCAUGCUU | AAGcAuGAcAAccuAuGAuUsU | 217 |
| R-008415672-000G | 619b | 39 | AUCAUAGGUUGUCAUGCUU | aagcAuGAcAAccuAuGAuUsU | 218 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008415672-000G | 619b | 39 | AUCAUAGGUUGUCAUGCUU | B AucAuAGGuuGucAuGcuuUsU B | 219 |
| R-008415671-000Y | 619b | 39 | AUCAUAGGUUGUCAUGCUU | aagcAuGAcAAccuAuGAuUsU | 220 |
| R-008415671-000Y | 619b | 39 | AUCAUAGGUUGUCAUGCUU | B AucAuAGGuuGucAuGcuuUsU B | 219 |
| R-008415685-000A | 619b | 39 | AUCAUAGGUUGUCAUGCUU | aagcAuGAcAAccuAuGAuUsU | 221 |
| R-008415685-000A | 619b | 39 | AUCAUAGGUUGUCAUGCUU | B AucAuAGGuuGucAuGcuuUsU B | 219 |
| R-008415673-000R | 619b | 39 | AUCAUAGGUUGUCAUGCUU | aagcAuGAcAAccuAuGAuUsU | 220 |
| R-008415673-000R | 619b | 39 | AUCAUAGGUUGUCAUGCUU | B AucAuAGGuuGucAuGcuuUsU B | 222 |
| R-008415626-000E | 619b | 39 | AUCAUAGGUUGUCAUGCUU | aagcAuGAcAAccuAuGAuUsU | 221 |
| R-008415626-000E | 619b | 39 | AUCAUAGGUUGUCAUGCUU | B AucAuAGGuuGucAuGcuuUsU B | 222 |
| R-008415648-000G | 619b | 39 | AUCAUAGGUUGUCAUGCUU | aagcAuGAcAAccuAuGAuUsU | 218 |
| R-008415648-000G | 619b | 39 | AUCAUAGGUUGUCAUGCUU | B AucAuAGGuuGucAuGcuuUsU B | 223 |
| R-008415557-000F | 619b | 39 | AUCAUAGGUUGUCAUGCUU | aagcAuGAcAAccuAuGAuUsU | 221 |
| R-008415557-000F | 619b | 39 | AUCAUAGGUUGUCAUGCUU | B AucAuAGGuuGucAuGcuuUsU B | 223 |
| R-008415459-000N | 619b | 39 | AUCAUAGGUUGUCAUGCUU | aagcAuGAcAAccuAuGAuUsU | 224 |
| R-008415459-000N | 619b | 39 | AUCAUAGGUUGUCAUGCUU | B AucAuAGGuuGucAuGcuuUsU B | 225 |
| R-008372835-000F | 620b | 40 | UCAUAGGUUGUCAUGCUUA | B UCAUAGGUUGUCAUGCUUAUsU B | 226 |
| R-008372835-000F | 620b | 40 | UCAUAGGUUGUCAUGCUUA | UAAGCAUGACAACCUAUGAUsU | 227 |
| R-008415504-000T | 620b | 40 | UCAUAGGUUGUCAUGCUUA | UAAGCAUGACAACCUAUGATT | 228 |
| R-008415504-000T | 620b | 40 | UCAUAGGUUGUCAUGCUUA | UCAUAGGUUGUCAUGCUUATT | 229 |
| R-008372886-000B | 621b | 41 | CAUAGGUUGUCAUGCUUAU | B CAUAGGUUGUCAUGCUUAUUsU B | 230 |
| R-008372886-000B | 621b | 41 | CAUAGGUUGUCAUGCUUAU | AUAAGCAUGACAACCUAUGUsU | 231 |
| R-008415541-000L | 621b | 41 | CAUAGGUUGUCAUGCUUAU | AUAAGCAUGACAACCUAUGTT | 232 |
| R-008415541-000L | 621b | 41 | CAUAGGUUGUCAUGCUUAU | CAUAGGUUGUCAUGCUUAUTT | 233 |
| R-008372876-000J | 622b | 42 | AUAGGUUGUCAUGCUUAUG | B AUAGGUUGUCAUGCUUAUGUsU B | 234 |
| R-008372876-000J | 622b | 42 | AUAGGUUGUCAUGCUUAUG | CAUAAGCAUGACAACCUAUUsU | 235 |
| R-008415618-000E | 622b | 42 | AUAGGUUGUCAUGCUUAUG | AUAGGUUGUCAUGCUUAUGTT | 236 |
| R-008415618-000E | 622b | 42 | AUAGGUUGUCAUGCUUAUG | CAUAAGCAUGACAACCUAUTT | 237 |
| R-008372852-000P | 623b | 43 | UAGGUUGUCAUGCUUAUGG | B UAGGUUGUCAUGCUUAUGGUsU B | 238 |
| R-008372852-000P | 623b | 43 | UAGGUUGUCAUGCUUAUGG | CCAUAAGCAUGACAACCUAUsU | 239 |
| R-008415582-000P | 623b | 43 | UAGGUUGUCAUGCUUAUGG | CCAUAAGCAUGACAACCUATT | 240 |
| R-008415582-000P | 623b | 43 | UAGGUUGUCAUGCUUAUGG | UAGGUUGUCAUGCUUAUGGTT | 241 |
| R-008372865-000H | 624b | 44 | AGGUUGUCAUGCUUAUGGG | B AGGUUGUCAUGCUUAUGGGUsU B | 242 |
| R-008372865-000H | 624b | 44 | AGGUUGUCAUGCUUAUGGG | CCCAUAAGCAUGACAACCUUsU | 243 |
| R-008415468-000X | 624b | 44 | AGGUUGUCAUGCUUAUGGG | AGGUUGUCAUGCUUAUGGGTT | 244 |
| R-008415468-000X | 624b | 44 | AGGUUGUCAUGCUUAUGGG | CCCAUAAGCAUGACAACCUTT | 245 |
| R-008372849-000H | 625b | 45 | GGUUGUCAUGCUUAUGGGG | B GGUUGUCAUGCUUAUGGGGUsU B | 246 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008372849-000H | 625b | 45 | GGUUGUCAUGCUUAUGGGG | CCCCAUAAGCAUGACAACC$\underline{U}$s$\underline{U}$ | 247 |
| R-008415538-000E | 625b | 45 | GGUUGUCAUGCUUAUGGGG | CCCCAUAAGCAUGACAACCTT | 248 |
| R-008415538-000E | 625b | 45 | GGUUGUCAUGCUUAUGGGG | GGUUGUCAUGCUUAUGGGGTT | 249 |
| R-008372862-000G | 626b | 46 | GUUGUCAUGCUUAUGGGGA | B GUUGUCAUGCUUAUGGGGAU$\underline{U}$ B | 250 |
| R-008372862-000G | 626b | 46 | GUUGUCAUGCUUAUGGGGA | UCCCCAUAAGCAUGACAAC$\underline{U}$s$\underline{U}$ | 251 |
| R-008415501-000S | 626b | 46 | GUUGUCAUGCUUAUGGGGA | GUUGUCAUGCUUAUGGGGATT | 252 |
| R-008415501-000S | 626b | 46 | GUUGUCAUGCUUAUGGGGA | UCCCCAUAAGCAUGACAACTT | 253 |
| R-008372775-000R | 627b | 47 | UUGUCAUGCUUAUGGGGAU | B UUGUCAUGCUUAUGGGGAUU$\underline{U}$ B | 254 |
| R-008372775-000R | 627b | 47 | UUGUCAUGCUUAUGGGGAU | AUCCCCAUAAGCAUGACAA$\underline{U}$s$\underline{U}$ | 255 |
| R-008415465-000W | 627b | 47 | UUGUCAUGCUUAUGGGGAU | AUCCCCAUAAGCAUGACAATT | 256 |
| R-008415465-000W | 627b | 47 | UUGUCAUGCUUAUGGGGAU | UUGUCAUGCUUAUGGGGAUTT | 257 |
| R-008372808-000E | 628b | 48 | UGUCAUGCUUAUGGGGAUC | B UGUCAUGCUUAUGGGGAUCU$\underline{U}$s$\underline{U}$ B | 258 |
| R-008372808-000E | 628b | 48 | UGUCAUGCUUAUGGGGAUC | GAUCCCCAUAAGCAUGACA$\underline{U}$s$\underline{U}$ | 259 |
| R-008415615-000D | 628b | 48 | UGUCAUGCUUAUGGGGAUC | GAUCCCCAUAAGCAUGACATT | 260 |
| R-008415615-000D | 628b | 48 | UGUCAUGCUUAUGGGGAUC | UGUCAUGCUUAUGGGGAUCTT | 261 |
| R-008364705-000U | 611c | 49 | AACCUAUCAUCAUAGGUCA | B AACCUAUCAUCAUAGGUCATT B | 262 |
| R-008364705-000U | 611c | 49 | AACCUAUCAUCAUAGGUCA | UGACCUAUGAUGAUAGGUU$\underline{UU}$ | 263 |
| R-008415661-000F | 611c | 49 | AACCUAUCAUCAUAGGUCA | AACCUAUCAUCAUAGGUCATT | 264 |
| R-008415661-000F | 611c | 49 | AACCUAUCAUCAUAGGUCA | UGACCUAUGAUGAUAGGUUTT | 265 |
| R-008364848-000Z | 612c | 50 | ACCUAUCAUCAUAGGUCAU | B ACCUAUCAUCAUAGGUCAUTT B | 266 |
| R-008364848-000Z | 612c | 50 | ACCUAUCAUCAUAGGUCAU | AUGACCUAUGAUGAUAGGU$\underline{UU}$ | 267 |
| R-008415576-000G | 612c | 50 | ACCUAUCAUCAUAGGUCAU | ACCUAUCAUCAUAGGUCAUTT | 268 |
| R-008415576-000G | 612c | 50 | ACCUAUCAUCAUAGGUCAU | AUGACCUAUGAUGAUAGGUTT | 269 |
| R-008364815-000W | 613c | 51 | CCUAUCAUCAUAGGUCAUC | B CCUAUCAUCAUAGGUCAUCTT B | 270 |
| R-008364815-000W | 613c | 51 | CCUAUCAUCAUAGGUCAUC | GAUGACCUAUGAUGAUAGG$\underline{UU}$ | 271 |
| R-008415658-000Z | 613c | 51 | CCUAUCAUCAUAGGUCAUC | CCUAUCAUCAUAGGUCAUCTT | 272 |
| R-008415658-000Z | 613c | 51 | CCUAUCAUCAUAGGUCAUC | GAUGACCUAUGAUGAUAGGTT | 273 |
| R-008364672-000E | 614c | 52 | CUAUCAUCAUAGGUCAUCA | B CUAUCAUCAUAGGUCAUCATT B | 274 |
| R-008364672-000E | 614c | 52 | CUAUCAUCAUAGGUCAUCA | UGAUGACCUAUGAUGAUAG$\underline{UU}$ | 275 |
| R-008415610-000K | 614c | 52 | CUAUCAUCAUAGGUCAUCA | CUAUCAUCAUAGGUCAUCATT | 276 |
| R-008415610-000K | 614c | 52 | CUAUCAUCAUAGGUCAUCA | UGAUGACCUAUGAUGAUAGTT | 277 |
| R-008364642-000C | 615c | 53 | UAUCAUCAUAGGUCAUCAU | B UAUCAUCAUAGGUCAUCAUTT B | 278 |
| R-008364642-000C | 615c | 53 | UAUCAUCAUAGGUCAUCAU | AUGAUGACCUAUGAUGAUA$\underline{UU}$ | 279 |
| R-008415573-000F | 615c | 53 | UAUCAUCAUAGGUCAUCAU | AUGAUGACCUAUGAUGAUATT | 280 |
| R-008415573-000F | 615c | 53 | UAUCAUCAUAGGUCAUCAU | UAUCAUCAUAGGUCAUCAUTT | 281 |
| R-008364845-000Y | 616c | 54 | AUCAUCAUAGGUCAUCAUG | B AUCAUCAUAGGUCAUCAUGTT B | 282 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008364845-000Y | 616c | 54 | AUCAUCAUAGGUCAUCAUG | CAUGAUGACCUAUGAUGAU<u>UU</u> | 283 |
| R-008415570-000E | 616c | 54 | AUCAUCAUAGGUCAUCAUG | AUCAUCAUAGGUCAUCAUGTT | 284 |
| R-008415570-000E | 616c | 54 | AUCAUCAUAGGUCAUCAUG | CAUGAUGACCUAUGAUGAUTT | 285 |
| R-008364711-000B | 617c | 55 | UCAUCAUAGGUCAUCAUGC | B UCAUCAUAGGUCAUCAUGCUU B | 286 |
| R-008364711-000B | 617c | 55 | UCAUCAUAGGUCAUCAUGC | GCAUGAUGACCUAUGAUGA<u>UU</u> | 287 |
| R-008415498-000Z | 617c | 55 | UCAUCAUAGGUCAUCAUGC | GCAUGAUGACCUAUGAUGATT | 288 |
| R-008415498-000Z | 617c | 55 | UCAUCAUAGGUCAUCAUGC | UCAUCAUAGGUCAUCAUGCTT | 289 |
| R-008364842-000X | 618c | 56 | CAUCAUAGGUCAUCAUGCU | B CAUCAUAGGUCAUCAUGCUU B | 290 |
| R-008364842-000X | 618c | 56 | CAUCAUAGGUCAUCAUGCU | AGCAUGAUGACCUAUGAUG<u>UU</u> | 291 |
| R-008415567-000Y | 618c | 56 | CAUCAUAGGUCAUCAUGCU | AGCAUGAUGACCUAUGAUGTT | 292 |
| R-008415567-000Y | 618c | 56 | CAUCAUAGGUCAUCAUGCU | CAUCAUAGGUCAUCAUGCUTT | 293 |
| R-008364738-000X | 619c | 57 | AUCAUAGGUCAUCAUGCUU | B AUCAUAGGUCAUCAUGCUUU B | 294 |
| R-008364738-000X | 619c | 57 | AUCAUAGGUCAUCAUGCUU | AAGCAUGAUGACCUAUGAU<u>UU</u> | 295 |
| R-008415677-000A | 619c | 57 | AUCAUAGGUCAUCAUGCUU | AAGCAUGAUGACCUAUGAUTT | 296 |
| R-008415677-000A | 619c | 57 | AUCAUAGGUCAUCAUGCUU | AUCAUAGGUCAUCAUGCUUTT | 297 |
| R-008364765-000Y | 620c | 58 | UCAUAGGUCAUCAUGCUUA | B UCAUAGGUCAUCAUGCUUATT B | 298 |
| R-008364765-000Y | 620c | 58 | UCAUAGGUCAUCAUGCUUA | UAAGCAUGAUGACCUAUGA<u>UU</u> | 299 |
| R-008415643-000N | 620c | 58 | UCAUAGGUCAUCAUGCUUA | UAAGCAUGAUGACCUAUGATT | 300 |
| R-008415643-000N | 620c | 58 | UCAUAGGUCAUCAUGCUUA | UCAUAGGUCAUCAUGCUUATT | 301 |
| R-008364714-000C | 621c | 59 | CAUAGGUCAUCAUGCUUAU | B CAUAGGUCAUCAUGCUUAUU B | 302 |
| R-008364714-000C | 621c | 59 | CAUAGGUCAUCAUGCUUAU | AUAAGCAUGAUGACCUAUG<u>UU</u> | 303 |
| R-008415607-000D | 621c | 59 | CAUAGGUCAUCAUGCUUAU | AUAAGCAUGAUGACCUAUGTT | 304 |
| R-008415607-000D | 621c | 59 | CAUAGGUCAUCAUGCUUAU | CAUAGGUCAUCAUGCUUAUTT | 305 |
| R-008415655-000Y | 621c | 59 | CAUAGGUCAUCAUGCUUAU | B cAuAGGucAucAuGcuuAuUs<u>U</u> B | 306 |
| R-008415655-000Y | 621c | 59 | CAUAGGUCAUCAUGCUUAU | AuAAGcAuGAuGAccuAuGUs<u>U</u> | 307 |
| R-008479888-000J | 621c | 59 | CAUAGGUCAUCAUGCUUAU | auaAGc<u>A</u>uG<u>A</u>uG<u>A</u>ccu<u>A</u>uGUs<u>U</u> | 308 |
| R-008479888-000J | 621c | 59 | CAUAGGUCAUCAUGCUUAU | B cAuAGGucAucAuGcuuAuUs<u>U</u> B | 306 |
| R-008480041-000N | 621c | 59 | CAUAGGUCAUCAUGCUUAU | B cAuAGGucAucAuGcuuAuUs<u>U</u> B | 306 |
| R-008480041-000N | 621c | 59 | CAUAGGUCAUCAUGCUUAU | AuAAGcAUGAuGAccuAuGUs<u>U</u> | 309 |
| R-008480043-000F | 621c | 59 | CAUAGGUCAUCAUGCUUAU | B cAuAGGucAucAuGcuuAuUs<u>U</u> B | 306 |
| R-008480043-000F | 621c | 59 | CAUAGGUCAUCAUGCUUAU | AUAAGcAuGAuGAccuAuGUs<u>U</u> | 310 |
| R-008480045-000Y | 621c | 59 | CAUAGGUCAUCAUGCUUAU | B cAuAGGucAucAuGcuuAuUs<u>U</u> B | 306 |
| R-008480045-000Y | 621c | 59 | CAUAGGUCAUCAUGCUUAU | AuAAGcAuGAuGAccuAuGUs<u>U</u> | 311 |
| R-008480047-000R | 621c | 59 | CAUAGGUCAUCAUGCUUAU | B cAuAGGucAucAuGcuuAuUs<u>U</u> B | 306 |
| R-008480047-000R | 621c | 59 | CAUAGGUCAUCAUGCUUAU | AuAAGcAUGAuGAccuAuGUs<u>U</u> | 312 |
| R-008480049-000H | 621c | 59 | CAUAGGUCAUCAUGCUUAU | B cAuAGGucAucAuGcuuAuUs<u>U</u> B | 306 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008480049-000H | 621c | 59 | CAUAGGUCAUCAUGCUUAU | AuAAGcAuGAuGAccuAuGUsU | 313 |
| R-008480051-000F | 621c | 59 | CAUAGGUCAUCAUGCUUAU | B cAuAGGucAucAuGcuuAuUsU B | 306 |
| R-008480051-000F | 621c | 59 | CAUAGGUCAUCAUGCUUAU | AuAAGcAuGAuGACcuAuGUsU | 314 |
| R-008480053-000Y | 621c | 59 | CAUAGGUCAUCAUGCUUAU | B cAuAGGucAucAuGcuuAuUsU B | 306 |
| R-008480053-000Y | 621c | 59 | CAUAGGUCAUCAUGCUUAU | AuAAGcAuGAuGAcCuAuGUsU | 315 |
| R-008480055-000R | 621c | 59 | CAUAGGUCAUCAUGCUUAU | B cAuAGGucAucAuGcuuAuUsU B | 306 |
| R-008480055-000R | 621c | 59 | CAUAGGUCAUCAUGCUUAU | AuAAGcAuGAuGAccUAuGUsU | 316 |
| R-008480057-000H | 621c | 59 | CAUAGGUCAUCAUGCUUAU | B cAuAGGucAucAuGcuuAuUsU B | 306 |
| R-008480057-000H | 621c | 59 | CAUAGGUCAUCAUGCUUAU | AuAAGcAuGAuGAccuAUGUsU | 317 |
| R-008480059-000A | 621c | 59 | CAUAGGUCAUCAUGCUUAU | B cAuAGGucAucAuGcuuAuUsU B | 306 |
| R-008480059-000A | 621c | 59 | CAUAGGUCAUCAUGCUUAU | AuAAGcAuGAuGAccUAuGUsU | 318 |
| R-008480061-000Y | 621c | 59 | CAUAGGUCAUCAUGCUUAU | B cAuAGGucAucAuGcuuAuUsU B | 306 |
| R-008480061-000Y | 621c | 59 | CAUAGGUCAUCAUGCUUAU | AuAAGcAuGAuGAccuAuGUsU | 319 |
| R-008480063-000R | 621c | 59 | CAUAGGUCAUCAUGCUUAU | B cAuAGGucAucAuGcuuAuUsU B | 306 |
| R-008480063-000R | 621c | 59 | CAUAGGUCAUCAUGCUUAU | AuAAGcAuGAuGAccuAuGUsU | 320 |
| R-008480065-000H | 621c | 59 | CAUAGGUCAUCAUGCUUAU | B cAuAGGucAucAuGcuuAuUsU B | 306 |
| R-008480065-000H | 621c | 59 | CAUAGGUCAUCAUGCUUAU | AuAAGcAuGAuGAccuAuGUsU | 321 |
| R-008480067-000A | 621c | 59 | CAUAGGUCAUCAUGCUUAU | B cAuAGGucAucAuGcuuAuUsU B | 306 |
| R-008480067-000A | 621c | 59 | CAUAGGUCAUCAUGCUUAU | AuAAGcAuGAuGAccuAuGUsU | 322 |
| R-008480069-000T | 621c | 59 | CAUAGGUCAUCAUGCUUAU | B cAuAGGucAucAuGcuuAuUsU B | 306 |
| R-008480069-000T | 621c | 59 | CAUAGGUCAUCAUGCUUAU | AuAAGcAuGAuGAccuAuGUsU | 323 |
| R-008480071-000R | 621c | 59 | CAUAGGUCAUCAUGCUUAU | B cAuAGGucAucAuGcuuAuUsU B | 306 |
| R-008480071-000R | 621c | 59 | CAUAGGUCAUCAUGCUUAU | AuAAGcAuGAuGAccuAuGUsU | 324 |
| R-008480073-000H | 621c | 59 | CAUAGGUCAUCAUGCUUAU | B cAuAGGucAucAuGcuuAuUsU B | 306 |
| R-008480073-000H | 621c | 59 | CAUAGGUCAUCAUGCUUAU | AuAAGcAuGAuGAccuAuGUsU | 325 |
| R-008480075-000A | 621c | 59 | CAUAGGUCAUCAUGCUUAU | B cAuAGGucAucAuGcuuAuUsU B | 306 |
| R-008480075-000A | 621c | 59 | CAUAGGUCAUCAUGCUUAU | AuAAGcAuGAuGAccuAuGUsU | 326 |
| R-008480077-000T | 621c | 59 | CAUAGGUCAUCAUGCUUAU | B cAuAGGucAucAuGcuuAuUsU B | 306 |
| R-008480077-000T | 621c | 59 | CAUAGGUCAUCAUGCUUAU | AuAAGcAuGAuGAccuAuGUsU | 327 |
| R-008480079-000K | 621c | 59 | CAUAGGUCAUCAUGCUUAU | B cAuAGGucAucAuGcuuAuUsU B | 306 |
| R-008480079-000K | 621c | 59 | CAUAGGUCAUCAUGCUUAU | AuAAGcAuGAuGAccuAuGUsU | 328 |
| R-008480081-000H | 621c | 59 | CAUAGGUCAUCAUGCUUAU | B cAuAGGucAucAuGcuuAuUsU B | 306 |
| R-008480081-000H | 621c | 59 | CAUAGGUCAUCAUGCUUAU | AuAAGcAuGAuGAccuAuGUsU | 329 |
| R-008480083-000A | 621c | 59 | CAUAGGUCAUCAUGCUUAU | B cAuAGGucAucAuGcuuAuUsU B | 306 |
| R-008480083-000A | 621c | 59 | CAUAGGUCAUCAUGCUUAU | AuAAGCAuGAUGAccuAuGUsU | 330 |
| R-008415678-000J | 621c | 59 | CAUAGGUCAUCAUGCUUAU | auaAGcAuGAuGAccuAuGUsU | 331 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008415678-000J | 621c | 59 | CAUAGGUCAUCAUGCUUAU | B cAuAGGucAucAuGcuuAuUsU B | 332 |
| R-008415664-000G | 621c | 59 | CAUAGGUCAUCAUGCUUAU | auaAGcAuGAuGAccuAuGUsU | 333 |
| R-008415664-000G | 621c | 59 | CAUAGGUCAUCAUGCUUAU | B cAuAGGucAucAuGcuuAuUsU B | 332 |
| R-008415646-000P | 621c | 59 | CAUAGGUCAUCAUGCUUAU | auaAGcAuGAuGAccuAuGUsU | 333 |
| R-008415646-000P | 621c | 59 | CAUAGGUCAUCAUGCUUAU | B cAuAGGucAucAuGcuuAuUsU B | 334 |
| R-008415662-000P | 621c | 59 | CAUAGGUCAUCAUGCUUAU | auaAGcAuGAuGAccuAuGUsU | 308 |
| R-008415662-000P | 621c | 59 | CAUAGGUCAUCAUGCUUAU | B cAuAGGucAucAuGcuuAuUsU B | 334 |
| R-008415612-000C | 621c | 59 | CAUAGGUCAUCAUGCUUAU | auaAGcAuGAuGAccuAuGUsU | 331 |
| R-008415612-000C | 621c | 59 | CAUAGGUCAUCAUGCUUAU | B cAuAGGucAucAuGcuuAuUsU B | 335 |
| R-008415674-000Z | 621c | 59 | CAUAGGUCAUCAUGCUUAU | auaAGcAuGAuGAccuAuGUsU | 333 |
| R-008415674-000Z | 621c | 59 | CAUAGGUCAUCAUGCUUAU | B cAuAGGucAucAuGcuuAuUsU B | 335 |
| R-008415535-000D | 621c | 59 | CAUAGGUCAUCAUGCUUAU | auaAGcAuGAuGAccuAuGUsU | 308 |
| R-008415535-000D | 621c | 59 | CAUAGGUCAUCAUGCUUAU | B cAuAGGucAucAuGcuuAuUsU B | 335 |
| R-008480085-000T | 621c | 59 | CAUAGGUCAUCAUGCUUAU | auaAGcAUGAuGAccuAuGUsU | 336 |
| R-008480085-000T | 621c | 59 | CAUAGGUCAUCAUGCUUAU | B cAuAGGucAucAuGcuuAuUsU B | 335 |
| R-008480087-000K | 621c | 59 | CAUAGGUCAUCAUGCUUAU | auaAGcAuGAuGAccuAuGUsU | 337 |
| R-008480087-000K | 621c | 59 | CAUAGGUCAUCAUGCUUAU | B cAuAGGucAucAuGcuuAuUsU B | 335 |
| R-008480089-000C | 621c | 59 | CAUAGGUCAUCAUGCUUAU | auaAGcAuGAuGAccuAuGUsU | 338 |
| R-008480089-000C | 621c | 59 | CAUAGGUCAUCAUGCUUAU | B cAuAGGucAucAuGcuuAuUsU B | 335 |
| R-008480091-000A | 621c | 59 | CAUAGGUCAUCAUGCUUAU | auaAGcAuGAuGAccuAuGUsU | 339 |
| R-008480091-000A | 621c | 59 | CAUAGGUCAUCAUGCUUAU | B cAuAGGucAucAuGcuuAuUsU B | 335 |
| R-008480093-000T | 621c | 59 | CAUAGGUCAUCAUGCUUAU | auaAGcAuGAuGAccuAuGUsU | 340 |
| R-008480093-000T | 621c | 59 | CAUAGGUCAUCAUGCUUAU | B cAuAGGucAucAuGcuuAuUsU B | 335 |
| R-008480095-000K | 621c | 59 | CAUAGGUCAUCAUGCUUAU | auaAGcAuGAuGAccuAuGUsU | 341 |
| R-008480095-000K | 621c | 59 | CAUAGGUCAUCAUGCUUAU | B cAuAGGucAucAuGcuuAuUsU B | 335 |
| R-008480097-000C | 621c | 59 | CAUAGGUCAUCAUGCUUAU | auaAGcAuGAuGAccuAuGUsU | 342 |
| R-008480097-000C | 621c | 59 | CAUAGGUCAUCAUGCUUAU | B cAuAGGucAucAuGcuuAuUsU B | 335 |
| R-008480099-000V | 621c | 59 | CAUAGGUCAUCAUGCUUAU | auaAGcAUGAuGAccuAuGUsU | 343 |
| R-008480099-000V | 621c | 59 | CAUAGGUCAUCAUGCUUAU | B cAuAGGucAucAuGcuuAuUsU B | 335 |
| R-008480101-000D | 621c | 59 | CAUAGGUCAUCAUGCUUAU | auaAGcAuGAuGAccuAuGUsU | 344 |
| R-008480101-000D | 621c | 59 | CAUAGGUCAUCAUGCUUAU | B cAuAGGucAucAuGcuuAuUsU B | 335 |
| R-008480103-000W | 621c | 59 | CAUAGGUCAUCAUGCUUAU | auaAGcAuGAuGAccuAuGUsU | 345 |
| R-008480103-000W | 621c | 59 | CAUAGGUCAUCAUGCUUAU | B cAuAGGucAucAuGcuuAuUsU B | 335 |
| R-008480105-000N | 621c | 59 | CAUAGGUCAUCAUGCUUAU | auaAGcAuGAuGAccuAuGUsU | 346 |
| R-008480105-000N | 621c | 59 | CAUAGGUCAUCAUGCUUAU | B cAuAGGucAucAuGcuuAuUsU B | 335 |
| R-008480107-000F | 621c | 59 | CAUAGGUCAUCAUGCUUAU | auaAGcAuGAuGAccuAuGUsU | 347 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008480107-000F | 621c | 59 | CAUAGGUCAUCAUGCUUAU | B cAuAGGucAucAuGcuuAuUsU B | 335 |
| R-008480109-000Y | 621c | 59 | CAUAGGUCAUCAUGCUUAU | auaAGcAuGAuGAccuAuGUsU | 348 |
| R-008480109-000Y | 621c | 59 | CAUAGGUCAUCAUGCUUAU | B cAuAGGucAucAuGcuuAuUsU B | 335 |
| R-008480111-000W | 621c | 59 | CAUAGGUCAUCAUGCUUAU | auaAGcAuGAuGAccuAuGUsU | 349 |
| R-008480111-000W | 621c | 59 | CAUAGGUCAUCAUGCUUAU | B cAuAGGucAucAuGcuuAuUsU B | 335 |
| R-008480113-000N | 621c | 59 | CAUAGGUCAUCAUGCUUAU | auaAGcAuGAuGAccuAuGUsU | 350 |
| R-008480113-000N | 621c | 59 | CAUAGGUCAUCAUGCUUAU | B cAuAGGucAucAuGcuuAuUsU B | 335 |
| R-008480115-000F | 621c | 59 | CAUAGGUCAUCAUGCUUAU | auaAGcAuGAuGAccuAuGUsU | 351 |
| R-008480115-000F | 621c | 59 | CAUAGGUCAUCAUGCUUAU | B cAuAGGucAucAuGcuuAuUsU B | 335 |
| R-008480117-000Y | 621c | 59 | CAUAGGUCAUCAUGCUUAU | auaAGcAuGAuGAccuAuGUsU | 352 |
| R-008480117-000Y | 621c | 59 | CAUAGGUCAUCAUGCUUAU | B cAuAGGucAucAuGcuuAuUsU B | 335 |
| R-008480119-000R | 621c | 59 | CAUAGGUCAUCAUGCUUAU | auaAGcAuGAuGAccuAuGUsU | 353 |
| R-008480119-000R | 621c | 59 | CAUAGGUCAUCAUGCUUAU | B cAuAGGucAucAuGcuuAuUsU B | 335 |
| R-008480121-000N | 621c | 59 | CAUAGGUCAUCAUGCUUAU | auaAGcAuGAuGAccuAuGUsU | 354 |
| R-008480121-000N | 621c | 59 | CAUAGGUCAUCAUGCUUAU | B cAuAGGucAucAuGcuuAuUsU B | 335 |
| R-008480123-000F | 621c | 59 | CAUAGGUCAUCAUGCUUAU | auaAGcAuGAuGAccuAuGUsU | 355 |
| R-008480123-000F | 621c | 59 | CAUAGGUCAUCAUGCUUAU | B cAuAGGucAucAuGcuuAuUsU B | 335 |
| R-008480125-000Y | 621c | 59 | CAUAGGUCAUCAUGCUUAU | auaAGcAuGAuGAccuAuGUsU | 356 |
| R-008480125-000Y | 621c | 59 | CAUAGGUCAUCAUGCUUAU | B cAuAGGucAucAuGcuuAuUsU B | 335 |
| R-008480127-000R | 621c | 59 | CAUAGGUCAUCAUGCUUAU | auaAGcAuGAuGAccuAuGUsU | 357 |
| R-008480127-000R | 621c | 59 | CAUAGGUCAUCAUGCUUAU | B cAuAGGucAucAuGcuuAuUsU B | 335 |
| R-008480129-000H | 621c | 59 | CAUAGGUCAUCAUGCUUAU | auaAGcAuGAuGAccuAuGUsU | 358 |
| R-008480129-000H | 621c | 59 | CAUAGGUCAUCAUGCUUAU | B cAuAGGucAucAuGcuuAuUsU B | 335 |
| R-008480131-000F | 621c | 59 | CAUAGGUCAUCAUGCUUAU | auaAGcAuGAuGAccUAuGUsU | 359 |
| R-008480131-000F | 621c | 59 | CAUAGGUCAUCAUGCUUAU | B cAuAGGucAucAuGcuuAuUsU B | 335 |
| R-008480133-000Y | 621c | 59 | CAUAGGUCAUCAUGCUUAU | auaAGcAuGAuGAccuAuGUsU | 360 |
| R-008480133-000Y | 621c | 59 | CAUAGGUCAUCAUGCUUAU | B cAuAGGucAucAuGcuuAuUsU B | 335 |
| R-008480135-000R | 621c | 59 | CAUAGGUCAUCAUGCUUAU | auaAGcAuGAuGAccUAuGUsU | 361 |
| R-008480135-000R | 621c | 59 | CAUAGGUCAUCAUGCUUAU | B cAuAGGucAucAuGcuuAuUsU B | 335 |
| R-008480137-000H | 621c | 59 | CAUAGGUCAUCAUGCUUAU | auaAGcAuGAuGAccuAuGUsU | 362 |
| R-008480137-000H | 621c | 59 | CAUAGGUCAUCAUGCUUAU | B cAuAGGucAucAuGcuuAuUsU B | 335 |
| R-008480139-000A | 621c | 59 | CAUAGGUCAUCAUGCUUAU | auaAGCAuGAUGAccuAuGUsU | 363 |
| R-008480139-000A | 621c | 59 | CAUAGGUCAUCAUGCUUAU | B cAuAGGucAucAuGcuuAuUsU B | 335 |
| R-008480141-000Y | 621c | 59 | CAUAGGUCAUCAUGCUUAU | auaAGCAuGAUGAccuAuGUsU | 364 |
| R-008480141-000Y | 621c | 59 | CAUAGGUCAUCAUGCUUAU | B cAuAGGucAucAuGcuuAuUsU B | 335 |
| R-008482284-000T | 621c | 59 | CAUAGGUCAUCAUGCUUAU | auaAGcAuGAuGAccuAuGUsU | 365 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008482284-000T | 621c | 59 | CAUAGGUCAUCAUGCUUAU | B cAuAGGucAucAuGcuuAuUsU B | 335 |
| R-008482286-000K | 621c | 59 | CAUAGGUCAUCAUGCUUAU | auaAGcAuGAuGAccuAuGUsU | 366 |
| R-008482286-000K | 621c | 59 | CAUAGGUCAUCAUGCUUAU | B cAuAGGucAucAuGcuuAuUsU B | 335 |
| R-008482288-000C | 621c | 59 | CAUAGGUCAUCAUGCUUAU | auaAGcAuGAuGAccuAuGUsU | 367 |
| R-008482288-000C | 621c | 59 | CAUAGGUCAUCAUGCUUAU | B cAuAGGucAucAuGcuuAuUsU B | 335 |
| R-008482290-000A | 621c | 59 | CAUAGGUCAUCAUGCUUAU | auaAGcAuGAuGAccuAuGUsU | 368 |
| R-008482290-000A | 621c | 59 | CAUAGGUCAUCAUGCUUAU | B cAuAGGucAucAuGcuuAuUsU B | 335 |
| R-008482292-000T | 621c | 59 | CAUAGGUCAUCAUGCUUAU | auaAGcAuGAuGAccuAuGUsU | 369 |
| R-008482292-000T | 621c | 59 | CAUAGGUCAUCAUGCUUAU | B cAuAGGucAucAuGcuuAuUsU B | 335 |
| R-008482294-000K | 621c | 59 | CAUAGGUCAUCAUGCUUAU | auaAGcAuGAuGAccuAuGUsU | 370 |
| R-008482294-000K | 621c | 59 | CAUAGGUCAUCAUGCUUAU | B cAuAGGucAucAuGcuuAuUsU B | 335 |
| R-008482296-000C | 621c | 59 | CAUAGGUCAUCAUGCUUAU | auaAGcAuGAuGAccuAuGUsU | 371 |
| R-008482296-000C | 621c | 59 | CAUAGGUCAUCAUGCUUAU | B cAuAGGucAucAuGcuuAuUsU B | 335 |
| R-008482298-000V | 621c | 59 | CAUAGGUCAUCAUGCUUAU | auaAGcAuGAuGAccuAuGUsU | 372 |
| R-008482298-000V | 621c | 59 | CAUAGGUCAUCAUGCUUAU | B cAuAGGucAucAuGcuuAuUsU B | 335 |
| R-008480025-000N | 621c | 59 | CAUAGGUCAUCAUGCUUAU | B CAUAGGUCAUCAUGCUUAUTT B | 302 |
| R-008480025-000N | 621c | 59 | CAUAGGUCAUCAUGCUUAU | AuAAGCAUGAUGACCUAUGUU | 373 |
| R-008480027-000F | 621c | 59 | CAUAGGUCAUCAUGCUUAU | B CAUAGGUCAUCAUGCUUAUTT B | 302 |
| R-008480027-000F | 621c | 59 | CAUAGGUCAUCAUGCUUAU | AUAAGcAUGAUGACCUAUGUU | 374 |
| R-008480029-000Y | 621c | 59 | CAUAGGUCAUCAUGCUUAU | B CAUAGGUCAUCAUGCUUAUTT B | 302 |
| R-008480029-000Y | 621c | 59 | CAUAGGUCAUCAUGCUUAU | AUAAGCAuGAUGACCUAUGUU | 375 |
| R-008480031-000W | 621c | 59 | CAUAGGUCAUCAUGCUUAU | B CAUAGGUCAUCAUGCUUAUTT B | 302 |
| R-008480031-000W | 621c | 59 | CAUAGGUCAUCAUGCUUAU | AUAAGCAUGAuGACCUAUGUU | 376 |
| R-008480033-000N | 621c | 59 | CAUAGGUCAUCAUGCUUAU | B CAUAGGUCAUCAUGCUUAUTT B | 302 |
| R-008480033-000N | 621c | 59 | CAUAGGUCAUCAUGCUUAU | AUAAGCAUGAUGAcCUAUGUU | 377 |
| R-008480035-000F | 621c | 59 | CAUAGGUCAUCAUGCUUAU | B CAUAGGUCAUCAUGCUUAUTT B | 302 |
| R-008480035-000F | 621c | 59 | CAUAGGUCAUCAUGCUUAU | AUAAGCAUGAUGACcUAUGUU | 378 |
| R-008480037-000Y | 621c | 59 | CAUAGGUCAUCAUGCUUAU | B CAUAGGUCAUCAUGCUUAUTT B | 302 |
| R-008480037-000Y | 621c | 59 | CAUAGGUCAUCAUGCUUAU | AUAAGCAUGAUGACCuAUGUU | 379 |
| R-008480039-000R | 621c | 59 | CAUAGGUCAUCAUGCUUAU | B CAUAGGUCAUCAUGCUUAUTT B | 302 |
| R-008480039-000R | 621c | 59 | CAUAGGUCAUCAUGCUUAU | AUAAGCAUGAUGACCUAuGUU | 380 |
| R-008482253-000G | 621c | 59 | CAUAGGUCAUCAUGCUUAU | B CAUAGGUCAUCAUGCUUAUTT B | 302 |
| R-008482253-000G | 621c | 59 | CAUAGGUCAUCAUGCUUAU | AUAAGcAuGAUGACCUAUGUU | 381 |
| R-008482255-000Z | 621c | 59 | CAUAGGUCAUCAUGCUUAU | B CAUAGGUCAUCAUGCUUAUTT B | 302 |
| R-008482255-000Z | 621c | 59 | CAUAGGUCAUCAUGCUUAU | AUAAGcAUGAUGACCUAuGUU | 382 |
| R-008482257-000S | 621c | 59 | CAUAGGUCAUCAUGCUUAU | B CAUAGGUCAUCAUGCUUAUTT B | 302 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008482257-000S | 621c | 59 | CAUAGGUCAUCAUGCUUAU | AUAAGCAuGAUGACCuAUGUU | 383 |
| R-008482259-000J | 621c | 59 | CAUAGGUCAUCAUGCUUAU | B CAUAGGUCAUCAUGCUUAUTT B | 302 |
| R-008482259-000J | 621c | 59 | CAUAGGUCAUCAUGCUUAU | AUAAGcAUGAUGACCuAUGUU | 384 |
| R-008482261-000G | 621c | 59 | CAUAGGUCAUCAUGCUUAU | B CAUAGGUCAUCAUGCUUAUTT B | 302 |
| R-008482261-000G | 621c | 59 | CAUAGGUCAUCAUGCUUAU | AUAAGCAuGAUGACCUAuGUU | 385 |
| R-008482263-000Z | 621c | 59 | CAUAGGUCAUCAUGCUUAU | B CAUAGGUCAUCAUGCUUAUTT B | 302 |
| R-008482263-000Z | 621c | 59 | CAUAGGUCAUCAUGCUUAU | AUAAGCAUGAUGACCuAuGUU | 386 |
| R-008482265-000S | 621c | 59 | CAUAGGUCAUCAUGCUUAU | B CAUAGGUCAUCAUGCUUAUTT B | 302 |
| R-008482265-000S | 621c | 59 | CAUAGGUCAUCAUGCUUAU | AuAAGcAuGAUGACCUAUGUU | 387 |
| R-008482267-000J | 621c | 59 | CAUAGGUCAUCAUGCUUAU | B CAUAGGUCAUCAUGCUUAUTT B | 302 |
| R-008482267-000J | 621c | 59 | CAUAGGUCAUCAUGCUUAU | AUAAGcAuGAuGACCUAUGUU | 388 |
| R-008482269-000B | 621c | 59 | CAUAGGUCAUCAUGCUUAU | B CAUAGGUCAUCAUGCUUAUTT B | 302 |
| R-008482269-000B | 621c | 59 | CAUAGGUCAUCAUGCUUAU | AUAAGCAUGAUGACcuAuGUU | 389 |
| R-008482271-000Z | 621c | 59 | CAUAGGUCAUCAUGCUUAU | B CAUAGGUCAUCAUGCUUAUTT B | 302 |
| R-008482271-000Z | 621c | 59 | CAUAGGUCAUCAUGCUUAU | AUAAGcAuGAUGACCuAUGUU | 390 |
| R-008482273-000S | 621c | 59 | CAUAGGUCAUCAUGCUUAU | B CAUAGGUCAUCAUGCUUAUTT B | 302 |
| R-008482273-000S | 621c | 59 | CAUAGGUCAUCAUGCUUAU | AUAAGcaUGAUGACCUAuGUU | 391 |
| R-008482275-000J | 621c | 59 | CAUAGGUCAUCAUGCUUAU | B CAUAGGUCAUCAUGCUUAUTT B | 302 |
| R-008482275-000J | 621c | 59 | CAUAGGUCAUCAUGCUUAU | AUAAGcAUGAUGACCuAuGUU | 392 |
| R-008482277-000B | 621c | 59 | CAUAGGUCAUCAUGCUUAU | B CAUAGGUCAUCAUGCUUAUTT B | 302 |
| R-008482277-000B | 621c | 59 | CAUAGGUCAUCAUGCUUAU | AUAAGCAuGAUGACCuAuGUU | 393 |
| R-008482279-000U | 621c | 59 | CAUAGGUCAUCAUGCUUAU | B CAUAGGUCAUCAUGCUUAUTT B | 302 |
| R-008482279-000U | 621c | 59 | CAUAGGUCAUCAUGCUUAU | AUAAGCAUGAUGAccuAuGUU | 394 |
| R-008482281-000S | 621c | 59 | CAUAGGUCAUCAUGCUUAU | B CAUAGGUCAUCAUGCUUAUTT B | 302 |
| R-008482281-000S | 621c | 59 | CAUAGGUCAUCAUGCUUAU | AUAAGcAuGAUGACCuAuGUU | 395 |
| R-008482282-000A | 621c | 59 | CAUAGGUCAUCAUGCUUAU | auaAGcAuGAuGAccuAuGUsU | 333 |
| R-008482282-000A | 621c | 59 | CAUAGGUCAUCAUGCUUAU | B cAuAGGucAucAuGcuuAuUsU B | 306 |
| R-008415637-000F | 621c | 59 | CAUAGGUCAUCAUGCUUAU | auaAGcAuGAuGAccuAuGUsU | 396 |
| R-008415637-000F | 621c | 59 | CAUAGGUCAUCAUGCUUAU | B cAuAGGucAucAuGcuuAuUsU B | 397 |
| R-008364603-000S | 622c | 60 | AUAGGUCAUCAUGCUUAUG | B AUAGGUCAUCAUGCUUAUGTT B | 398 |
| R-008364603-000S | 622c | 60 | AUAGGUCAUCAUGCUUAUG | CAUAAGCAUGAUGACCUAUUU | 399 |
| R-008415640-000M | 622c | 60 | AUAGGUCAUCAUGCUUAUG | AUAGGUCAUCAUGCUUAUGTT | 400 |
| R-008415640-000M | 622c | 60 | AUAGGUCAUCAUGCUUAUG | CAUAAGCAUGAUGACCUAUTT | 401 |
| R-008364708-000V | 623c | 61 | UAGGUCAUCAUGCUUAUGG | B UAGGUCAUCAUGCUUAUGGTT B | 402 |
| R-008364708-000V | 623c | 61 | UAGGUCAUCAUGCUUAUGG | CCAUAAGCAUGAUGACCUAUU | 403 |
| R-008415604-000C | 623c | 61 | UAGGUCAUCAUGCUUAUGG | CCAUAAGCAUGAUGACCUATT | 404 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008415604-000C | 623c | 61 | UAGGUCAUCAUGCUUAUGG | UAGGUCAUCAUGCUUAUGGTT | 405 |
| R-008364762-000X | 624c | 62 | AGGUCAUCAUGCUUAUGGG | B AGGUCAUCAUGCUUAUGGGTT B | 406 |
| R-008364762-000X | 624c | 62 | AGGUCAUCAUGCUUAUGGG | CCCAUAAGCAUGAUGACCUUU | 407 |
| R-008415532-000C | 624c | 62 | AGGUCAUCAUGCUUAUGGG | AGGUCAUCAUGCUUAUGGGTT | 408 |
| R-008415532-000C | 624c | 62 | AGGUCAUCAUGCUUAUGGG | CCCAUAAGCAUGAUGACCUTT | 409 |
| R-008364600-000R | 625c | 63 | GGUCAUCAUGCUUAUGGGG | B GGUCAUCAUGCUUAUGGGGTT B | 410 |
| R-008364600-000R | 625c | 63 | GGUCAUCAUGCUUAUGGGG | CCCCAUAAGCAUGAUGACCUU | 411 |
| R-008415456-000M | 625c | 63 | GGUCAUCAUGCUUAUGGGG | CCCCAUAAGCAUGAUGACCTT | 412 |
| R-008415456-000M | 625c | 63 | GGUCAUCAUGCUUAUGGGG | GGUCAUCAUGCUUAUGGGGTT | 413 |
| R-008415526-000V | 625c | 63 | GGUCAUCAUGCUUAUGGGG | ccccAuAAGcAuGAuGAccUsU | 414 |
| R-008415526-000V | 625c | 63 | GGUCAUCAUGCUUAUGGGG | B GGucAucAuGcuuAuGGGGUsU B | 415 |
| R-008415453-000L | 625c | 63 | GGUCAUCAUGCUUAUGGGG | ccccAuAAGcAuGAuGAccUsU | 416 |
| R-008415453-000L | 625c | 63 | GGUCAUCAUGCUUAUGGGG | B GGucAucAuGcuuAuGGGGUsU B | 417 |
| R-008415598-000J | 625c | 63 | GGUCAUCAUGCUUAUGGGG | ccccAuAAGcAuGAuGAccUsU | 418 |
| R-008415598-000J | 625c | 63 | GGUCAUCAUGCUUAUGGGG | B GGucAucAuGcuuAuGGGGUsU B | 417 |
| R-008415564-000X | 625c | 63 | GGUCAUCAUGCUUAUGGGG | ccccAuAAGcAuGAuGAccUsU | 419 |
| R-008415564-000X | 625c | 63 | GGUCAUCAUGCUUAUGGGG | B GGucAucAuGcuuAuGGGGUsU B | 417 |
| R-008415634-000E | 625c | 63 | GGUCAUCAUGCUUAUGGGG | ccccAuAAGcAuGAuGAccUsU | 416 |
| R-008415634-000E | 625c | 63 | GGUCAUCAUGCUUAUGGGG | B GGucAucAuGcuuAuGGGGUsU B | 420 |
| R-008415652-000X | 625c | 63 | GGUCAUCAUGCUUAUGGGG | ccccAuAAGcAuGAuGAccUsU | 419 |
| R-008415652-000X | 625c | 63 | GGUCAUCAUGCUUAUGGGG | B GGucAucAuGcuuAuGGGGUsU B | 420 |
| R-008415523-000U | 625c | 63 | GGUCAUCAUGCUUAUGGGG | ccccAuAAGcAuGAuGAccUsU | 416 |
| R-008415523-000U | 625c | 63 | GGUCAUCAUGCUUAUGGGG | B GGucAucAuGcuuAuGGGGUsU B | 421 |
| R-008415450-000K | 625c | 63 | GGUCAUCAUGCUUAUGGGG | ccccAuAAGcAuGAuGAccUsU | 419 |
| R-008415450-000K | 625c | 63 | GGUCAUCAUGCUUAUGGGG | B GGucAucAuGcuuAuGGGGUsU B | 421 |
| R-008415489-000R | 625c | 63 | GGUCAUCAUGCUUAUGGGG | ccccAuAAGcAuGAuGAccUsU | 422 |
| R-008415489-000R | 625c | 63 | GGUCAUCAUGCUUAUGGGG | B GGucAucAuGcuuAuGGGGUsU B | 423 |
| R-008364811-000L | 626c | 64 | GUCAUCAUGCUUAUGGGGA | B GUCAUCAUGCUUAUGGGGATT B | 424 |
| R-008364811-000L | 626c | 64 | GUCAUCAUGCUUAUGGGGA | UCCCCAUAAGCAUGAUGACUU | 425 |
| R-008415495-000Y | 626c | 64 | GUCAUCAUGCUUAUGGGGA | GUCAUCAUGCUUAUGGGGATT | 426 |
| R-008415495-000Y | 626c | 64 | GUCAUCAUGCUUAUGGGGA | UCCCCAUAAGCAUGAUGACTT | 427 |
| R-008364675-000F | 627c | 65 | UCAUCAUGCUUAUGGGGAU | B UCAUCAUGCUUAUGGGGAUTT B | 428 |
| R-008364675-000F | 627c | 65 | UCAUCAUGCUUAUGGGGAU | AUCCCCAUAAGCAUGAUGAUU | 429 |
| R-008415529-000W | 627c | 65 | UCAUCAUGCUUAUGGGGAU | AUCCCCAUAAGCAUGAUGATT | 430 |

TABLE 1c-continued

IDH1-related siNA duplexes. The SEQ ID NOs listed in column 3 correspond to the Target Sequences listed in column 4. The SEQ ID NOs listed in column 6 correspond to the Modified Sequences listed in column 5.

| siNA duplex ID | Target Site (human) | SEQ ID NO: | Target Sequence (5' to 3') | Modified Sequence (5' to 3') | SEQ ID NO: |
|---|---|---|---|---|---|
| R-008415529-000W | 627c | 65 | UCAUCAUGCUUAUGGGGAU | UCAUCAUGCUUAUGGGGAUTT | 431 |
| R-008364645-000D | 628c | 66 | CAUCAUGCUUAUGGGGAUC | B CAUCAUGCUUAUGGGGAUCTT B | 432 |
| R-008364645-000D | 628c | 66 | CAUCAUGCUUAUGGGGAUC | GAUCCCCAUAAGCAUGAUG<u>UU</u> | 433 |
| R-008415492-000X | 628 | 66 | CAUCAUGCUUAUGGGGAUC | CAUCAUGCUUAUGGGGAUCTT | 434 |
| R-008415492-000X | 628 | 66 | CAUCAUGCUUAUGGGGAUC | GAUCCCCAUAAGCAUGAUGTT | 435 |
| R-008364851-000F | 629c | 67 | AUCAUGCUUAUGGGGAUCA | B AUCAUGCUUAUGGGGAUCATT B | 436 |
| R-008364851-000F | 629c | 67 | AUCAUGCUUAUGGGGAUCA | UGAUCCCCAUAAGCAUGAU<u>UU</u> | 437 |
| R-008415601-000B | 629c | 67 | AUCAUGCUUAUGGGGAUCA | AUCAUGCUUAUGGGGAUCATT | 438 |
| R-008415601-000B | 629c | 67 | AUCAUGCUUAUGGGGAUCA | UGAUCCCCAUAAGCAUGAUTT | 439 | wherein:
A, C, G, and U = ribose A, C, G or U
a, g, c and u = 2'-deoxy-2'-fluoro A, G, C or U
<u>A</u>, <u>U</u>, <u>C</u> and <u>G</u> = 2'-O-methyl(2'-OMe) A, U, C, or G
A, U, C, and G = deoxy A, U, C, or G
B = inverted abasic
T = thymidine
s = phosphorothioate linkage Further Synthesis Steps for Commercial Preparation—

Once analysis indicates that the target product purity has been achieved after the annealing step, the material is transferred to a tangential flow filtration (TFF) system for concentration and desalting, as opposed to doing this prior to the annealing step.

Ultrafiltration: The annealed product solution is concentrated using a TFF system containing an appropriate molecular weight cut-off membrane. Following concentration, the product solution is desalted via diafiltration using Milli-Q water until the conductivity of the filtrate is that of water.

Lyophilization: The concentrated solution is transferred to a bottle, flash frozen and attached to a lyophilizer. The product is then freeze-dried to a powder. The bottle is removed from the lyophilizer and is now ready for use.

Example 2

Initial Screening to Identify siNAs Active Against IDH1 Gene Expression

Luciferase Reporter Plasmid Design—

The reporter constructs specific for wild-type, R132H and R132C mutant IDH1 alleles were generated using a modified version of psiCHECK™-2 vector (Promega Cat# C8021). Two-hundred basepair regions surrounding the single point mutation sites were cloned between XhoI and NotI restriction sites to generate transcriptional fusion products between Renilla luciferase and the IDH1 inserts (Genscript). The Renilla luciferase open reading frame is upstream of the IDH1 insert in each fusion transcript. siNAs targeting the IDH1-related insert of the fusion transcript may result in knockdown of the Renilla luciferase expression. The level of Renilla luciferase expression can be determined by directly measuring the amount of Renilla luciferase activity. The plasmid also expresses the firefly luciferase gene that is unaffected by the IDH1 siNAs and can be used to normalize the data to take into account any variations in the amount of plasmid transfected into the cells.

The IDH1 insert sequences for the 3 reporters are as follows:

Wild-type IDH1 - (SEQ ID NO: 507)
CGGTCTTCAGAGAAGCCATTATCTGCAAAAATATCCCCCGGCTTGTGAGT

GGATGGGTAAAACCTATCATCATAGGTCGTCATGCTTATGGGGATCAATA

CAGAGCAACTGATTTTGTTGTTCCTGGGCCTGGAAAAGTAGAGATAACCT

ACACACCAAGTGACGGAACCCAAAAGGTGACATACCTGGTACATAACTT

T;

IDH1-R132H mutant - (SEQ ID NO: 508)
CGGTCTTCAGAGAAGCCATTATCTGCAAAAATATCCCCCGGCTTGTGAGT

GGATGGGTAAAACCTATCATCATAGGTCATCATGCTTATGGGGATCAATA

CAGAGCAACTGATTTTGTTGTTCCTGGGCCTGGAAAAGTAGAGATAACCT

ACACACCAAGTGACGGAACCCAAAAGGTGACATACCTGGTACATAACTT

T;
and

IDH1-R132C mutant - (SEQ ID NO: 509)
CGGTCTTCAGAGAAGCCATTATCTGCAAAAATATCCCCCGGCTTGTGAGT

GGATGGGTAAAACCTATCATCATAGGTTGTCATGCTTATGGGGATCAATA

CAGAGCAACTGATTTTGTTGTTCCTGGGCCTGGAAAAGTAGAGATAACCT

ACACACCAAGTGACGGAACCCAAAAGGTGACATACCTGGTACATAACTT

T.

The full length DNA and protein sequences of wildtype, IDH1-R132H and IDH1-R132C are set forth in Table 2:

| IDH1 | Protein | DNA |
|---|---|---|
| Wild-type | SEQ ID NO: 510 | SEQ ID NO: 511 |
| R132H | SEQ ID NO: 512 | SEQ ID NO: 513 |
| R132C | SEQ ID NO: 514 | SEQ ID NO: 515 |

Cell Culture Preparation—

Human hepatoma cell line, HepG2, was grown in modified Eagle's medium. Mouse hepatoma cell line, Hepa1-6, was grown in Dulbecco's modified Eagle's medium. All the culture media were supplemented with 10% fetal bovine serum, 100 μg/mL streptomycin, 100 U/mL penicillin, and 1% sodium bicarbonate.

Transfection and Screening—

Cells were plated in 96-well tissue culture plates at a density of 10,000 cells per well and incubated at 37° C. overnight. Reporter plasmids and siNAs were cotransfected with Lipofectamine™ 2000 Reagent (Invitrogen) the next day. For initial screens, the final concentrations of siNA and plasmid were 10 nM and 600 ng/ml, respectively.

For 12-point dose response curve experiments, the siNA series are 4-fold serial dilution starting at 40 nM whereas plasmid concentration remained constant at 600 ng/ml. All transfections were set up as multiple biological replicates. One day after transfection, the culture medium was replaced with fresh media and the cells were incubated at 37° C. for another day. Two days after transfection, Renilla luciferase and firefly luciferase activities from the reporter plasmids were measured using Dual-Glo™ Luciferase Assay System (Promega Cat # E2940) according to manufacturer's instruction.

Data Analysis—

Renilla luciferase activity of each well was divided by firefly luciferase activity from the same cell to normalize for different transfection efficiencies across different wells. The normalized luciferase activities produced by wild-type and mutant IDH1 siNAs were further divided by the normalized luciferase activity generated by non-targeting control siNA to calculate the percent knockdown (% KD) of reporter expression. Log 2(fold change) ("log 2FC") was calculated according to the following formula: log 2FC=log 2[100/(100-% KD)]

All calculations of Potency50s and IC50s were performed using R.2.9.2 software. The data were analyzed using the sigmoidal dose-response (fixed slope) equation for simple ligand binding. Potency50 is the calculated siNA transfection concentration that produces 50% target mRNA knockdown. For siNAs with poor maximum knockdown (log 2(fold change)<1), Potency50 cannot be calculated.

Results—

The IDH1-related siNAs were designed and synthesized as described previously. Various siNAs were screened in Hepa1-6 cells transfected with a reporter plasmids based on a modified psiCHECK™-2 vector that generate transcriptional fusion products between Renilla luciferase and the IDH1-related inserts (either wild-type, R13211 mutant, or R132C mutant). The Log 2FC in IDH1-related mRNA expression levels (either wild-type, R132H mutant, or R132C mutant) upon treatment with various modified IDH1-related siNAs in the mouse cells is shown in Table 3a, Table 3b, Table 3c, and Table 3d. For each experiment, n=2-4. The screening data shown in Table 3c primarily encompasses data from chemically-modified siNAs having the Stab 04/05 chemistries (see Table 6), but also includes some data from unmodified siNAs with the exception of the 3'-overhangs. The screening data shown in Table 3d only encompasses data from unmodified siNAs, with the exception of the 3'-overhangs. Each screen was performed at 48 hours using the luciferase assay method.

TABLE 3a

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1.

| Target specificity | siNA duplex ID | IDH1 reporter Mean log2FC | IDH1 reporter SD log2FC | IDH1-R132H reporter Mean log2FC | IDH1-R132H reporter SD log2FC | IDH1-R132C reporter Mean log2FC | IDH1-R132C reporter SD log2FC |
|---|---|---|---|---|---|---|---|
| IDH1 | R-008364795-000A | 4.46 | 0.13 | 0.18 | 0.07 | 1.64 | 0.16 |
| IDH1R132H | R-008364705-000U | -0.02 | 0.07 | 0.01 | 0.10 | -0.06 | 0.03 |
| IDH1R132H | R-008364848-000Z | -0.28 | 0.07 | 1.95 | 0.20 | -0.56 | 0.11 |
| IDH1R132H | R-008364815-000W | 0.68 | 0.10 | 2.83 | 0.26 | 1.20 | 0.15 |
| IDH1R132H | R-008364672-000E | 0.45 | 0.09 | 4.71 | 0.11 | -0.09 | 0.13 |
| IDH1R132H | R-008364642-000C | 0.11 | 0.12 | 1.72 | 0.19 | -0.16 | 0.10 |
| IDH1R132H | R-008364845-000Y | -0.18 | 0.04 | -0.04 | 0.03 | -0.15 | 0.04 |
| IDH1R132H | R-008364711-000B | -0.04 | 0.13 | 2.27 | 0.11 | -0.20 | 0.14 |
| IDH1R132H | R-008364842-000X | 1.70 | 0.10 | 3.88 | 0.24 | 1.50 | 0.05 |
| IDH1R132H | R-008364738-000X | 0.14 | 0.05 | 2.94 | 0.08 | 0.03 | 0.06 |
| IDH1R132H | R-008364765-000Y | -0.20 | 0.07 | 2.86 | 0.06 | -0.11 | 0.04 |
| IDH1R132H | R-008364714-000C | 0.29 | 0.10 | 3.94 | 0.11 | -0.18 | 0.09 |
| IDH1R132H | R-008364603-000S | -0.49 | 0.12 | 1.19 | 0.10 | -0.64 | 0.17 |
| IDH1R132H | R-008364708-000V | -0.06 | 0.06 | 1.18 | 0.05 | -0.22 | 0.16 |
| IDH1R132H | R-008364762-000X | 0.26 | 0.20 | 2.34 | 0.15 | -0.21 | 0.16 |
| IDH1R132H | R-008364600-000R | 0.14 | 0.07 | 2.63 | 0.12 | -0.18 | 0.11 |
| IDH1R132H | R-008364811-000L | -0.07 | 0.10 | 2.13 | 0.19 | -0.11 | 0.18 |
| IDH1R132H | R-008364675-000F | 1.64 | 0.12 | 3.19 | 0.09 | 2.17 | 0.06 |
| IDH1R132H | R-008364645-000D | 0.68 | 0.15 | 1.97 | 0.11 | 1.39 | 0.06 |
| IDH1R132H | R-008364851-000F | 2.34 | 0.06 | 3.06 | 0.05 | 3.65 | 0.05 |
| IDH1R132C | R-008372792-000Z | -0.03 | 0.02 | -0.30 | 0.08 | -0.09 | 0.07 |
| IDH1R132C | R-008372838-000G | -0.23 | 0.12 | -0.57 | 0.19 | -0.20 | 0.19 |
| IDH1R132C | R-008372817-000N | -0.12 | 0.10 | -0.49 | 0.10 | 0.12 | 0.06 |
| IDH1R132C | R-008372814-000M | -0.44 | 0.10 | -0.87 | 0.08 | 2.07 | 0.10 |

TABLE 3a-continued

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1.

| Target specificity | siNA duplex ID | IDH1 reporter | | IDH1-R132H reporter | | IDH1-R132C reporter | |
|---|---|---|---|---|---|---|---|
| | | Mean log2FC | SD log2FC | Mean log2FC | SD log2FC | Mean log2FC | SD log2FC |
| IDH1R132C | R-008372889-000C | 0.08 | 0.17 | −0.42 | 0.13 | 3.99 | 0.12 |
| IDH1R132C | R-008372789-000T | −0.13 | 0.02 | −0.42 | 0.08 | 1.15 | 0.08 |
| IDH1R132C | R-008372868-000J | −0.31 | 0.08 | −0.67 | 0.04 | −0.25 | 0.02 |
| IDH1R132C | R-008372786-000S | 0.16 | 0.12 | −0.28 | 0.17 | 1.76 | 0.16 |
| IDH1R132C | R-008372855-000R | 0.04 | 0.22 | −0.29 | 0.17 | 4.86 | 0.25 |
| IDH1R132C | R-008372811-000L | −0.10 | 0.07 | −0.22 | 0.14 | 3.94 | 0.05 |
| IDH1R132C | R-008372835-000F | −0.23 | 0.04 | −0.35 | 0.04 | 4.20 | 0.01 |
| IDH1R132C | R-008372886-000B | −0.43 | 0.21 | −0.71 | 0.09 | 5.18 | 0.11 |
| IDH1R132C | R-008372876-000J | −0.38 | 0.08 | −0.64 | 0.11 | 1.91 | 0.06 |
| IDH1R132C | R-008372852-000P | −0.09 | 0.08 | −0.37 | 0.09 | 2.51 | 0.06 |
| IDH1R132C | R-008372865-000H | −0.13 | 0.05 | −0.49 | 0.06 | 2.80 | 0.05 |
| IDH1R132C | R-008372849-000H | −0.11 | 0.20 | −0.51 | 0.17 | 3.98 | 0.15 |
| IDH1R132C | R-008372862-000G | 0.04 | 0.11 | −0.46 | 0.14 | 2.39 | 0.07 |
| IDH1R132C | R-008372775-000R | 2.69 | 0.11 | 0.84 | 0.12 | 4.01 | 0.12 |
| IDH1R132C | R-008372808-000E | 1.49 | 0.53 | 0.39 | 0.24 | 3.28 | 0.40 |

TABLE 3b

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1.

| Target specificity | siNA duplex ID | IDH1 reporter | | IDH1-R132H reporter | | IDH1-R132C reporter | |
|---|---|---|---|---|---|---|---|
| | | Mean log2FC | SD log2FC | Mean log2FC | SD log2FC | Mean log2FC | SD log2FC |
| IDH1 | R-008364795-000A | 4.46 | 0.07 | 0.23 | 0.31 | 1.80 | 0.14 |
| IDH1 | R-008405466-000R | 3.82 | 0.34 | −0.22 | 0.15 | 1.68 | 0.20 |
| IDH1 | R-008405049-000T | 3.64 | 0.27 | 0.59 | 0.19 | 2.43 | 0.14 |
| IDH1 | R-008405379-000Z | 3.62 | 0.24 | 2.34 | 0.19 | 4.57 | 0.23 |
| IDH1 | R-008405463-000P | 3.50 | 0.26 | 0.16 | 0.24 | 0.55 | 0.17 |
| IDH1 | R-008405382-000F | 3.48 | 0.20 | 0.76 | 0.14 | 3.51 | 0.10 |
| IDH1 | R-008405181-000C | 3.17 | 0.20 | 0.32 | 0.16 | 1.26 | 0.31 |
| IDH1 | R-008405253-000C | 3.01 | 0.12 | −0.11 | 0.08 | 0.51 | 0.07 |
| IDH1 | R-008405178-000W | 2.89 | 0.10 | 0.74 | 0.28 | 4.25 | 0.19 |
| IDH1 | R-008404956-000C | 2.86 | 0.12 | 2.14 | 0.33 | 4.23 | 0.09 |
| IDH1 | R-008405457-000G | 2.66 | 0.21 | 0.11 | 0.11 | 1.79 | 0.18 |
| IDH1 | R-008405100-000E | 2.32 | 0.17 | −0.24 | 0.21 | 1.20 | 0.15 |
| IDH1 | R-008405310-000S | 2.16 | 0.14 | 0.27 | 0.12 | 2.02 | 0.22 |
| IDH1 | R-008404959-000D | 2.05 | 0.20 | 0.37 | 0.26 | 1.40 | 0.27 |
| IDH1 | R-008405472-000Y | 1.41 | 0.04 | 0.00 | 0.14 | 0.17 | 0.09 |
| IDH1 | R-008405460-000N | 1.14 | 0.08 | −0.17 | 0.11 | 0.22 | 0.08 |
| IDH1 | R-008405469-000S | 0.90 | 0.09 | 0.03 | 0.15 | 0.99 | 0.16 |
| IDH1 | R-008405046-000S | 0.72 | 0.21 | −0.66 | 0.10 | −0.43 | 0.15 |
| IDH1 | R-008405184-000D | 0.31 | 0.10 | −0.07 | 0.12 | 0.16 | 0.14 |
| IDH1 | R-008405385-000G | 0.26 | 0.15 | −0.30 | 0.22 | 0.13 | 0.16 |
| IDH1R132C | R-008372886-000B | 0.00 | 0.04 | −0.21 | 0.10 | 4.71 | 0.24 |
| IDH1R132C | R-008372855-000R | 0.21 | 0.14 | −0.27 | 0.04 | 4.66 | 0.17 |
| IDH1R132C | R-008372775-000R | 2.83 | 0.06 | 0.92 | 0.04 | 4.50 | 0.17 |
| IDH1R132C | R-008372849-000H | −0.26 | 0.10 | −0.59 | 0.08 | 4.44 | 0.04 |
| IDH1R132C | R-008372889-000C | 0.37 | 0.04 | −0.16 | 0.21 | 4.28 | 0.10 |
| IDH1R132C | R-008372811-000L | −0.17 | 0.06 | −0.26 | 0.25 | 4.01 | 0.01 |
| IDH1R132C | R-008372835-000F | −0.22 | 0.10 | −0.39 | 0.15 | 3.97 | 0.08 |
| IDH1R132C | R-008372808-000E | 1.91 | 0.03 | 0.48 | 0.14 | 3.42 | 0.06 |
| IDH1R132C | R-008372865-000H | −0.35 | 0.11 | −0.73 | 0.12 | 3.14 | 0.04 |
| IDH1R132C | R-008372852-000P | −0.33 | 0.10 | −0.44 | 0.15 | 2.94 | 0.19 |
| IDH1R132C | R-008372862-000G | −0.03 | 0.06 | −0.50 | 0.08 | 2.74 | 0.08 |
| IDH1R132C | R-008372786-000S | 0.45 | 0.14 | −0.11 | 0.14 | 2.49 | 0.21 |
| IDH1R132C | R-008372814-000M | −0.72 | 0.10 | −1.12 | 0.14 | 2.44 | 0.07 |
| IDH1R132C | R-008372876-000J | −0.61 | 0.11 | −0.69 | 0.13 | 2.33 | 0.16 |
| IDH1R132C | R-008372789-000T | −0.27 | 0.08 | −0.54 | 0.17 | 1.40 | 0.18 |
| IDH1R132C | R-008372838-000G | −0.04 | 0.12 | −0.34 | 0.10 | 0.71 | 0.11 |
| IDH1R132C | R-008372868-000J | −0.12 | 0.11 | −0.36 | 0.17 | 0.67 | 0.08 |
| IDH1R132C | R-008372817-000N | −0.42 | 0.05 | −0.68 | 0.11 | 0.23 | 0.05 |
| IDH1R132C | R-008372792-000Z | −0.39 | 0.10 | −0.68 | 0.08 | 0.10 | 0.07 |

TABLE 3b-continued

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1.

| Target specificity | siNA duplex ID | IDH1 reporter Mean log2FC | IDH1 reporter SD log2FC | IDH1-R132H reporter Mean log2FC | IDH1-R132H reporter SD log2FC | IDH1-R132C reporter Mean log2FC | IDH1-R132C reporter SD log2FC |
|---|---|---|---|---|---|---|---|
| IDH1R132H | R-008364672-000E | 0.48 | 0.13 | 4.83 | 0.18 | 0.06 | 0.14 |
| IDH1R132H | R-008364842-000X | 2.14 | 0.13 | 4.44 | 0.08 | 2.18 | 0.18 |
| IDH1R132H | R-008364714-000C | 0.37 | 0.21 | 3.88 | 0.31 | 0.18 | 0.11 |
| IDH1R132H | R-008364675-000F | 1.50 | 0.23 | 3.69 | 0.19 | 2.26 | 0.10 |
| IDH1R132H | R-008364815-000W | 1.09 | 0.04 | 3.28 | 0.17 | 1.72 | 0.04 |
| IDH1R132H | R-008364851-000F | 2.48 | 0.09 | 3.25 | 0.16 | 3.73 | 0.06 |
| IDH1R132H | R-008364600-000R | 0.35 | 0.10 | 3.16 | 0.13 | 0.00 | 0.06 |
| IDH1R132H | R-008364711-000B | 0.10 | 0.17 | 3.09 | 0.40 | −0.14 | 0.06 |
| IDH1R132H | R-008364765-000Y | −0.15 | 0.11 | 2.99 | 0.14 | −0.29 | 0.08 |
| IDH1R132H | R-008364738-000X | 0.40 | 0.05 | 2.86 | 0.19 | 0.12 | 0.09 |
| IDH1R132H | R-008364762-000X | 0.35 | 0.13 | 2.70 | 0.21 | −0.14 | 0.08 |
| IDH1R132H | R-008364848-000Z | −0.10 | 0.08 | 2.61 | 0.18 | −0.27 | 0.07 |
| IDH1R132H | R-008364811-000L | 0.10 | 0.08 | 2.34 | 0.19 | −0.12 | 0.12 |
| IDH1R132H | R-008364645-000D | 0.70 | 0.10 | 2.16 | 0.15 | 1.57 | 0.07 |
| IDH1R132H | R-008364642-000C | 0.26 | 0.17 | 2.01 | 0.11 | 0.11 | 0.18 |
| IDH1R132H | R-008364603-000S | −0.65 | 0.09 | 1.37 | 0.04 | −0.51 | 0.04 |
| IDH1R132H | R-008364708-000V | −0.33 | 0.15 | 1.08 | 0.08 | −0.47 | 0.17 |
| IDH1R132H | R-008364845-000Y | −0.08 | 0.11 | 0.45 | 0.13 | −0.11 | 0.09 |
| IDH1R132H | R-008364705-000U | −0.10 | 0.04 | 0.20 | 0.09 | 0.15 | 0.13 |

TABLE 3c

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1. In this experiment, the siNA duplexes tested have either a Stab 04/05 based chemistry (see Table 6) or are unmodified (with the exception of the 3'-overhangs).

| Target specificity | siNA duplex ID | IDH1 reporter Mean Log2FC | IDH1 reporter SD log2FC | IDH1-R132H reporter Mean log2FC | IDH1-R132H reporter SD log2FC | IDH1-R132C reporter Mean log2FC | IDH1-R132C reporter SD log2FC |
|---|---|---|---|---|---|---|---|
| IDH1 | R-008364795-000A | 3.89 | 0.22 | 0.26 | 0.08 | 1.02 | 0.09 |
| IDH1 | R-008405466-000R | 3.29 | 0.30 | UD | UD | 2.65 | 0.34 |
| IDH1 | R-008405253-000C | 2.81 | 0.13 | −0.11 | 0.13 | −0.13 | 0.15 |
| IDH1 | R-008405463-000P | 3.52 | 0.11 | −0.10 | 0.46 | 0.46 | 0.07 |
| IDH1R132C | R-008372855-000R | −0.09 | 0.10 | −0.18 | 0.08 | 4.21 | 0.21 |
| IDH1R132C | R-008415579-000H | 0.24 | 0.42 | UD | UD | 3.62 | 0.18 |
| IDH1R132C | R-008415590-000P | −0.34 | 0.06 | 0.45 | 0.42 | 1.78 | 0.10 |
| IDH1R132C | R-008415554-000E | −0.31 | 0.09 | −0.19 | 0.09 | 1.49 | 0.42 |
| IDH1R132C | R-008415622-000V | −0.25 | 0.06 | −0.26 | 0.06 | 1.13 | 0.13 |
| IDH1R132C | R-008415668-000S | −0.31 | 0.15 | −0.09 | 0.26 | 1.03 | 0.31 |
| IDH1R132C | R-008415624-000M | −0.30 | 0.13 | 0.02 | 0.24 | 0.81 | 0.24 |
| IDH1R132C | R-008415513-000B | −0.22 | 0.13 | 0.46 | 0.75 | 0.66 | 0.08 |
| IDH1R132C | R-008415552-000M | −0.33 | 0.14 | −0.27 | 0.17 | 0.52 | 0.06 |
| IDH1R132C | R-008415667-000H | −0.42 | 0.12 | −0.27 | 0.22 | 0.39 | 0.21 |
| IDH1R132C | R-008415462-000V | 0.83 | 0.13 | 0.16 | 0.17 | 5.27 | 0.25 |
| IDH1R132C | R-008415671-000Y | 0.37 | 0.12 | 0.33 | 0.07 | 5.10 | 0.24 |
| IDH1R132C | R-008415685-000A | 0.47 | 0.27 | 0.42 | 0.09 | 5.03 | 0.26 |
| IDH1R132C | R-008415672-000G | 0.86 | 0.24 | 0.52 | 0.52 | 4.74 | 0.22 |
| IDH1R132C | R-008415626-000E | 0.08 | 0.13 | 0.16 | 0.12 | 4.73 | 0.36 |
| IDH1R132C | R-008415557-000F | 0.11 | 0.10 | 0.30 | 0.18 | 4.66 | 0.10 |
| IDH1R132C | R-008415673-000R | 0.06 | 0.15 | 0.27 | 0.07 | 4.33 | 0.23 |
| IDH1R132C | R-008415648-000G | 0.25 | 0.19 | 0.04 | 0.27 | 4.06 | 0.45 |
| IDH1R132C | R-008372811-000L | −0.32 | 0.13 | −0.34 | 0.14 | 3.53 | 0.35 |
| IDH1R132C | R-008415459-000N | 0.08 | 0.02 | −0.09 | 0.14 | 2.93 | 0.12 |
| IDH1R132H | R-008415535-000D | 0.73 | 0.12 | 4.25 | 0.13 | 0.41 | 0.30 |
| IDH1R132H | R-008415664-000G | 2.56 | 0.14 | 4.23 | 0.13 | 2.47 | 0.35 |
| IDH1R132H | R-008415612-000C | 2.94 | 0.13 | 4.04 | 0.30 | 1.60 | 0.18 |
| IDH1R132H | R-008415674-000Z | 2.70 | 0.16 | 4.02 | 0.11 | 2.48 | 0.29 |
| IDH1R132H | R-008364714-000C | 0.34 | 0.11 | 3.99 | 0.10 | −0.19 | 0.15 |
| IDH1R132H | R-008415678-000J | 2.89 | 0.23 | 3.98 | 0.29 | 1.37 | 0.14 |
| IDH1R132H | R-008415655-000Y | 2.31 | 0.12 | 3.98 | 0.44 | 1.65 | 0.32 |
| IDH1R132H | R-008415646-000P | 1.83 | 0.09 | 3.53 | 0.29 | 1.36 | 0.34 |
| IDH1R132H | R-008415662-000P | 0.41 | 0.26 | 3.51 | 0.17 | 0.42 | 0.07 |

TABLE 3c-continued

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1. In this experiment, the siNA duplexes tested have either a Stab 04/05 based chemistry (see Table 6) or are unmodified (with the exception of the 3'-overhangs).

| Target specificity | siNA duplex ID | IDH1 reporter Mean Log2FC | IDH1 reporter SD log2FC | IDH1-R132H reporter Mean log2FC | IDH1-R132H reporter SD log2FC | IDH1-R132C reporter Mean log2FC | IDH1-R132C reporter SD log2FC |
|---|---|---|---|---|---|---|---|
| IDH1R132H | R-008415637-000F | 0.48 | 0.07 | 2.85 | 0.38 | −0.14 | 0.22 |
| IDH1R132H | R-008415598-000J | 0.31 | 0.13 | 3.15 | 0.09 | −0.04 | 0.15 |
| IDH1R132H | R-008415526-000V | 0.29 | 0.26 | 3.01 | 0.19 | −0.21 | 0.13 |
| IDH1R132H | R-008415564-000X | 0.48 | 0.17 | 2.97 | 0.21 | 0.08 | 0.26 |
| IDH1R132H | R-008364600-000R | 0.10 | 0.18 | 2.87 | 0.13 | UD | UD |
| IDH1R132H | R-008415634-000E | −0.09 | 0.14 | 2.85 | 0.20 | −0.25 | 0.05 |
| IDH1R132H | R-008415652-000X | −0.20 | 0.16 | 2.65 | 0.14 | −0.44 | 0.09 |
| IDH1R132H | R-008415523-000U | −0.13 | 0.11 | 2.53 | 0.16 | 0.26 | 0.96 |
| IDH1R132H | R-008415450-000K | 0.02 | 0.17 | 2.53 | 0.26 | −0.20 | 0.17 |
| IDH1R132H | R-008415453-000L | −0.24 | 0.16 | 2.51 | 0.39 | −0.31 | 0.14 |
| IDH1R132H | R-008415489-000R | −0.51 | 0.17 | 0.89 | 0.20 | −0.47 | 0.28 |

TABLE 3d

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1. In this experiment, each siNA duplex tested is unmodified with the exception of the 3'-overhangs.

| Target specificity | siNA duplex ID | IDH1 reporter Mean log2FC | IDH1 reporter SD log2FC | IDH1-R132H reporter Mean log2FC | IDH1-R132H reporter SD log2FC | IDH1-R132C reporter Mean log2FC | IDH1-R132C reporter SD log2FC |
|---|---|---|---|---|---|---|---|
| IDH1 | R-008364795-000A | 4.07 | 0.02 | −0.10 | 0.08 | 1.04 | 0.15 |
| IDH1 | R-008415691-000H | 3.72 | 0.01 | 0.09 | 0.11 | 1.44 | 0.05 |
| IDH1 | R-008405466-000R | 3.62 | 0.00 | −0.14 | 0.19 | 1.39 | 0.22 |
| IDH1 | R-008405463-000P | 3.61 | 0.21 | 0.24 | 0.07 | 0.22 | 0.09 |
| IDH1 | R-000372127-000H | 3.23 | 0.20 | −0.09 | 0.09 | 1.57 | 0.19 |
| IDH1 | R-000372128-000S | 2.85 | 0.12 | 0.87 | 0.45 | 3.33 | 0.02 |
| IDH1 | R-008415480-000M | 2.43 | 0.24 | 0.37 | 0.04 | 0.13 | 0.11 |
| IDH1 | R-008415560-000M | 2.40 | 0.07 | 2.28 | 0.11 | 4.02 | 0.29 |
| IDH1 | R-008405253-000C | 2.37 | 0.18 | −0.23 | 0.23 | 0.06 | 0.08 |
| IDH1 | R-008415516-000C | 2.06 | 0.03 | 1.26 | 0.05 | 2.50 | 0.21 |
| IDH1 | R-008415651-000N | 1.91 | 0.01 | −0.37 | 0.04 | 0.12 | 0.14 |
| IDH1 | R-008415596-000S | 1.90 | 0.13 | −0.13 | 0.16 | 0.17 | 0.05 |
| IDH1 | R-008415471-000D | 1.89 | 0.02 | 0.03 | 0.12 | 0.69 | 0.03 |
| IDH1 | R-008415593-000R | 1.63 | 0.01 | 0.80 | 0.07 | 2.81 | 0.19 |
| IDH1 | R-008415629-000F | 1.06 | 0.05 | −0.44 | 0.26 | −0.39 | 0.14 |
| IDH1 | R-008415474-000E | 0.64 | 0.07 | −0.58 | 0.01 | 0.14 | 0.01 |
| IDH1 | R-008415694-000J | 0.56 | 0.07 | −0.42 | 0.08 | −0.19 | 0.08 |
| IDH1 | R-008415477-000F | 0.23 | 0.09 | −0.16 | 0.19 | −0.10 | 0.09 |
| IDH1 | R-008415697-000K | 0.22 | 0.07 | −0.08 | 0.17 | −0.32 | 0.13 |
| IDH1 | R-008415688-000B | −0.13 | 0.00 | −0.47 | 0.00 | −0.38 | 0.00 |
| IDH1 | R-008415522-000K | −0.24 | 0.02 | −0.30 | 0.23 | −0.34 | 0.11 |
| IDH1 | R-008415519-000D | −0.24 | 0.05 | −0.34 | 0.20 | −0.20 | 0.04 |
| IDH1 | R-008415483-000N | −0.32 | 0.19 | −0.64 | 0.19 | −0.38 | 0.04 |
| IDH1 | R-008415563-000N | −0.41 | 0.09 | −0.42 | 0.09 | −0.33 | 0.14 |
| IDH1R132C | R-008415588-000S | 0.30 | 0.03 | −0.52 | 0.18 | 4.44 | 0.21 |
| IDH1R132C | R-008415547-000N | −0.07 | 0.10 | −0.24 | 0.11 | 4.34 | 0.10 |
| IDH1R132C | R-008415541-000L | −0.28 | 0.03 | −0.22 | 0.21 | 4.05 | 0.06 |
| IDH1R132C | R-008372855-000R | −0.10 | 0.03 | −0.09 | 0.15 | 3.90 | 0.16 |
| IDH1R132C | R-008372811-000L | −0.16 | 0.09 | −0.22 | 0.16 | 3.27 | 0.14 |
| IDH1R132C | R-008415504-000T | −0.24 | 0.17 | −0.08 | 0.39 | 3.18 | 0.25 |
| IDH1R132C | R-008415544-000M | −0.09 | 0.13 | −0.12 | 0.20 | 3.08 | 0.04 |
| IDH1R132C | R-008415538-000E | −0.23 | 0.05 | −0.49 | 0.18 | 3.02 | 0.07 |
| IDH1R132C | R-008415501-000S | −0.14 | 0.07 | −0.39 | 0.02 | 1.95 | 0.21 |
| IDH1R132C | R-008415615-000D | 0.59 | 0.02 | −0.03 | 0.30 | 1.43 | 0.01 |
| IDH1R132C | R-008415465-000W | 0.84 | 0.53 | 0.07 | 0.06 | 1.38 | 0.12 |
| IDH1R132C | R-008415618-000E | 0.35 | 0.05 | 0.06 | 0.08 | 1.21 | 0.07 |
| IDH1R132C | R-008415468-000X | −0.32 | 0.23 | −0.48 | 0.35 | 1.20 | 0.03 |
| IDH1R132C | R-008415507-000U | −0.28 | 0.11 | −0.35 | 0.22 | 1.08 | 0.08 |
| IDH1R132C | R-008415621-000L | −0.58 | 0.02 | −0.36 | 0.04 | 1.00 | 0.04 |

TABLE 3d-continued

Screening data in Hepa1-6 cells recorded as Log2(fold change) ("log2FC") in expression of the specific IDH1-related reporter. The target specificity (IDH1, IDH1-R132H, or IDH1-R132C) of the tested siNA duplex is provided in column 1. In this experiment, each siNA duplex tested is unmodified with the exception of the 3'-overhangs.

| Target specificity | siNA duplex ID | IDH1 reporter Mean log2FC | IDH1 reporter SD log2FC | IDH1-R132H reporter Mean log2FC | IDH1-R132H reporter SD log2FC | IDH1-R132C reporter Mean log2FC | IDH1-R132C reporter SD log2FC |
|---|---|---|---|---|---|---|---|
| IDH1R132C | R-008415582-000P | −0.33 | 0.00 | −0.47 | 0.24 | 0.28 | 0.13 |
| IDH1R132C | R-008415684-000S | −0.33 | 0.22 | −0.22 | 0.14 | 0.08 | 0.18 |
| IDH1R132C | R-008415681-000R | −0.28 | 0.09 | −0.41 | 0.08 | −0.21 | 0.12 |
| IDH1R132C | R-008415585-000R | −0.36 | 0.20 | −0.66 | 0.06 | −0.28 | 0.03 |
| IDH1R132C | R-008415550-000V | −0.57 | 0.06 | −0.48 | 0.08 | −0.34 | 0.24 |
| IDH1R132C | R-008415510-000A | −0.25 | 0.02 | −0.31 | 0.10 | −0.36 | 0.24 |
| IDH1R132H | R-008415610-000K | 0.19 | 0.18 | 4.21 | 0.35 | −0.26 | 0.02 |
| IDH1R132H | R-008364714-000C | 0.34 | 0.09 | 4.17 | 0.12 | −0.02 | 0.17 |
| IDH1R132H | R-008415607-000D | 0.66 | 0.14 | 3.24 | 0.05 | 0.21 | 0.02 |
| IDH1R132H | R-008415567-000Y | 1.13 | 0.35 | 2.97 | 0.36 | 1.38 | 0.24 |
| IDH1R132H | R-008364600-000R | −0.27 | 0.23 | 2.59 | 0.08 | −0.33 | 0.00 |
| IDH1R132H | R-008415643-000N | −0.02 | 0.18 | 2.52 | 0.01 | −0.11 | 0.19 |
| IDH1R132H | R-008415456-000M | −0.20 | 0.09 | 2.22 | 0.19 | −0.37 | 0.04 |
| IDH1R132H | R-008415677-000A | 0.11 | 0.14 | 2.17 | 0.29 | −0.04 | 0.19 |
| IDH1R132H | R-008415573-000F | −0.04 | 0.28 | 1.66 | 0.36 | −0.40 | 0.08 |
| IDH1R132H | R-008415495-000Y | −0.25 | 0.01 | 1.54 | 0.08 | −0.32 | 0.20 |
| IDH1R132H | R-008415532-000C | −0.04 | 0.08 | 1.43 | 0.25 | −0.38 | 0.00 |
| IDH1R132H | R-008415576-000G | −0.16 | 0.04 | 1.41 | 0.05 | −0.46 | 0.09 |
| IDH1R132H | R-008415492-000X | 0.49 | 0.01 | 1.34 | 0.14 | 1.21 | 0.13 |
| IDH1R132H | R-008415601-000B | 1.30 | 0.10 | 1.18 | 0.24 | 2.74 | 0.03 |
| IDH1R132H | R-008415529-000W | 0.43 | 0.17 | 1.02 | 0.21 | 0.48 | 0.10 |
| IDH1R132H | R-008415658-000Z | −0.43 | 0.03 | 0.87 | 0.46 | −0.54 | 0.12 |
| IDH1R132H | R-008415640-000M | −0.19 | 0.19 | 0.21 | 0.27 | −0.22 | 0.02 |
| IDH1R132H | R-008415604-000C | 0.02 | 0.02 | 0.18 | 0.02 | 0.12 | 0.07 |
| IDH1R132H | R-008415661-000F | −0.18 | 0.15 | −0.05 | 0.17 | −0.13 | 0.10 |
| IDH1R132H | R-008415570-000E | −0.33 | 0.11 | −0.14 | 0.09 | −0.25 | 0.09 |
| IDH1R132H | R-008415498-000Z | −0.44 | 0.14 | −0.41 | 0.10 | −0.33 | 0.09 |

Select high ranking siNAs from Tables 3a-d were further analyzed for efficacy and potency in human HepG2 and mouse Hepa1-6 cells using dose response curves. The results for these siNAs are shown in Table 4a, Table 4b, Table 4c and Table 4d. Potency50 ("P50" in Tables 4a-d) was determined after 48 hour exposure time.

TABLE 4a

Dose response data for various siNAs targeting IDH1-R132H expression in human HepG2 and mouse Hepa1-6 cells. Calculated maximum log2(fold change) ("ssDRC max log2(FC)") is determined from the dose response curve. P50 is the Potency 50 calculation.

| | HepG2 cells | | | | Hepa1-6 cells | | | |
|---|---|---|---|---|---|---|---|---|
| | IDH1 reporter | | IDH1-R132H reporter | | IDH1 reporter | | IDH1-R132H reporter | |
| siNA duplex ID | ssDRC max log2(FC) | P50 (pM) | ssDRC max log2(FC) | Pot. 50 (pM) | ssDRC max log2(FC) | P50 (pM) | ssDRC max log2(FC) | P50 (pM) |
| R-008364600-000R | −0.12 | ND | 3.08 | 496 | 0.40 | ND | 3.72 | 263 |
| R-008364675-000F | 0.86 | ND | 4.20 | 226 | 1.77 | 225 | 4.03 | 40 |
| R-008364711-000B | 0.12 | ND | 2.17 | 1040 | 0.25 | ND | 3.08 | 180 |
| R-008364714-000C | 0.04 | ND | 3.86 | 67 | 0.50 | ND | 4.59 | 22 |
| R-008364765-000Y | 0.16 | ND | 2.51 | 294 | 0.00 | ND | 3.36 | 101 |
| R-008364842-000X | 1.28 | 3830 | 4.54 | 124 | 1.99 | 228 | 4.49 | 22 |

TABLE 4b

Dose response data for various siNAs targeting IDH1-R132C expression in mouse Hepa1-6 cells. Calculated maximum log2(foldchange) ("ssDRC max log2(FC)") is determined from the dose response curve. P50 is the Potency 50 calculation.

| | IDH1 reporter | | IDH1-R132C reporter | |
|---|---|---|---|---|
| siNA duplex ID | ssDRC max log2(FC) | P50 (pM) | ssDRC max log2(FC) | P50 (pM) |
| R-008372811-000L | 0.30 | ND | 4.26 | 45 |
| R-008372835-000F | 0.27 | ND | 4.54 | 64 |
| R-008372849-000H | 0.29 | ND | 5.07 | 313 |
| R-008372855-000R | 0.48 | ND | 4.90 | 57 |
| R-008372886-000B | 0.32 | ND | 5.62 | 36 |
| R-008372889-000C | 0.50 | ND | 4.16 | 67 |

TABLE 4c

Dose response data for various siNAs targeting wildtype IDH1 expression in mouse Hepa1-6 cells. Calculated maximum log2(fold change) ("ssDRC max log2(FC)") is determined from the dose response curve. P50 is the Potency 50 calculation.

| | IDH1 reporter | | IDH1-R132H reporter | | IDH1-R132C reporter | |
|---|---|---|---|---|---|---|
| siNA duplex ID | ssDRC max log2(FC) | P50 (pM) | ssDRC max log2(FC) | P50 (pM) | ssDRC max log2(FC) | P50 (pM) |
| R-008364795-000A | 5.07 | 81 | 0.69 | ND | 2.08 | 966 |
| R-008405466-000R | 4.19 | 78 | 0.17 | ND | 1.81 | 196 |
| R-008405463-000P | 3.98 | 40 | 0.47 | ND | 0.58 | ND |
| R-008405049-000T | 3.39 | 147 | 0.71 | ND | 2.36 | 589 |
| R-008405253-000C | 3.17 | 64 | 0.12 | ND | 0.31 | ND |
| R-008405181-000C | 3.13 | 192 | 0.33 | ND | 1.33 | 2890 |

TABLE 4d

Dose response data for various siNAs targeting wildtype IDH1, IDH1-R132H ("R132H"), or IDH1-R132C ("R132C") expression in mouse Hepa1-6 cells. Calculated maximum log2(fold change) ("ssDRC max log2(FC)") is determined from the dose response curve. P50 is the Potency 50 calculation.

| | | IDH1 reporter | | IDH1-R132H reporter | | IDH1-R132C reporter | |
|---|---|---|---|---|---|---|---|
| Target spec. | siNA duplex ID | ssDRC max log2(FC) | P50 (pM) | ssDRC max log2(FC) | P50 (pM) | ssDRC max log2(FC) | P50 (pM) |
| IDH1 | R-008405463-000P | 3.31 | 50 | | | | 886 |
| IDH1 | R-008405466-000R | | | 0.19 | 233 | 1.28 | 1300 |
| IDH1 | R-008415516-000C | | | | 13 | 2.09 | 179 |
| IDH1 | R-008415593-000R | | | | 624 | 2.68 | |
| R132H | R-008364600-000R | 0.56 | | 3.30 | 24 | 0.10 | |
| R132H | R-008364714-000C | 0.45 | | 4.08 | 301 | | |
| R132H | R-008415453-000L | 0.22 | | 2.55 | 36 | | |
| R132H | R-008415535-000D | 1.05 | | 4.30 | 20 | | |
| R132H | R-008415598-000J | 0.67 | | 3.25 | 74 | | |
| R132H | R-008415662-000P | 1.11 | | 3.82 | | | |
| R132H | R-008415664-000G | 2.80 | 171 | 4.09 | | 3.03 | 100 |
| R132H | R-008415674-000Z | 3.04 | 94 | 4.33 | | 3.01 | 360 |
| R132C | R-008372811-000L | 0.09 | | 0.13 | | 3.33 | 50 |
| R132C | R-008372855-000R | 0.15 | | 0.18 | | 3.73 | 73 |
| R132C | R-008415462-000V | 0.94 | | 0.23 | | 5.52 | 16 |
| R132C | R-008415465-000W | | | | | 1.24 | 7850 |
| R132C | R-008415579-000H | 0.24 | | 0.24 | | 4.12 | 50 |
| R132C | R-008415615-000D | | | | | 1.43 | 3560 |
| R132C | R-008415671-000Y | | | | | 5.33 | 19 |

Example 3

In Vitro IDH1 Protein Knockdown

In Vitro Cell Culture System—

Human glioma cell line, MOG-G-UVW, were grown as suggested by the European Collection of Cell Cultures (ECACC (UK)). MOG-G-UVW cells were engineered to express human IDH1-R132H using the pLENTI6.2 C-terminal V5 lentiviral expression system (Invitrogen). Post-lentiviral infection, MOG-G-UVW IDH1 R132H cells were grown in DMEM-F12 supplemented with GLUTAMAX (Invitrogen), 1% sodium bicarbonate, sodium pyruvate, 5 micrograms/ml of blasticidin and 10% fetal bovine serum. For the 2-HG measurements a sarcoma cell line was grown in Dulbecco's modified Eagle's medium GLUTAMAX (Invitrogen), D-glucose, sodium pyruvate & 10% fetal bovine serum.

Experiments to Assess IDH1 Protein Knockdown—

For siRNA protein knockdown experiments, cells were plated in 6-well tissue culture plates and incubated at 37° C. overnight. The next day, siNAs or siGLO transfection control (Dharmacon) were transfected at 20 nM final concentration using Lipofectamine™ RNAiMAX Reagent (Invitrogen). The next morning cell media was replaced. At 72 hours post transfection, cells were washed once with PBS and lysed with m-PER lysis buffer (Pierce) and Western blots were run. Protein expression was assessed with the following antibodies at 1:1000 dilutions unless otherwise noted: V5-tagged IDH1-R132H (Invitrogen), endogenous anti-human IDH1 at 1:400 dilution (Protein Tech Group), anti-human GAPDH (Cell Signaling Technologies) and anti-human Tubulin (Cell Signal Technologies).

Mass-Spectrometry for 2-Hydroxyglutarate Assessment—

To measure 2-hydroxyglutarate (2-HG) upon siNA knockdown of mutant IDH1, cells were plated in 6-well tissue culture plates and incubated at 37° C. overnight. The next day, siNAs were transfected at 20 nM final concentration using Lipofectamine™ RNAiMAX Reagent (Invitrogen). All transfections were set up as multiple biological replicates. The next morning cell media was replaced. At 72 hours post transfection for MOG-G-UVW IDH1-R132H and 96 hrs post-transfection for HT-1080 cells, media supernatant was harvested and transferred to a 96-well plate and diluted with acetonitrile. Plates were spun at room temperature for 10 min at 3200 RPM to clear precipitated proteins and 2-HG was analyzed by mass spectrometry on an API-400 mass spectrometer.

Results—

1) Preferential IDH1-R132H-Specific RNAi Knockdown in MOG-G-UVM Human Glioma Cells—

The western blot data in FIG. 10 displays the ability for several human IDH1-based siNA sequences to inhibit IDH1 expression in a human glioma MOG-G-UVW cell line. A C-terminal V5-tag was introduced into either wildtype or mutant IDH protein and expression was measured by blotting with a V5-specific antibody. FIG. 10 shows the activity of siNA duplex ID no. R-008364600-000R to effectively abrogate the expression of mutant IDH1-R132H while leaving wildtype IDH1 expression intact. siNA duplex ID no. R-008364714-000C also has mutant-specific IDH1-R132H RNAi activity, however to a lesser degree than siNA R-008364600-000R. In contrast, siNA sequences R-008364798-000B and R-008364836-000P indiscriminantly prevented the expression of either wildtype or mutant IDH1-R132H alleles.

2) Inhibition of IDH1-R132C by RNAi Decreases 2-HG in Media—

FIGS. 11A and 11B represent the ability for several human IDH1 based siNA sequences to prevent the production and secretion of the metabolite, 2-hydroxyglutarate (2-HG) into cell culture media. FIG. 11A and FIG. 11B differ only by cell plating density at the start of each experiment. As shown, R132C-specific sequences R-008372811-000L, R-008372886-000B, R-008372855-000R, or the indiscriminant IDH1 siNA R-008364798-000B (mentioned above) are each able to reduce the levels of secreted 2-HG in culture media 96 hours post-transfection. Mock transfected cells or a non-targeting control siNA sequence maintained high levels of 2-HG.

3) IDH1 siRNA Knockdown Correlates with a Decrease in 2-HG—

FIG. 12 confirms that siNA knockdown of IDH1 correlates with a reduction in secreted 2-hydroxyglutarate (2-HG). IDH1 protein and 2-HG was significantly reduced in cells transfected with either siNA duplex ID nos. R-008364836-000B or R-008364798-000B after a 96 hour incubation period. Quantitatively, a reduction of 85% IDH1 protein resulted in a 78% reduction of 2-HG as both R-008364836-000B and R-008364798-000B have a similar level of knockdown activity in this assay. Control samples consisted of mock transfection (RNAiMax), non-targeting control, or the fluorescent transfection control siGLO neither of which significantly perturbed either IDH1 protein expression or 2-HG production.

Example 4

Determining In Vitro Serum Stability of siNAs siNAs are reconstituted as 50 µM to 100 µM stock solution with $H_2O$ and added to human serum pre-warmed to 37° C. to a final concentration of 20 µg/mL. The mixture is then incubated at 37° C. for 0, 1 and 2 hours. At the end of each time point, the reactions are stopped by mixing with equal volume of Phenomenex Lysis-Loading Buffer. Oligonucleotides are purified in 96-well format by Phenomenex Solid Phase Extraction and lyophilized until dry with Labconco Triad Lyo-00417. The lyophilized samples are reconstituted in 150 µL of 1 mM EDTA prepared with RNase-free $H_2O$. The sample solutions are then diluted 5 fold with 1 mM EDTA for liquid chromatography/mass spectrometry (LC/MS) analysis on ThermoFisher Orbitrap. Serum metabolites of the siNAs were determined based on the measured molecular weights.

Example 5

Testing of Cytokine Induction

To assess immunostimulative effects of various siNAs of the invention loaded in lipid nanoparticles (e.g., DLinDMA/Cholesterol/S-PEG-C-DMA/DSPC in a 40/48/2/10 ratio), C57Bl/6 mice are dosed with a single 3mpk dose of LNP formulated siNAs through tail vein injection. Serum or plasma samples are collected at 3 and 24 hours post-dose. The cytokine and chemokine levels in these samples are measured with the SearchLight IR Cytokine Array from Aushon Biosciences according to the manufacturer's instruction. The cytokines and chemokines measured are IL-1α, IL-1β, IL-6, KC, IL-10, IFNγ, TNF, GMCSF, MIP-1β, MCP-1/JE, and RANTES.

Example 6

Pharmacodynamic Study in Non-Human Primates

Rhesus macaque monkeys are dosed with a single 2.5 mpk dose of siNA loaded in lipid nanoparticles (e.g., DLinDMA/Cholesterol/S-PEG-C-DMA/DSPC in a 40/48/2/10 ratio) through intravenous infusion. To monitor target mRNA knockdown, liver biopsies are performed at various time points pre- and post-dose with 16T gauge Menghini needles for about 20 mg tissue per animal. Whole blood and serum/plasma is also collected at different time points pre- and post-dose to monitor potential toxicity associated with the treatments. All procedures adhere to the regulations outlined in the USDA Animal Welfare Act (9 CFR, Parts 1, 2 and 3) and the conditions specified in The Guide for Care and Use of Laboratory Animals (ILAR publication, 1996, National Academy Press). Log 2(fold change) in target gene expression is determined at different timepoints post-dosing. Pre-dose target gene expression levels for the monkey is measured 7 days before the first dosing.

Example 7 siNA Lipid Nanoparticle (LNP) Formulations

General LNP Process Description for DLinDMA Formulations—

Lipid nanoparticles are prepared by an impinging jet process. The particles are formed by mixing lipids dissolved in alcohol with siNA dissolved in a citrate buffer. The mixing ratio of lipids to siNA is targeted at approximately 45-55% lipid and 35-45% siNA. The lipid solution contains a cationic lipid, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids has a mole percent range of 25-98 for the cationic lipid with a target of 35-65; the helper lipid has a mole percent range from 0-75 with a target of 30-50; the PEG lipid has a mole percent range from 1-15 with a target of 1-6; and the DSPC has a mole percent range of 0-15 with a target of 0-12. The siNA solution contains one or more siNA sequences at a concentration range from 0.3 to 1.0 mg/mL with a target of 0.3-0.9 mg/mL in a sodium citrate-buffered salt solution with pH in the range of 3.5-5. The two liquids are heated to a temperature in the range of 15-40° C., targeting 30-40° C., and then mixed in an impinging jet mixer instantly forming the LNP. The tubing ID has a range from 0.25 to 1.0 mm and a total flow rate from 10-600 mL/minute. The combination of flow rate and tubing ID has the effect of controlling the particle size of the LNPs between 30 and 200 nm. The solution is then mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating, the solution is filtered through a 0.8 μm filter containing an anion exchange separation step. This process uses tubing IDs ranging from 1 mm ID to 5 mm ID and a flow rate from 10 to 2000 mL/minute. The LNPs are concentrated and diafiltered via an ultrafiltration process where the alcohol is removed and the citrate buffer is exchanged for the final buffer solution, such as phosphate buffered saline. The ultrafiltration process uses a tangential flow filtration format (TFF). This process uses a membrane nominal molecular weight cutoff range from 30-500 KD. The membrane format is hollow fiber or flat sheet cassette. The TFF processes, with the proper molecular weight cutoff, retains the LNP in the retentate, and the filtrate or permeate contains the alcohol, citrate buffer, and final buffer wastes. The TFF process is a multiple step process with an initial concentration to a siNA concentration of 1-3 mg/mL. Following concentration, the LNP solution is diafiltered against the final buffer for 10-20 volumes to remove the alcohol and perform buffer exchange. The material is then concentrated an additional 1-3 fold. The final steps of the LNP process are to sterile filter the concentrated LNP solution and vial the product.

Analytical Procedure:

1) siNA concentration—The siNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siNA and analyzed by SAX separation using a Dionex BioLC DNAPac PA 200 (4×250 mm) column with UV detection at 254 nm. Mobile phase is composed of A: 25 mM $NaClO_4$, 10 mM Tris, 20% EtOH, pH 7.0 and B: 250 mM $NaClO_4$, 10 mM Tris, 20% EtOH, pH 7.0 with a liner gradient from 0-15 min and a flow rate of 1 ml/minute. The siNA amount is determined by comparing to the siNA standard curve.

2) Encapsulation rate—Fluorescence reagent SYBR Gold is employed for RNA quantitation to monitor the encapsulation rate of RDVs. RDVs with or without Triton X-100 are used to determine the free siNA and total siNA amount. The assay is performed using a SpectraMax M5e microplate spectrophotometer from Molecular Devices (Sunnyvale, Calif.). Samples are excited at 485 nm and fluorescence emission is measured at 530 nm. The siNA amount is determined by comparing to a siNA standard curve: Encapsulation rate=(1−free siNA/total siNA)×100%

3) Particle size and polydispersity—RDVs containing 1 μg siNA are diluted to a final volume of 3 ml with 1×PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis—RDVs containing 1 μg siNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid analysis—Individual lipid concentrations are determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 μm particle size) column with CAD at 60° C. The mobile phase is composed of A: 0.1% TFA in $H_2O$ and B: 0.1% TFA in IPA. The gradient changes from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 min with a flow rate of 1 ml/minute. The individual lipid concentration is determined by comparing to the standard curve with all the lipid components in the RDVs with a quadratic curve fit. The molar percentage of each lipid is calculated based on its molecular weight.

General LNP Preparation for Various Formulations in Table 8— siNA nanoparticle solutions in Table 8 are prepared by dissolving siNAs and/or carrier molecules in 25 mM citrate buffer (pH 4.0) at a concentration of 0.9 mg/mL. Lipid solutions are prepared by dissolving a mixture of cationic lipid (e.g., CLinDMA or DOBMA, see structures and ratios for Formulations in Table 8), DSPC, Cholesterol, and PEG- DMG (ratios shown in Table 8) in absolute ethanol at a concentration of about 15 mg/mL. The nitrogen to phosphate ratio is approximate to 3:1.

Equal volume of siNA/carrier and lipid solutions are delivered with two FPLC pumps at the same flow rates to a mixing T connector. A back pressure valve is used to adjust to the desired particle size. The resulting milky mixture is collected in a sterile glass bottle. This mixture is then diluted slowly with an equal volume of citrate buffer, and filtered through an ion-exchange membrane to remove any free siNA/carrier in the mixture. Ultrafiltration against citrate buffer (pH 4.0) is employed to remove ethanol (test stick from ALCO screen), and against PBS (pH 7.4) to exchange buffer. The final LNP is obtained by concentrating to a desired volume and sterile filtered through a 0.2 μm filter. The obtained LNPs are characterized in terms of particle size, Zeta potential, alcohol content, total lipid content, nucleic acid encapsulated, and total nucleic acid concentration.

LNP Manufacture Process—

In a non-limiting example, a LNP-086 siNA/carrier formulation is prepared in bulk as follows. The process consists of (1) preparing a lipid solution; (2) preparing an siNA/carrier solution; (3) mixing/particle formation; (4) incubation; (5) dilution; and (6) ultrafiltration and concentration.

1) Preparation of Lipid Solution—A 3-necked 2 L round bottom flask, a condenser, measuring cylinders, and two 10 L conical glass vessels are depyrogenated. The lipids are warmed to room temperature. Into the 3-necked round bottom flask is transferred 50.44 g of CLinDMA with a pipette and 43.32 g of DSPC, 5.32 g of Cholesterol, 6.96 g of PEG-DMG, and 2.64 g of linoleyl alcohol. To the mixture is added 1 L of ethanol. The round bottom flask is placed in a heating mantle that is connected to a J-CHEM process controller. The lipid suspension is stirred under Argon with a stir bar and a condenser on top. A thermocouple probe is placed into the suspension through one neck of the round bottom flask with a sealed adapter. The suspension is heated at 30° C. until it becomes clear. The solution is allowed to cool to room temperature and transferred to a conical glass vessel and sealed with a cap.

2) Preparation of siNA/Carrier Solution—Into a sterile container, such as a Corning storage bottle, is weighed 3.6 g times the water correction factor (approximately 1.2) of a first siNA powder, "siNA-1." The siNA is transferred to a depyrogenated 5 L glass vessel. The weighing container is rinsed 3× with citrate buffer (25 mM, pH 4.0, and 100 mM NaCl) and the rinses are placed into the 5 L vessel, QS with citrate buffer to 4 L. The concentration of the siNA solution is determined with a UV spectrometer using the following procedure. 20 μL is removed from the solution, diluted 50 times to 1000 and the UV reading recorded at A260 nm after blanking with citrate buffer. This is repeated. If the readings for the two samples are consistent, an average is taken and the concentration is calculated based on the extinction coefficients of the siNAs. If the final concentration is out of the range of 0.90±0.01 mg/mL, the concentration is adjusted by adding more siNA/carrier powder, or adding more citrate buffer. This process is repeated for a second siNA, "siNA-2." Into a depyrogenated 10 L glass vessel, 4 L of each 0.9 mg/mL siNA solution is transferred.

Alternatively, if the siNA/carrier solution comprised a single siNA duplex and or carrier, instead of a cocktail of two or more siNA duplexes and/or carriers, then the siNA/carrier is dissolved in 25 mM citrate buffer (pH 4.0, 100 mM of NaCl) to give a final concentration of 0.9 mg/mL.

The lipid/ethanol solution is then sterile filtered through a Pall Acropak 20 0.8/0.2 μm sterile filter PN 12203 into a depyrogenated glass vessel using a Master Flex Peristaltic Pump Model 7520-40 to provide a sterile starting material for the encapsulation process. The filtration process is run at an 80 mL scale with a membrane area of 20 cm$^2$. The flow rate is 280 mL/minute. This process is scaleable by increasing the tubing diameter and the filtration area.

3) Particle formation—Mixing step—An AKTA P900 pump is turned on and sanitized by placing 1000 mL of 1 N NaOH into a 1 L glass vessel and 1000 mL of 70% ethanol into a 1 L glass vessel and attaching the pump with a pressure lid to each vessel. A 2000 mL glass vessel is placed below the pump outlet and the flow rate is set to 40 mL/min for a 40 minute time period with argon flushing the system at 10 psi. When the sanitation is complete, the gas is turned off and the pump is stored in the solutions until ready for use. Prior to use, the pump flow is verified by using 200 mL of ethanol and 200 mL of sterile citrate buffer.

To the AKTA pump is attached the sterile lipid/ethanol solution, the sterile siNA/carrier or siNA/carrier cocktail/citrate buffer solution and a depyrogenated receiving vessel (2× batch size) with lid. The gas is turned on and the pressure maintained between 5 to 10 psi during mixing.

4) Incubation—The solution is held after mixing for a 22±2 hour incubation. The incubation is done at room temperature (20-25° C.) and the in-process solution is protected from light.

5) Dilution—The lipid siNA solution is diluted with an equal volume of citrate buffer using a dual head peristaltic pump, Master Flex Peristaltic Pump, Model 7520-40 that is set up with equal lengths of tubing and a Tee connection and a flow rate of 360 mL/minute.

6) Ultrafiltration and concentration—The ultrafiltration process is a timed process and the flow rates must be monitored carefully. This is a two step process: the first is a concentration step taking the diluted material from 32 L to 3600 mLs and to a concentration of approximately 2 mg/mL.

In the first step, a Flexstand installed with an ultrafiltration membrane GE PN UFP-100-C-35A is attached to the quatro-flow pump. 200 mL of WFI is added to the reservoir, followed by 3 L of 0.5 N sodium hydroxide which is then flushed through the retentate to waste. This process is repeated 3×. Then 3 L WFI is flushed through the system 2×, followed by 3 L of citrate buffer. The pump is then drained.

The diluted LNP solution is placed into the reservoir to the 4 L mark. The pump is turned on and the pump speed adjusted so the permeate flow rate is 300 mL/minute and the liquid level is constant at 4 L in the reservoir. The pump is stopped when all the diluted LNP solution has been transferred to the reservoir. The diluted LNP solution is concentrated to 3600 mL in 240 minutes by adjusting the pump speed as necessary.

The second step is a diafiltration step exchanging the ethanol citrate buffer to phosphate buffered saline. The diafiltration step takes 3 hrs and, again, the flow rates must be carefully monitored. During this step, the ethanol concentration is monitored by head space GC. After 3 hours (20 diafiltration volumes), a second concentration is undertaken to concentrate the solution to approximately 6 mg/mL or a volume of 1.2 L. This material is collected into a depyrogenated glass vessel. The system is rinsed with 400 mL of PBS at high flow rate and the permeate line closed. This material is collected and added to the first collection. The expected concentration at this point is 4.5 mg/mL. The concentration and volume are determined.

The feed tubing of the peristaltic pump is placed into a container containing 72 L of PBS (0.05 μm filtered) and the flow rate is adjusted initially to maintain a constant volume of 3600 mL in the reservoir and then increased to 400 mL/minute. The LNP solution is diafiltered with PBS (20 volumes) for 180 minutes.

The LNP solution is concentrated to the 1.2 L mark and collected into a depyrogenated 2 L graduated cylinder. 400 mL of PBS are added to the reservoir and the pump is recirculated for 2 minutes. The rinse is collected and added to the collected LNP solution in the graduated cylinder.

The obtained LNPs are characterized in terms of particle size, Zeta potential, alcohol content, total lipid content, nucleic acid encapsulated, and total nucleic acid concentration.

One skilled in the art will readily appreciate that the present invention is well adapted to carry out the objects and obtain the ends and advantages mentioned, as well as those inherent therein. The methods and compositions described herein, as presently representative of preferred embodiments, are exemplary and are not intended as limitations on the scope of the invention. Changes therein and other uses will occur to those skilled in the art, which are encompassed within the spirit of the invention and are defined by the scope of the claims.

TABLE 5

IDH1-related NCBI Genbank Accession Numbers

NM_005896—SEQ ID NO: 516
*Homo sapiens* IDH1
GI: 28178824

TABLE 6

Non-limiting examples of Stabilization Chemistries for chemically modified siNA constructs

| Chemistry | pyrimidine | purine | caps | p = S | Strand |
|---|---|---|---|---|---|
| "Stab 00" | Ribo | Ribo | TT at 3'-ends | — | S/AS |
| "Stab 1" | Ribo | Ribo | — | 5 at 5'-end 1 at 3'-end | S/AS |
| "Stab 2" | Ribo | Ribo | — | All linkages | Usually AS |
| "Stab 3" | 2'-fluoro | Ribo | — | 4 at 5'-end 4 at 3'-end | Usually S |
| "Stab 4" | 2'-fluoro | Ribo | 5' and 3'-ends | — | Usually S |
| "Stab 5" | 2'-fluoro | Ribo | — | 1 at 3'-end | Usually AS |
| "Stab 6" | 2'-O-Methyl | Ribo | 5' and 3'-ends | — | Usually S |
| "Stab 7" | 2'-fluoro | 2'-deoxy | 5' and 3'-ends | — | Usually S |
| "Stab 8" | 2'-fluoro | 2'-O-Methyl | — | 1 at 3'-end | S/AS |
| "Stab 9" | Ribo | Ribo | 5' and 3'-ends | — | Usually S |
| "Stab 10" | Ribo | Ribo | — | 1 at 3'-end | Usually AS |
| "Stab 11" | 2'-fluoro | 2'-deoxy | — | 1 at 3'-end | Usually AS |
| "Stab 12" | 2'-fluoro | LNA | 5' and 3'-ends | — | Usually S |
| "Stab 13" | 2'-fluoro | LNA | — | 1 at 3'-end | Usually AS |
| "Stab 14" | 2'-fluoro | 2'-deoxy | — | 2 at 5'-end 1 at 3'-end | Usually AS |
| "Stab 15" | 2'-deoxy | 2'-deoxy | — | 2 at 5'-end 1 at 3'-end | Usually AS |
| "Stab 16" | Ribo | 2'-O-Methyl | 5' and 3'-ends | — | Usually S |
| "Stab 17" | 2'-O-Methyl | 2'-O-Methyl | 5' and 3'-ends | — | Usually S |
| "Stab 18" | 2'-fluoro | 2'-O-Methyl | 5' and 3'-ends | — | Usually S |
| "Stab 19" | 2'-fluoro | 2'-O-Methyl | 3'-end | — | S/AS |
| "Stab 20" | 2'-fluoro | 2'-deoxy | 3'-end | — | Usually AS |
| "Stab 21" | 2'-fluoro | Ribo | 3'-end | — | Usually AS |
| "Stab 22" | Ribo | Ribo | 3'-end | — | Usually AS |
| "Stab 23" | 2'-fluoro* | 2'-deoxy* | 5' and 3'-ends | — | Usually S |
| "Stab 24" | 2'-fluoro* | 2'-O-Methyl* | — | 1 at 3'-end | S/AS |
| "Stab 25" | 2'-fluoro* | 2'-O-Methyl* | — | 1 at 3'-end | S/AS |
| "Stab 26" | 2'-fluoro* | 2'-O-Methyl* | — | — | S/AS |
| "Stab 27" | 2'-fluoro* | 2'-O-Methyl* | 3'-end | — | S/AS |
| "Stab 28" | 2'-fluoro* | 2'-O-Methyl* | 3'-end | — | S/AS |
| "Stab 29" | 2'-fluoro* | 2'-O-Methyl* | — | 1 at 3'-end | S/AS |
| "Stab 30" | 2'-fluoro* | 2'-O-Methyl* | — | — | S/AS |
| "Stab 31" | 2'-fluoro* | 2'-O-Methyl* | 3'-end | — | S/AS |
| "Stab 32" | 2'-fluoro | 2'-O-Methyl | — | — | S/AS |
| "Stab 33" | 2'-fluoro | 2'-deoxy* | 5' and 3'-ends | — | Usually S |
| "Stab 34" | 2'-fluoro | 2'-O-Methyl* | 5' and 3'-ends | — | Usually S |
| "Stab 35" | 2'-fluoro*† | 2'-O-Methyl*† | | | Usually AS |

TABLE 6-continued

Non-limiting examples of Stabilization Chemistries for chemically modified siNA constructs

| Chemistry | pyrimidine | purine | caps | p = S | Strand |
|---|---|---|---|---|---|
| "Stab 36" | 2'-fluoro*† | 2'-O-Methyl*† | | | Usually AS |
| "Stab04H" | 2'-fluoro*‡ | Ribo‡ | 5' and 3'-ends | 1 at 3'-end | Ususally S |
| "Stab06C" | 2'-O-Methyl‡ | Ribo‡ | 5' and 3'-ends | | Ususally S |
| "Stab07H" | 2'-fluoro‡ | 2'-deoxy‡ | 5' and 3'-ends | 1 at 3'-end | Ususally S |
| "Stab07mU" | 2'-fluoro‡ | 2'-deoxy‡ | 5' and 3'-ends | | Ususally S |
| "Stab09H" | Ribo‡ | Ribo‡ | 5' and 3'-ends | 1 at 3'-end | Ususally S |
| "Stab16C" | Ribo‡ | 2'-O-Methyl‡ | 5' and 3'-ends | | Ususally S |
| "Stab16H" | Ribo‡ | 2'-O-Methyl‡ | 5' and 3'-ends | 1 at 3'-end | Ususally S |
| "Stab18C" | 2'-fluoro‡ | 2'-O-Methyl‡ | 5' and 3'-ends | | Ususally S |
| "Stab18H" | 2'-fluoro‡ | 2'-O-Methyl‡ | 5' and 3'-ends | 1 at 3'-end | Ususally S |
| "Stab52H" | 2'-O-Methyl‡ | Ribo‡ | 5' and 3'-ends | 1 at 3'-end | Ususally S |
| "Stab05C" | 2'-fluoro‡ | Ribo‡ | | | Ususally AS |
| "Stab05N" | 2'-fluoro‡ | Ribo‡ | | 1 at 3'-end | Ususally AS |
| "Stab10C" | Ribo‡ | Ribo‡ | | | Ususally AS |
| "Stab10N" | Ribo‡ | Ribo‡ | | 1 at 3'-end | Ususally AS |
| "Stab35G*" | 2'-fluoro‡ | 2'-O-Methyl‡ | | | Ususally AS |
| "Stab35N*" | 2'-fluoro‡ | 2'-O-Methyl‡ | | 1 at 3'-end | Ususally AS |
| "Stab35rev*" | 2'-O-Methyl‡ | 2'-fluoro‡ | | | Ususally AS |
| "Stab50*" | Ribo‡ | 2'-O-Methy‡ | | | Ususally AS |
| "Stab53*" | 2'-O-Methyl‡ | Ribo‡ | | | Ususally AS |
| "Stab53N*" | 2'-O-Methyl‡ | Ribo‡ | | 1 at 3'-end | Ususally AS |
| Stab54 | Ribo‡ | 2'-fluoro‡ | | | Ususally AS |

CAP = any terminal cap, see for example FIG. 5.
All Stab chemistries can be used in combination with each other for duplexes of the invention (e.g., as combinations of sense and antisense strand chemistries), or alternately can be used in isolation, e.g., for single stranded nucleic acid molecules of the invention.
All Stab chemistries can comprise 3'-overhang nucleotides having 2'-O-alkyl, 2'-deoxy-2'-fluoro, 2'-deoxy, LNA or other modified nucleotides or non-nucleotides.
All Stab chemistries typically comprise about 19-21 nucleotides, but can vary as described herein.
All Stab chemistries can also include a single ribonucleotide in the sense or passenger strand at the 11th base paired position of the double-stranded nucleic acid duplex as determined from the 5'-end of the antisense or guide strand (see FIG. 4C).
All Stab chemistries can also have in place of the Stab designation above a 2'-deoxy-2'-fluoro modification at position 14 from the 5' end of the antisense strand regardless of whether it is a purine or pyrimidine at that position (see FIG. 4C).
All Stab chemistries of the antisense strand presented above can have a thymidine in place of a 2'-deoxy uridine at position 1, 2, and/or 3 from the 5' end of the antisense strand (see FIG. 4C).
S = sense strand.
AS = antisense strand
*Stab 23 has a single ribonucleotide adjacent to 3'-CAP.
*Stab 24 and Stab 28 have a single ribonucleotide at 5'-terminus.
*Stab 25, Stab 26, Stab 27, Stab 35, Stab35G*, Stab 35N*, Stab 35rev*, Stab 36, Stab 50*, Stab53*, Stab 53N*, and Stab 54 have three ribonucleotides at 5'-terminus.
*Stab 29, Stab 30, Stab 31, Stab 33, and Stab 34 any purine at first three nucleotide positions from 5'-terminus are ribonucleotides.
p = phosphorothioate linkage.
†Stab 35 has 2'-O-methyl U at 3'-overhangs and three ribonucleotides at 5'-terminus.
†Stab 36 has 2'-O-methyl overhangs that are complementary to the target sequence. (naturally occurring overhangs) and three ribonucleotides at 5'-terminus.
‡Stab 04H, Stab 06C, Stab107H, Stab07mU, Stab09H, Stab16C, Stab 16H, Stab18C, Stab 18H, Stab 52H, Stab 05C, Stab05N, Stab10C, Stab10N, Stab35G*, Stab35N*, Stab35N*, Stab35rev*, Stab 50*, Stab 53*, Stab 53N*, Stab 54 have two 2'-O-methyl U 3'-overhangs. Stab35G*, Stab 35N*, Stab35rev*, Stab50*, Stab53*, and Stab53N* do not allow for a 2'-O-methyl modification at position 14 of the guide strand as determined from the 5'-end.

TABLE 7

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument | | | | | |
| Phosphor-amidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-PCSK9hyl Imidazole | 186 | 233 μL | 5 sec | 5 sec | 5 sec |
| TCA | 176 | 2.3 μL | 21 sec | 21 sec | 21 sec |
| Iodine | 11.2 | 1.7 μL | 45 sec | 45 sec | 45 sec |

TABLE 7-continued

| | | | | | |
|---|---|---|---|---|---|
| Beaucage | 12.9 | 645 μL | 100 sec | 300 sec | 300 sec |
| Acetonitrile | NA | 6.67 μL | NA | NA | NA |

B. 0.2 μmol Synthesis Cycle ABI 394 Instrument

| | | | | | |
|---|---|---|---|---|---|
| Phosphor-amidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-PCSK9hyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 μL | NA | NA | NA |

C. 0.2 μmol Synthesis Cycle 96 well Instrument

| Reagent | Equivalents: DNA/2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphor-amidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-PCSK9hyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

*Wait time does not include contact time during delivery.
*Tandem synthesis utilizes double coupling of linker molecule

TABLE 8

Lipid Nanoparticle (LNP) Formulations

| Formulation # | Composition | Mole Ratio |
|---|---|---|
| L051 | CLinDMA/DSPC/Chol/PEG-n-DMG | 48/40/10/2 |
| L053 | DMOBA/DSPC/Chol/PEG-n-DMG | 30/20/48/2 |
| L054 | DMOBA/DSPC/Chol/PEG-n-DMG | 50/20/28/2 |
| L069 | CLinDMA/DSPC/Cholesterol/PEG-Cholesterol | 48/40/10/2 |
| L073 | pCLinDMA or CLin DMA/DMOBA/DSPC/Chol/PEG-n-DMG | 25/25/20/28/2 |
| L077 | eCLinDMA/DSPC/Cholesterol/2KPEG-Chol | 48/40/10/2 |
| L080 | eCLinDMA/DSPC/Cholesterol/2KPEG-DMG | 48/40/10/2 |
| L082 | pCLinDMA/DSPC/Cholesterol/2KPEG-DMG | 48/40/10/2 |
| L083 | pCLinDMA/DSPC/Cholesterol/2KPEG-Chol | 48/40/10/2 |
| L086 | CLinDMA/DSPC/Cholesterol/2KPEG-DMG/Linoleyl alcohol | 43/38/10/2/7 |
| L061 | DMLBA/Cholesterol/2KPEG-DMG | 52/45/3 |
| L060 | DMOBA/Cholesterol/2KPEG-DMG N/P ratio of 5 | 52/45/3 |
| L097 | DMLBA/DSPC/Cholesterol/2KPEG-DMG | 50/20/28/2 |
| L098 | DMOBA/Cholesterol/2KPEG-DMG, N/P ratio of 3 | 52/45/3 |
| L099 | DMOBA/Cholesterol/2KPEG-DMG, N/P ratio of 4 | 52/45/3 |
| L100 | DMOBA/DOBA/3% PEG-DMG, N/P ratio of 3 | 52/45/3 |
| L101 | DMOBA/Cholesterol/2KPEG-Cholesterol | 52/45/3 |
| L102 | DMOBA/Cholesterol/2KPEG-Cholesterol, N/P ratio of 5 | 52/45/3 |
| L103 | DMLBA/Cholesterol/2KPEG-Cholesterol | 52/45/3 |
| L104 | CLinDMA/DSPC/Cholesterol/2KPEG-cholesterol/Linoleyl alcohol | 43/38/10/2/7 |
| L105 | DMOBA/Cholesterol/2KPEG-Chol, N/P ratio of 2 | 52/45/3 |
| L106 | DMOBA/Cholesterol/2KPEG-Chol, N/P ratio of 3 | 67/30/3 |
| L107 | DMOBA/Cholesterol/2KPEG-Chol, N/P ratio of 1.5 | 52/45/3 |
| L108 | DMOBA/Cholesterol/2KPEG-Chol, N/P ratio of 2 | 67/30/3 |
| L109 | DMOBA/DSPC/Cholesterol/2KPEG-Chol, N/P ratio of 2 | 50/20/28/2 |
| L110 | DMOBA/Cholesterol/2KPEG-DMG, N/P ratio of 1.5 | 52/45/3 |
| L111 | DMOBA/Cholesterol/2KPEG-DMG, N/P ratio of 1.5 | 67/30/3 |
| L112 | DMLBA/Cholesterol/2KPEG-DMG, N/P ratio of 1.5 | 52/45/3 |

TABLE 8-continued

Lipid Nanoparticle (LNP) Formulations

| Formulation # | Composition | Mole Ratio |
|---|---|---|
| L113 | DMLBA/Cholesterol/2KPEG-DMG, N/P ratio of 1.5 | 67/30/3 |
| L114 | DMOBA/Cholesterol/2KPEG-DMG, N/P ratio of 2 | 52/45/3 |
| L115 | DMOBA/Cholesterol/2KPEG-DMG, N/P ratio of 2 | 67/30/3 |
| L116 | DMLBA/Cholesterol/2KPEG-DMG, N/P ratio of 2 | 52/45/3 |
| L117 | DMLBA/Cholesterol/2KPEG-DMG, N/P ratio of 2 | 52/45/3 |
| L118 | LinCDMA/DSPC/Cholesterol/2KPEG-DMG/Linoleyl alcohol, N/P ratio of 2.85 | 43/38/10/2/7 |
| L121 | 2-CLIM/DSPC/Cholesterol/2KPEG-DMG/, N/P ratio of 3 | 48/40/10/2 |
| L122 | 2-CLIM/Cholesterol/2KPEG-DMG/, N/P ratio of 3 | 68/30/2 |
| L123 | CLinDMA/DSPC/Cholesterol/2KPEG-DMG/Linoleyl alcohol, N/P ratio of 2.85 | 43/37/10/3/7 |
| L124 | CLinDMA/DSPC/Cholesterol/2KPEG-DMG/Linoleyl alcohol, N/P ratio of 2.85 | 43/36/10/4/7 |
| L130 | CLinDMA/DOPC/Chol/PEG-n-DMG, N/P ratio of 3 | 48/39/10/3 |
| L131 | DMLBA/Cholesterol/2KPEG-DMG, N/P ratio of 3 | 52/43/5 |
| L132 | DMOBA/Cholesterol/2KPEG-DMG, N/P ratio of 3 | 52/43/5 |
| L133 | CLinDMA/DOPC/Chol/PEG-n-DMG, N/P ratio of 3 | 48/4/10/2 |
| L134 | CLinDMA/DOPC/Chol/PEG-n-DMG, N/P ratio of 3 | 48/37/10/5 |
| L149 | COIM/DSPC/Cholesterol/2KPEG-DMG/, N/P ratio of 3 | 48/40/10/2 |
| L155 | CLinDMA/DOPC/Cholesterol/2KPEG-DMG/Linoleyl alcohol, N/P ratio of 2.85 | 43/38/10/2/7 |
| L156 | CLinDMA/DOPC/Cholesterol/2KPEG-DMG, N/P ratio of 2.85 | 45/43/10/2 |
| L162 | CLinDMA/DOPC/Cholesterol/2KPEG-DMG, N/P ratio of 2.5 | 45/43/10/2 |
| L163 | CLinDMA/DOPC/Cholesterol/2KPEG-DMG, N/P ratio of 2 | 45/43/10/2 |
| L164 | CLinDMA/DOPC/Cholesterol/2KPEG-DMG, N/P ratio of 2.25 | 45/43/10/2 |
| L165 | CLinDMA/DOPC/Cholesterol/2KPEG-DMG, N/P ratio of 2.25 | 40/43/15/2 |
| L166 | CLinDMA/DOPC/Cholesterol/2KPEG-DMG, N/P ratio of 2.5 | 40/43/15/2 |
| L167 | CLinDMA/DOPC/Cholesterol/2KPEG-DMG, N/P ratio of 2 | 40/43/15/2 |
| L174 | CLinDMA/DSPC/DOPC/Cholesterol/2KPEG-DMG/Linoleyl alcohol, N/P ratio of 2.85 | 43/9/27/10/4/7 |
| L175 | CLinDMA/DSPC/DOPC/Cholesterol/2KPEG-DMG/Linoleyl alcohol, N/P ratio of 2.85 | 43/27/9/10/4/7 |
| L176 | CLinDMA/DOPC/Cholesterol/2KPEG-DMG/Linoleyl alcohol, N/P ratio of 2.85 | 43/36/10/4/7 |
| L180 | CLinDMA/DOPC/Cholesterol/2KPEG-DMG/Linoleyl alcohol, N/P ratio of 2.25 | 43/36/10/4/7 |
| L181 | CLinDMA/DOPC/Cholesterol/2KPEG-DMG/Linoleyl alcohol, N/P ratio of 2 | 43/36/10/4/7 |
| L182 | CLinDMA/DOPC/Cholesterol/2KPEG-DMG, N/P ratio of 2.25 | 45/41/10/4 |
| L197 | CODMA/DOPC/Cholesterol/2KPEG-DMG, N/P ratio of 2.85 | 43/36/10/4/7 |
| L198 | CLinDMA/DOPC/Cholesterol/2KPEG-DMG/2KPEG-DSG/Linoleyl alcohol, N/P ratio of 2.85 | 43/34/10/4/2/7 |
| L199 | CLinDMA/DOPC/Cholesterol/2KPEG-DMG/Linoleyl alcohol, N/P ratio of 2.85 | 43/34/10/6/7 |
| L200 | CLinDMA/Cholesterol/2KPEG-DMG, N/P ratio of 3.0 | 50/46/4 |
| L201 | CLinDMA/Cholesterol/2KPEG-DMG, N/P ratio of 3.0 | 50/44/6 |
| L206 | CLinDMA/Cholesterol/2KPEG-DMG, N/P ratio of 3.0 | 40/56/4 |
| L207 | CLinDMA/Cholesterol/2KPEG-DMG, N/P ratio of 3.0 | 60/36/4 |
| L208 | CLinDMA/DOPC/Cholesterol/2KPEG-DMG, N/P ratio of 3.0 | 40/10/46/4 |
| L209 | CLinDMA/DOPC/Cholesterol/2KPEG-DMG, N/P ratio of 3.0 | 60/10/26/4 |
| D000 | DLinDMA/Cholesterol/PEG-DMG/DSPC, N/P ratio of 2.8 | 40/48/2/10 |
| D001 | DLinDMA/Cholesterol/S-PEG-C-DMA/DSPC, N/P ratio of 6 | 40/48/2/10 |
| L278 | L-278/Cholesterol/PEG-DMG N/P ratio of 3.3 | 60/38/2 |
| OCD | Octyl ClinDMA/Cholesterol/PEG-DMG N/P ratio of 3.3 | 60/38/2 |

N/P ratio = Nitrogen:Phosphorous ratio between cationic lipid and nucleic acid

The 2KPEG utilized is PEG2000, a polydispersion which can typically vary from ~1500 to ~3000 Da (i.e., where PEG(n) is about 33 to about 67, or on average ~45).

TABLE 9
CLinDMA structure
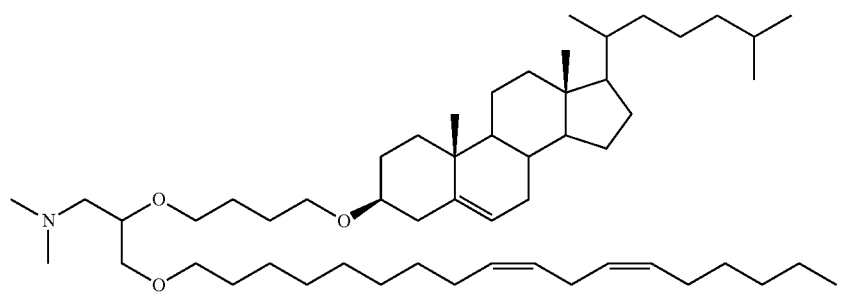 [SMILES: CCCCC/C=C\C/C=C\CCCCCCCCOCC(CN(C)C)OCCCCO[C@H]1CC[C@@]2(C)C(=CCC3C4CCC(C(C)CCCC(C)C)[C@@]4(C)CCC32)C1]
pCLinDMA structure
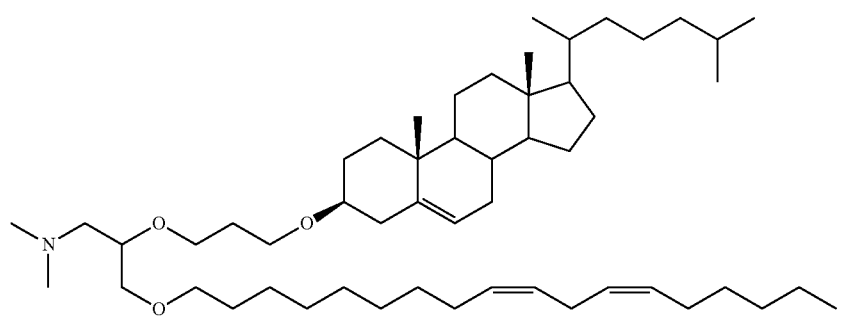 [SMILES: CCCCC/C=C\C/C=C\CCCCCCCCOCC(CN(C)C)OCCCO[C@H]1CC[C@@]2(C)C(=CCC3C4CCC(C(C)CCCC(C)C)[C@@]4(C)CCC32)C1]
eCLinDMA structure
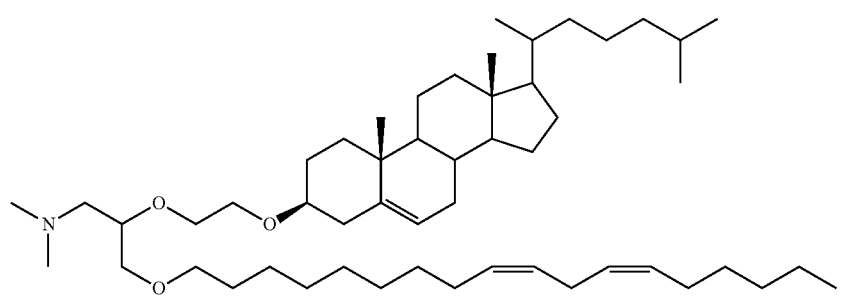 [SMILES: CCCCC/C=C\C/C=C\CCCCCCCCOCC(CN(C)C)OCCO[C@H]1CC[C@@]2(C)C(=CCC3C4CCC(C(C)CCCC(C)C)[C@@]4(C)CCC32)C1]
DEGCLinDMA structure
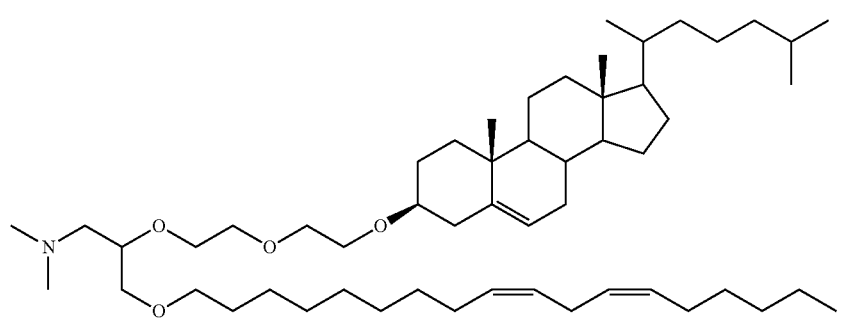 [SMILES: CCCCC/C=C\C/C=C\CCCCCCCCOCC(CN(C)C)OCCOCCO[C@H]1CC[C@@]2(C)C(=CCC3C4CCC(C(C)CCCC(C)C)[C@@]4(C)CCC32)C1]
PEG-n-DMG structure
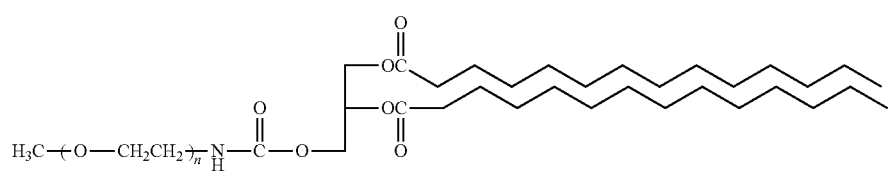
n = about 33 to 67, average = 45 for 2KPEG/PEG2000

TABLE 9-continued
DMOBA structure
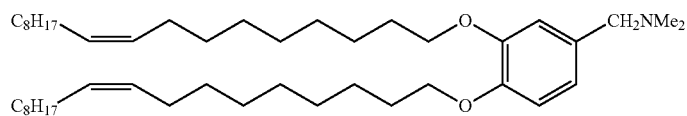
DMLBA structure
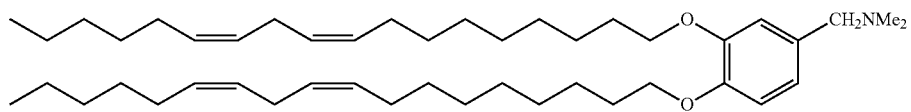
DOBA structure
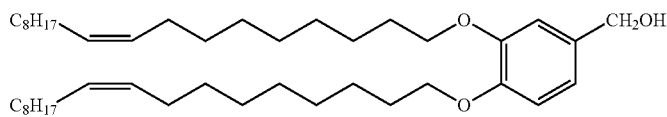
DSPC structure
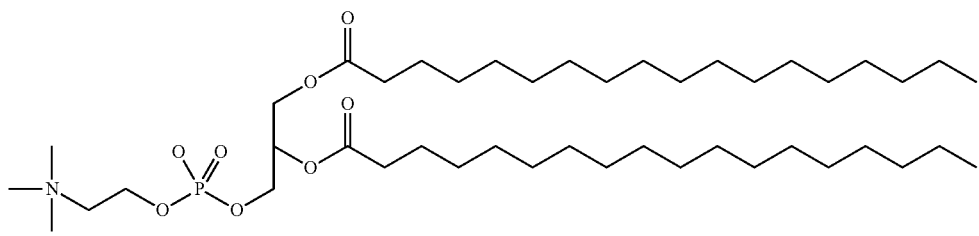
Cholesterol structure
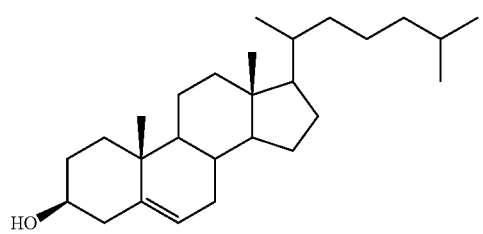 [SMILES: CC(C)CCCC(C)C1CCC2C3CC=C4C[C@@H](O)CC[C@]4(C)C3CC[C@]12C]
2KPEG-Cholesterol structure
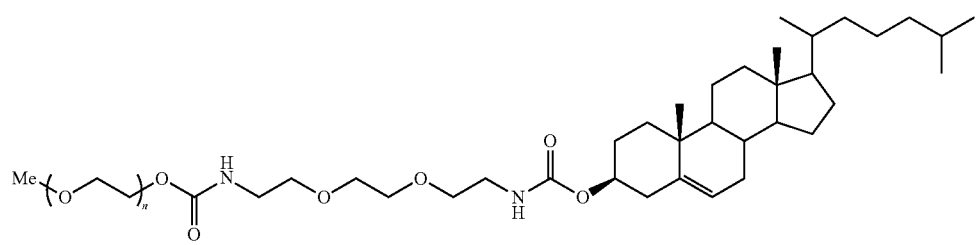
n = about 33 to 67, average = 45 for 2KPEG/PEG2000
2KPEG-DMG structure TABLE 9-continued
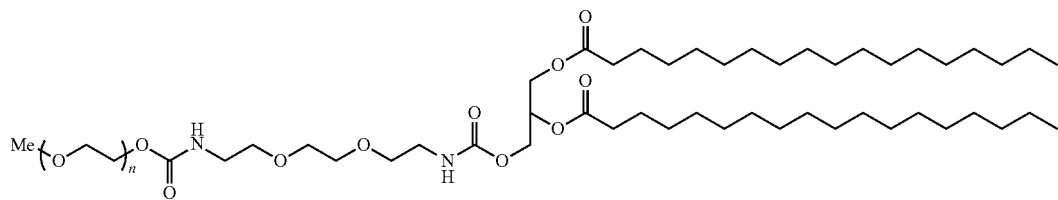
n = about 33 to 67, average = 45 for 2KPEG/PEG2000
COIM STRUCTURE
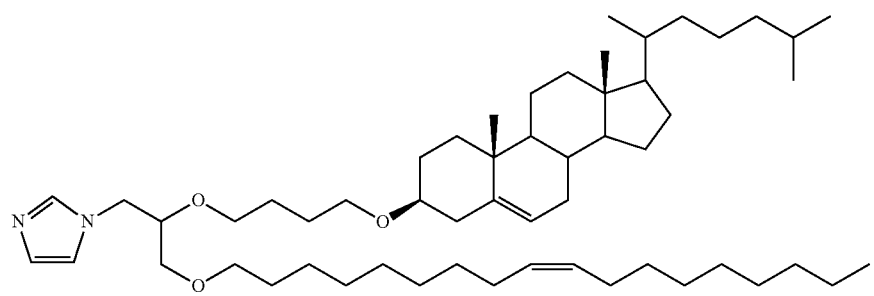 [SMILES: CCCCCCCC/C=C\CCCCCCCCOCC(Cn1ccnc1)OCCCCO[C@H]1CC[C@@]2(C)C(=CCC3C4CCC(C(C)CCCC(C)C)[C@@]4(C)CCC32)C1]
5-CLIM and 2-CLIM structures
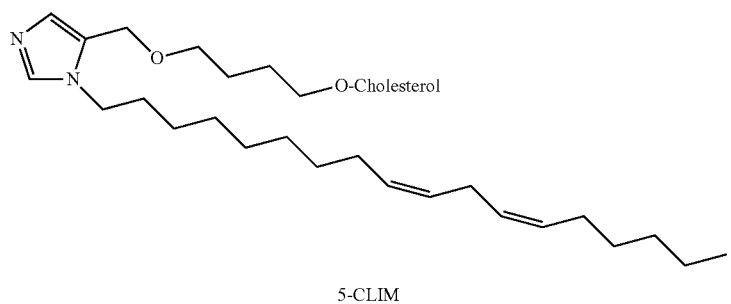
5-CLIM
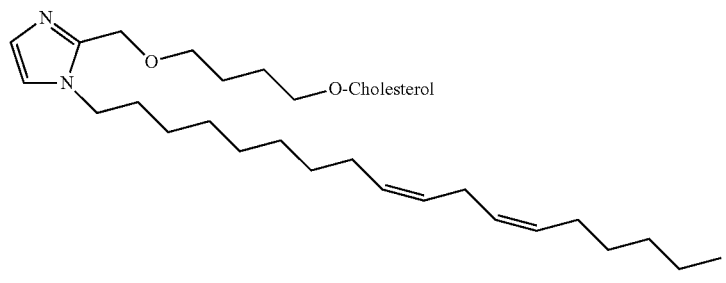
2-CLIM
DLinDMA structure
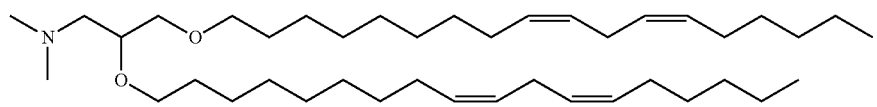 [SMILES: CCCCC/C=C\C/C=C\CCCCCCCCOCC(CN(C)C)OCCCCCCCC/C=C\C/C=C\CCCCC]
L-278 Structure TABLE 9-continued

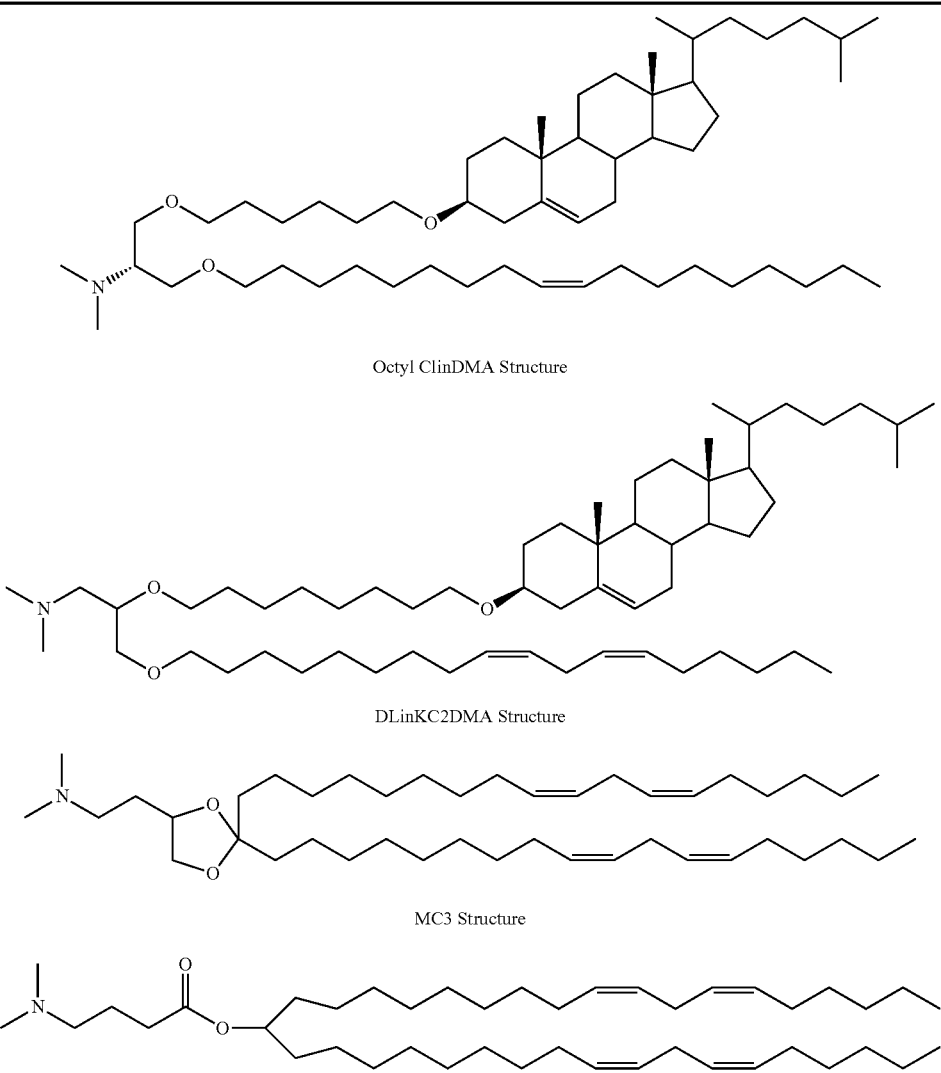

Octyl ClinDMA Structure

DLinKC2DMA Structure

MC3 Structure

What is claimed:

1. A double-stranded short interfering nucleic acid (siNA) molecule that inhibits the expression of mutant isocitrate dehydrogenase 1 (IDH1), comprising formula (A) having a sense strand and an antisense strand:

$$5'-B-N_{X3}-(N)_{X2}B-3'$$
$$3'-(N)_{X1}-N_{X4}-[N3]-[N2]-[N1]-5' \quad (A)$$

wherein, the upper strand is the sense strand and the lower strand is the antisense strand of the double-stranded nucleic acid molecule;

wherein the antisense strand comprises at least 15 contiguous nucleotides of a nucleotide sequence selected from the group consisting of SEQ ID NO: 477, SEQ ID NO: 478, SEQ ID NO: 479, SEQ ID NO: 480, SEQ ID NO: 498, and SEQ ID NO: 502; and the sense strand comprises a nucleotide sequence having complementarity to the antisense nucleotide sequence;

each N is independently either a nucleotide that is unmodified or chemically modified, or a non-nucleotide;

each B is a terminal cap;

$(N)_{X1}$ is 2 and represents overhanging nucleotides which each independently comprise a 2'-O-methyl modification;

$(N)_{X2}$ is 2 and represents overhanging nucleotides which each independently comprise a 2'-O-methyl modification or which each independently comprise a thymine;

X3 is an integer from 18 to 24;

X4 is an integer from 15 to 21; and,

[N1]-[N2]-[N3] are modified nucleotides or ribonucleotides.

2. A double-stranded siNA molecule according to claim 1, comprising one or more phosphorothioate internucleotide linkages.

3. A composition comprising a double-stranded siNA molecule of claim 1 in a pharmaceutically acceptable carrier or diluent.

4. A method of treating a human subject suffering from a condition that is mediated by the action or loss of action of mutant IDH1, which comprises administering to said subject an effective amount of a double-stranded siNA molecule according to claim 1; or, (b) a composition according to claim 3.

5. The method according to claim 4, wherein the condition is cancer.

6. The method of claim 5, wherein the cancer is cancer of the central nervous system.

7. The method of claim 6, wherein cancer of the central nervous system is glioma.

8. The method of claim 5, wherein the cancer is acute myeloid leukemia (AML).

9. The method of claim 4, further comprising administering to the subject an additional therapeutic agent.

10. The method of claim 9, wherein the additional therapeutic agent is an anti-cancer agent.

11. The double-stranded siNA molecule according to claim 1, wherein the sense strand comprises at least 15 nucleotides of a nucleotide sequence selected from the group consisting of SEQ ID NO:38, SEQ ID NO:39, SEQ ID NO:40, SEQ ID NO:41, SEQ ID NO:59, and SEQ ID NO:63.

12. The double-stranded siNA molecule according to claim 1, wherein the sense and antisense strands comprise nucleotide sequences selected from the group consisting of

```
5'-CAUCAUAGGUUGUCAUGCU-3'      (SEQ ID NO: 38)
and

5'-AGCAUGACAACCUAUGAUG-3';     (SEQ ID NO: 477)

5'-AUCAUAGGUUGUCAUGCUU-3'      (SEQ ID NO: 39)
and

5'-AAGCAUGACAACCUAUGAU-3';     (SEQ ID NO: 478)

5'-UCAUAGGUUGUCAUGCUUA-3'      (SEQ ID NO: 40)
and

5'-UAAGCAUGACAACCUAUGA-3';     (SEQ ID NO: 479)

5'-CAUAGGUUGUCAUGCUUAU-3'      (SEQ ID NO: 41)
and

5'-AUAAGCAUGACAACCUAUG-3';     (SEQ ID NO: 480)

5'-CAUAGGUCAUCAUGCUUAU-3'      (SEQ ID NO: 59)
and

5'-AUAAGCAUGAUGACCUAUG-3';     (SEQ ID NO: 498)
and
```

```
5'-GGUCAUCAUGCUUAUGGGG-3'      (SEQ ID NO: 63)
and

5'-CCCCAUAAGCAUGAUGACC-3'.     (SEQ ID NO: 502)
```

13. The double-stranded siNA molecule according to claim 12, wherein the sense and antisense strands comprise nucleotide sequences selected from the group consisting of

```
5'-B CAUAGGUUGUCAUGCUUAUUsU B-3'   (SEQ ID NO: 230)
and

5'-AUAAGCAUGACAACCUAUGUsU-3';      (SEQ ID NO: 231)

5'-B CAUCAUAGGUUGUCAUGCUUsU B-3'   (SEQ ID NO: 198)
and

5'-AGCAUGACAACCUAUGAUGsU-3';       (SEQ ID NO: 199)

5'-B AUCAUAGGUUGUCAUGCUUUsU B-3'   (SEQ ID NO: 212)
and

5'-AAGCAUGACAACCUAUGAUUsU-3';      (SEQ ID NO: 213)

5'-B CAUAGGUCAUCAUGCUUAUTT B-3'    (SEQ ID NO: 302)
and

5'-AUAAGCAUGAUGACCUAUGUU-3';       (SEQ ID NO: 303)

5'-B GGUCAUCAUGCUUAUGGGGTT B-3'    (SEQ ID NO: 410)
and

5'-CCCCAUAAGCAUGAUGACCUU-3',       (SEQ ID NO: 411)
``` wherein A, C, G, and U are ribose A, C, G or U; A, G, C, and U are 2'-O-methyl (2'-OMe) A, G, C, or U; B is an inverted abasic cap; and T is a thymine.

14. The double-stranded siNA molecule according to claim 13, wherein the inverted abasic cap is an inverted abasic sugar moiety.

* * * * *

UNITED STATES PATENT AND TRADEMARK OFFICE
CERTIFICATE OF CORRECTION

PATENT NO. : 9,322,020 B2  
APPLICATION NO. : 14/123822  
DATED : April 26, 2016  
INVENTOR(S) : Yong Ma et al.

Page 1 of 1

It is certified that error appears in the above-identified patent and that said Letters Patent is hereby corrected as shown below:

In the Claims

At column 460, claim number 13, line number 33, delete "and T is a thymine." and replace it with --and $T$ is a thymine.--

Signed and Sealed this  
Second Day of August, 2016

Michelle K. Lee  
*Director of the United States Patent and Trademark Office*